United States Patent
Koerber et al.

(10) Patent No.: US 8,999,889 B2
(45) Date of Patent: Apr. 7, 2015

(54) SUBSTITUTED KETONIC ISOXAZOLINE COMPOUNDS AND DERIVATIVES FOR COMBATING ANIMAL PESTS

(75) Inventors: Karsten Koerber, Eppelheim (DE); Florian Kaiser, Mannheim (DE); Wolfgang von Deyn, Neustadt (DE); Steffen Gross, Ludwigshafen (DE); Joachim Dickhaut, Heidelberg (DE); Prashant Deshmukh, Mannheim (DE); Nina Gertrud Bandur, Mannheim (DE); Arun Narine, Mannheim (DE); Deborah L. Culbertson, Fuquay Varina, NC (US); Douglas D. Anspaugh, Apex, NC (US); Franz Josef Braun, Durham, NC (US)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/576,039

(22) PCT Filed: Jan. 28, 2011

(86) PCT No.: PCT/EP2011/051215
§ 371 (c)(1),
(2), (4) Date: Jul. 30, 2012

(87) PCT Pub. No.: WO2011/092287
PCT Pub. Date: Aug. 4, 2011

(65) Prior Publication Data
US 2012/0309620 A1 Dec. 6, 2012

Related U.S. Application Data

(60) Provisional application No. 61/300,060, filed on Feb. 1, 2010.

(30) Foreign Application Priority Data

Feb. 1, 2010 (EP) .................................... 10152316

(51) Int. Cl.
*A01C 1/06* (2006.01)
*A01N 43/80* (2006.01)
*C07D 261/04* (2006.01)

(52) U.S. Cl.
CPC .............. *C07D 261/04* (2013.01); *A01N 43/80* (2013.01); *A01C 1/06* (2013.01)

(58) Field of Classification Search
None
See application file for complete search history.

(56) References Cited

U.S. PATENT DOCUMENTS

| | | | |
|---|---|---|---|
| 3,917,698 A | 11/1975 | Breslow | |
| 4,863,947 A | 9/1989 | Jacobson | |
| 6,313,344 B1 | 11/2001 | Trah et al. | |
| 6,521,643 B1 | 2/2003 | Tomishima et al. | |
| 6,980,676 B2 | 12/2005 | Pineau | |
| 7,662,972 B2 | 2/2010 | Mita et al. | |
| 7,947,715 B2 | 5/2011 | Mita et al. | |
| 7,951,828 B1 | 5/2011 | Mita et al. | |
| 8,119,671 B2 | 2/2012 | Mita et al. | |
| 2003/0119806 A1 | 6/2003 | Lindell et al. | |
| 2004/0014801 A1 | 1/2004 | Cohen et al. | |
| 2004/0110637 A1 | 6/2004 | Ziemer et al. | |

(Continued)

FOREIGN PATENT DOCUMENTS

| | | |
|---|---|---|
| CA | 2 547 744 | 12/2006 |
| CH | 577487 | 7/1976 |

(Continued)

OTHER PUBLICATIONS

International Search Report completed Mar. 11, 2011, in International Application No. PCT/EP2011/051215, filed Jan. 28, 2011.
English language translation of the International Preliminary Report on Patentability dated Aug. 7, 2012, from corresponding International Application No. PCT/EP2011/051215, filed Jan. 28, 2011.
Bhar, Sanjay, et al., "Highly Selective Regeneration of Carbonyl Compounds from Their Oximes and Semicarbazones in Aqueous Medium", Synthetic Communications, 2005, pp. 1183-1188, vol. 35.
Slee, Deborah H. et al., Development of Potent Non-Carbohydrate Imidazole-Based Small molecule Selection Inhibitors with Antiinflammatory Activity, Journal of Medicinal Chemistry, 2001, pp. 2094-2107, vol. 44, No. 13.
Belen'Kii et al, Database: Beilstein, XP002580907 database accession No. 1988095, Russian Chem. Bull., (1997), pp. 101-104, vol. 46, No. 1.

(Continued)

*Primary Examiner* — Alicia L Otton
(74) *Attorney, Agent, or Firm* — Brinks Gilson & Lione

(57) ABSTRACT

The invention relates to substituted ketonic isoxazoline compounds of formula (I), to the enantiomers, diastereomers and salts thereof and to compositions comprising such compounds. The invention also relates to the use of the substituted ketonic isoxazoline compounds, of their salts or of compositions comprising them for combating animal pests. Furthermore the invention relates also to methods of applying such substituted ketonic isoxazoline compounds.

The substituted ketonic isoxazoline compounds of the present invention are defined by the following formula I:

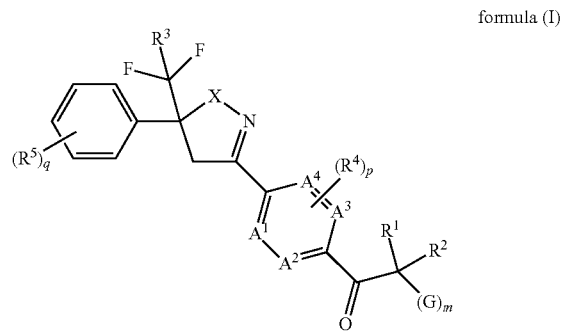

formula (I)

wherein $A^1$ to $A^4$, $R^1$ to $R^3$, $(R^4)_p$, $(R^5)_q$, X and $(G)_m$ are defined as in the description.

31 Claims, No Drawings

(56) References Cited

U.S. PATENT DOCUMENTS

| | | |
|---|---|---|
| 2007/0066617 A1 | 3/2007 | Mita et al. |
| 2008/0262057 A1 | 10/2008 | Tisdell et al. |
| 2009/0023923 A1 | 1/2009 | Mizukoshi et al. |
| 2009/0156643 A1 | 6/2009 | Mita et al. |
| 2010/0144797 A1 | 6/2010 | Mita et al. |
| 2010/0144808 A1 | 6/2010 | Mita et al. |
| 2010/0160683 A1 | 6/2010 | Matoba et al. |
| 2010/0286175 A1 | 11/2010 | Grammenos et al. |
| 2011/0172414 A1 | 7/2011 | Mita et al. |

FOREIGN PATENT DOCUMENTS

| | | |
|---|---|---|
| CH | 595365 | 2/1978 |
| CH | 608011 | 12/1978 |
| CN | 1 927 860 | 3/2007 |
| DE | 10 2004 010 086 | 9/2004 |
| EP | 0 539 676 | 5/1993 |
| EP | 1 538 138 | 6/2005 |
| EP | 1 731 512 | 12/2006 |
| EP | 1932836 | 6/2008 |
| EP | 1 997 813 | 12/2008 |
| EP | 2 151 437 | 2/2010 |
| EP | 2 186 804 | 5/2010 |
| EP | 2199287 | 6/2010 |
| JP | 8 217754 | 8/1996 |
| JP | 2007 016017 | 1/2007 |
| JP | 2007-016017 | 1/2007 |
| JP | 2007-106756 | 4/2007 |
| JP | 2007 106756 | 4/2007 |
| JP | 2007 308471 | 11/2007 |
| JP | 2008 239611 | 10/2008 |
| JP | 2008-239611 | 10/2008 |
| JP | 2009 108046 | 5/2009 |
| WO | WO 88/05046 | 7/1988 |
| WO | WO 88/06583 | 9/1988 |
| WO | WO 00/61009 | 10/2000 |
| WO | WO 01/17964 | 3/2001 |
| WO | WO 02/068392 | 9/2002 |
| WO | WO 03/022808 | 3/2003 |
| WO | WO 03/062222 | 7/2003 |
| WO | WO 03/067987 | 8/2003 |
| WO | WO 2004/018410 | 3/2004 |
| WO | WO 2004/056735 | 7/2004 |
| WO | WO 2004/060371 | 7/2004 |
| WO | WO 2004/060865 | 7/2004 |
| WO | WO 2005/036961 | 4/2005 |
| WO | WO 2005/085216 | 9/2005 |
| WO | WO 2006/010570 | 2/2006 |
| WO | WO 2006/021833 | 3/2006 |
| WO | WO 2006/065659 | 6/2006 |
| WO | WO 2007/026965 | 3/2007 |
| WO | WO 2007/070606 | 6/2007 |
| WO | WO 2007/074789 | 7/2007 |
| WO | WO 2007/075459 | 7/2007 |
| WO | WO 2007/079162 | 7/2007 |
| WO | WO 2007/081019 | 7/2007 |
| WO | WO 2007/093599 | 8/2007 |
| WO | WO 2007/094313 | 8/2007 |
| WO | WO 2007/105814 | 9/2007 |
| WO | WO 2007/125984 | 11/2007 |
| WO | WO 2008/012027 | 1/2008 |
| WO | WO 2008/019760 | 2/2008 |
| WO | WO 2008/022937 | 2/2008 |
| WO | WO 2008/070831 | 6/2008 |
| WO | WO 2008/108448 | 9/2008 |
| WO | WO 2008/122375 | 10/2008 |
| WO | WO 2008/126665 | 10/2008 |
| WO | WO 2008/130651 | 10/2008 |
| WO | WO 2008/154528 | 12/2008 |
| WO | WO 2009/002809 | 12/2008 |
| WO | WO 2009/005015 | 1/2009 |
| WO | WO 2009/022746 | 2/2009 |
| WO | WO 2009/025983 | 2/2009 |
| WO | WO 2009/035004 | 3/2009 |
| WO | WO 2009/045999 | 4/2009 |
| WO | WO 2009/049846 | 4/2009 |
| WO | WO 2009/051956 | 4/2009 |
| WO | WO 2009/077197 | 6/2009 |
| WO | WO 2009/080250 | 7/2009 |
| WO | WO 2009/112275 | 9/2009 |
| WO | WO 2009/126668 | 10/2009 |
| WO | WO 2010/003877 | 1/2010 |
| WO | WO 2010/003923 | 1/2010 |
| WO | WO 2010/020521 | 2/2010 |
| WO | WO 2010/020522 | 2/2010 |
| WO | WO 2010/072602 | 7/2010 |
| WO | WO 2010/072781 | 7/2010 |
| WO | WO 2010/112545 | 10/2010 |
| WO | WO 2011/073444 | 6/2011 |

OTHER PUBLICATIONS

"DMP 754 Roxifiban Acetate", Drugs of the Future, (1998), pp. 707-711, vol. 23(7).

Hosking, M., et al., "Roxifiban DuPont", Current Opinion in Cardiovascular, Pulmonary & Renal Investigational Drugs, (2000), pp. 165-171, vol. 2(2).

Kaugars, G. et al., "Miticidal activity of benzoyl chloride phenylhydrazones", Journal of Agriculture and Food Chem., (1973), pp. 647-650, vol. 21, No. 4.

Kiriyama, K. et al., "Insecticidal and Neuroblocking Activities of Acetamiprid and Related Compounds", Journal of Pesticide Science, (2003), pp. 8-17, vol. 28.

Wierenga, J. et al., "Insecticidal activity of N-arylalkylbenzhydrolpiperidines", Pest Management Science, (2002), pp. 1266-1272, vol. 58.

Walters, Matthew J. et al., "The preparation of 5-Aryl-5-methyl-4,5-dihydroisoxazoles from dilithiated C($\alpha$), O-oximes and Select Acetyl Ketones", Synthetic Communications, 2003, p. 4163-4171, vol. 33, No. 23.

SUBSTITUTED KETONIC ISOXAZOLINE COMPOUNDS AND DERIVATIVES FOR COMBATING ANIMAL PESTS

This application is a National Stage application of International Application No. PCT/EP2011/051215, filed Jan. 28, 2011, which claims the benefit of U.S. Provisional Application No. 61/300,060, filed Feb. 1, 2010 the entire contents of which are hereby incorporated herein by reference. This application also claims priority under 35 U.S.C. §119 to European Patent Application No. 10152316.5, filed Feb. 1, 2010, the entire contents of which is hereby incorporated herein by reference.

The present invention relates to substituted ketonic isoxazoline compounds, to the enantiomers, diastereomers, derivatives and salts thereof and to compositions comprising such compounds. The invention also relates to the use of the substituted ketonic isoxazoline compounds, of their salts or of compositions comprising them for combating animal pests. Furthermore the invention relates also to methods of applying such compounds.

Animal pests destroy growing and harvested crops and attack wooden dwelling and commercial structures, causing large economic loss to the food supply and to property. While a large number of pesticidal agents are known, due to the ability of target pests to develop resistance to said agents, there is an ongoing need for new agents for combating animal pests. In particular, animal pests such as insects and acaridae are difficult to be effectively controlled.

It is therefore an object of the present invention to provide compounds having a good pesticidal activity, especially against difficult to control insects and acaridae.

It has been found that these objects are solved by substituted ketonic isoxazoline derivatives of the general formula I:

Substituted ketonic isoxazoline compounds of the general formula (I)

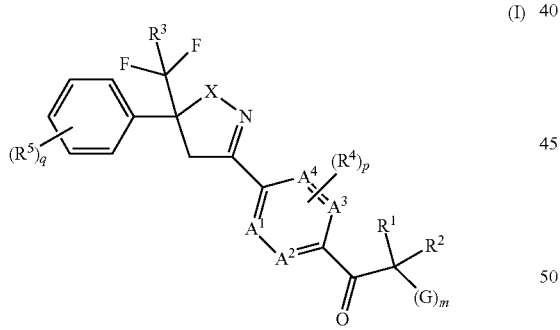

wherein $A^1$, $A^2$, $A^3$ and $A^4$ are N or CH, with the proviso that no more than two nitrogen are present in the ring;

X is O, S or $CH_2$;

p is 0, 1, 2, 3 or 4;

q is 0, 1, 2, 3, 4 or 5;

m is 0 or 1;

G is selected from the group consisting of hydrogen, nitro, cyano, —SCN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, wherein the carbon atoms of the aforementioned aliphatic and cyclo-aliphatic radicals may optionally be substituted with one or more $R^6$, which are independently selected from one another; $NR^{9a}R^{9b}$, $S(O)_nR^7$, —$S(O)_nNR^{9a}R^{9b}$, C(=O)$R^6$, C(=O)$OR^7$, C(=O)$NR^{9a}R^{9b}$, C(=S)$R^6$, C(=S)$SR^7$, C(=S)$NR^{9a}R^{9b}$, C(=$NR^8$)$R^6$;

phenyl, optionally substituted with one or more substituents $R^{10}$, which are selected independently from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, selected independently from one another, and wherein the nitrogen and/or the sulfur atom(s) of the heterocyclic ring may optionally be oxidized;

$R^1$, $R^2$ are selected independent from one another from the group consisting of hydrogen, halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, wherein the carbon atoms of the aforementioned aliphatic and cyclo-aliphatic radicals may optionally be substituted with one or more $R^6$, which are independently selected from one another; Si($R^{11}$)$_2R^{12}$, $OR^7$, $OSO_2R^7$, $S(O)_nR^7$, $S(O)_nNR^{9a}R^{9b}$, $NR^{9a}R^{9b}$, C(=O)$NR^{9a}R^{9b}$, C(=S)$NR^{9a}R^{9b}$, C(=O)$OR^7$, phenyl, optionally substituted with one or more substituents $R^{10}$, which are independently selected from one another;

a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, selected independently from one another, and wherein the nitrogen and/or the sulfur atom(s) of the heterocyclic ring may optionally be oxidized, or $R^1$ and $R^2$ may together form =O, =$CR^{13}R^{14}$; =$CR^{13}NR^{17a}R^{17b}$, =$S(O)_nR^{16}$; =$S(O)_nNR^{17a}R^{17b}$, =$NR^{17a}$, =$NOR^{16}$; =$NNR^{17a}$;

or $R^1$ and $R^2$ may form together with the carbon atoms to which $R^1$ and $R^2$ are bonded to a 3-, 4-, 5-, 6-, 7- or 8-membered saturated, partly or fully unsaturated or aromatic carbocyclic or heterocyclic ring optionally comprising 1, 2 or 3 heteroatoms selected from oxygen, nitrogen and/or sulfur and/or optionally substituted with k substituents $R^{10}$, selected independently from one another, and wherein the nitrogen and/or the sulfur atom(s) of the heterocyclic ring may optionally be oxidized;

$R^3$ is preferably selected from the group consisting of hydrogen, halogen, hydroxyl, nitrile, SCN, $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_3$-$C_6$-cycloalkyl $C_3$-$C_6$-halocycloalkyl and $C_1$-$C_4$-halothioalkyl;

$R^4$ is attached to the carbon atom of the ring and is selected, independently from each other if p>1, from the group consisting of hydrogen, halogen, cyano, azido, nitro, —SCN, $SF_5$, $C_1$-$C_6$-alkyl, $C_3$-$C_8$-cycloalkyl, $C_2$-$C_6$-alkenyl, $C_2$-$C_6$-alkinyl, wherein the carbon atoms of the aforementioned aliphatic and cyclo-aliphatic radicals may optionally be substituted with one or more $R^6$, which are independently selected from one another;

$Si(R^{11})_2R^{12}$, $OR^7$, $-OS(O)_nR^7$, $S(O)_nR^7$, $NR^{9a}R^{9b}$, $N(R^{9a})C(=O)R^6$, $C(=O)R^6$, $-C(=O)OR^7$, $C(=NR^8)R^6$, $C(=S)R^6$, phenyl, optionally substituted with one or more substituents independently selected from $R^{10}$, which are selected independently from one another;

a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized, or, when p is 2 or more and two of $R^4$ are adjacent, the two adjacent $R^4$ may form a bridge selected from the group consisting of $CH_2CH_2CH_2CH_2$, $CH=CH-CH=CH$, $N=CH-CH=CH$, $CH=N-CH=CH$, $N=CH-N=CH$, $OCH_2CH_2CH_2$, $OCH=CHCH_2$, $CH_2OCH_2CH_2$, $OCH_2CH_2O$, $OCH_2OCH_2$, $CH_2CH_2CH_2$, $CH=CHCH_2$, $CH_2CH_2O$, $CH=CHO$, $CH_2OCH_2$, $CH_2C(=O)O$, $C(=O)OCH_2$, $O(CH_2)O$, $SCH_2CH_2CH_2$, $SCH=CHCH_2$, $CH_2SCH_2CH_2$, $SCH_2CH_2S$, $SCH_2SCH_2$, $CH_2CH_2S$, $CH=CHS$, $CH_2SCH_2$, $CH_2C(=S)S$, $C(=S)SCH_2$, $S(CH_2)S$, $CH_2CH_2NR^{9a}$, $CH_2CH=N$, $OCH=N$, $SCH=N$, $CH=CH-NR^{9a}$, wherein the carbon atoms of the bridge may optionally be substituted with one or two substituents selected from the group consisting of $=O$, $OH$, $CH_3$, $OCH_3$, halogen, halomethyl or halomethoxy, and with the proviso, that G, $R^1$ and $R^2$ are not hydrogen simultaneously;

$R^5$ is selected independently from each other if q>1 from the group consisting of hydrogen, halogen, cyano, azido, nitro, SCN, $SF_5$, $C_1$-$C_6$-alkyl, $C_3$-$C_8$-cycloalkyl, $C_2$-$C_6$-alkenyl, $C_2$-$C_6$-alkinyl, wherein the carbon atoms of the aforementioned aliphatic and cyclo-aliphatic radicals may optionally be substituted with one or more $R^6$, which are independently selected from one another;
$Si(R^{11})_2R^{12}$, $OR^7$, $-OS(O)_nR^7$, $S(O)_nR^7$, $NR^{9a}R^{9b}$, $N(=R^{9a})C(=O)R^6$, $C(=O)R^6$, $C(=O)OR^7$, $C(=NR^8)R^6$, $C(=S)R^6$, phenyl, optionally substituted with one or more substituents $R^{10}$; which are independently selected from one another;

a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized;

$R^6$ is selected from the group consisting of hydrogen, halogen, cyano, azido, nitro, $-SCN$, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, $Si(R^{11})_2R^{12}$, $OR^{16}$, $OSO_2R^{16}$, $S(O)_nR^{16}$, $S(O)_nNR^{17a}R^{17b}$, $NR^{17a}R^{17b}$, $NR^{17a}C(=O)R^{16}C(=O)NR^{17a}R^{17b}$, $C(=S)NR^{17a}R^{17b}$, $C(=O)OR^{16}$, phenyl, optionally substituted with one or more substituents $R^{18}$, which are independently selected from one another;

a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized; or two $R^6$ present on one carbon atom may together form $=O$, $=CR^{13}R^{14}$; $=S(O)_nR^{16}$; $=S(O)_nNR^{17a}R^{17b}$, $=NR^{17a}$, $=NOR^{16}$; $=NNR^{17a}R^{17b}$;

or two $R^6$ may form a 3-, 4-, 5-, 6-, 7- or 8-membered saturated or partly unsaturated carbocyclic or heterocyclic ring together with the carbon atoms to which the two $R^6$ are bonded to;

$R^7$ is, independent from each other, selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_4$-$C_8$-alkylcycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, $-Si(R^{11})_2R^{12}$, $OR^{16}$, $-S(O)_nNR^{17a}R^{17b}$, $NR^{17a}R^{17b}$, $-N=CR^{13}R^{14}$, $-C(=O)R^{16}$, $C(=O)NR^{17a}R^{17b}$, $C(=S)NR^{17a}R^{17b}$, $C(=O)OR^{16}$, phenyl, optionally substituted with one or more substituents $R^{18}$; which are selected independently from one another;

a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized;

$R^8$ is selected from the group consisting of hydrogen, nitro, cyano, $C_1$-$C_{10}$-alkyl, $C_3$-$C_8$-cycloalkyl, $C_2$-$C_{10}$-alkenyl, $C_2$-$C_{10}$-alkinyl, wherein the carbon atoms of the aforementioned aliphatic and cyclo-aliphatic radicals may optionally be substituted with one or more $R^{15}$, which are selected independently from one another;

$NR^{17a}R^{17b}$, $Si(R^{11})_2R^{12}$, $OR^{16}$, $S(O)_nR^{16}$, $S(O)_nNR^{17a}R^{17b}$, $C(=O)R^{15}$, $-C(=O)OR^{16}$, $C(=O)NR^{17a}R^{17b}$, $C(=S)R^{15}$, $C(=S)SR^{16}$, $C(=S)NR^{17a}R^{17b}$; $C(=NR^{17a})R^{15}$;

phenyl, optionally substituted with one or more substituents $R^{18}$, which are selected independently from one another;

a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, independently selected from one another, and wherein the nitrogen and/or the sulfur atom(s) of the heterocyclic ring may optionally be oxidized;

$R^{9a}$, $R^{9b}$ are selected independent from one another from the group consisting of hydrogen, $C_1$-$C_6$-alkyl, optionally substituted with one or more substituents $R^{10}$;

$C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, $S(O)_nR^{16}$, $-S(O)_nNR^{17a}R^{17b}$, $C(=O)R^{15}$, $C(=O)OR^{16}$, $C(=O)NR^{17a}R^{17b}$, $C(=S)R^{15}$, $C(=S)SR^{16}$, $C(=S)NR^{17a}R^{17b}$, $C(=NR^{17a})R^{15}$, phenyl, optionally substituted with one or more substituents $R^{18}$, which are selected independently from one another;

a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized;

or, $R^{9a}$ and $R^{9b}$ are together a $C_2$-$C_7$ alkylene chain and form a 3-, 4-, 5-, 6-, 7- or 8-membered saturated, partly saturated or unsaturated aromatic ring together with the nitrogen atom they are bonded to, wherein the alkylene chain may contain one or two heteroatoms selected from oxygen, sulfur or nitrogen, and may optionally be substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl;

phenyl, optionally substituted with one or more substituents $R^{18}$; which are selected independently from one another;

a 3-, 4-, 5-, 6-, or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized;

$R^{10}$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkinyl, wherein the carbon atoms of the aforementioned aliphatic and cyclo-aliphatic radicals may optionally be substituted with one or more $R^{15}$, which are selected independently from one another;

$Si(R^{11})_2R^{12}$, $OR^{16}$, $OS(O)_nR^{16}$, $-S(O)_nR^{16}$, $S(O)_nNR^{17a}R^{17b}$, $NR^{17a}R^{17b}$, $C(=O)R^{15}$, $C(=O)OR^{16}$, $-C(=NR^{17a})R^{15}$, $C(=O)NR^{17a}R^{17b}$, $C(=S)NR^{17a}R^{17b}$, phenyl, optionally substituted with halogen, cyano, nitro, $C_1$-$C_6$-alkyl, $C_1$-$C_6$-haloalkyl, $C_1$-$C_6$-alkoxy or $C_1$-$C_6$-haloalkoxy;

a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents selected independently from one another from halogen, cyano, $NO_2$, $C_1$-$C_6$-alkyl, $C_1$-$C_6$-haloalkyl, $C_1$-$C_6$-alkoxy or $C_1$-$C_6$-haloalkoxy, and wherein the nitrogen and/or the sulfur atom(s) of the heterocyclic ring may optionally be oxidized;

or two $R^{10}$ present together on one atom of a partly saturated heterocyclic may be $=O$, $=CR^{13}R^{14}$; $=S(O)_nR^{16}$; $=S(O)_nNR^{17a}R^{17b}$, $=NR^{17a}$, $=NOR^{16}$ or $=NNR^{17a}$, or, two $R^{10}$ on adjacent carbon atoms may be a bridge selected from $CH_2CH_2CH_2CH_2$, $CH=CH-CH=CH$, $N=CH-CH=CH$, $CH=N-CH=CH$, $N=CH-N=CH$, $OCH_2CH_2CH_2$, $OCH=CHCH_2$, $CH_2OCH_2CH_2$, $OCH_2CH_2O$, $OCH_2OCH_2$, $CH_2CH_2CH_2$, $CH=CHCH_2$, $CH_2CH_2O$, $CH=CHO$, $CH_2OCH_2$, $CH_2C(=O)O$, $C(=O)OCH_2$, $O(CH_2)O$, $SCH_2CH_2CH_2$, $SCH=CHCH_2$, $CH_2SCH_2CH_2$, $SCH_2CH_2S$, $SCH_2SCH_2$, $CH_2CH_2S$, $CH=CHS$, $CH_2SCH_2$, $CH_2C(=S)S$, $C(=S)SCH_2$, $S(CH_2)S$, $CH_2CH_2NR^{9a}$, $CH_2CH=N$, $CH=CH-NR^{9a}$, $OCH=N$, $SCH=N$ and form together with the carbon atoms to which the two $R^{10}$ are bonded to a 5-membered or 6-membered partly saturated or unsaturated, aromatic carbocyclic or heterocyclic ring, wherein the ring may optionally be substituted with one or two substituents selected from $=O$, OH, $CH_3$, $OCH_3$, halogen, halomethyl or halomethoxy;

$R^{11}$, $R^{12}$ are selected independent from one another from the group consisting of hydrogen, halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkinyl, $C_2$-$C_6$ haloalkinyl, $C_3$-$C_8$ cycloalkyl, $C_3$-$C_8$ halocycloalkyl, $C_1$-$C_6$ alkoxyalkyl, $C_1$-$C_6$ haloalkoxyalkyl, phenyl, optionally substituted with one or more substituents $R^{18}$; which are selected independently from one another;

a 3-, 4-, 5-, 6- to 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized;

$R^{13}$, $R^{14}$ are selected independent from one another from hydrogen, $C_1$-$C_4$ alkyl, $C_1$-$C_6$ cycloalkyl, $C_1$-$C_4$ alkoxyalkyl, phenyl or benzyl;

$R^{15}$ is selected from the group consisting of hydrogen, halogen, cyano, azido, nitro, OH, SH, SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, ($C_1$-$C_6$-alkyl)amino or di-($C_1$-$C_6$-alkyl)amino, ($C_1$-$C_6$-haloalkyl)amino or di-($C_1$-$C_6$-haloalkyl)amino, $C_1$-$C_6$-alkyl, $C_2$-$C_6$-alkenyl, $C_2$-$C_6$-alkinyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $C_1$-$C_4$ alkoxy;

phenyl, benzyl, pyridyl, phenoxy, wherein the last four radicals may be unsubstituted, partially or fully halogenated and/or to carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino or di-($C_1$-$C_6$-alkyl)amino;

or two $R^{15}$ present on the same carbon atom may together be $=O$, $=CH(C_1$-$C_4$-alkyl), $=C(C_1$-$C_4$-alkyl)$C_1$-$C_4$-alkyl, $=N(C_1$-$C_6$-alkyl) or $=NO(C_1$-$C_6$-alkyl);

$R^{16}$ is selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkinyl, $C_3$-$C_8$-cycloalkyl, wherein the four last mentioned radicals may be unsubstituted, partially or fully halogenated and/or oxygenated and/or may carry 1 or 2 radicals selected from $C_1$-$C_4$ alkoxy cyclopropyl or halocyclopropyl;

phenyl, benzyl, pyridyl, phenoxy, wherein the last four radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy or ($C_1$-$C_6$-alkoxy)carbonyl;

$R^{17a}$, $R^{17b}$ is selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkinyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $C_1$-$C_4$-alkoxy, $C_1$-$C_4$-alkyl, cyclopropyl, halocyclopropyl or pyridyl;

phenyl, benzyl, pyridyl, phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy or ($C_1$-$C_6$-alkoxy)carbonyl;

or, $R^{17a}$ and $R^{17b}$ may together be a $C_2$-$C_6$ alkylene chain forming a 3- to 7-membered saturated, partly saturated or unsaturated ring together with the nitrogen atom $R^{17a}$ and $R^{17b}$ are bonded to, wherein the alkylene chain may contain 1 or 2 heteroatoms selected from oxygen, sulfur or nitrogen, and may optionally be substituted with halogen, $C_1$-$C_4$-haloalkyl, $C_1$-$C_4$-alkoxy or $C_1$-$C_4$-haloalkoxy, and wherein the nitrogen and/or the sulfur atom(s) of the heterocyclic ring may optionally be oxidized;

$R^{18}$ is selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkinyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $C_1$-$C_4$-alkoxy;

phenyl, benzyl, pyridyl, phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy), ($C_1$-$C_6$-alkoxy)carbonyl;

or two $R^{18}$ present together on one atom of a partly saturated atom may be =O, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

or, two $R^{18}$ on two adjacent carbon atoms may be together a $C_2$-$C_6$ alkylene chain, which form together with the carbon atom they are bonded to a 3-, 4-, 5-, 6- or 7-membered saturated, partly saturated or unsaturated aromatic, wherein the alkylene chain may contain 1 or 2 heteroatoms selected from oxygen, sulfur or nitrogen, and may optionally be substituted with halogen, $C_1$-$C_4$-haloalkyl, $C_1$-$C_4$-alkoxy or $C_1$-$C_4$-haloalkoxy, and wherein the nitrogen and/or the sulfur atom(s) of the heterocyclic ring may optionally be oxidized;

n is 0, 1 or 2;

k is an integer selected from 0 to 10;

or an enantiomer, diastereomer and salt thereof.

Aryl isoxazolines in general have been previously described. Insecticidal aryl isoxazolines of the following formula

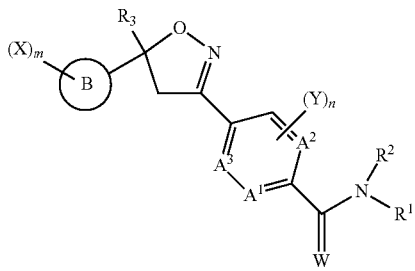

wherein, inter alia, each of $A^1$, $A^2$ and $A^3$ are independently carbon or nitrogen, B is a benzene ring, and W being defined as oxygen or sulfur are disclosed in WO 2005/085216 (corresponding US 20070066617). Similar aryl isoxazoline to those used in pesticidal mixtures have been described in JP 2009-108046 and international applications WO2010/003923 and WO 0000061009. These documents do not disclose isoxazolins that incorporate a substituted aryl amidine group according to the present invention.

Related insecticidal aryl isoxazolines are further described in JP 2007-016017, WO 2007/026965, JP 2007-106756, WO 2007/070606, WO 2007/075459, WO 2007/079162, WO 2007/105814, WO 2007/125984, WO 2008/012027, WO 2008/019760, WO 2008/108448, JP 2008-239611, WO 2008/122375, WO 2008/130651, WO 2007/026965, WO 2009/126668, WO2009/051956, WO 2009/080250, WO 2009/002809, WO 2009/112275 and US 20080262057. None of these documents discloses isoxazolines incorporating a substituted aryl ketone group according to the present invention. Same applies to unpublished international applications PCT/EP2009/067037 and PCT/EP2009/067777. Aryl isoxazoline with a different substitution pattern on the aryl moiety of the molecule have been described in U.S. Prov 61/287,895.

Insecticidal aryl ketones are disclosed in WO 2009/002809 and WO 2009/112275. These documents disclose isoxazoline substituted naphthyl ketones as intermediates (for WO 2009/002809, see page 26, Tab. I.1) and tied back cyclic ketones (WO 2009/112275) with 5 prepared examples. These documents do not disclose aryl ketones according to the present invention.

Insecticidal aryl ketones are also disclosed in WO 88/05046, WO 88/06583, U.S. Pat. No. 4,863,947 and JP 08217754. These documents do not disclose aryl ketones that incorporate an isoxazoline-group according to the present invention.

Insecticidal aryl ketones are also disclosed in WO 2004/056735. This document do not disclose aryl ketones that incorporate an isoxazoline-group bearing a quarternary carbon atom at the 5-position of the isoxazoline according to the present invention.

Various 3-aryl-2-isoxazolines compounds have been described to represent a novel series of sLeX mimetics with anti-inflammatory activity, and are disclosed in, for example, Journal of Medicinal Chemistry (2001), 44(13), 2094-2107 However, these documents do not disclose aryl ketones that incorporate an isoxazoline-group bearing a quarternary carbon atom at the 5-position of the isoxazoline according to the present invention. Further, the usefulness thereof as a pesticide is neither disclosed.

The substituted ketone compounds of the formula I, and their agriculturally acceptable salts are highly active against animal pest, i.e. harmful arthropodes and nematodes, especially against difficult to control insects and acaridae.

Accordingly, the present invention relates to substituted ketone compounds of the general formula I, to their agriculturally or veterinarily useful salts, their enantiomers or diasteromers.

The substituted ketonic isoxazoline compounds of the formula I, and their agriculturally acceptable salts are highly active against animal pest, i.e. harmful arthropodes and nematodes, especially against difficult to control insects and acaridae.

Accordingly, the present invention relates to substituted ketonic isoxazoline compounds of the general formula I, to their agriculturally or veterinarily useful salts, their enantiomers or diasteromers.

Moreover, the present invention relates to and includes the following embodiments:

- agricultural and veterinary compositions comprising an amount of at least one compound of the formula I or an enantiomer, diasteromer or salt thereof;
- the use of a compound of formula I or an enantiomer, diasteromer or salt thereof for combating animal pests;
- a method of combating animal pests which comprises contacting the animal pests, their habit, breeding ground, food supply, plant, seed, soil, area, material or environment in which the animal pests are growing or may grow, or the materials, plants, seeds, soils, surfaces or spaces to be protected from animal attack or infestation with a pesticidally effective amount of at least one compound of the formula I or an enantiomer, diasteromer or salt thereof;
- a method for protecting crops from attack or infestation by animal pests, which comprises contacting a crop with a pesticidally effective amount of at least one compound of the formula I or an enantiomer, diasteromer or salt thereof;
- a method for the protection of plant propagation, especially seeds, from soil insects and of the seedlings' roots and shoots from soil and foliar insects comprising contacting the seeds before sowing and/or after pregermination with at least one compound of the formula I, or the enantiomers, diastereomers or salts thereof;
- seeds comprising a compound of the formula I or an enantiomer, diasteromer or salt thereof;
- the use of compounds of formula I or the enantiomers, diastereomers or veterinary acceptable salts thereof for combating parasites in and on animals.
- a method for treating, controlling, preventing or protecting animals against infestation or infection by parasites which comprises orally, topically or parenterally administering or applying to the animals a parasiticidally effective amount of an compound of formula I or the enantiomers, diastereomers and/or veterinary acceptable salt thereof;
- a process for the preparation of a veterinary composition for treating, controlling, preventing or protecting animals against infestation or infection by parasites which comprises adding a parasiticidally effective amount of an compound of formula I or the enantiomers, diastereomers and/or veterinary acceptable salt thereof to a carrier composition suitable for veterinary use;
- the use of a compound of formula I or the enantiomers, diastereomers and/or veterinary acceptable salt thereof for the preparation of a medicament for treating, controlling, preventing or protecting animals against infestation or infection by parasites;

The present invention also relates to plant propagation materials, in particular seed, comprising at least one compound of formula I and/or an agriculturally acceptable salt thereof.

The present invention relates to every possible stereoisomer of the compounds of formula I, i.e. to single enantiomers or diastereomers, as well as to mixtures thereof.

The compounds of the present invention may be amorphous or may exist in one or more different crystalline states (polymorphs) or modifications which may have a different macroscopic properties such as stability or show different biological properties such as activities. The present invention includes both amorphous and crystalline compounds of the formula I, mixtures of different crystalline states or modifications of the respective compound I, as well as amorphous or crystalline salts thereof.

Salts of the compounds of the formula I are preferably agriculturally and/or veterinary acceptable salts. They can be formed in a customary method, e.g. by reacting the compound with an acid of the anion in question if the compound of formula I has a basic functionality or by reacting an acidic compound of formula I with a suitable base.

Suitable agriculturally or veterinary useful salts are especially the salts of those cations or the acid addition salts of those acids whose cations and anions, respectively, do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH_4^+$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or benzyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethyl-ammonium, bis(2-hydroxyethyl)ammonium, benzyltrimethylammonium and benzyltriethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the compounds of the formulae I with an acid of the corresponding anion, preferably of hydrochloric acid, hydrobromic acid, sulfuric acid, phosphoric acid or nitric acid.

The organic moieties mentioned in the above definitions of the variables are—like the term halogen—collective terms for individual listings of the individual group members. The prefix $C_n$-$C_m$ indicates in each case the possible number of carbon atoms in the group.

"Halogen" will be taken to mean fluoro, chloro, bromo and iodo.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "$C_n$-$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $C_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $C_n$-$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and penta-fluoromethyl.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propyl-thio, isopropylthio, and n-butylthio.

Accordingly, the terms "$C_n$-$C_m$-haloalkoxy" and "$C_n$-$C_m$-haloalkylthio" (or $C_n$-$C_m$-haloalkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chloro-difluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloro-methylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoro-ethylthio and the like. Similarly the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The term "$C_1$-$C_4$-alkoxy-$C_1$-$C_4$-alkyl" as used herein refers to alkyl having 1 to 4 carbon atoms, e.g. like specific examples mentioned above, wherein one hydrogen atom of the alkyl radical is replaced by an $C_1$-$C_4$-alkoxy group.

The term "$C_3$-$C_m$-cycloalkyl" as used herein refers to a monocyclic 3- to m-membered saturated cycloaliphatic radicals, e.g. cyclopropyl, cyclobutyl, cyclopentyl, cyclohexyl, cycloheptyl, cyclooctyl and cyclodecyl.

The term "aryl" as used herein refers to an aromatic hydrocarbon radical such as naphthyl or in particular phenyl.

The term "3- to 6-membered carbocyclic ring" as used herein refers to cyclopropane, cyclobutane, cyclopentane and cyclohexane rings.

The term "3-, 4-, 5-, 6- or 7-membered saturated, partially unsaturated or aromatic heterocyclic ring containing 1, 2 or 3 heteroatoms" or "containing heteroatom groups", wherein those heteroatom(s) (group(s)) are selected from N, O, S, NO, SO and $SO_2$ and are ring members, as used herein refers to monocyclic radicals, the monocyclic radicals being saturated, partially unsaturated or aromatic. The heterocyclic radical may be attached to the remainder of the molecule via a carbon ring member or via a nitrogen ring member.

Examples of 3-, 4-, 5-, 6- or 7-membered saturated heterocyclyl or heterocyclic rings include: Oxiranyl, aziridinyl, azetidinyl, 2 tetrahydrofuranyl, 3-tetrahydrofuranyl, 2 tetrahydrothienyl, 3 tetrahydrothienyl, 2-pyrrolidinyl, 3-pyrrolidinyl, 3 pyrazolidinyl, 4 pyrazolidinyl, 5-pyrazolidinyl, 2 imidazolidinyl, 4 imidazolidinyl, 2-oxazolidinyl, 4-oxazolidinyl, 5 oxazolidinyl, 3-isoxazolidinyl, 4 isoxazolidinyl, 5 isoxazolidinyl, 2 thiazolidinyl, 4-thiazolidinyl, 5-thiazolidinyl, 3 isothiazolidinyl, 4-isothiazolidinyl, 5 isothiazolidinyl, 1,2,4-oxadiazolidin-3-yl, 1,2,4 oxadiazolidin 5 yl, 1,2,4-thiadiazolidin-3-yl, 1,2,4 thiadiazolidin-5-yl, 1,2,4 triazolidin-3-yl, 1,3,4-oxadiazolidin-2-yl, 1,3,4 thiadiazolidin-2-yl, 1,3,4 triazolidin-2-yl, 2-tetrahydropyranyl, 4 tetrahydropyranyl, 1,3-dioxan-5-yl, 1,4-dioxan-2-yl, 2-piperidinyl, 3-piperidinyl, 4-piperidinyl, 3-hexahydropyridazinyl, 4 hexahydropyridazinyl, 2-hexahydropyrimidinyl, 4-hexahydropyrimidinyl, 5 hexahydropyrimidinyl, 2-piperazinyl, 1,3,5-hexahydrotriazin-2-yl and 1,2,4 hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl or heterocyclic rings include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3 dihydrothien-3-yl, 2,4 dihydrothien-2-yl, 2,4-dihydrothien-3-yl, 2-pyrrolin-2-yl, 2-pyrrolin-3-yl, 3 pyrrolin-2-yl, 3-pyrrolin-3-yl, 2-isoxazolin-3-yl, 3-isoxazolin-3-yl, 4 isoxazolin 3 yl, 2-isoxazolin-4-yl, 3-isoxazolin-4-yl, 4-isoxazolin-4-yl, 2 isoxazolin-5-yl, 3-isoxazolin-5-yl, 4-isoxazolin-5-yl, 2-isothiazolin-3-yl, 3 isothiazolin-3-yl, 4-isothiazolin-3-yl, 2-isothiazolin-4-yl, 3-isothiazolin-4-yl, 4 isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3 dihydropyrazol-4-yl, 2,3-dihydropyrazol-5-yl, 3,4-dihydropyrazol-1-yl, 3,4 dihydropyrazol-3-yl, 3,4-dihydropyrazol-4-yl, 3,4-dihydropyrazol-5-yl, 4,5 dihydropyrazol-1-yl, 4,5-dihydropyrazol-3-yl, 4,5-dihydropyrazol-4-yl, 4,5 dihydropyrazol-5-yl, 2,3-dihydrooxazol-2-yl, 2,3-dihydrooxazol-3-yl, 2,3 dihydrooxazol-4-yl, 2,3-dihydrooxazol-5-yl, 3,4-dihydrooxazol-2-yl, 3,4 dihydrooxazol-3-yl, 3,4-dihydrooxazol-4-yl, 3,4-dihydrooxazol-5-yl, 3,4 dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4 di- or tetrahydropyridazinyl, 2-di- or tetrahydropyrimidinyl, 4-di- or tetrahydropyrimidinyl, 5 di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7 tetrahydro[1H]azepin-1-, -2-, -3-, -4-, -5-, -6- or -7-yl, 2,3,6,7 tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples of 5- or 6-membered aromatic heterocyclyl (hetaryl) or heteroaromatic rings are: 2-furyl, 3-furyl, 2-thienyl, 3-thienyl, 2-pyrrolyl, 3-pyrrolyl, 3-pyrazolyl, 4-pyrazo¬lyl, 5-pyrazolyl, 2-oxazolyl, 4-oxazolyl, 5-oxazolyl, 2-thiazolyl, 4 thiazolyl, 5-thiazo¬lyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

A "$C_2$-$C_m$-alkylene" is divalent branched or preferably unbranched saturated aliphatic chain having 2 to m, e.g. 2 to 7 carbon atoms, for example $CH_2CH_2$, —$CH(CH_3)$—, $CH_2CH_2CH_2$, $CH(CH_3)CH_2$, $CH_2CH(CH_3)$, $CH_2CH_2CH_2CH_2$, $CH_2CH_2CH_2CH_2CH_2$, $CH_2CH_2CH_2CH_2CH_2CH_2$, and $CH_2CH_2CH_2CH_2CH_2CH_2CH_2$.

Preferences

Embodiments and preferred compounds of the present invention are outlined in the following paragraphs.

The remarks made below concerning preferred embodiments of the variables of the compounds of formula I, especially with respect to their substituents, $A^1$, $A^2$, $A^3$, $A^4$, $R^1$, $R^2$, $R^3$, $R^4$, $R^5$, G, m, p and q, the features of the use and method according to the invention and of the composition of the invention are valid both on their own and, in particular, in every possible combination with each other.

As a matter of course, the q radicals $R^5$ replace a hydrogen atom on a carbon ring atom. If there is more than one radical $R^5$, these can be the same or different.

As a matter of course, the p radicals $R^4$ replace a hydrogen atom on a carbon ring atom. For instance, if $A^1$, $A^2$, $A^3$ or $A^4$ is defined to be CH and if this position is to be substituted by a radical $R^4$, then $A^1$, $A^2$, $A^3$ and/or $A^4$ are/is C—$R^4$. If there is more than one radical $R^4$, these can be the same or different.

At most two of $A^1$, $A^2$, $A^3$ and $A^4$ are N. In one preferred embodiment, $A^1$, $A^2$, $A^3$ and $A^4$ are CH. In an alternative preferred embodiment, $A^1$, $A^3$ and $A^4$ are CH and $A^2$ is N. In another alternative embodiment, $A^1$ and $A^4$ are CH and $A^2$ and $A^3$ are N. In further another alternative embodiment, $A^1$ and $A^2$ are CH and $A^3$ and $A^4$ are N. Another alternative embodiment is also when $A^2$ and $A^4$ are CH and $A^1$ and $A^3$ are N.

More preferably, $A^4$ is CH.

More preferably, $A^1$ and $A^3$ are CH.

Even more preferably, $A^1$, $A^3$ and $A^4$ are CH and $A^2$ is CH or N and in particular CH.

In a preferred embodiment, the ring comprising the groups $A^1$, $A^2$, $A^3$ or $A^4$ as ring members carries 0, 1 or 2, preferably 1 or 2 and in particular 1 substituent $R^4$. In other words, p is preferably 0, 1 or 2, more preferably 1 or 2 and in particular 1. In case $A^2$ is CH and p is 1, the substituent $R^4$ is preferably bound on the position of $A^2$. In other words, $A^2$ is in this case preferably C—$R^4$. In case $A^2$ is N and p is 1, the substituent $R^4$ is preferably bound on the position of $A^3$. In other words, $A^3$ is in this case preferably C—$R^4$.

Alternatively, also preferred is an embodiment comprising two substituents $R^4$, where individual $R^4$ radicals are bound to the positions $A^2$ and $A^3$ simultaneously. In other words, $A^2$ and $A^3$ are in this case preferably C—$R^4$.

In case p is 2, two substituents $R^4$ bound on adjacent carbon atoms preferably form together a group selected from —$CH_2CH_2CH_2CH_2$— and —CH═CH—CH═CH— and more preferably —CH═CH—CH═CH—, thus yielding a fused phenyl ring.

q is preferably 0, 1, 2 or 3, more preferably 1, 2 or 3, even more preferably 2 or 3 and in particular 2. If q is 3, then the three substituents $R^5$ are preferably bound in the positions of 3, 4 and 5 of the aromat.

If q is 2, then the two substituents $R^5$ are preferably bound in the positions 3 and 5 of the aromat. Then both $R^5$ are preferably selected independently from one another from the group consisting of hydrogen, halogen, cyano, $OR^7$, $C_1$-$C_6$-alkyl, $C_3$-$C_8$-cycloalkyl, wherein the carbon atoms of the two last aliphatic and cyclo-aliphatic radicals may optionally be substituted with one or more $R^6$ and are selected independently from one another.

If q is 1, then the substituent is preferably bound in the 3-position of the aromat. Then $R^5$ is preferably selected from the group consisting of hydrogen, halogen, cyano, $C_1$-$C_6$-alkyl, $C_1$-$C_6$-alkyl, $C_3$-$C_8$-cycloalkyl, wherein the five last aliphatic and cyclo-aliphatic radicals may optionally be substituted with one or more $R^{15}$, selected independently from one another;

$Si(R^{11})_2R^{12}$, $OR^7$, $OS(O)_nR^7$, $S(O)_nR^7$, $NR^{9a}R^{9b}$, $N(R^{9a})C(=O)R^6$, $C(=O)R^6$, $C(=O)OR^7$, $C(=NR^{9a})R^6$ and $C(=S)R^6$.

$R^3$ is preferably selected from the group consisting of hydrogen, halogen, hydroxyl, nitrile, SCN, $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_3$-$C_6$-cycloalkyl $C_3$-$C_6$-halocycloalkyl and $C_1$-$C_4$-halothioalkyl. More preferably, $R^3$ is selected from the group consisting of hydrogen, halogen, hydroxyl, nitrile, SCN, $C_1$-$C_4$-haloalkyl, and $C_3$-$C_6$-halocycloalkyl. Even more preferably, $R^3$ is selected from the group consisting of, halogen, $C_1$-$C_4$-alkyl, $C_1$-$C_4$-haloalkyl. In particular, $R^3$ is halogen, specifically chlorine, bromine and fluorine and more specifically fluorine, in particular fluorine.

Preferred are substituted ketonic compounds of the following formula (I-2):

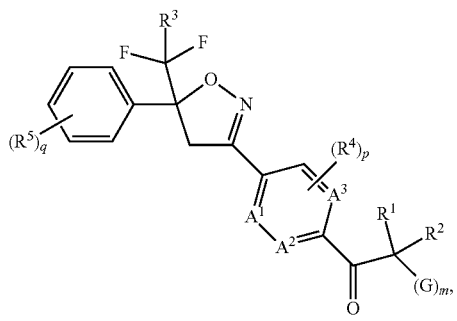

wherein $R^3$ is selected from the group consisting of hydrogen, halogen, hydroxyl, nitrile, SCN, $C_1$-$C_4$-alkyl, $C_1$-$C_4$-haloalkyl, and $C_3$-$C_6$-halocycloalkyl, more preferred wherein $R^3$ is selected from the group consisting of halogen, $C_1$-$C_4$-alkyl, $C_1$-$C_4$-haloalkyl.

Preferred are substituted ketonic compounds of the following formula (I-3):

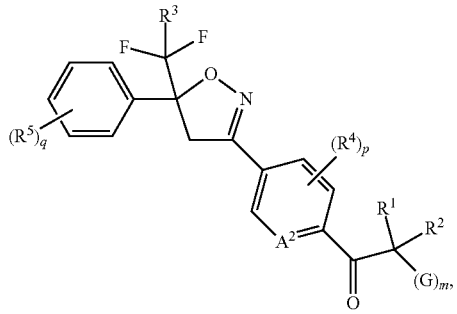

wherein $R^3$ is selected from the group consisting of hydrogen, halogen, hydroxyl, nitrile, SCN, $C_1$-$C_4$-alkyl, $C_1$-$C_4$-haloalkyl, and $C_3$-$C_6$-halocycloalkyl, more preferred wherein $R^3$ is selected from the group consisting of halogen, $C_1$-$C_4$-alkyl, $C_1$-$C_4$-haloalkyl.

Preferred are substituted ketonic compounds of the following formula (I-4):

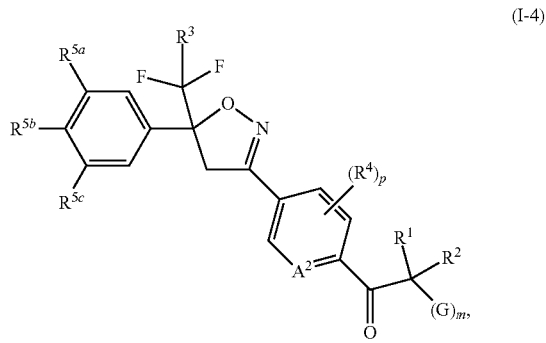

wherein $R^3$ is selected from the group consisting of hydrogen, halogen, hydroxyl, $C_1$-$C_4$-alkyl, $C_1$-$C_4$-haloalkyl, and $C_3$-$C_6$-halocycloalkyl, more preferred wherein $R^3$ is selected from the group consisting of halogen, $C_1$-$C_4$-alkyl, $C_1$-$C_4$-haloalkyl;

p is 0, 1 or 2;

$R^4$ is selected independently from p from the group consisting of hydrogen, halogen, cyano, azido, nitro, —SCN, $SF_5$, $C_1$-$C_6$-alkyl, $C_3$-$C_8$-cycloalkyl, $C_2$-$C_6$-alkenyl, $C_2$-$C_6$-alkinyl, wherein the carbon atoms of the aforementioned aliphatic and cyclo-aliphatic radicals may optionally be substituted with one or more $R^6$, which are independently selected from one another, $Si(R^{11})_2R^{12}$, $OR^7$, $-OS(O)_nR^7$, $S(O)_nR^7$, $NR^{9a}R^{9b}$, $N(R^{9a})C(=O)R^6$, $C(=O)R^6$, $C(=O)OR^7$, $C(=NR^{9a})R^6$, $C(=S)R^6$, phenyl, optionally substituted with one or more substituents independently selected from $R^{10}$, which are selected independently from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized, or, when p is 2 and two of $R^4$ are adjacent, the two adjacent $R^4$ may be a bridge selected from the group consisting of $CH_2CH_2CH_2CH_2$, CH=CH—CH=CH, N=CH—CH=CH, CH=N—CH=CH, N=CH—N=CH, $OCH_2CH_2CH_2$, OCH=$CHCH_2$, $CH_2OCH_2CH_2$, $OCH_2CH_2O$, $OCH_2OCH_2$, $CH_2CH_2CH_2$, CH=$CHCH_2$, $CH_2CH_2O$, CH=CHO, $CH_2OCH_2$, $CH_2C(=O)O$, C(=O)$OCH_2$, $O(CH_2)O$, $SCH_2CH_2CH_2$, SCH=$CHCH_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, C(=S)$SCH_2$, $S(CH_2)S$, $CH_2CH_2NR^{9a}$, $CH_2CH=N$, CH=CH—$NR^{9a}$, OCH=N, SCH=N and with the proviso, that in this case G, $R^1$ and $R^2$ are not hydrogen simultaneously;

$R^{5a}$ and $R^{5c}$ are selected independently from one another from the group consisting of hydrogen, halogen, cyano, nitro, SCN, $SF_5$, $C_1$-$C_6$-alkyl, $C_3$-$C_8$-cycloalkyl, wherein the carbon atoms of the two last aliphatic and cyclo-aliphatic radicals may optionally be substituted with one or more $R^6$, selected independently from one another, $OR^7$, $S(O)nR^7$, $NR^{9a}R^{9b}$, $C(=O)R^6$, —$C(=O)OR^7$, $C(=NR^8)R^6$, $C(=S)NR^6$;

and $R^{5b}$ is selected from the group consisting of hydrogen, halogen, cyano, nitro, —SCN, $SF_5$, $C_1$-$C_6$-alkyl, $C_1$-$C_6$-alkyl, $C_3$-$C_8$-cycloalkyl, $C_2$-$C_6$-alkenyl, $C_2$-$C_6$-alkinyl, wherein the five last aliphatic and cyclo-aliphatic radicals may optionally be substituted with one or more $R^6$, selected independently from one another,
$Si(R^{11})_2R^{12}$, $OR^7$, $OS(O)_nR^7$, $S(O)_nR^7$, $NR^{9a}R^{9b}$, $N(R^{9a})C(=O)R^6$, CHO, $C(=O)R^6$, $C(=O)OR^7$, $C(=NR^9)R^6$, $C(=S)NR^6$,
phenyl, optionally substituted with one or more substituents $R^{10}$, which are selected independently from one another;
a 3-, 4-, 5-, 6- to 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized.

Preferred are substituted ketonic isoxazoline compounds of the following formula (I-5):

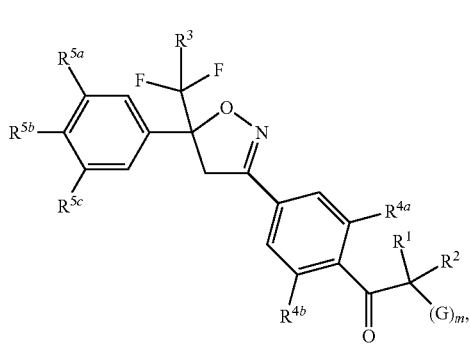

(I-5)

wherein
$R^{4a}$, $R^{4b}$ are selected independently from one another from the group consisting of hydrogen, halogen, cyano, azido, nitro, —SCN, $SF_5$, $C_1$-$C_6$-alkyl, $C_3$-$C_8$-cycloalkyl, wherein the carbon atoms of the last two aliphatic and cyclo-aliphatic radicals may optionally be substituted with one or more $R^6$, which are independently selected from one another,
$OR^7$, —$OS(O)_nR^7$, $S(O)nR^7$, $NR^{9a}R^{9b}$, $N(R^{9a})C(=O)R^6$, CHO, $C(=O)R^6$, —$C(=O)OR^7$, $C(=NR^{9a})R^6$, $C(=S)R^6$,
phenyl, optionally substituted with one or more substituents independently selected from $R^{10}$, which are selected independently from one another,
a 3-, 4-, 5-, 6- or 7-membered saturated, partly saturated or unsaturated aromatic heterocyclic ring;
$R^{5a}$ and $R^{5c}$ are selected independently from one another from the group consisting of hydrogen, halogen, cyano, nitro, SCN, $SF_5$, $C_1$-$C_6$-alkyl, $C_3$-$C_8$-cycloalkyl, wherein the carbon atoms of the two last aliphatic and cyclo-aliphatic radicals may optionally be substituted with one or more $R^6$, selected independently from one another,
$OR^7$, $S(O)nR^7$, $NR^{9a}R^{9b}$, $C(=O)R^6$, —$C(=O)OR^7$, $C(=NR^8)R^6$, $C(=S)NR^6$;
and
$R^{5b}$ is selected from the group consisting of hydrogen, halogen, cyano, nitro, —SCN, $SF_5$, $C_1$-$C_6$-alkyl, $C_1$-$C_6$-alkyl, $C_3$-$C_8$-cycloalkyl, $C_2$-$C_6$-alkenyl, $C_2$-$C_6$-alkinyl, wherein the aliphatic chains of the five last radicals may optionally be substituted with one or more $R^6$, selected independently from one another,
$Si(R^{11})_2R^{12}$, $OR^7$, $OS(O)_nR^7$, $S(O)_nR^7$, $NR^{9a}R^{9b}$, $N(R^{9a})C(=O)R^6$, $C(=O)R^6$, $C(=O)OR^7$, $C(=NR^{9a})R^6$, $C(=S)NR^6$,
phenyl, optionally substituted with one or more substituents $R^{10}$, which are selected independently from one another;
a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized.

Especially preferred substituted ketonic compounds of formula (I-5) are those, wherein $R^{4a}$, $R^{4b}$ are selected independently from one another from the group consisting of hydrogen, halogen, cyano, nitro, SCN, $C_1$-$C_6$-alkyl, $C_3$-$C_8$-cycloalkyl, wherein the carbon atoms of the of the last two aliphatic and cyclo-aliphatic radicals may optionally be substituted with one or more $R^6$, which are independently selected from one another, $OR^7$, —$OS(O)_nR^7$, $S(O)nR^7$, $NR^{9a}R^{9b}$, $N(R^{9a})C(=O)R^6$, $C(=O)R^6$, —$C(=O)OR^7$, $C(=NR^{9a})R^6$, $C(=S)R^6$;
$R^{5a}$ and $R^{5c}$ are selected independently from one another from the group consisting of hydrogen, halogen, cyano, $OR^7$, $C_1$-$C_6$-alkyl, $C_3$-$C_8$-cycloalkyl, wherein the carbon atoms of the two last aliphatic and cyclo-aliphatic radicals may optionally be substituted with one or more $R^6$, selected independently from one another;
and
$R^{5b}$ is selected from the group consisting of hydrogen, halogen, cyano, $C_1$-$C_6$-alkyl, $C_1$-$C_6$-alkyl, $C_3$-$C_8$-cycloalkyl, wherein the five last aliphatic and cyclo-aliphatic radicals may optionally be substituted with one or more $R^{15}$, selected independently from one another,
$Si(R^{11})_2R^{12}$, $OR^7$, $OS(O)_nR^7$, $S(O)_nR^7$, $NR^{9a}R^{9b}$, $N(R^{9a})C(=O)R^6$, $C(=O)R^6$, $C(=O)OR^7$, $C(=NR^{9a})R^6$ and $C(=S)R^6$.

Preferred are S-configured enantiomers of substituted ketonic compounds of formula (I-S)

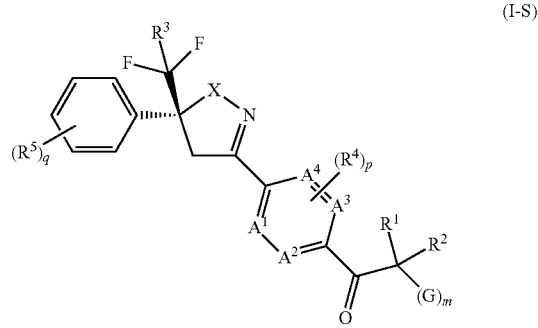

(I-S)

More preferred are enantiomers of formula (I-S), wherein the variables corresponds to the definitions as given for formula (I-2), (I-3), (I-4) or (I-5).

Preferred are R-configured enantiomers of substituted ketonic isoxazoline compounds of formula (I-R)

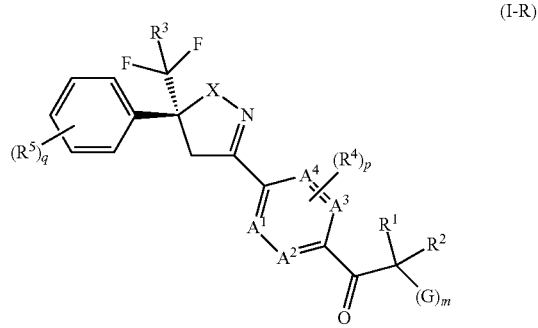

(I-R)

More preferred are enantiomers of formula (I-R), wherein the variables corresponds to the definitions as given for formula (I-2), (I-3), (I-4) or (I-5).

Preferred are substituted ketonic isoxazoline compounds as of formula (I), (I-2), (I-3), (I-4) or (I-5), wherein
G is present in the respective formula, which means that m is 1, and
$R^1$, $R^2$ are preferably selected independent from one another from the group consisting of hydrogen, halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, wherein the carbon atoms of the aforementioned aliphatic and cyclo-aliphatic radicals may optionally be substituted with one or more $R^6$, which are independently selected from one another, $Si(R^{11})_2R^{12}$, $OR^7$, $OSO_2R^7$, $S(O)_nR^7$, $S(O)_nNR^{9a}R^{9b}$, $NR^{9a}R^{9b}$, $C(=O)NR^{9a}R^{9b}$, $C(=S)NR^{9a}R^{9b}$, $C(=O)OR^7$, or phenyl, optionally substituted with one or more substituents $R^{10}$, which are independently selected from one another,
or a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, selected independently from one another, and wherein the nitrogen and/or the sulfur atom(s) of the heterocyclic ring may optionally be oxidized.

Preferred are also substituted ketonic isoxazoline compounds as of formula (I), (I-2), (I-3), (I-4) or (I-5), wherein
$R^1$ and $R^2$ from together =O, =$CR^{13}R^{14}$; =$CR^{13}NR^{17a}R^{17b}$, =$S(O)_nR^{16}$, =$S(O)_nNR^{17a}R^{17b}$, =$NR^{17a}$, =$NOR^{16}$; =$NNR^{17a}$; or
$R^1$ and $R^2$ from together with the carbon atom, to which $R^1$ and $R^2$ are bonded to, a 3-, 4-, 5-, 6-, 7- or 8-membered saturated, partly unsaturated carbocyclic or heterocyclic ring optionally comprising 1, 2 or 3 heteroatoms selected from oxygen, nitrogen and/or sulfur and/or optionally substituted with k substituents $R^{10}$, selected independently from one another, and wherein the nitrogen and/or the sulfur atom(s) of the heterocyclic ring may optionally be oxidized;
and
G is selected from the group consisting of hydrogen, cyano, —SCN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkinyl, $C_2$-$C_6$ haloalkinyl, wherein the carbon atoms of the aforementioned aliphatic and cyclo-aliphatic radicals may optionally be substituted with one or more $R^6$, which are independently selected from one another, or
$NR^{9a}R^{9b}$, $S(O)_nR^7$, —$S(O)_nNR^{9a}R^{9b}$, $C(=O)R^6$, $C(=O)OR^7$, $C(=O)NR^{9a}R^{9b}$, $C(=NR^8)R^6$, phenyl, optionally substituted with one or more substituents $R^{10}$, selected independently from one another, or
a 3-, 4-, 5-, 6- or 7-membered saturated, partly saturated, partly or fully unsaturated or aromatic heterocyclic ring comprising 1, 2 or 3 heteroatoms selected from oxygen, nitrogen and/or sulfur, optionally substituted with k substituents $R^{10}$, selected independently from one another, and wherein the nitrogen and/or the sulfur atom(s) of the heterocyclic ring may optionally be oxidized;

Preferred are also substituted ketonic isoxazoline compounds as of formula (I), (I-2), (I-3), (I-4) or (I-5), wherein
G is not present in formula (I), which means that m is 0, and $R^1$ and $R^2$ form together with the carbon atom to which $R^1$ and $R^2$ are bonded to a 5- or 6-membered carboaromatic or heteroaromatic ring, optionally comprising 1, 2 or 3 heteroatoms selected from oxygen nitrogen and/or sulfur and/or optionally substituted with k substituents $R^{10}$, selected independently from one another.

As noted above, some of the variables of formula (I), (I-2), (I-3), (I-4) or (I-5) may optionally be further substituted by an unsaturated (aromatic), partly saturated or saturated 3-7 membered heterocyclic ring, which may arbitrarily be substituted with k substituents $R^{10}$, selected independently from the integer of k.

Preferred examples of a 6-membered unsaturated (aromatic) heterocyclic ring, optionally substituted with k substituents $R^{10}$, selected independently from the integer of K, include the rings D-1 through D-14:

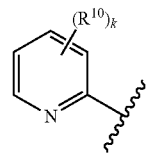

D-1

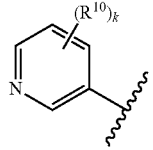

D-2

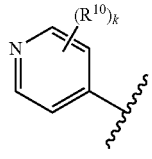

D-3

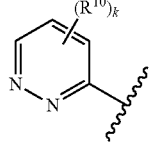

D-4

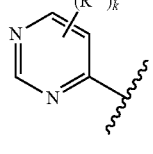

D-5

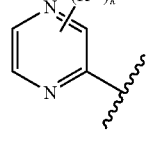

D-6

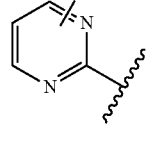

D-7

-continued
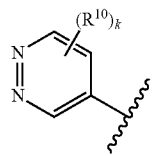 D-8
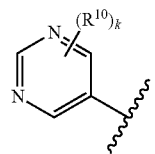 D-9
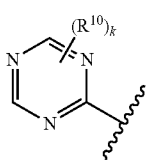 D-10
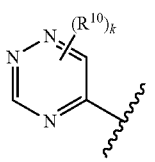 D-11
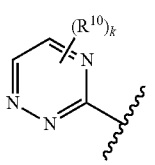 D-12
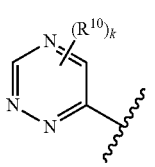 D-13
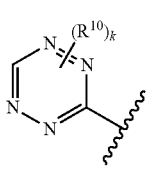 D-14
Preferred examples of a 5-membered unsaturated (aromatic) heterocyclic ring, optionally substituted with k substituents $R^{10}$, selected independently from the integer of k, include the rings D-15 through D-65:
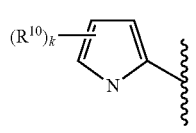 D-15
-continued
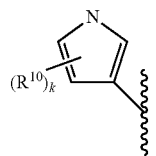 D-16
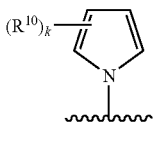 D-17
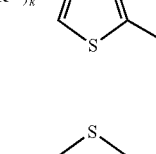 D-18
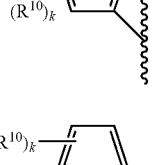 D-19
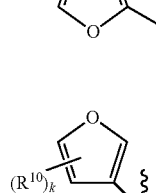 D-20
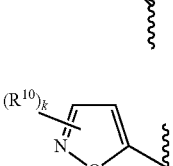 D-21
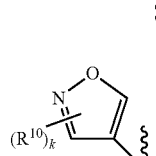 D-22
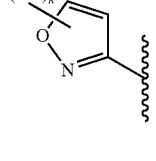 D-23
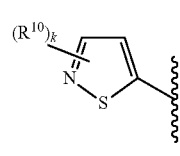 D-24
D-25

| | |
|---|---|
| 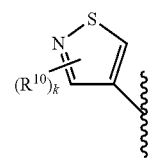 | D-26 |
| 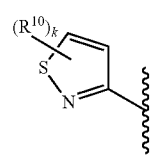 | D-27 |
| 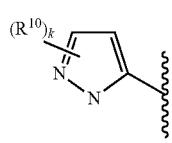 | D-28 |
| 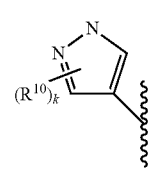 | D-29 |
| 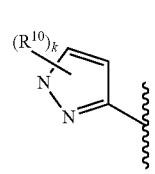 | D-30 |
| 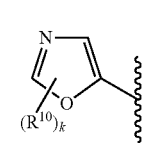 | D-31 |
| 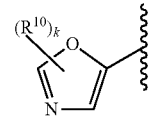 | D-32 |
| 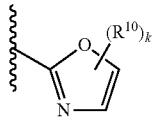 | D-33 |
| 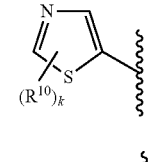 | D-34 |
| 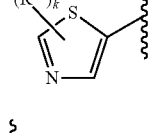 | D-35 |
| 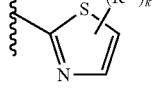 | D-36 |
| | |
|---|---|
| 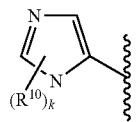 | D-37 |
| 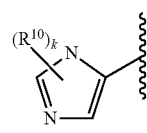 | D-38 |
| 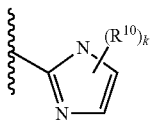 | D-39 |
| 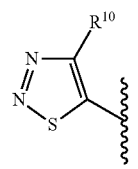 | D-40 |
| 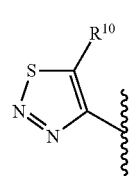 | D-41 |
| 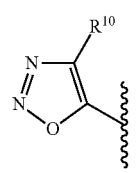 | D-42 |
| 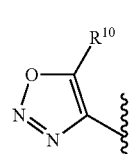 | D-43 |
| 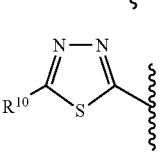 | D-44 |
| 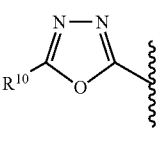 | D-45 |
| 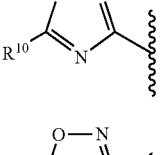 | D-46 |

| D-48 | 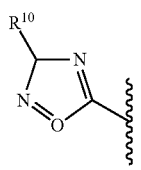 |
| D-49 | 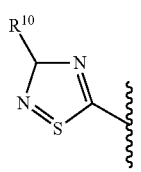 |
| D-50 | 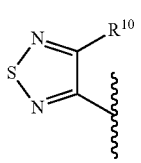 |
| D-51 | 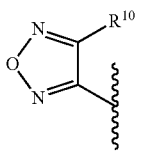 |
| D-52 | 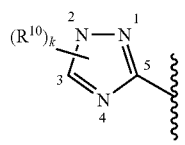 |
| D-53 | 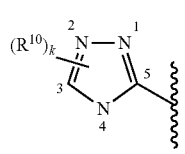 |
| D-54 | 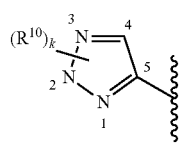 |
| D-55 | 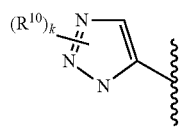 |
| D-56 | 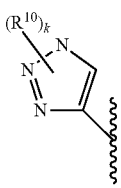 |
| D-57 | 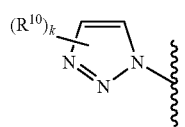 |
| D-58 | 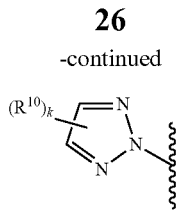 |
| D-59 | 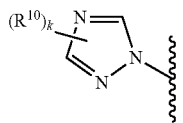 |
| D-60 | 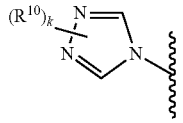 |
| D-61 | 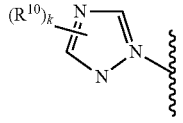 |
| D-62 | 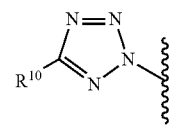 |
| D-63 | 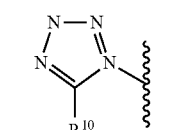 |
| D-64 | 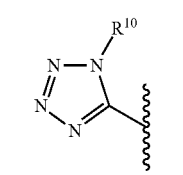 |
Preferred examples of a 3-7-membered saturated heterocyclic ring, optionally substituted with k substituents $R^{10}$, selected independently from the integer of k, include the rings D-66 through D-120:
| D-66 | 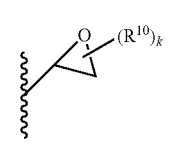 |
| D-67 | 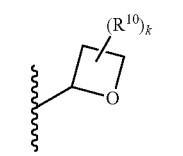 |

-continued
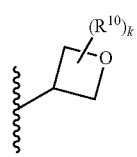 D-68
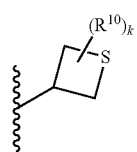 D-69
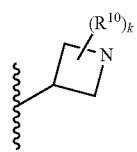 D-70
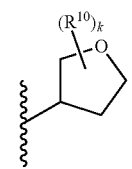 D-71
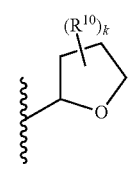 D-72
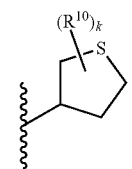 D-73
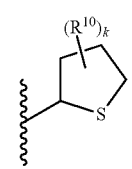 D-74
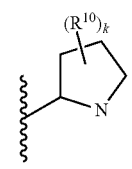 D-75
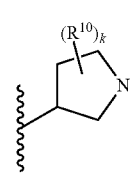 D-76
-continued
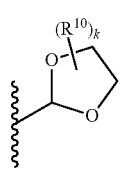 D-77
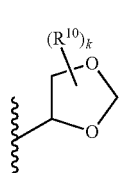 D-78
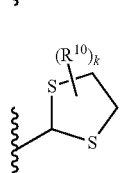 D-79
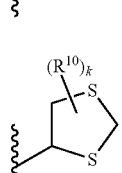 D-80
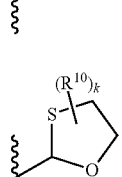 D-81
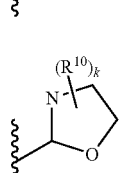 D-82
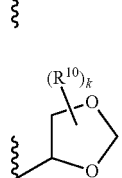 D-83
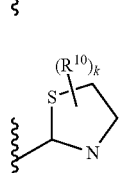 D-84
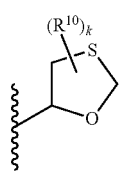 D-85

| | | | |
|---|---|---|---|
| 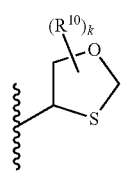 | D-86 | 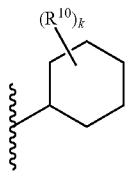 | D-95 |
| 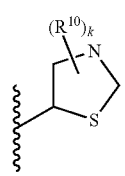 | D-87 | 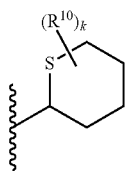 | D-96 |
| 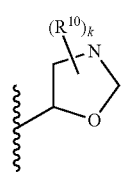 | D-88 | 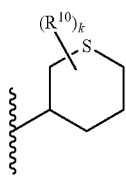 | D-97 |
| 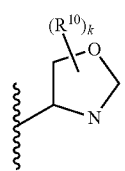 | D-89 | 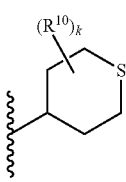 | D-98 |
| 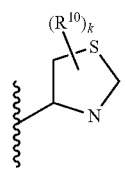 | D-90 | 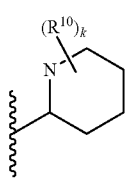 | D-99 |
| 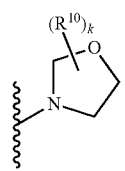 | D-91 | 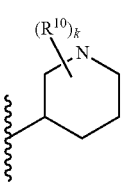 | D-100 |
| 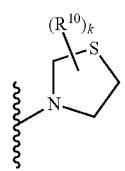 | D-92 | 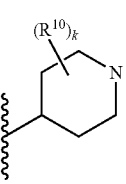 | D-101 |
| 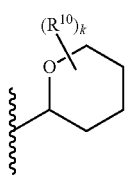 | D-93 | 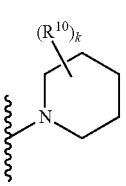 | D-102 |
| 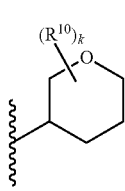 | D-94 | 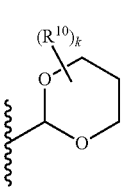 | D-103 |

| | | | |
|---|---|---|---|
| 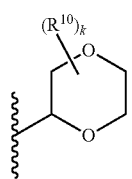 | D-104 | 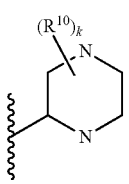 | D-112 |
| 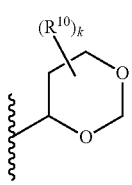 | D-105 | 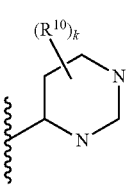 | D-113 |
| 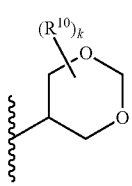 | D-106 | 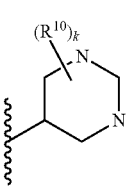 | D-114 |
| 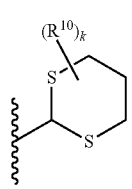 | D-107 | 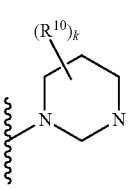 | D-115 |
| 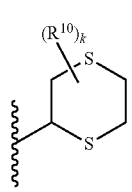 | D-108 | 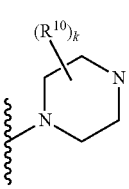 | D-116 |
| 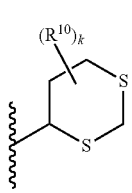 | D-109 | 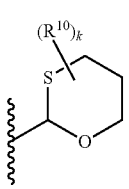 | D-117 |
| 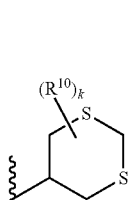 | D-110 | 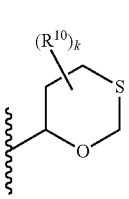 | D-118 |
| 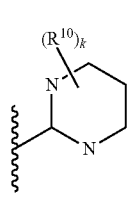 | D-111 | 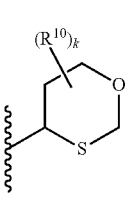 | D-119 |

-continued
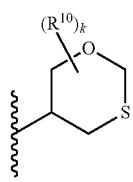
D-120
Preferred examples of a 5-7-membered, partly saturated heterocyclic ring, optionally substituted with k substituents R$^{10}$, selected independently from the integer of k, include the rings D-121 through D-169:
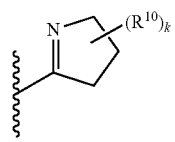
D-121
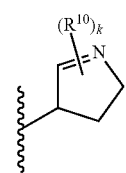
D-122
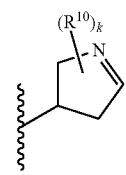
D-123
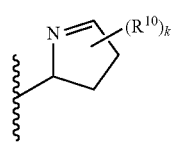
D-124
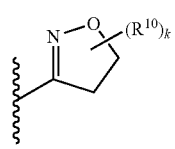
D-125
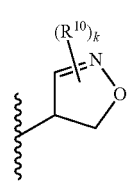
D-126
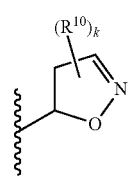
D-127
-continued
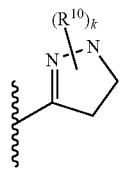
D-128
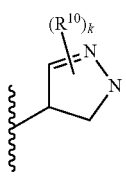
D-129
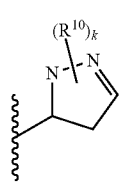
D-130
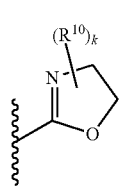
D-131
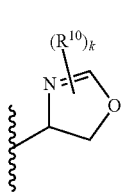
D-132
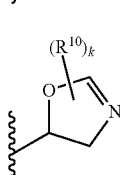
D-133
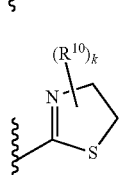
D-134
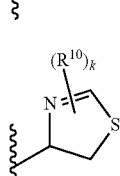
D-135
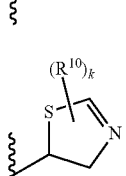
D-136

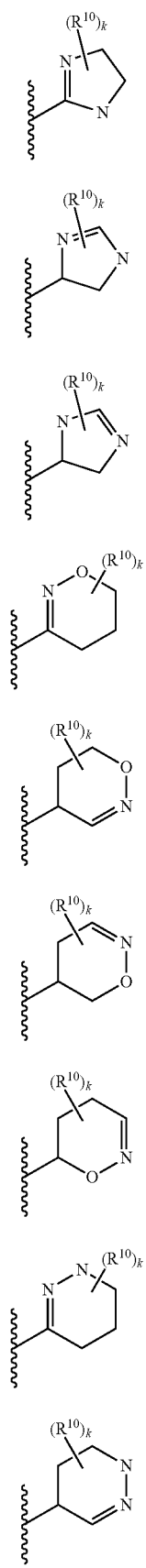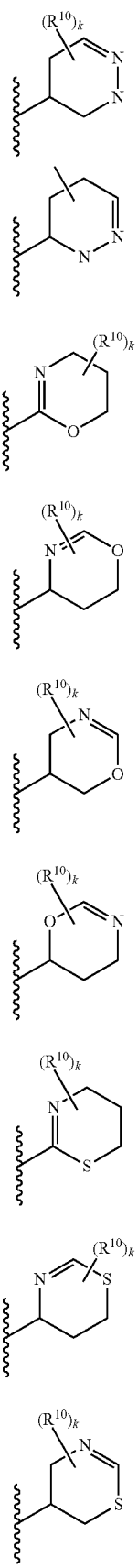

-continued

D-155 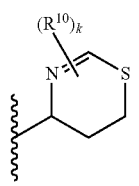

D-156 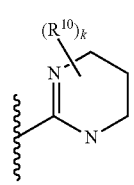

D-157 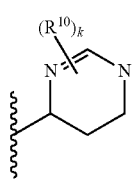

D-158 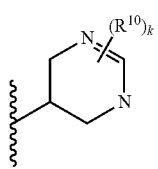

D-159 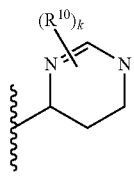

D-160 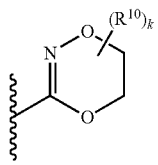

D-161 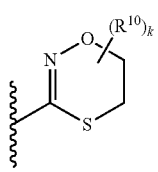

D-162 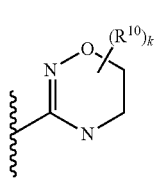

D-163 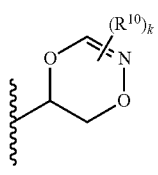

-continued

D-164 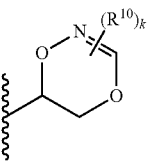

D-165 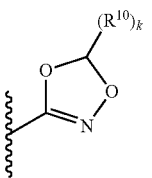

D-166 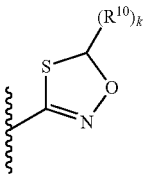

D-167 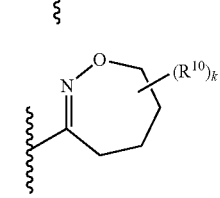

D-168 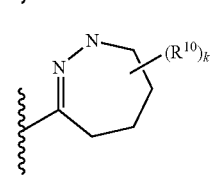

D-169

Another embodiment of the present invention are also intermediate 4-hydroxyiminomethyl substituted ketonic compound of the general formula (I-A)

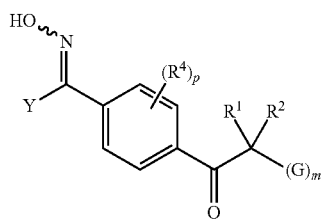

(I-A)

wherein

Y is hydrogen or halogen;

and wherein $R^1$, $R^2$, $R^4$, G, m and p are defined as for compounds of formula (I); and intermediate 4-hydroxy-iminomethyl substituted ketonic compound of the general formula (I-B)

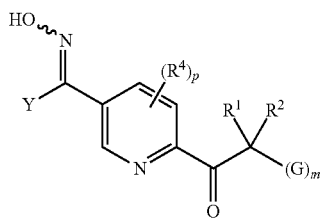
(I-B)

wherein

Y is hydrogen or halogen;

and wherein $R^1$, $R^2$, $R^4$, G, m and p are defined as for compounds of formula (I).

EXAMPLES OF PREFERRED COMPOUNDS

Examples of preferred compounds of the present invention are described in the following without imposing any limitation to the invention.

Preferred are compounds of the following the formulae I-a to I-bb, wherein the variables have one of the general or preferred meanings given above.

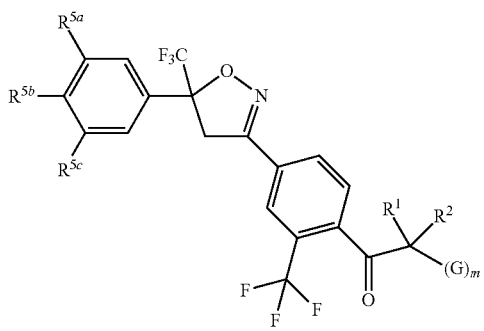
(I-a)

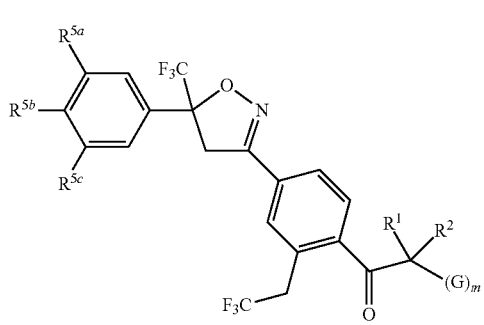
(I-b)

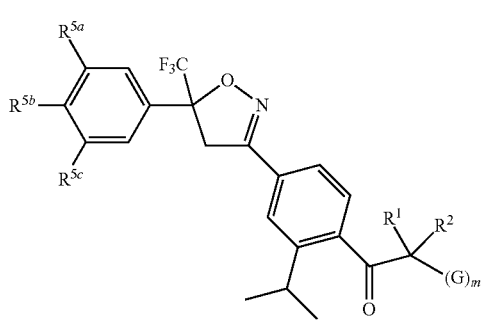
(I-c)

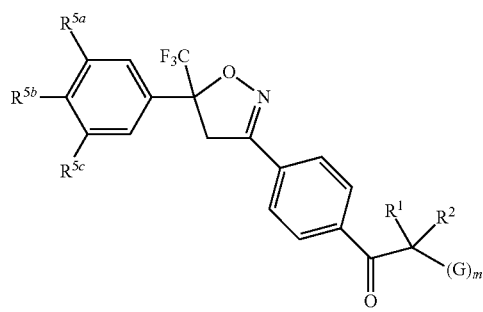
(I-d)

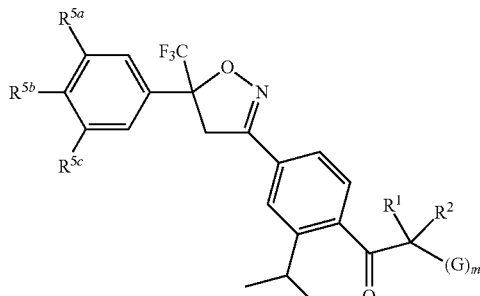
(I-e)

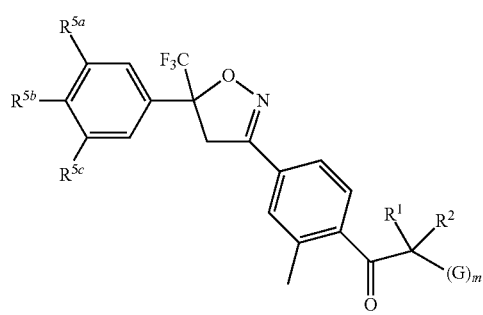
(I-f)

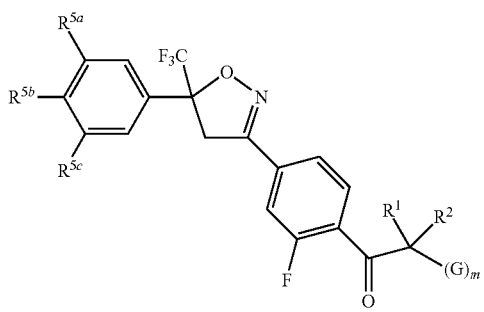
(I-g)

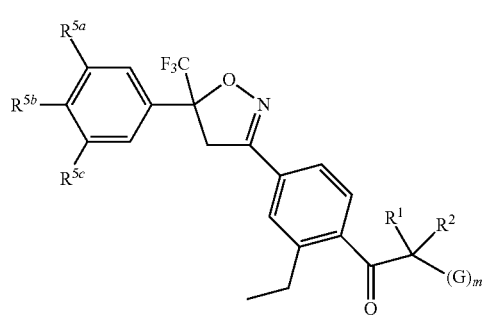
(I-h)

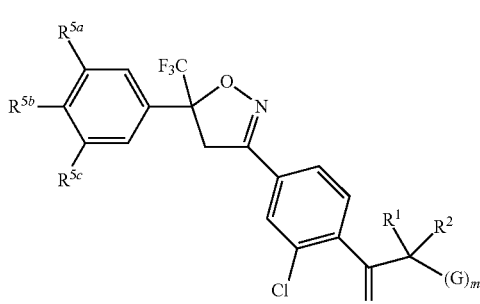

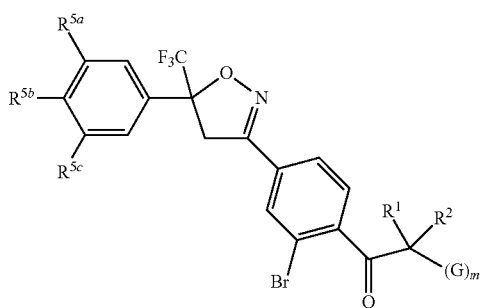 (I-i)
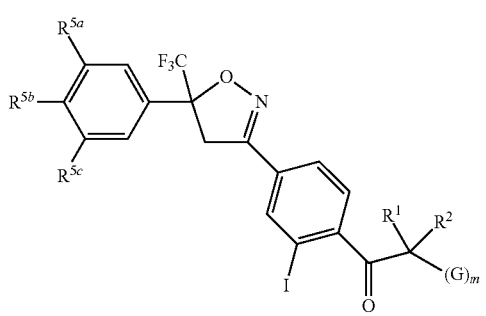 (I-j)
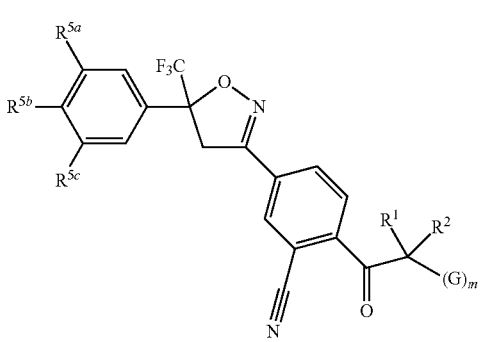 (I-k)
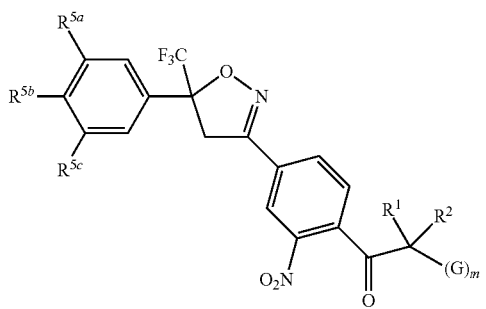 (I-l)
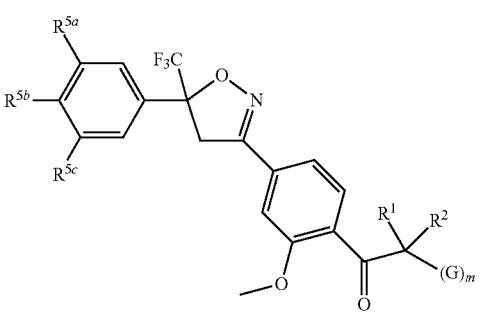 (I-m)
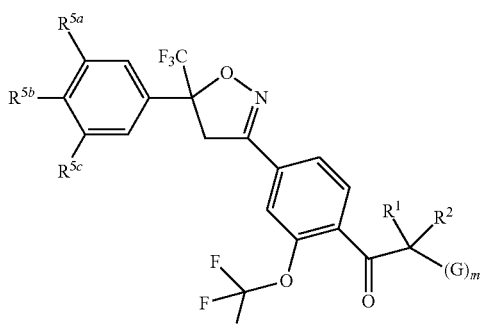 (I-n)
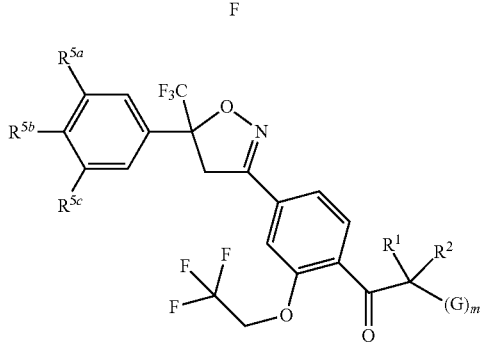 (I-o)
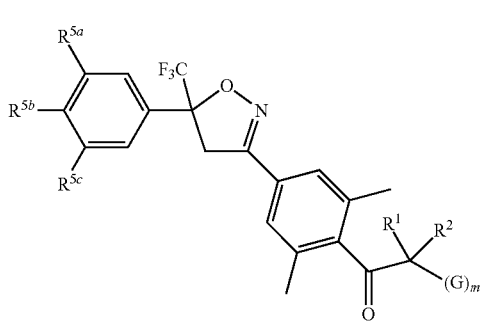 (I-p)
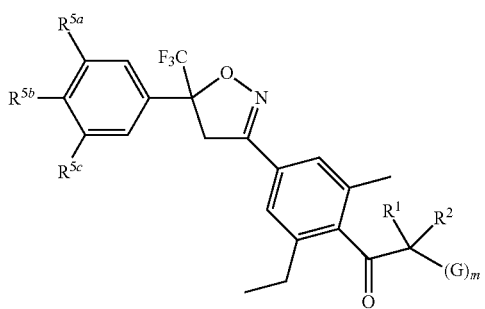 (I-q)
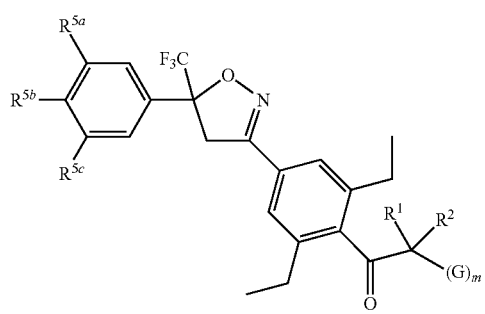 (I-r)

-continued
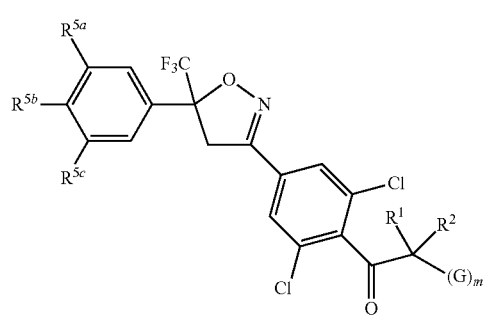
(I-s)
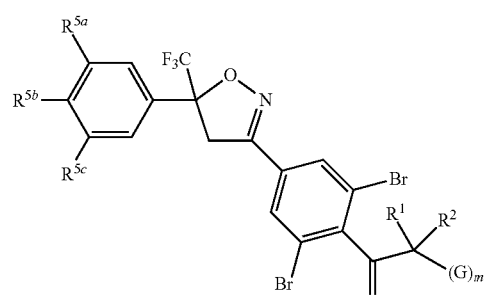
(I-t)
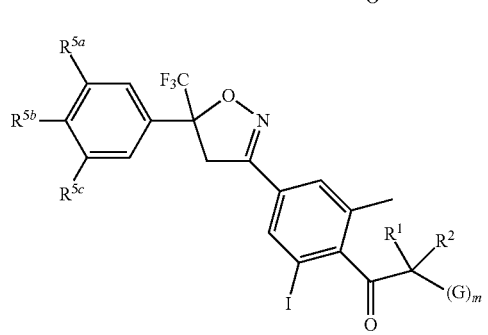
(I-u)
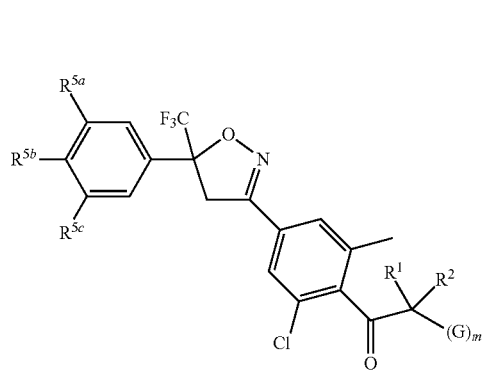
(I-v)
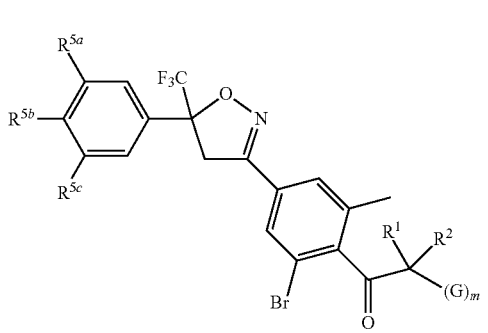
(I-w)
-continued
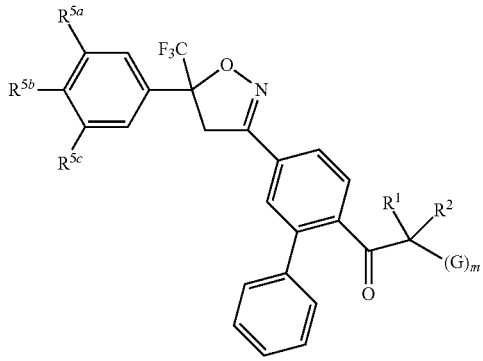
(I-x)
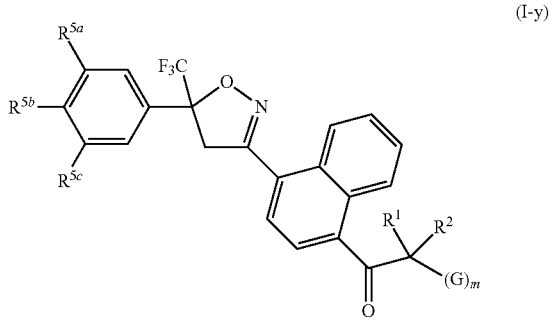
(I-y)
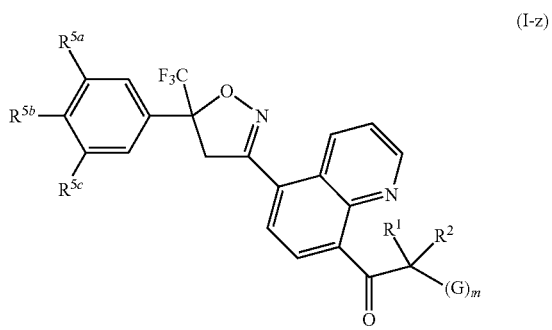
(I-z)
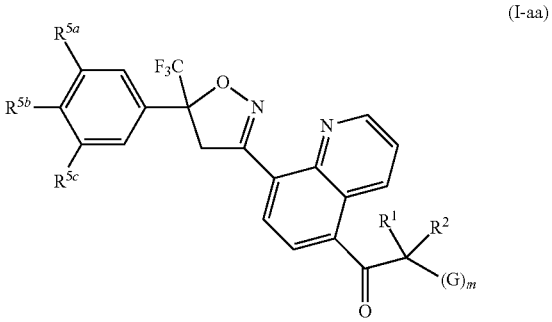
(I-aa)
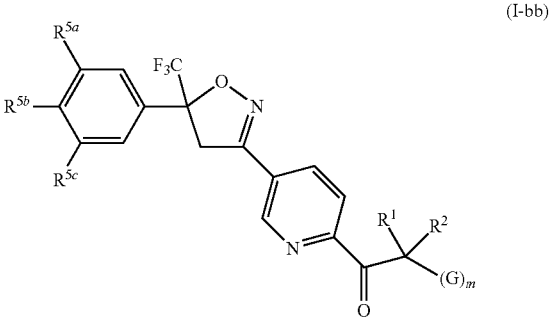
(I-bb)

Examples of more preferred compounds are represented by the following individual compounds compiled in the tables hereafter. The meaning of the respective individual variables $R^{5a}$, $R^{5b}$ and $R^{5c}$ are defined therein, and the radicals $R^1$ and $R^2$ alone, when m is 0, or in combination with G, when m is 1, are individually identified as outlined in tables Q1, Q2 and Q3.

Moreover, the meanings mentioned for the individual variables in the tables are per se, independently of the combination in which they are mentioned, a particularly preferred embodiment of the substituents in question.

Some individual variables in the tables are selected from the following substituents A, wherein the "#" in the formulae of variables A indicate the bond to formulae:

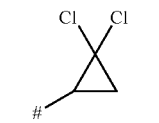
A-1

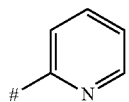
A-2

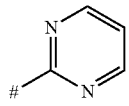
A-3

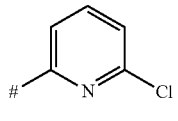
A-4

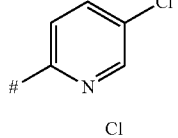
A-5

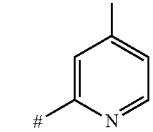
A-6

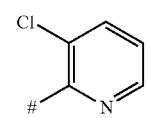
A-7

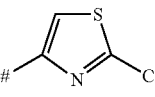
A-8

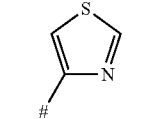
A-9

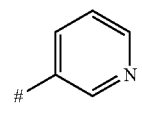
A-10

-continued

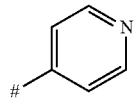
A-11

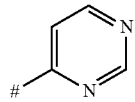
A-12

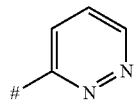
A-13

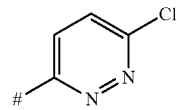
A-14

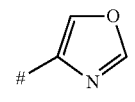
A-15

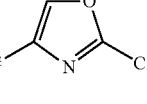
A-16

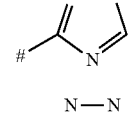
A-17

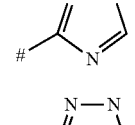
A-18

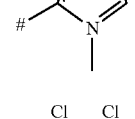
A-19

A-20

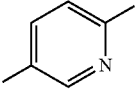
A-21

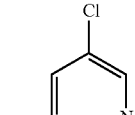
A-22

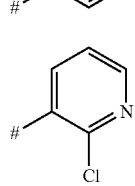
A-23

A-24

A-25

A-26

A-27

A-28

Tables 1-308 of preferred compounds:

Table 1

Compounds of the formula I-a in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 2

Compounds of the formula I-a in which $R^{5a}$ and $R^{5c}$ are bromine, $R^{5b}$ is H, and the combination of $R^1$ and $R^2$ and G, if G is present, for a compound corresponds in each case to one row of Table Q1.

Table 3

Compounds of the formula I-a in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 4

Compounds of the formula I-a in which $R^{5a}$ and $R^{5c}$ are methyl, $R^{5b}$ is H, and the combination of $R^1$ and $R^2$ and G, if G is present, for a compound corresponds in each case to one row of Table Q1.

Table 5

Compounds of the formula I-a in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 6

Compounds of the formula I-a in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 7

Compounds of the formula I-a in which $R^{5a}$ and $R^{5b}$ are methyl, $R^{5c}$ is H, and the combination of $R^1$ and $R^2$ and G, if G is present, for a compound corresponds in each case to one row of Table Q1.

Table 8

Compounds of the formula I-a in which $R^{5a}$ is CF3, $R^{5b}$ and $R^{5c}$ are H, and the combination of $R^1$ and $R^2$ and G, if G is present, for a compound corresponds in each case to one row of Table Q1.

Table 9

Compounds of the formula I-a in which $R^{5a}$, $R^{5b}$ and $R^{5c}$ are chlorine, and the combination of $R^1$ and $R^2$ and G, if G is present, for a compound corresponds in each case to one row of Table Q1.

Table 10

Compounds of the formula I-a in which $R^{5a}$, $R^{5b}$ and $R^{5c}$ are fluorine, and the combination of $R^1$ and $R^2$ and G, if G is present, for a compound corresponds in each case to one row of Table Q1.

Table 11

Compounds of the formula I-a in which $R^{5a}$, $R^{5b}$ and $R^{5c}$ are methyl, and the combination of $R^1$ and $R^2$ and G, if G is present, for a compound corresponds in each case to one row of Table Q1.

Table 12

Compounds of the formula I-b in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 13

Compounds of the formula I-b in which $R^{5a}$ and $R^{5c}$ are bromine, $R^{5b}$ is H, and the combination of $R^1$ and $R^2$ and G, if G is present, for a compound corresponds in each case to one row of Table Q1.

Table 14

Compounds of the formula I-b in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 15

Compounds of the formula I-b in which $R^{5a}$ and $R^{5c}$ are methyl, $R^{5b}$ is H, and the combination of $R^1$ and $R^2$ and G, if G is present, for a compound corresponds in each case to one row of Table Q1.

Table 16

Compounds of the formula I-b in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 17

Compounds of the formula I-b in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 18

Compounds of the formula I-b in which $R^{5a}$ and $R^{5b}$ are methyl, $R^{5c}$ is H, and the combination of $R^1$ and $R^2$ and G, if G is present, for a compound corresponds in each case to one row of Table Q1.

Table 19

Compounds of the formula I-b in which $R^{5a}$ is CF3, $R^{5b}$ and $R^{5c}$ are H, and the combination of $R^1$ and $R^2$ and G, if G is present, for a compound corresponds in each case to one row of Table Q1.

Table 20

Compounds of the formula I-b in which $R^{5a}$, $R^{5b}$ and $R^{5c}$ are chlorine, and the combination of $R^1$ and $R^2$ and G, if G is present, for a compound corresponds in each case to one row of Table Q1.

Table 21

Compounds of the formula I-b in which $R^{5a}$, $R^{5b}$ and $R^{5c}$ are fluorine, and the combination of $R^1$ and $R^2$ and G, if G is present, for a compound corresponds in each case to one row of Table Q1.

Table 22
Compounds of the formula I-b in which $R^{5a}$, $R^{5b}$ and $R^{5c}$ are methyl, and the combination of $R^1$ and $R^2$ and G, if G is present, for a compound corresponds in each case to one row of Table Q1.

Table 23
Compounds of the formula I-c in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 24
Compounds of the formula I-c in which $R^{5a}$ and $R^{5c}$ are bromine, $R^{5b}$ is H, and the combination of $R^1$ and $R^2$ and G, if G is present, for a compound corresponds in each case to one row of Table Q1.

Table 25
Compounds of the formula I-c in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 26
Compounds of the formula I-c in which $R^{5a}$ and $R^{5c}$ are methyl, $R^{5b}$ is H, and the combination of $R^1$ and $R^2$ and G, if G is present, for a compound corresponds in each case to one row of Table Q1.

Table 27
Compounds of the formula I-c in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 28
Compounds of the formula I-c in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 29
Compounds of the formula I-c in which $R^{5a}$ and $R^{5b}$ are methyl, $R^{5c}$ is H, and the combination of $R^1$ and $R^2$ and G, if G is present, for a compound corresponds in each case to one row of Table Q1.

Table 30
Compounds of the formula I-c in which $R^{5a}$ is CF3, $R^{5b}$ and $R^{5c}$ are H, and the combination of $R^1$ and $R^2$ and G, if G is present, for a compound corresponds in each case to one row of Table Q1.

Table 31
Compounds of the formula I-c in which $R^{5a}$, $R^{5b}$ and $R^{5c}$ are chlorine, and the combination of $R^1$ and $R^2$ and G, if G is present, for a compound corresponds in each case to one row of Table Q1.

Table 32
Compounds of the formula I-c in which $R^{5a}$, $R^{5b}$ and $R^{5c}$ are fluorine, and the combination of $R^1$ and $R^2$ and G, if G is present, for a compound corresponds in each case to one row of Table Q1.

Table 33
Compounds of the formula I-c in which $R^{5a}$, $R^{5b}$ and $R^{5c}$ are methyl, and the combination of $R^1$ and $R^2$ and G, if G is present, for a compound corresponds in each case to one row of Table Q1.

Table 34
Compounds of the formula I-d in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 35
Compounds of the formula I-d in which $R^{5a}$ and $R^{5c}$ are bromine, $R^{5b}$ is H, and the combination of $R^1$ and $R^2$ and G, if G is present, for a compound corresponds in each case to one row of Table Q1.

Table 36
Compounds of the formula I-d in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 37
Compounds of the formula I-d in which $R^{5a}$ and $R^{5c}$ are methyl, $R^{5b}$ is H, and the combination of $R^1$ and $R^2$ and G, if G is present, for a compound corresponds in each case to one row of Table Q1.

Table 38
Compounds of the formula I-d in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 39
Compounds of the formula I-d in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 40
Compounds of the formula I-d in which $R^{5a}$ and $R^{5b}$ are methyl, $R^{5c}$ is H, and the combination of $R^1$ and $R^2$ and G, if G is present, for a compound corresponds in each case to one row of Table Q1.

Table 41
Compounds of the formula I-d in which $R^{5a}$ is CF3, $R^{5b}$ and $R^{5c}$ are H, and the combination of $R^1$ and $R^2$ and G, if G is present, for a compound corresponds in each case to one row of Table Q1.

Table 42
Compounds of the formula I-d in which $R^{5a}$, $R^{5b}$ and $R^{5c}$ are chlorine, and the combination of $R^1$ and $R^2$ and G, if G is present, for a compound corresponds in each case to one row of Table Q1.

Table 43
Compounds of the formula I-d in which $R^{5a}$, $R^{5b}$ and $R^{5c}$ are fluorine, and the combination of $R^1$ and $R^2$ and G, if G is present, for a compound corresponds in each case to one row of Table Q1.

Table 44
Compounds of the formula I-d in which $R^{5a}$, $R^{5b}$ and $R^{5c}$ are methyl, and the combination of $R^1$ and $R^2$ and G, if G is present, for a compound corresponds in each case to one row of Table Q1.

Table 45
Compounds of the formula I-e in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 46
Compounds of the formula I-e in which $R^{5a}$ and $R^{5c}$ are bromine, $R^{5b}$ is H, and the combination of $R^1$ and $R^2$ and G, if G is present, for a compound corresponds in each case to one row of Table Q1.

Table 47
Compounds of the formula I-e in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 48
Compounds of the formula I-e in which $R^{5a}$ and $R^{5c}$ are methyl, $R^{5b}$ is H, and the combination of $R^1$ and $R^2$ and G, if G is present, for a compound corresponds in each case to one row of Table Q1.

Table 49
Compounds of the formula I-e in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 50
Compounds of the formula I-e in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 51
Compounds of the formula I-e in which $R^{5a}$ and $R^{5b}$ are methyl, $R^{5c}$ is H, and the combination of $R^1$ and $R^2$ and G, if G is present, for a compound corresponds in each case to one row of Table Q1.

Table 52
Compounds of the formula I-e in which $R^{5a}$ is CF3, $R^{5b}$ and $R^{5c}$ are H, and the combination of $R^1$ and $R^2$ and G, if G is present, for a compound corresponds in each case to one row of Table Q1.

Table 53
Compounds of the formula I-e in which $R^{5a}$, $R^{5b}$ and $R^{5c}$ are chlorine, and the combination of $R^1$ and $R^2$ and G, if G is present, for a compound corresponds in each case to one row of Table Q1.

Table 54
Compounds of the formula I-e in which $R^{5a}$, $R^{5b}$ and $R^{5c}$ are fluorine, and the combination of $R^1$ and $R^2$ and G, if G is present, for a compound corresponds in each case to one row of Table Q1.

Table 55
Compounds of the formula I-e in which $R^{5a}$, $R^{5b}$ and $R^{5c}$ are methyl, and the combination of $R^1$ and $R^2$ and G, if G is present, for a compound corresponds in each case to one row of Table Q1.

Table 56
Compounds of the formula I-f in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 57
Compounds of the formula I-f in which $R^{5a}$ and $R^{5c}$ are bromine, $R^{5b}$ is H, and the combination of $R^1$ and $R^2$ and G, if G is present, for a compound corresponds in each case to one row of Table Q1.

Table 58
Compounds of the formula I-f in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 59
Compounds of the formula I-f in which $R^{5a}$ and $R^{5c}$ are methyl, $R^{5b}$ is H, and the combination of $R^1$ and $R^2$ and G, if G is present, for a compound corresponds in each case to one row of Table Q1.

Table 60
Compounds of the formula I-f in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 61
Compounds of the formula I-f in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 62
Compounds of the formula I-f in which $R^{5a}$ and $R^{5b}$ are methyl, $R^{5c}$ is H, and the combination of $R^1$ and $R^2$ and G, if G is present, for a compound corresponds in each case to one row of Table Q1.

Table 63
Compounds of the formula I-f in which $R^{5a}$ is CF3, $R^{5b}$ and $R^{5c}$ are H, and the combination of $R^1$ and $R^2$ and G, if G is present, for a compound corresponds in each case to one row of Table Q1.

Table 64
Compounds of the formula I-f in which $R^{5a}$, $R^{5b}$ and $R^{5c}$ are chlorine, and the combination of $R^1$ and $R^2$ and G, if G is present, for a compound corresponds in each case to one row of Table Q1.

Table 65
Compounds of the formula I-f in which $R^{5a}$, $R^{5b}$ and $R^{5c}$ are fluorine, and the combination of $R^1$ and $R^2$ and G, if G is present, for a compound corresponds in each case to one row of Table Q1.

Table 66
Compounds of the formula I-f in which $R^{5a}$, $R^{5b}$ and $R^{5c}$ are methyl, and the combination of $R^1$ and $R^2$ and G, if G is present, for a compound corresponds in each case to one row of Table Q1.

Table 67
Compounds of the formula I-g in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 68
Compounds of the formula I-g in which $R^{5a}$ and $R^{5c}$ are bromine, $R^{5b}$ is H, and the combination of $R^1$ and $R^2$ and G, if G is present, for a compound corresponds in each case to one row of Table Q1.

Table 69
Compounds of the formula I-g in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 70
Compounds of the formula I-g in which $R^{5a}$ and $R^{5c}$ are methyl, $R^{5b}$ is H, and the combination of $R^1$ and $R^2$ and G, if G is present, for a compound corresponds in each case to one row of Table Q1.

Table 71
Compounds of the formula I-g in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 72
Compounds of the formula I-g in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 73
Compounds of the formula I-g in which $R^{5a}$ and $R^{5b}$ are methyl, $R^{5c}$ is H, and the combination of $R^1$ and $R^2$ and G, if G is present, for a compound corresponds in each case to one row of Table Q1.

Table 74
Compounds of the formula I-g in which $R^{5a}$ is CF3, $R^{5b}$ and $R^{5c}$ are H, and the combination of $R^1$ and $R^2$ and G, if G is present, for a compound corresponds in each case to one row of Table Q1.

Table 75
Compounds of the formula I-g in which $R^{5a}$, $R^{5b}$ and $R^{5c}$ are chlorine, and the combination of $R^1$ and $R^2$ and G, if G is present, for a compound corresponds in each case to one row of Table Q1.

Table 76
Compounds of the formula I-g in which $R^{5a}$, $R^{5b}$ and $R^{5c}$ are fluorine, and the combination of $R^1$ and $R^2$ and G, if G is present, for a compound corresponds in each case to one row of Table Q1.

Table 77
Compounds of the formula I-g in which $R^{5a}$, $R^{5b}$ and $R^{5c}$ are methyl, and the combination of $R^1$ and $R^2$ and G, if G is present, for a compound corresponds in each case to one row of Table Q1.

Table 78
Compounds of the formula I-h in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 79
Compounds of the formula I-h in which $R^{5a}$ and $R^{5c}$ are bromine, $R^{5b}$ is H, and the combination of $R^1$ and $R^2$ and G, if G is present, for a compound corresponds in each case to one row of Table Q1.

Table 80
Compounds of the formula I-h in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 81
Compounds of the formula I-h in which $R^{5a}$ and $R^{5c}$ are methyl, $R^{5b}$ is H, and the combination of $R^1$ and $R^2$ and G, if G is present, for a compound corresponds in each case to one row of Table Q1.

Table 82
Compounds of the formula I-h in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 83
Compounds of the formula I-h in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 84
Compounds of the formula I-h in which $R^{5a}$ and $R^{5b}$ are methyl, $R^{5c}$ is H, and the combination of $R^1$ and $R^2$ and G, if G is present, for a compound corresponds in each case to one row of Table Q1.

Table 85
Compounds of the formula I-h in which $R^{5a}$ is CF3, $R^{5b}$ and $R^{5c}$ are H, and the combination of $R^1$ and $R^2$ and G, if G is present, for a compound corresponds in each case to one row of Table Q1.

Table 86
Compounds of the formula I-h in which $R^{5a}$, $R^{5b}$ and $R^{5c}$ are chlorine, and the combination of $R^1$ and $R^2$ and G, if G is present, for a compound corresponds in each case to one row of Table Q1.

Table 87
Compounds of the formula I-h in which $R^{5a}$, $R^{5b}$ and $R^{5c}$ are fluorine, and the combination of $R^1$ and $R^2$ and G, if G is present, for a compound corresponds in each case to one row of Table Q1.

Table 88
Compounds of the formula I-h in which $R^{5a}$, $R^{5b}$ and $R^{5c}$ are methyl, and the combination of $R^1$ and $R^2$ and G, if G is present, for a compound corresponds in each case to one row of Table Q1.

Table 89
Compounds of the formula I-i in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 90
Compounds of the formula I-i in which $R^{5a}$ and $R^{5c}$ are bromine, $R^{5b}$ is H, and the combination of $R^1$ and $R^2$ and G, if G is present, for a compound corresponds in each case to one row of Table Q1.

Table 91
Compounds of the formula I-i in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 92
Compounds of the formula I-i in which $R^{5a}$ and $R^{5c}$ are methyl, $R^{5b}$ is H, and the combination of $R^1$ and $R^2$ and G, if G is present, for a compound corresponds in each case to one row of Table Q1.

Table 93
Compounds of the formula I-i in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 94
Compounds of the formula I-i in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 95
Compounds of the formula I-i in which $R^{5a}$ and $R^{5b}$ are methyl, $R^{5c}$ is H, and the combination of $R^1$ and $R^2$ and G, if G is present, for a compound corresponds in each case to one row of Table Q1.

Table 96
Compounds of the formula I-i in which $R^{5a}$ is CF3, $R^{5b}$ and $R^{5c}$ are H, and the combination of $R^1$ and $R^2$ and G, if G is present, for a compound corresponds in each case to one row of Table Q1.

Table 97
Compounds of the formula I-i in which $R^{5a}$, $R^{5b}$ and $R^{5c}$ are chlorine, and the combination of $R^1$ and $R^2$ and G, if G is present, for a compound corresponds in each case to one row of Table Q1.

Table 98
Compounds of the formula I-i in which $R^{5a}$, $R^{5b}$ and $R^{5c}$ are fluorine, and the combination of $R^1$ and $R^2$ and G, if G is present, for a compound corresponds in each case to one row of Table Q1.

Table 99
Compounds of the formula I-i in which $R^{5a}$, $R^{5b}$ and $R^{5c}$ are methyl, and the combination of $R^1$ and $R^2$ and G, if G is present, for a compound corresponds in each case to one row of Table Q1.

Table 100
Compounds of the formula I-j in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 101
Compounds of the formula I-j in which $R^{5a}$ and $R^{5c}$ are bromine, $R^{5b}$ is H, and the combination of $R^1$ and $R^2$ and G, if G is present, for a compound corresponds in each case to one row of Table Q1.

Table 102
Compounds of the formula I-j in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 103
Compounds of the formula I-j in which $R^{5a}$ and $R^{5c}$ are methyl, $R^{5b}$ is H, and the combination of $R^1$ and $R^2$ and G, if G is present, for a compound corresponds in each case to one row of Table Q1.

Table 104
Compounds of the formula I-j in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 105
Compounds of the formula I-j in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 106
Compounds of the formula I-j in which $R^{5a}$ and $R^{5b}$ are methyl, $R^{5c}$ is H, and the combination of $R^1$ and $R^2$ and G, if G is present, for a compound corresponds in each case to one row of Table Q1.

Table 107
Compounds of the formula I-j in which $R^{5a}$ is CF3, $R^{5b}$ and $R^{5c}$ are H, and the combination of $R^1$ and $R^2$ and G, if G is present, for a compound corresponds in each case to one row of Table Q1.

Table 108
Compounds of the formula I-j in which $R^{5a}$, $R^{5b}$ and $R^{5c}$ are chlorine, and the combination of $R^1$ and $R^2$ and G, if G is present, for a compound corresponds in each case to one row of Table Q1.

Table 109
Compounds of the formula I-j in which $R^{5a}$, $R^{5b}$ and $R^{5c}$ are fluorine, and the combination of $R^1$ and $R^2$ and G, if G is present, for a compound corresponds in each case to one row of Table Q1.

Table 110
Compounds of the formula I-j in which $R^{5a}$, $R^{5b}$ and $R^{5c}$ are methyl, and the combination of $R^1$ and $R^2$ and G, if G is present, for a compound corresponds in each case to one row of Table Q1.

Table 111
Compounds of the formula I-k in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 112
Compounds of the formula I-k in which $R^{5a}$ and $R^{5c}$ are bromine, $R^{5b}$ is H, and the combination of $R^1$ and $R^2$ and G, if G is present, for a compound corresponds in each case to one row of Table Q1.

Table 113
Compounds of the formula I-k in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 114
Compounds of the formula I-k in which $R^{5a}$ and $R^{5c}$ are methyl, $R^{5b}$ is H, and the combination of $R^1$ and $R^2$ and G, if G is present, for a compound corresponds in each case to one row of Table Q1.

Table 115
Compounds of the formula I-k in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 116
Compounds of the formula I-k in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 117
Compounds of the formula I-k in which $R^{5a}$ and $R^{5b}$ are methyl, $R^{5c}$ is H, and the combination of $R^1$ and $R^2$ and G, if G is present, for a compound corresponds in each case to one row of Table Q1.

Table 118
Compounds of the formula I-k in which $R^{5a}$ is CF3, $R^{5b}$ and $R^{5c}$ are H, and the combination of $R^1$ and $R^2$ and G, if G is present, for a compound corresponds in each case to one row of Table Q1.

Table 119
Compounds of the formula I-k in which $R^{5a}$, $R^{5b}$ and $R^{5c}$ are chlorine, and the combination of $R^1$ and $R^2$ and G, if G is present, for a compound corresponds in each case to one row of Table Q1.

Table 120
Compounds of the formula I-k in which $R^{5a}$, $R^{5b}$ and $R^{5c}$ are fluorine, and the combination of $R^1$ and $R^2$ and G, if G is present, for a compound corresponds in each case to one row of Table Q1.

Table 121
Compounds of the formula I-k in which $R^{5a}$, $R^{5b}$ and $R^{5c}$ are methyl, and the combination of $R^1$ and $R^2$ and G, if G is present, for a compound corresponds in each case to one row of Table Q1.

Table 122
Compounds of the formula I-l in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 123
Compounds of the formula I-l in which $R^{5a}$ and $R^{5c}$ are bromine, $R^{5b}$ is H, and the combination of $R^1$ and $R^2$ and G, if G is present, for a compound corresponds in each case to one row of Table Q1.

Table 124
Compounds of the formula I-l which $R^{5a}$ and $R^{5c}$ are fluorine, $R^{5b}$ is H, and the combination of $R^1$ and $R^2$ and G, if G is present, for a compound corresponds in each case to one row of Table Q1.

Table 125
Compounds of the formula I-l in which $R^{5a}$ and $R^{5c}$ are methyl, $R^{5b}$ is H, and the combination of $R^1$ and $R^2$ and G, if G is present, for a compound corresponds in each case to one row of Table Q1.

Table 126
Compounds of the formula I-l in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 127
Compounds of the formula I-l in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 128
Compounds of the formula I-l in which $R^{5a}$ and $R^{5b}$ are methyl, $R^{5c}$ is H, and the combination of $R^1$ and $R^2$ and G, if G is present, for a compound corresponds in each case to one row of Table Q1.

Table 129
Compounds of the formula I-l in which $R^{5a}$ is CF3, $R^{5b}$ and $R^{5c}$ are H, and the combination of $R^1$ and $R^2$ and G, if G is present, for a compound corresponds in each case to one row of Table Q1.

Table 130
Compounds of the formula I-l in which $R^{5a}$, $R^{5b}$ and $R^{5c}$ are chlorine, and the combination of $R^1$ and $R^2$ and G, if G is present, for a compound corresponds in each case to one row of Table Q1.

Table 131
Compounds of the formula I-l in which $R^{5a}$, $R^{5b}$ and $R^{5c}$ are fluorine, and the combination of $R^1$ and $R^2$ and G, if G is present, for a compound corresponds in each case to one row of Table Q1.

Table 132
Compounds of the formula I-l in which $R^{5a}$, $R^{5b}$ and $R^{5c}$ are methyl, and the combination of $R^1$ and $R^2$ and G, if G is present, for a compound corresponds in each case to one row of Table Q1.

Table 133
Compounds of the formula I-m in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 134
Compounds of the formula I-m in which $R^{5a}$ and $R^{5c}$ are bromine, $R^{5b}$ is H, and the combination of $R^1$ and $R^2$ and G, if G is present, for a compound corresponds in each case to one row of Table Q1.

Table 135
Compounds of the formula I-m in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 136
Compounds of the formula I-m in which $R^{5a}$ and $R^{5c}$ are methyl, $R^{5b}$ is H, and the combination of $R^1$ and $R^2$ and G, if G is present, for a compound corresponds in each case to one row of Table Q1.

Table 137
Compounds of the formula I-m in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 138
Compounds of the formula I-m in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 139
Compounds of the formula I-m in which $R^{5a}$ and $R^{5b}$ are methyl, $R^{5c}$ is H, and the combination of $R^1$ and $R^2$ and G, if G is present, for a compound corresponds in each case to one row of Table Q1.

Table 140
Compounds of the formula I-m in which $R^{5a}$ is CF3, $R^{5b}$ and $R^{5c}$ are H, and the combination of $R^1$ and $R^2$ and G, if G is present, for a compound corresponds in each case to one row of Table Q1.

Table 141
Compounds of the formula I-m in which $R^{5a}$, $R^{5b}$ and $R^{5c}$ are chlorine, and the combination of $R^1$ and $R^2$ and G, if G is present, for a compound corresponds in each case to one row of Table Q1.

Table 142
Compounds of the formula I-m in which $R^{5a}$, $R^{5b}$ and $R^{5c}$ are fluorine, and the combination of $R^1$ and $R^2$ and G, if G is present, for a compound corresponds in each case to one row of Table Q1.

Table 143
Compounds of the formula I-m in which $R^{5a}$, $R^{5b}$ and $R^{5c}$ are methyl, and the combination of $R^1$ and $R^2$ and G, if G is present, for a compound corresponds in each case to one row of Table Q1.

Table 144
Compounds of the formula I-n in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 145
Compounds of the formula I-n in which $R^{5a}$ and $R^{5c}$ are bromine, $R^{5b}$ is H, and the combination of $R^1$ and $R^2$ and G, if G is present, for a compound corresponds in each case to one row of Table Q1.

Table 146
Compounds of the formula I-n in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 147
Compounds of the formula I-n in which $R^{5a}$ and $R^{5c}$ are methyl, $R^{5b}$ is H, and the combination of $R^1$ and $R^2$ and G, if G is present, for a compound corresponds in each case to one row of Table Q1.

Table 148
Compounds of the formula I-n in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 149
Compounds of the formula I-n in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 150
Compounds of the formula I-n in which $R^{5a}$ and $R^{5b}$ are methyl, $R^{5c}$ is H, and the combination of $R^1$ and $R^2$ and G, if G is present, for a compound corresponds in each case to one row of Table Q1.

Table 151
Compounds of the formula I-n in which $R^{5a}$ is CF3, $R^{5b}$ and $R^{5c}$ are H, and the combination of $R^1$ and $R^2$ and G, if G is present, for a compound corresponds in each case to one row of Table Q1.

Table 152
Compounds of the formula I-n in which $R^{5a}$, $R^{5b}$ and $R^{5c}$ are chlorine, and the combination of $R^1$ and $R^2$ and G, if G is present, for a compound corresponds in each case to one row of Table Q1.

Table 153
Compounds of the formula I-n in which $R^{5a}$, $R^{5b}$ and $R^{5c}$ are fluorine, and the combination of $R^1$ and $R^2$ and G, if G is present, for a compound corresponds in each case to one row of Table Q1.

Table 154
Compounds of the formula I-n in which $R^{5a}$, $R^{5b}$ and $R^{5c}$ are methyl, and the combination of $R^1$ and $R^2$ and G, if G is present, for a compound corresponds in each case to one row of Table Q1.

Table 155
Compounds of the formula I-o in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 156
Compounds of the formula I-o in which $R^{5a}$ and $R^{5c}$ are bromine, $R^{5b}$ is H, and the combination of $R^1$ and $R^2$ and G, if G is present, for a compound corresponds in each case to one row of Table Q1.

Table 157
Compounds of the formula I-o in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 158
Compounds of the formula I-o in which $R^{5a}$ and $R^{5c}$ are methyl, $R^{5b}$ is H, and the combination of $R^1$ and $R^2$ and G, if G is present, for a compound corresponds in each case to one row of Table Q1.

Table 159
Compounds of the formula I-o in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 160
Compounds of the formula I-o in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 161
Compounds of the formula I-o in which $R^{5a}$ and $R^{5b}$ are methyl, $R^{5c}$ is H, and the combination of $R^1$ and $R^2$ and G, if G is present, for a compound corresponds in each case to one row of Table Q1.

Table 162
Compounds of the formula I-o in which $R^{5a}$ is CF3, $R^{5b}$ and $R^{5c}$ are H, and the combination of $R^1$ and $R^2$ and G, if G is present, for a compound corresponds in each case to one row of Table Q1.

Table 163
Compounds of the formula I-o in which $R^{5a}$, $R^{5b}$ and $R^{5c}$ are chlorine, and the combination of $R^1$ and $R^2$ and G, if G is present, for a compound corresponds in each case to one row of Table Q1.

Table 164
Compounds of the formula I-o in which $R^{5a}$, $R^{5b}$ and $R^{5c}$ are fluorine, and the combination of $R^1$ and $R^2$ and G, if G is present, for a compound corresponds in each case to one row of Table Q1.

Table 165
Compounds of the formula I-o in which $R^{5a}$, $R^{5b}$ and $R^{5c}$ are methyl, and the combination of $R^1$ and $R^2$ and G, if G is present, for a compound corresponds in each case to one row of Table Q1.

Table 166
Compounds of the formula I-p in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 167
Compounds of the formula I-p in which $R^{5a}$ and $R^{5c}$ are bromine, $R^{5b}$ is H, and the combination of $R^1$ and $R^2$ and G, if G is present, for a compound corresponds in each case to one row of Table Q1.

Table 168
Compounds of the formula I-p in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 169
Compounds of the formula I-p in which $R^{5a}$ and $R^{5c}$ are methyl, $R^{5b}$ is H, and the combination of $R^1$ and $R^2$ and G, if G is present, for a compound corresponds in each case to one row of Table Q1.

Table 170
Compounds of the formula I-p in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 171
Compounds of the formula I-p in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 172
Compounds of the formula I-p in which $R^{5a}$ and $R^{5b}$ are methyl, $R^{5c}$ is H, and the combination of $R^1$ and $R^2$ and G, if G is present, for a compound corresponds in each case to one row of Table Q1.

Table 173
Compounds of the formula I-p in which $R^{5a}$ is CF3, $R^{5b}$ and $R^{5c}$ are H, and the combination of $R^1$ and $R^2$ and G, if G is present, for a compound corresponds in each case to one row of Table Q1.

Table 174
Compounds of the formula I-p in which $R^{5a}$, $R^{5b}$ and $R^{5c}$ are chlorine, and the combination of $R^1$ and $R^2$ and G, if G is present, for a compound corresponds in each case to one row of Table Q1.

Table 175
Compounds of the formula I-p in which $R^{5a}$, $R^{5b}$ and $R^{5c}$ are fluorine, and the combination of $R^1$ and $R^2$ and G, if G is present, for a compound corresponds in each case to one row of Table Q1.

Table 176
Compounds of the formula I-p in which $R^{5a}$, $R^{5b}$ and $R^{5c}$ are methyl, and the of $R^1$ and $R^2$ and G, if G is present, for a compound corresponds in each case to one row of Table Q1.

Table 177
Compounds of the formula I-q in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 178
Compounds of the formula I-q in which $R^{5a}$ and $R^{5c}$ are bromine, $R^{5b}$ is H, and the combination of $R^1$ and $R^2$ and G, if G is present, for a compound corresponds in each case to one row of Table Q1.

Table 179
Compounds of the formula I-q in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 180
Compounds of the formula I-q in which $R^{5a}$ and $R^{5c}$ are methyl, $R^{5b}$ is H, and the combination of $R^1$ and $R^2$ and G, if G is present, for a compound corresponds in each case to one row of Table Q1.

Table 181
Compounds of the formula I-q in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 182
Compounds of the formula I-q in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 183
Compounds of the formula I-q in which $R^{5a}$ and $R^{5b}$ are methyl, $R^{5c}$ is H, and the combination of $R^1$ and $R^2$ and G, if G is present, for a compound corresponds in each case to one row of Table Q1.

Table 184
Compounds of the formula I-q in which $R^{5a}$ is CF3, $R^{5b}$ and $R^{5c}$ are H, and the combination of $R^1$ and $R^2$ and G, if G is present, for a compound corresponds in each case to one row of Table Q1.

Table 185
Compounds of the formula I-q in which $R^{5a}$, $R^{5b}$ and $R^{5c}$ are chlorine, and the combination of $R^1$ and $R^2$ and G, if G is present, for a compound corresponds in each case to one row of Table Q1.

Table 186
Compounds of the formula I-q in which $R^{5a}$, $R^{5b}$ and $R^{5c}$ are fluorine, and the combination of $R^1$ and $R^2$ and G, if G is present, for a compound corresponds in each case to one row of Table Q1.

Table 187
Compounds of the formula I-q in which $R^{5a}$, $R^{5b}$ and $R^{5c}$ are methyl, and the combination of $R^1$ and $R^2$ and G, if G is present, for a compound corresponds in each case to one row of Table Q1.

Table 188
Compounds of the formula I-r in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 189
Compounds of the formula I-r in which $R^{5a}$ and $R^{5c}$ are bromine, $R^{5b}$ is H, and the combination of $R^1$ and $R^2$ and G, if G is present, for a compound corresponds in each case to one row of Table Q1.

Table 190
Compounds of the formula I-r in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 191
Compounds of the formula I-r in which $R^{5a}$ and $R^{5c}$ are methyl, $R^{5b}$ is H, and the combination of $R^1$ and $R^2$ and G, if G is present, for a compound corresponds in each case to one row of Table Q1.

Table 192
Compounds of the formula I-r in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 193
Compounds of the formula I-r in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 194
Compounds of the formula I-r in which $R^{5a}$ and $R^{5b}$ are methyl, $R^{5c}$ is H, and the combination of $R^1$ and $R^2$ and G, if G is present, for a compound corresponds in each case to one row of Table Q1.

Table 195
Compounds of the formula I-r in which $R^{5a}$ is CF3, $R^{5b}$ and $R^{5c}$ are H, and the combination of $R^1$ and $R^2$ and G, if G is present, for a compound corresponds in each case to one row of Table Q1.

Table 196
Compounds of the formula I-r in which $R^{5a}$, $R^{5b}$ and $R^{5c}$ are chlorine, and the combination of $R^1$ and $R^2$ and G, if G is present, for a compound corresponds in each case to one row of Table Q1.

Table 197
Compounds of the formula I-r in which $R^{5a}$, $R^{5b}$ and $R^{5c}$ are fluorine, and the combination of $R^1$ and $R^2$ and G, if G is present, for a compound corresponds in each case to one row of Table Q1.

Table 198
Compounds of the formula I-r in which $R^{5a}$, $R^{5b}$ and $R^{5c}$ are methyl, and the combination of $R^1$ and $R^2$ and G, if G is present, for a compound corresponds in each case to one row of Table Q1.

Table 199
Compounds of the formula I-s in which $R^{5a}$ and $R^{5b}$ are chlorine, $R^{5b}$ is H, and the combination of $R^1$ and $R^2$ and G, if G is present, for a compound corresponds in each case to one row of Table Q1.

Table 200
Compounds of the formula I-s in which $R^{5a}$ and $R^{5c}$ are bromine, $R^{5b}$ is H, and the combination of $R^1$ and $R^2$ and G, if G is present, for a compound corresponds in each case to one row of Table Q1.

Table 201
Compounds of the formula I-s in which $R^{5a}$ and $R^{5b}$ are fluorine, $R^{5b}$ is H, and the combination of $R^1$ and $R^2$ and G, if G is present, for a compound corresponds in each case to one row of Table Q1.

Table 202
Compounds of the formula I-s in which $R^{5a}$ and $R^{5c}$ are methyl, $R^{5b}$ is H, and the combination of $R^1$ and $R^2$ and G, if G is present, for a compound corresponds in each case to one row of Table Q1.

Table 203
Compounds of the formula I-s in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 204
Compounds of the formula I-s in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 205
Compounds of the formula I-s in which $R^{5a}$ and $R^{5b}$ are methyl, $R^{5c}$ is H, and the combination of $R^1$ and $R^2$ and G, if G is present, for a compound corresponds in each case to one row of Table Q1.

Table 206
Compounds of the formula I-s in which $R^{5a}$ is CF3, $R^{5b}$ and $R^{5c}$ are H, and the combination of $R^1$ and $R^2$ and G, if G is present, for a compound corresponds in each case to one row of Table Q1.

Table 207
Compounds of the formula I-s in which $R^{5a}$, $R^{5b}$ and $R^{5c}$ are chlorine, and the combination of $R^1$ and $R^2$ and G, if G is present, for a compound corresponds in each case to one row of Table Q1.

Table 208
Compounds of the formula I-s in which $R^{5a}$, $R^{5b}$ and $R^{5c}$ are fluorine, and the combination of $R^1$ and $R^2$ and G, if G is present, for a compound corresponds in each case to one row of Table Q1.

Table 209
Compounds of the formula I-s in which $R^{5a}$, $R^{5b}$ and $R^{5c}$ are methyl, and the combination of $R^1$ and $R^2$ and G, if G is present, for a compound corresponds in each case to one row of Table Q1.

Table 210
Compounds of the formula I-t in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 211
Compounds of the formula I-t in which $R^{5a}$ and $R^{5c}$ are bromine, $R^{5b}$ is H, and the combination of $R^1$ and $R^2$ and G, if G is present, for a compound corresponds in each case to one row of Table Q1.

Table 212
Compounds of the formula I-t in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 213
Compounds of the formula I-t in which $R^{5a}$ and $R^{5c}$ are methyl, $R^{5b}$ is H, and the combination of $R^1$ and $R^2$ and G, if G is present, for a compound corresponds in each case to one row of Table Q1.

Table 214
Compounds of the formula I-t in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 215
Compounds of the formula I-t in which $R^{5a}$ and $R^{5b}$ are chlorine, Rx is H, and the combination of $R^1$ and $R^2$ and G, if G is present, for a compound corresponds in each case to one row of Table Q1.

Table 216
Compounds of the formula I-t in which $R^{5a}$ and $R^{5b}$ are methyl, $R^{5c}$ is H, and the combination of $R^1$ and $R^2$ and G, if G is present, for a compound corresponds in each case to one row of Table Q1.

Table 217
Compounds of the formula I-t in which $R^{5a}$ is CF3, $R^{5b}$ and $R^{5c}$ are H, and the combination of $R^1$ and $R^2$ and G, if G is present, for a compound corresponds in each case to one row of Table Q1.

Table 218
Compounds of the formula I-t in which $R^{5a}$, $R^{5b}$ and $R^{5c}$ are chlorine, and the combination of $R^1$ and $R^2$ and G, if G is present, for a compound corresponds in each case to one row of Table Q1.

Table 219
Compounds of the formula I-t in which $R^{5a}$, $R^{5b}$ and $R^{5c}$ are fluorine, and the combination of $R^1$ and $R^2$ and G, if G is present, for a compound corresponds in each case to one row of Table Q1.

Table 220
Compounds of the formula I-t in which $R^{5a}$, $R^{5b}$ and $R^{5c}$ are methyl, and the combination of $R^1$ and $R^2$ and G, if G is present, for a compound corresponds in each case to one row of Table Q1.

Table 221
Compounds of the formula I-u in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 222
Compounds of the formula I-u in which $R^{5a}$ and $R^{5c}$ are bromine, $R^{5b}$ is H, and the combination of $R^1$ and $R^2$ and G, if G is present, for a compound corresponds in each case to one row of Table Q1.

Table 223
Compounds of the formula I-u in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 224
Compounds of the formula I-u in which $R^{5a}$ and $R^{5c}$ are methyl, $R^{5b}$ is H, and the combination of $R^1$ and $R^2$ and G, if G is present, for a compound corresponds in each case to one row of Table Q1.

Table 225
Compounds of the formula I-u in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 226
Compounds of the formula I-u in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 227
Compounds of the formula I-u in which $R^{5a}$ and $R^{5b}$ are methyl, $R^{5c}$ is H, and the combination of $R^1$ and $R^2$ and G, if G is present, for a compound corresponds in each case to one row of Table Q1.

Table 228
Compounds of the formula I-u in which $R^{5a}$ is CF3, $R^{5b}$ and $R^{5c}$ are H, and the combination of $R^1$ and $R^2$ and G, if G is present, for a compound corresponds in each case to one row of Table Q1.

Table 229
Compounds of the formula I-u in which $R^{5a}$, $R^{5b}$ and $R^{5c}$ are chlorine, and the combination of $R^1$ and $R^2$ and G, if G is present, for a compound corresponds in each case to one row of Table Q1.

Table 230
Compounds of the formula I-u in which $R^{5a}$, $R^{5b}$ and $R^{5c}$ are fluorine, and the combination of $R^1$ and $R^2$ and G, if G is present, for a compound corresponds in each case to one row of Table Q1.

Table 231
Compounds of the formula I-u in which $R^{5a}$, $R^{5b}$ and $R^{5c}$ are methyl, and the combination of $R^1$ and $R^2$ and G, if G is present, for a compound corresponds in each case to one row of Table Q1.

Table 232
Compounds of the formula I-v in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 233
Compounds of the formula I-v in which $R^{5a}$ and $R^{5c}$ are bromine, $R^{5b}$ is H, and the combination of $R^1$ and $R^2$ and G, if G is present, for a compound corresponds in each case to one row of Table Q1.

Table 234
Compounds of the formula I-v in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 235
Compounds of the formula I-v in which $R^{5a}$ and $R^{5c}$ are methyl, $R^{5b}$ is H, and the combination of $R^1$ and $R^2$ and G, if G is present, for a compound corresponds in each case to one row of Table Q1.

Table 236
Compounds of the formula I-v in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 237
Compounds of the formula I-v in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 238
Compounds of the formula I-v in which $R^{5a}$ and $R^{5b}$ are methyl, $R^{5c}$ is H, and the combination of $R^1$ and $R^2$ and G, if G is present, for a compound corresponds in each case to one row of Table Q1.

Table 239
Compounds of the formula I-v in which $R^{5a}$ is CF3, $R^{5b}$ and $R^{5c}$ are H, and the combination of $R^1$ and $R^2$ and G, if G is present, for a compound corresponds in each case to one row of Table Q1.

Table 240
Compounds of the formula I-v in which $R^{5a}$, $R^{5b}$ and $R^{5c}$ are chlorine, and the combination of $R^1$ and $R^2$ and G, if G is present, for a compound corresponds in each case to one row of Table Q1.

Table 241
Compounds of the formula I-v in which $R^{5a}$, $R^{5b}$ and $R^{5c}$ are fluorine, and the combination of $R^1$ and $R^2$ and G, if G is present, for a compound corresponds in each case to one row of Table Q1.

Table 242
Compounds of the formula I-v in which $R^{5a}$, $R^{5b}$ and $R^{5c}$ are methyl, and the combination of $R^1$ and $R^2$ and G, if G is present, for a compound corresponds in each case to one row of Table Q1.

Table 243
Compounds of the formula I-w in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 244
Compounds of the formula I-w in which $R^{5a}$ and $R^{5c}$ are bromine, $R^{5b}$ is H, and the combination of $R^1$ and $R^2$ and G, if G is present, for a compound corresponds in each case to one row of Table Q1.

Table 245
Compounds of the formula I-w in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 246
Compounds of the formula I-w in which $R^{5a}$ and $R^{5c}$ are methyl, $R^{5b}$ is H, and the combination of $R^1$ and $R^2$ and G, if G is present, for a compound corresponds in each case to one row of Table Q1.

Table 247
Compounds of the formula I-w in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 248
Compounds of the formula I-w in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 249
Compounds of the formula I-w in which $R^{5a}$ and $R^{5b}$ are methyl, $R^{5c}$ is H, and the combination of $R^1$ and $R^2$ and G, if G is present, for a compound corresponds in each case to one row of Table Q1.

Table 250
Compounds of the formula I-w in which $R^{5a}$ is CF3, $R^{5b}$ and $R^{5c}$ are H, and the combination of $R^1$ and $R^2$ and G, if G is present, for a compound corresponds in each case to one row of Table Q1.

Table 251
Compounds of the formula I-w in which $R^{5a}$, $R^{5b}$ and $R^{5c}$ are chlorine, and the combination of $R^1$ and $R^2$ and G, if G is present, for a compound corresponds in each case to one row of Table Q1.

Table 252
Compounds of the formula I-w in which $R^{5a}$, $R^{5b}$ and $R^{5c}$ are fluorine, and the combination of $R^1$ and $R^2$ and G, if G is present, for a compound corresponds in each case to one row of Table Q1.

Table 253
Compounds of the formula I-w in which $R^{5a}$, $R^{5b}$ and $R^{5c}$ are methyl, and the combination of $R^1$ and $R^2$ and G, if G is present, for a compound corresponds in each case to one row of Table Q1.

Table 254
Compounds of the formula I-x in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 255
Compounds of the formula I-x in which $R^{5a}$ and $R^{5c}$ are bromine, $R^{5b}$ is H, and the combination of $R^1$ and $R^2$ and G, if G is present, for a compound corresponds in each case to one row of Table Q1.

Table 256
Compounds of the formula I-x in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 257
Compounds of the formula I-x in which $R^{5a}$ and $R^{5c}$ are methyl, $R^{5b}$ is H, and the combination of $R^1$ and $R^2$ and G, if G is present, for a compound corresponds in each case to one row of Table Q1.

Table 258
Compounds of the formula I-x in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 259
Compounds of the formula I-x in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 260
Compounds of the formula I-x in which $R^{5a}$ and $R^{5b}$ are methyl, $R^{5c}$ is H, and the combination of $R^1$ and $R^2$ and G, if G is present, for a compound corresponds in each case to one row of Table Q1.

Table 261
Compounds of the formula I-x in which $R^{5a}$ is CF3, $R^{5b}$ and $R^{5c}$ are H, and the combination of $R^1$ and $R^2$ and G, if G is present, for a compound corresponds in each case to one row of Table Q1.

Table 262
Compounds of the formula I-x in which $R^{5a}$, $R^{5b}$ and $R^{5c}$ are chlorine, and the combination of $R^1$ and $R^2$ and G, if G is present, for a compound corresponds in each case to one row of Table Q1.

Table 263
Compounds of the formula I-x in which $R^{5a}$, $R^{5b}$ and $R^{5a}$ are fluorine, and the combination of $R^1$ and $R^2$ and G, if G is present, for a compound corresponds in each case to one row of Table Q1.

Table 264
Compounds of the formula I-x in which $R^{5a}$, $R^{5b}$ and $R^{5c}$ are methyl, and the combination of $R^1$ and $R^2$ and G, if G is present, for a compound corresponds in each case to one row of Table Q1.

Table 265
Compounds of the formula I-y in which $R^{5a}$ and $R^{5c}$ are chlorine, $R^{5b}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 266
Compounds of the formula I-y in which $R^{5a}$ and $R^{5c}$ are bromine, $R^{5b}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 267
Compounds of the formula I-y in which $R^{5a}$ and $R^{5c}$ are fluorine, $R^{5b}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 268
Compounds of the formula I-y in which $R^{5a}$ and $R^{5c}$ are methyl, $R^{5b}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 269
Compounds of the formula I-y in which $R^{5a}$ and $R^{5c}$ are $CF_3$, $R^{5b}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 270
Compounds of the formula I-y in which $R^{5a}$ and $R^{5b}$ are chlorine, $R^{5c}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 271
Compounds of the formula I-y in which $R^{5a}$ and $R^{5b}$ are methyl, $R^{5c}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 272
Compounds of the formula I-y in which $R^{5a}$ is CF3, $R^{5b}$ and $R^{5c}$ are H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 273
Compounds of the formula I-y in which $R^{5a}$, $R^{5b}$ and $R^{5c}$ are chlorine, and the combination of $R^1$ and $R^2$ and G, if G is present, for a compound corresponds in each case to one row of Table Q1, but excluding compounds Q1-1, wherein $R^1$, $R^2$ and G are hydrogen.

Table 274
Compounds of the formula I-y in which $R^{5a}$, $R^{5b}$ and $R^{5c}$ are fluorine, and the combination of $R^1$ and $R^2$ and G, if G is present, for a compound corresponds in each case to one row of Table Q1, but excluding compounds Q1-1, wherein $R^1$, $R^2$ and G are hydrogen.

Table 275
Compounds of the formula I-y in which $R^{5a}$, $R^{5b}$ and $R^{5c}$ are methyl, and the combination of $R^1$ and $R^2$ and G, if G is present, for a compound corresponds in each case to one row of Table Q1, but excluding compounds Q1-1, wherein $R^1$, $R^2$ and G are hydrogen.

Table 276
Compounds of the formula I-z in which $R^{5a}$ and $R^{5c}$ are chlorine, $R^{5b}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 277
Compounds of the formula I-z in which $R^{5a}$ and $R^{5c}$ are bromine, $R^{5b}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 278
Compounds of the formula I-z in which $R^{5a}$ and $R^{5c}$ are fluorine, $R^{5b}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 279
Compounds of the formula I-z in which $R^{5a}$ and $R^{5c}$ are methyl, $R^{5b}$ is H, and the combination of $R^1$ and $R^2$ and G, if Table 280
Compounds of the formula I-z in which $R^{5a}$ and $R^{5b}$ are $CF_3$, $R^{5c}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 281
Compounds of the formula I-z in which $R^{5a}$ and $R^{5b}$ are chlorine, $R^{5c}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 282
Compounds of the formula I-z in which $R^{5a}$ and $R^{5b}$ are methyl, $R^{5c}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 283
Compounds of the formula I-z in which $R^{5a}$ is CF3, $R^{5b}$ and $R^{5c}$ are H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 284
Compounds of the formula I-z in which $R^{5a}$, $R^{5b}$ and $R^{5c}$ are chlorine, and the combination of $R^1$ and $R^2$ and G, if G is present, for a compound corresponds in each case to one row of Table Q1, but excluding compounds Q1-1, wherein $R^1$, $R^2$ and G are hydrogen.

Table 285
Compounds of the formula I-z in which $R^{5a}$, $R^{5b}$ and $R^{5c}$ are fluorine, and the combination of $R^1$ and $R^2$ and G, if G is present, for a compound corresponds in each case to one row of Table Q1, but excluding compounds Q1-1, wherein $R^1$, $R^2$ and G are hydrogen.

Table 286
Compounds of the formula I-z in which $R^{5a}$, $R^{5b}$ and $R^{5c}$ are methyl, and the combination of $R^1$ and $R^2$ and G, if G is present, for a compound corresponds in each case to one row of Table Q1, but excluding compounds Q1-1, wherein $R^1$, $R^2$ and G are hydrogen.

Table 287
Compounds of the formula I-aa in which $R^{5a}$ and $R^{5c}$ are chlorine, $R^{5b}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 288
Compounds of the formula I-aa in which $R^{5a}$ and $R^{5c}$ are bromine, $R^{5b}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 289
Compounds of the formula I-aa in which $R^{5a}$ and $R^{5c}$ are fluorine, $R^{5b}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 290
Compounds of the formula I-aa in which $R^{5a}$ and $R^{5c}$ are methyl, $R^{5b}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 291
Compounds of the formula I-aa in which $R^{5a}$ and $R^{5c}$ are $CF_3$, $R^{5b}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 292
Compounds of the formula I-aa in which $R^{5a}$ and $R^{5b}$ are chlorine, $R^{5c}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 293
Compounds of the formula I-aa in which $R^{5a}$ and $R^{5b}$ are methyl, $R^{5c}$ is H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 294
Compounds of the formula I-aa in which $R^{5a}$ is CF3, $R^{5b}$ and $R^{5c}$ are H, and the combination of $R^1$ and $R^2$ and G, if G is present, for a compound corresponds in each case to one row of Table Q1, but excluding compounds Q1-1, wherein $R^1$, $R^2$ and G are hydrogen.

Table 295
Compounds of the formula I-aa in which $R^{5a}$, $R^{5b}$ and $R^{5c}$ are chlorine, and the combination of $R^1$ and $R^2$ and G, if G is present, for a compound corresponds in each case to one row of Table Q1, but excluding compounds Q1-1, wherein $R^1$, $R^2$ and G are hydrogen.

Table 296
Compounds of the formula I-aa in which $R^{5a}$, $R^{5b}$ and $R^{5c}$ are fluorine, and the combination of $R^1$ and $R^2$ and G, if G is present, for a compound corresponds in each case to one row of Table Q1, but excluding compounds Q1-1, wherein $R^1$, $R^2$ and G are hydrogen.

Table 297
Compounds of the formula I-aa in which $R^{5a}$, $R^{5b}$ and $R^{5c}$ are methyl, and the combination of $R^1$ and $R^2$ and G, if G is present, for a compound corresponds in each case to one row of Table Q1, but excluding compounds Q1-1, wherein $R^1$, $R^2$ and G are hydrogen.

Table 298
Compounds of the formula I-bb in which $R^{5a}$ and $R^{5c}$ are chlorine, $R^{5b}$ is H, and the combination of $R^1$ and $R^2$ and G, if G is present, for a compound corresponds in each case to one row of Table Q1.

Table 299
Compounds of the formula I-bb in which $R^{5a}$ and $R^{5c}$ are bromine, $R^{5b}$ is H, and the combination of $R^1$ and $R^2$ and G, if G is present, for a compound corresponds in each case to one row of Table Q1.

Table 300
Compounds of the formula I-bb in which $R^{5a}$ and $R^{5c}$ are fluorine, $R^{5b}$ is H, and the combination of $R^1$ and $R^2$ and G, if G is present, for a compound corresponds in each case to one row of Table Q1.

Table 301
Compounds of the formula I-bb in which $R^{5a}$ and $R^{5c}$ are methyl, $R^{5b}$ is H, and the combination of $R^1$ and $R^2$ and G, if G is present, for a compound corresponds in each case to one row of Table Q1.

Table 302
Compounds of the formula I-bb in which $R^{5a}$ and $R^{5c}$ are $CF_3$, $R^{5b}$ is H, and the combination of $R^1$ and $R^2$ and G, if G is present, for a compound corresponds in each case to one row of Table Q1.

Table 303
Compounds of the formula I-bb in which $R^{5a}$ and $R^{5b}$ are chlorine, $R^{5c}$ is H, and the combination of $R^1$ and $R^2$ and G, if G is present, for a compound corresponds in each case to one row of Table Q1.

Table 304
Compounds of the formula I-bb in which $R^{5a}$ and $R^{5b}$ are methyl, $R^{5c}$ is H, and the combination of $R^1$ and $R^2$ and G, if G is present, for a compound corresponds in each case to one row of Table Q1.

Table 305
Compounds of the formula I-bb in which $R^{5a}$ is CF3, $R^{5b}$ and $R^{5c}$ are H, and the combination of $R^1$ and $R^2$ and G, if G is present, for a compound corresponds in each case to one row of Table Q1.

Table 306
Compounds of the formula I-bb in which $R^{5a}$, $R^{5b}$ and $R^{5c}$ are chlorine, and the combination of $R^1$ and $R^2$ and G, if G is present, for a compound corresponds in each case to one row of Table Q1.

Table 307
Compounds of the formula I-bb in which $R^{5a}$, $R^{5b}$ and $R^{5c}$ are fluorine, and the combination of $R^1$ and $R^2$ and G, if G is present, for a compound corresponds in each case to one row of Table Q1.

Table 308
Compounds of the formula I-bb in which $R^{5a}$, $R^{5b}$ and $R^{5c}$ are methyl, and the combination of $R^1$ and $R^2$ and G, if G is present, for a compound corresponds in each case to one row of Table Q1.

TABLE Q1

| Compound No | $R^1$ | $R^2$ | G |
|---|---|---|---|
| Q1-1. | H | H | H |
| Q1-2. | H | H | F |
| Q1-3. | H | H | $CH_3$ |
| Q1-4. | H | H | $OCH_3$ |
| Q1-5. | H | H | $OCH_2CH_3$ |
| Q1-6. | H | H | $NHCH_3$ |
| Q1-7. | H | H | $NHCH_2CH_3$ |
| Q1-8. | H | H | $NHCH_2CH_2CH_3$ |
| Q1-9. | H | H | $NHCH_2CF_3$ |
| Q1-10. | H | H | $CH_2CH_3$ |
| Q1-11. | H | H | $CH_2CH_2CH_3$ |
| Q1-12. | H | H | $CH(CH_3)_2$ |
| Q1-13. | H | H | Ph |
| Q1-14. | H | H | $CH_2Ph$ |
| Q1-15. | H | H | 2-Cl—$C_6H_4$ |
| Q1-16. | H | H | 3-Cl—$C_6H_4$ |
| Q1-17. | H | H | 4-Cl—$C_6H_4$ |
| Q1-18. | H | H | 2-$CH_3$—$C_6H_4$ |
| Q1-19. | H | H | 3-$CH_3$—$C_6H_4$ |
| Q1-20. | H | H | 4-$CF_3$—$C_6H_4$ |
| Q1-21. | H | H | 2-$CF_3$—$C_6H_4$ |
| Q1-22. | H | H | 3-$CF_3$—$C_6H_4$ |
| Q1-23. | H | H | 4-$CH_3$—$C_6H_4$ |
| Q1-24. | H | H | 2-$OCH_3$—$C_6H_4$ |
| Q1-25. | H | H | 3-$OCH_3$—$C_6H_4$ |
| Q1-26. | H | H | 4-$OCH_3$—$C_6H_4$ |
| Q1-27. | H | H | 2-$OCF_3$—$C_6H_4$ |
| Q1-28. | H | H | 3-$OCF_3$—$C_6H_4$ |
| Q1-29. | H | H | 4-$OCF_3$—$C_6H_4$ |
| Q1-30. | H | H | —O—$CH_2CH_2$—O—$CH_3$ |
| Q1-31. | H | H | A-2 |
| Q1-32. | H | H | A-3 |
| Q1-33. | H | H | A-4 |
| Q1-34. | H | H | A-5 |
| Q1-35. | H | H | A-6 |
| Q1-36. | H | H | A-7 |
| Q1-37. | H | H | A-8 |
| Q1-38. | H | H | A-9 |
| Q1-39. | H | H | A-10 |
| Q1-40. | H | H | A-11 |
| Q1-41. | H | H | A-12 |
| Q1-42. | H | H | A-13 |
| Q1-43. | H | H | A-14 |
| Q1-44. | H | H | A-15 |
| Q1-45. | H | H | A-16 |
| Q1-46. | H | H | A-17 |
| Q1-47. | H | H | A-18 |
| Q1-48. | H | H | A-19 |
| Q1-49. | H | H | A-21 |
| Q1-50. | H | H | A-22 |
| Q1-51. | H | H | A-23 |
| Q1-52. | H | H | A-24 |

TABLE Q1-continued

| Compound No | R¹ | R² | G |
|---|---|---|---|
| Q1-53. | H | H | A-25 |
| Q1-54. | H | H | A-26 |
| Q1-55. | H | H | A-27 |
| Q1-56. | H | H | A-28 |
| Q1-57. | H | H | —CH$_2$-4-OCH$_3$—C$_6$H$_4$ |
| Q1-58. | H | H | C(=O)OCH$_3$ |
| Q1-59. | H | H | C(=O)OC$_2$H$_5$ |
| Q1-60. | H | H | C(=O)NHCH$_3$ |
| Q1-61. | H | H | C(=O)NHC$_2$H$_5$ |
| Q1-62. | H | H | C(=O)NH—CH$_2$(CH$_3$)$_2$ |
| Q1-63. | H | H | C(=O)NH—CH$_2$CF$_3$ |
| Q1-64. | H | H | C(=O)NH—CH$_2$Cyclopropyl |
| Q1-65. | H | H | C(=O)NH—CH(CH$_3$)Cyclopropyl |
| Q1-66. | H | H | C(=O)NH—CH$_2$C(=O)NH—CH$_2$Cyclopropyl |
| Q1-67. | H | H | C(=O)NH—CH$_2$C(=O)NH—CH$_2$CF$_3$ |
| Q1-68. | H | H | C(=O)NH—CH$_2$(A-1) |
| Q1-69. | H | H | C(=O)NH—CH$_2$(A-2) |
| Q1-70. | H | H | CH$_2$C(=O)OCH$_3$ |
| Q1-71. | H | H | CH$_2$C(=O)OC$_2$H$_5$ |
| Q1-72. | H | H | CH$_2$C(=O)NHCH$_3$ |
| Q1-73. | H | H | CH$_2$C(=O)NHC$_2$H$_5$ |
| Q1-74. | H | H | CH$_2$C(=O)NH—CH$_2$(CH$_3$)$_2$ |
| Q1-75. | H | H | CH$_2$C(=O)NH—CH$_2$CF$_3$ |
| Q1-76. | H | H | CH$_2$C(=O)NH—CH$_2$Cyclopropyl |
| Q1-77. | H | H | CH$_2$C(=O)NH—CH(CH$_3$)Cyclopropyl |
| Q1-78. | H | H | CH$_2$C(=O)NH—CH$_2$C(=O)NH—CH$_2$Cyclopropyl |
| Q1-79. | H | H | CH$_2$C(=O)NH—CH$_2$C(=O)NH—CH$_2$CF$_3$ |
| Q1-80. | H | H | CH$_2$C(=O)NH—CH$_2$(A-1) |
| Q1-81. | H | H | CH$_2$C(=O)NH—CH$_2$(A-2) |
| Q1-82. | H | H | (CH$_2$)$_2$C(=O)OCH$_3$ |
| Q1-83. | H | H | (CH$_2$)$_2$C(=O)OC$_2$H$_5$ |
| Q1-84. | H | H | (CH$_2$)$_2$C(=O)NHCH$_3$ |
| Q1-85. | H | H | (CH$_2$)$_2$C(=O)NHC$_2$H$_5$ |
| Q1-86. | H | H | (CH$_2$)$_2$C(=O)NH—CH$_2$(CH$_3$)$_2$ |
| Q1-87. | H | H | (CH$_2$)$_2$C(=O)NH—CH$_2$CF$_3$ |
| Q1-88. | H | H | (CH$_2$)$_2$C(=O)NH—CH$_2$Cyclopropyl |
| Q1-89. | H | H | (CH$_2$)$_2$C(=O)NH—CH(CH$_3$)Cyclopropyl |
| Q1-90. | H | H | (CH$_2$)$_2$C(=O)NH—CH$_2$C(=O)NH—CH$_2$Cyclopropyl |
| Q1-91. | H | H | (CH$_2$)$_2$C(=O)NH—CH$_2$C(=O)NH—CH$_2$CF$_3$ |
| Q1-92. | H | H | (CH$_2$)$_2$C(=O)NH—CH$_2$(A-1) |
| Q1-93. | H | H | (CH$_2$)$_2$C(=O)NH—CH$_2$(A-2) |
| Q1-94. | H | H | SO$_2$CH$_3$ |
| Q1-95. | H | H | CF$_3$ |
| Q1-96. | H | H | CH$_2$CF$_3$ |
| Q1-97. | H | H | CH$_2$CH$_2$CF$_3$ |
| Q1-98. | H | H | CH$_2$CF(CF$_3$)$_2$ |
| Q1-99. | H | H | CH$_2$(CF$_2$)$_3$CF$_3$ |
| Q1-100. | CH$_3$ | H | H |
| Q1-101. | CH$_3$ | H | F |
| Q1-102. | CH$_3$ | H | CH$_3$ |
| Q1-103. | CH$_3$ | H | OCH$_3$ |
| Q1-104. | CH$_3$ | H | OCH$_2$CH$_3$ |
| Q1-105. | CH$_3$ | H | NHCH$_3$ |
| Q1-106. | CH$_3$ | H | NHCH$_2$CH$_3$ |
| Q1-107. | CH$_3$ | H | NHCH$_2$CH$_2$CH$_3$ |
| Q1-108. | CH$_3$ | H | NHCH$_2$CF$_3$ |
| Q1-109. | CH$_3$ | H | CH$_2$CH$_3$ |
| Q1-110. | CH$_3$ | H | CH$_2$CH$_2$CH$_3$ |
| Q1-111. | CH$_3$ | H | CH(CH$_3$)$_2$ |
| Q1-112. | CH$_3$ | H | Ph |
| Q1-113. | CH$_3$ | H | CH$_2$Ph |
| Q1-114. | CH$_3$ | H | 2-Cl—C$_6$H$_4$ |
| Q1-115. | CH$_3$ | H | 3-Cl—C$_6$H$_4$ |
| Q1-116. | CH$_3$ | H | 4-Cl—C$_6$H$_4$ |
| Q1-117. | CH$_3$ | H | 2-CH$_3$—C$_6$H$_4$ |
| Q1-118. | CH$_3$ | H | 3-CH$_3$—C$_6$H$_4$ |
| Q1-119. | CH$_3$ | H | 4-CF$_3$—C$_6$H$_4$ |
| Q1-120. | CH$_3$ | H | 2-CF$_3$—C$_6$H$_4$ |
| Q1-121. | CH$_3$ | H | 3-CF$_3$—C$_6$H$_4$ |
| Q1-122. | CH$_3$ | H | 4-CH$_3$—C$_6$H$_4$ |
| Q1-123. | CH$_3$ | H | 2-OCH$_3$—C$_6$H$_4$ |
| Q1-124. | CH$_3$ | H | 3-OCH$_3$—C$_6$H$_4$ |
| Q1-125. | CH$_3$ | H | 4-OCH$_3$—C$_6$H$_4$ |
| Q1-126. | CH$_3$ | H | 2-OCF$_3$—C$_6$H$_4$ |
| Q1-127. | CH$_3$ | H | 3-OCF$_3$—C$_6$H$_4$ |
| Q1-128. | CH$_3$ | H | 4-OCF$_3$—C$_6$H$_4$ |
| Q1-129. | CH$_3$ | H | —O—CH$_2$CH$_2$—O—CH$_3$ |
| Q1-130. | CH$_3$ | H | A-2 |

TABLE Q1-continued

| Compound No | R¹ | R² | G |
|---|---|---|---|
| Q1-131. | CH₃ | H | A-3 |
| Q1-132. | CH₃ | H | A-4 |
| Q1-133. | CH₃ | H | A-5 |
| Q1-134. | CH₃ | H | A-6 |
| Q1-135. | CH₃ | H | A-7 |
| Q1-136. | CH₃ | H | A-8 |
| Q1-137. | CH₃ | H | A-9 |
| Q1-138. | CH₃ | H | A-10 |
| Q1-139. | CH₃ | H | A-11 |
| Q1-140. | CH₃ | H | A-12 |
| Q1-141. | CH₃ | H | A-13 |
| Q1-142. | CH₃ | H | A-14 |
| Q1-143. | CH₃ | H | A-15 |
| Q1-144. | CH₃ | H | A-16 |
| Q1-145. | CH₃ | H | A-17 |
| Q1-146. | CH₃ | H | A-18 |
| Q1-147. | CH₃ | H | A-19 |
| Q1-148. | CH₃ | H | A-21 |
| Q1-149. | CH₃ | H | A-22 |
| Q1-150. | CH₃ | H | A-23 |
| Q1-151. | CH₃ | H | A-24 |
| Q1-152. | CH₃ | H | A-25 |
| Q1-153. | CH₃ | H | A-26 |
| Q1-154. | CH₃ | H | A-27 |
| Q1-155. | CH₃ | H | A-28 |
| Q1-156. | CH₃ | H | —CH₂-4-OCH₃—C₆H₄ |
| Q1-157. | CH₃ | H | C(=O)OCH₃ |
| Q1-158. | CH₃ | H | C(=O)OC₂H₅ |
| Q1-159. | CH₃ | H | C(=O)NHCH₃ |
| Q1-160. | CH₃ | H | C(=O)NHC₂H₅ |
| Q1-161. | CH₃ | H | C(=O)NH—CH₂(CH₃)₂ |
| Q1-162. | CH₃ | H | C(=O)NH—CH₂CF₃ |
| Q1-163. | CH₃ | H | C(=O)NH—CH₂Cyclopropyl |
| Q1-164. | CH₃ | H | C(=O)NH—CH(CH₃)Cyclopropyl |
| Q1-165. | CH₃ | H | C(=O)NH—CH₂C(=O)NH—CH₂Cyclopropyl |
| Q1-166. | CH₃ | H | C(=O)NH—CH₂C(=O)NH—CH₂CF₃ |
| Q1-167. | CH₃ | H | C(=O)NH—CH₂(A-1) |
| Q1-168. | CH₃ | H | C(=O)NH—CH₂(A-2) |
| Q1-169. | CH₃ | H | CH₂C(=O)OCH₃ |
| Q1-170. | CH₃ | H | CH₂C(=O)OC₂H₅ |
| Q1-171. | CH₃ | H | CH₂C(=O)NHCH₃ |
| Q1-172. | CH₃ | H | CH₂C(=O)NHC₂H₅ |
| Q1-173. | CH₃ | H | CH₂C(=O)NH—CH₂(CH₃)₂ |
| Q1-174. | CH₃ | H | CH₂C(=O)NH—CH₂CF₃ |
| Q1-175. | CH₃ | H | CH₂C(=O)NH—CH₂Cyclopropyl |
| Q1-176. | CH₃ | H | CH₂C(=O)NH—CH(CH₃)Cyclopropyl |
| Q1-177. | CH₃ | H | CH₂C(=O)NH—CH₂C(=O)NH—CH₂Cyclopropyl |
| Q1-178. | CH₃ | H | CH₂C(=O)NH—CH₂C(=O)NH—CH₂CF₃ |
| Q1-179. | CH₃ | H | CH₂C(=O)NH—CH₂(A-1) |
| Q1-180. | CH₃ | H | CH₂C(=O)NH—CH₂(A-2) |
| Q1-181. | CH₃ | H | (CH₂)₂C(=O)OCH₃ |
| Q1-182. | CH₃ | H | (CH₂)₂C(=O)OC₂H₅ |
| Q1-183. | CH₃ | H | (CH₂)₂C(=O)NHCH₃ |
| Q1-184. | CH₃ | H | (CH₂)₂C(=O)NHC₂H₅ |
| Q1-185. | CH₃ | H | (CH₂)₂C(=O)NH—CH₂(CH₃)₂ |
| Q1-186. | CH₃ | H | (CH₂)₂C(=O)NH—CH₂CF₃ |
| Q1-187. | CH₃ | H | (CH₂)₂C(=O)NH—CH₂Cyclopropyl |
| Q1-188. | CH₃ | H | (CH₂)₂C(=O)NH—CH(CH₃)Cyclopropyl |
| Q1-189. | CH₃ | H | (CH₂)₂C(=O)NH—CH₂C(=O)NH—CH₂Cyclopropyl |
| Q1-190. | CH₃ | H | (CH₂)₂C(=O)NH—CH₂C(=O)NH—CH₂CF₃ |
| Q1-191. | CH₃ | H | (CH₂)₂C(=O)NH—CH₂(A-1) |
| Q1-192. | CH₃ | H | (CH₂)₂C(=O)NH—CH₂(A-2) |
| Q1-193. | CH₃ | H | SO₂CH₃ |
| Q1-194. | CH₃ | H | CF₃ |
| Q1-195. | CH₃ | H | CH₂CF₃ |
| Q1-196. | CH₃ | H | CH₂CH₂CF₃ |
| Q1-197. | CH₃ | H | CH₂CF(CF₃)₂ |
| Q1-198. | CH₃ | H | CH₂(CF₂)₃CF₃ |
| Q1-199. | CH₃ | CH₃ | H |
| Q1-200. | CH₃ | CH₃ | F |
| Q1-201. | CH₃ | CH₃ | CH₃ |
| Q1-202. | CH₃ | CH₃ | OCH₃ |
| Q1-203. | CH₃ | CH₃ | OCH₂CH₃ |
| Q1-204. | CH₃ | CH₃ | NHCH₃ |
| Q1-205. | CH₃ | CH₃ | NHCH₂CH₃ |
| Q1-206. | CH₃ | CH₃ | NHCH₂CH₂CH₃ |
| Q1-207. | CH₃ | CH₃ | NHCH₂CF₃ |
| Q1-208. | CH₃ | CH₃ | CH₂CH₃ |

TABLE Q1-continued

| Compound No | R¹ | R² | G |
|---|---|---|---|
| Q1-209. | $CH_3$ | $CH_3$ | $CH_2CH_2CH_3$ |
| Q1-210. | $CH_3$ | $CH_3$ | $CH(CH_3)_2$ |
| Q1-211. | $CH_3$ | $CH_3$ | Ph |
| Q1-212. | $CH_3$ | $CH_3$ | $CH_2Ph$ |
| Q1-213. | $CH_3$ | $CH_3$ | 2-Cl—$C_6H_4$ |
| Q1-214. | $CH_3$ | $CH_3$ | 3-Cl—$C_6H_4$ |
| Q1-215. | $CH_3$ | $CH_3$ | 4-Cl—$C_6H_4$ |
| Q1-216. | $CH_3$ | $CH_3$ | 2-$CH_3$—$C_6H_4$ |
| Q1-217. | $CH_3$ | $CH_3$ | 3-$CH_3$—$C_6H_4$ |
| Q1-218. | $CH_3$ | $CH_3$ | 4-$CF_3$—$C_6H_4$ |
| Q1-219. | $CH_3$ | $CH_3$ | 2-$CF_3$—$C_6H_4$ |
| Q1-220. | $CH_3$ | $CH_3$ | 3-$CF_3$—$C_6H_4$ |
| Q1-221. | $CH_3$ | $CH_3$ | 4-$CH_3$—$C_6H_4$ |
| Q1-222. | $CH_3$ | $CH_3$ | 2-$OCH_3$—$C_6H_4$ |
| Q1-223. | $CH_3$ | $CH_3$ | 3-$OCH_3$—$C_6H_4$ |
| Q1-224. | $CH_3$ | $CH_3$ | 4-$OCH_3$—$C_6H_4$ |
| Q1-225. | $CH_3$ | $CH_3$ | 2-$OCF_3$—$C_6H_4$ |
| Q1-226. | $CH_3$ | $CH_3$ | 3-$OCF_3$—$C_6H_4$ |
| Q1-227. | $CH_3$ | $CH_3$ | 4-$OCF_3$—$C_6H_4$ |
| Q1-228. | $CH_3$ | $CH_3$ | —O—$CH_2CH_2$—O—$CH_3$ |
| Q1-229. | $CH_3$ | $CH_3$ | A-2 |
| Q1-230. | $CH_3$ | $CH_3$ | A-3 |
| Q1-231. | $CH_3$ | $CH_3$ | A-4 |
| Q1-232. | $CH_3$ | $CH_3$ | A-5 |
| Q1-233. | $CH_3$ | $CH_3$ | A-6 |
| Q1-234. | $CH_3$ | $CH_3$ | A-7 |
| Q1-235. | $CH_3$ | $CH_3$ | A-8 |
| Q1-236. | $CH_3$ | $CH_3$ | A-9 |
| Q1-237. | $CH_3$ | $CH_3$ | A-10 |
| Q1-238. | $CH_3$ | $CH_3$ | A-11 |
| Q1-239. | $CH_3$ | $CH_3$ | A-12 |
| Q1-240. | $CH_3$ | $CH_3$ | A-13 |
| Q1-241. | $CH_3$ | $CH_3$ | A-14 |
| Q1-242. | $CH_3$ | $CH_3$ | A-15 |
| Q1-243. | $CH_3$ | $CH_3$ | A-16 |
| Q1-244. | $CH_3$ | $CH_3$ | A-17 |
| Q1-245. | $CH_3$ | $CH_3$ | A-18 |
| Q1-246. | $CH_3$ | $CH_3$ | A-19 |
| Q1-247. | $CH_3$ | $CH_3$ | A-21 |
| Q1-248. | $CH_3$ | $CH_3$ | A-22 |
| Q1-249. | $CH_3$ | $CH_3$ | A-23 |
| Q1-250. | $CH_3$ | $CH_3$ | A-24 |
| Q1-251. | $CH_3$ | $CH_3$ | A-25 |
| Q1-252. | $CH_3$ | $CH_3$ | A-26 |
| Q1-253. | $CH_3$ | $CH_3$ | A-27 |
| Q1-254. | $CH_3$ | $CH_3$ | A-28 |
| Q1-255. | $CH_3$ | $CH_3$ | —$CH_2$-4-$OCH_3$—$C_6H_4$ |
| Q1-256. | $CH_3$ | $CH_3$ | C(=O)$OCH_3$ |
| Q1-257. | $CH_3$ | $CH_3$ | C(=O)$OC_2H_5$ |
| Q1-258. | $CH_3$ | $CH_3$ | C(=O)$NHCH_3$ |
| Q1-259. | $CH_3$ | $CH_3$ | C(=O)$NHC_2H_5$ |
| Q1-260. | $CH_3$ | $CH_3$ | C(=O)NH—$CH_2(CH_3)_2$ |
| Q1-261. | $CH_3$ | $CH_3$ | C(=O)NH—$CH_2CF_3$ |
| Q1-262. | $CH_3$ | $CH_3$ | C(=O)NH—$CH_2$Cyclopropyl |
| Q1-263. | $CH_3$ | $CH_3$ | C(=O)NH—CH($CH_3$)Cyclopropyl |
| Q1-264. | $CH_3$ | $CH_3$ | C(=O)NH—$CH_2$C(=O)NH—$CH_2$Cyclopropyl |
| Q1-265. | $CH_3$ | $CH_3$ | C(=O)NH—$CH_2$C(=O)NH—$CH_2CF_3$ |
| Q1-266. | $CH_3$ | $CH_3$ | C(=O)NH—$CH_2$(A-1) |
| Q1-267. | $CH_3$ | $CH_3$ | C(=O)NH—$CH_2$(A-2) |
| Q1-268. | $CH_3$ | $CH_3$ | $CH_2$C(=O)$OCH_3$ |
| Q1-269. | $CH_3$ | $CH_3$ | $CH_2$C(=O)$OC_2H_5$ |
| Q1-270. | $CH_3$ | $CH_3$ | $CH_2$C(=O)$NHCH_3$ |
| Q1-271. | $CH_3$ | $CH_3$ | $CH_2$C(=O)$NHC_2H_5$ |
| Q1-272. | $CH_3$ | $CH_3$ | $CH_2$C(=O)NH—$CH_2(CH_3)_2$ |
| Q1-273. | $CH_3$ | $CH_3$ | $CH_2$C(=O)NH—$CH_2CF_3$ |
| Q1-274. | $CH_3$ | $CH_3$ | $CH_2$C(=O)NH—$CH_2$Cyclopropyl |
| Q1-275. | $CH_3$ | $CH_3$ | $CH_2$C(=O)NH—CH($CH_3$)Cyclopropyl |
| Q1-276. | $CH_3$ | $CH_3$ | $CH_2$C(=O)NH—$CH_2$C(=O)NH—$CH_2$Cyclopropyl |
| Q1-277. | $CH_3$ | $CH_3$ | $CH_2$C(=O)NH—$CH_2$C(=O)NH—$CH_2CF_3$ |
| Q1-278. | $CH_3$ | $CH_3$ | $CH_2$C(=O)NH—$CH_2$(A-1) |
| Q1-279. | $CH_3$ | $CH_3$ | $CH_2$C(=O)NH—$CH_2$(A-2) |
| Q1-280. | $CH_3$ | $CH_3$ | $(CH_2)_2$C(=O)$OCH_3$ |
| Q1-281. | $CH_3$ | $CH_3$ | $(CH_2)_2$C(=O)$OC_2H_5$ |
| Q1-282. | $CH_3$ | $CH_3$ | $(CH_2)_2$C(=O)$NHCH_3$ |
| Q1-283. | $CH_3$ | $CH_3$ | $(CH_2)_2$C(=O)$NHC_2H_5$ |
| Q1-284. | $CH_3$ | $CH_3$ | $(CH_2)_2$C(=O)NH—$CH_2(CH_3)_2$ |
| Q1-285. | $CH_3$ | $CH_3$ | $(CH_2)_2$C(=O)NH—$CH_2CF_3$ |
| Q1-286. | $CH_3$ | $CH_3$ | $(CH_2)_2$C(=O)NH—$CH_2$Cyclopropyl |

TABLE Q1-continued

| Compound No | R$^1$ | R$^2$ | G |
|---|---|---|---|
| Q1-287. | CH$_3$ | CH$_3$ | (CH$_2$)$_2$C(=O)NH—CH(CH$_3$)Cyclopropyl |
| Q1-288. | CH$_3$ | CH$_3$ | (CH$_2$)$_2$C(=O)NH—CH$_2$C(=O)NH—CH$_2$Cyclopropyl |
| Q1-289. | CH$_3$ | CH$_3$ | (CH$_2$)$_2$C(=O)NH—CH$_2$C(=O)NH—CH$_2$CF$_3$ |
| Q1-290. | CH$_3$ | CH$_3$ | (CH$_2$)$_2$C(=O)NH—CH$_2$(A-1) |
| Q1-291. | CH$_3$ | CH$_3$ | (CH$_2$)$_2$C(=O)NH—CH$_2$(A-2) |
| Q1-292. | CH$_3$ | CH$_3$ | SO$_2$CH$_3$ |
| Q1-293. | CH$_3$ | CH$_3$ | CF$_3$ |
| Q1-294. | CH$_3$ | CH$_3$ | CH$_2$CF$_3$ |
| Q1-295. | CH$_3$ | CH$_3$ | CH$_2$CH$_2$CF$_3$ |
| Q1-296. | CH$_3$ | CH$_3$ | CH$_2$CF(CF$_3$)$_2$ |
| Q1-297. | CH$_3$ | CH$_3$ | CH$_2$(CF$_2$)$_3$CF$_3$ |
| Q1-298. | CF$_3$ | H | H |
| Q1-299. | CF$_3$ | H | F |
| Q1-300. | CF$_3$ | H | CH$_3$ |
| Q1-301. | CF$_3$ | H | OCH$_3$ |
| Q1-302. | CF$_3$ | H | OCH$_2$CH$_3$ |
| Q1-303. | CF$_3$ | H | NHCH$_3$ |
| Q1-304. | CF$_3$ | H | NHCH$_2$CH$_3$ |
| Q1-305. | CF$_3$ | H | NHCH$_2$CH$_2$CH$_3$ |
| Q1-306. | CF$_3$ | H | NHCH$_2$CF$_3$ |
| Q1-307. | CF$_3$ | H | CH$_2$CH$_3$ |
| Q1-308. | CF$_3$ | H | CH$_2$CH$_2$CH$_3$ |
| Q1-309. | CF$_3$ | H | CH(CH$_3$)$_2$ |
| Q1-310. | CF$_3$ | H | Ph |
| Q1-311. | CF$_3$ | H | CH$_2$Ph |
| Q1-312. | CF$_3$ | H | 2-Cl—C$_6$H$_4$ |
| Q1-313. | CF$_3$ | H | 3-Cl—C$_6$H$_4$ |
| Q1-314. | CF$_3$ | H | 4-Cl—C$_6$H$_4$ |
| Q1-315. | CF$_3$ | H | 2-CH$_3$—C$_6$H$_4$ |
| Q1-316. | CF$_3$ | H | 3-CH$_3$—C$_6$H$_4$ |
| Q1-317. | CF$_3$ | H | 4-CF$_3$—C$_6$H$_4$ |
| Q1-318. | CF$_3$ | H | 2-CF$_3$—C$_6$H$_4$ |
| Q1-319. | CF$_3$ | H | 3-CF$_3$—C$_6$H$_4$ |
| Q1-320. | CF$_3$ | H | 4-CH$_3$—C$_6$H$_4$ |
| Q1-321. | CF$_3$ | H | 2-OCH$_3$—C$_6$H$_4$ |
| Q1-322. | CF$_3$ | H | 3-OCH$_3$—C$_6$H$_4$ |
| Q1-323. | CF$_3$ | H | 4-OCH$_3$—C$_6$H$_4$ |
| Q1-324. | CF$_3$ | H | 2-OCF$_3$—C$_6$H$_4$ |
| Q1-325. | CF$_3$ | H | 3-OCF$_3$—C$_6$H$_4$ |
| Q1-326. | CF$_3$ | H | 4-OCF$_3$—C$_6$H$_4$ |
| Q1-327. | CF$_3$ | H | —O—CH$_2$CH$_2$—O—CH$_3$ |
| Q1-328. | CF$_3$ | H | A-2 |
| Q1-329. | CF$_3$ | H | A-3 |
| Q1-330. | CF$_3$ | H | A-4 |
| Q1-331. | CF$_3$ | H | A-5 |
| Q1-332. | CF$_3$ | H | A-6 |
| Q1-333. | CF$_3$ | H | A-7 |
| Q1-334. | CF$_3$ | H | A-8 |
| Q1-335. | CF$_3$ | H | A-9 |
| Q1-336. | CF$_3$ | H | A-10 |
| Q1-337. | CF$_3$ | H | A-11 |
| Q1-338. | CF$_3$ | H | A-12 |
| Q1-339. | CF$_3$ | H | A-13 |
| Q1-340. | CF$_3$ | H | A-14 |
| Q1-341. | CF$_3$ | H | A-15 |
| Q1-342. | CF$_3$ | H | A-16 |
| Q1-343. | CF$_3$ | H | A-17 |
| Q1-344. | CF$_3$ | H | A-18 |
| Q1-345. | CF$_3$ | H | A-19 |
| Q1-346. | CF$_3$ | H | A-21 |
| Q1-347. | CF$_3$ | H | A-22 |
| Q1-348. | CF$_3$ | H | A-23 |
| Q1-349. | CF$_3$ | H | A-24 |
| Q1-350. | CF$_3$ | H | A-25 |
| Q1-351. | CF$_3$ | H | A-26 |
| Q1-352. | CF$_3$ | H | A-27 |
| Q1-353. | CF$_3$ | H | A-28 |
| Q1-354. | CF$_3$ | H | —CH$_2$-4-OCH$_3$—C$_6$H$_4$ |
| Q1-355. | CF$_3$ | H | C(=O)OCH$_3$ |
| Q1-356. | CF$_3$ | H | C(=O)OC$_2$H$_5$ |
| Q1-357. | CF$_3$ | H | C(=O)NHCH$_3$ |
| Q1-358. | CF$_3$ | H | C(=O)NHC$_2$H$_5$ |
| Q1-359. | CF$_3$ | H | C(=O)NH—CH$_2$(CH$_3$)$_2$ |
| Q1-360. | CF$_3$ | H | C(=O)NH—CH$_2$CF$_3$ |
| Q1-361. | CF$_3$ | H | C(=O)NH—CH$_2$Cyclopropyl |
| Q1-362. | CF$_3$ | H | C(=O)NH—CH(CH$_3$)Cyclopropyl |
| Q1-363. | CF$_3$ | H | C(=O)NH—CH$_2$C(=O)NH—CH$_2$Cyclopropyl |
| Q1-364. | CF$_3$ | H | C(=O)NH—CH$_2$C(=O)NH—CH$_2$CF$_3$ |

TABLE Q1-continued

| Compound No | R¹ | R² | G |
|---|---|---|---|
| Q1-365. | CF₃ | H | C(=O)NH—CH₂(A-1) |
| Q1-366. | CF₃ | H | C(=O)NH—CH₂(A-2) |
| Q1-367. | CF₃ | H | CH₂C(=O)OCH₃ |
| Q1-368. | CF₃ | H | CH₂C(=O)OC₂H₅ |
| Q1-369. | CF₃ | H | CH₂C(=O)NHCH₃ |
| Q1-370. | CF₃ | H | CH₂C(=O)NHC₂H₅ |
| Q1-371. | CF₃ | H | CH₂C(=O)NH—CH₂(CH₃)₂ |
| Q1-372. | CF₃ | H | CH₂C(=O)NH—CH₂CF₃ |
| Q1-373. | CF₃ | H | CH₂C(=O)NH—CH₂Cyclopropyl |
| Q1-374. | CF₃ | H | CH₂C(=O)NH—CH(CH₃)Cyclopropyl |
| Q1-375. | CF₃ | H | CH₂C(=O)NH—CH₂C(=O)NH—CH₂Cyclopropyl |
| Q1-376. | CF₃ | H | CH₂C(=O)NH—CH₂C(=O)NH—CH₂CF₃ |
| Q1-377. | CF₃ | H | CH₂C(=O)NH—CH₂(A-1) |
| Q1-378. | CF₃ | H | CH₂C(=O)NH—CH₂(A-2) |
| Q1-379. | CF₃ | H | (CH₂)₂C(=O)OCH₃ |
| Q1-380. | CF₃ | H | (CH₂)₂C(=O)OC₂H₅ |
| Q1-381. | CF₃ | H | (CH₂)₂C(=O)NHCH₃ |
| Q1-382. | CF₃ | H | (CH₂)₂C(=O)NHC₂H₅ |
| Q1-383. | CF₃ | H | (CH₂)₂C(=O)NH—CH₂(CH₃)₂ |
| Q1-384. | CF₃ | H | (CH₂)₂C(=O)NH—CH₂CF₃ |
| Q1-385. | CF₃ | H | (CH₂)₂C(=O)NH—CH₂Cyclopropyl |
| Q1-386. | CF₃ | H | (CH₂)₂C(=O)NH—CH(CH₃)Cyclopropyl |
| Q1-387. | CF₃ | H | (CH₂)₂C(=O)NH—CH₂C(=O)NH—CH₂Cyclopropyl |
| Q1-388. | CF₃ | H | (CH₂)₂C(=O)NH—CH₂C(=O)NH—CH₂CF₃ |
| Q1-389. | CF₃ | H | (CH₂)₂C(=O)NH—CH₂(A-1) |
| Q1-390. | CF₃ | H | (CH₂)₂C(=O)NH—CH₂(A-2) |
| Q1-391. | CF₃ | H | SO₂CH₃ |
| Q1-392. | CF₃ | H | CF₃ |
| Q1-393. | CF₃ | H | CH₂CF₃ |
| Q1-394. | CF₃ | H | CH₂CH₂CF₃ |
| Q1-395. | CF₃ | H | CH₂CF(CF₃)₂ |
| Q1-396. | CF₃ | H | CH₂(CF₂)₃CF₃ |
| Q1-397. | F | H | H |
| Q1-398. | F | H | F |
| Q1-399. | F | H | CH₃ |
| Q1-400. | F | H | OCH₃ |
| Q1-401. | F | H | OCH₂CH₃ |
| Q1-402. | F | H | NHCH₃ |
| Q1-403. | F | H | NHCH₂CH₃ |
| Q1-404. | F | H | NHCH₂CH₂CH₃ |
| Q1-405. | F | H | NHCH₂CF₃ |
| Q1-406. | F | H | CH₂CH₃ |
| Q1-407. | F | H | CH₂CH₂CH₃ |
| Q1-408. | F | H | CH(CH₃)₂ |
| Q1-409. | F | H | Ph |
| Q1-410. | F | H | CH₂Ph |
| Q1-411. | F | H | 2-Cl—C₆H₄ |
| Q1-412. | F | H | 3-Cl—C₆H₄ |
| Q1-413. | F | H | 4-Cl—C₆H₄ |
| Q1-414. | F | H | 2-CH₃—C₆H₄ |
| Q1-415. | F | H | 3-CH₃—C₆H₄ |
| Q1-416. | F | H | 4-CF₃—C₆H₄ |
| Q1-417. | F | H | 2-CF₃—C₆H₄ |
| Q1-418. | F | H | 3-CF₃—C₆H₄ |
| Q1-419. | F | H | 4-CH₃—C₆H₄ |
| Q1-420. | F | H | 2-OCH₃—C₆H₄ |
| Q1-421. | F | H | 3-OCH₃—C₆H₄ |
| Q1-422. | F | H | 4-OCH₃—C₆H₄ |
| Q1-423. | F | H | 2-OCF₃—C₆H₄ |
| Q1-424. | F | H | 3-OCF₃—C₆H₄ |
| Q1-425. | F | H | 4-OCF₃—C₆H₄ |
| Q1-426. | F | H | —O—CH₂CH₂—O—CH₃ |
| Q1-427. | F | H | A-2 |
| Q1-428. | F | H | A-3 |
| Q1-429. | F | H | A-4 |
| Q1-430. | F | H | A-5 |
| Q1-431. | F | H | A-6 |
| Q1-432. | F | H | A-7 |
| Q1-433. | F | H | A-8 |
| Q1-434. | F | H | A-9 |
| Q1-435. | F | H | A-10 |
| Q1-436. | F | H | A-11 |
| Q1-437. | F | H | A-12 |
| Q1-438. | F | H | A-13 |
| Q1-439. | F | H | A-14 |
| Q1-440. | F | H | A-15 |
| Q1-441. | F | H | A-16 |
| Q1-442. | F | H | A-17 |

TABLE Q1-continued

| Compound No | R¹ | R² | G |
|---|---|---|---|
| Q1-443. | F | H | A-18 |
| Q1-444. | F | H | A-19 |
| Q1-445. | F | H | A-21 |
| Q1-446. | F | H | A-22 |
| Q1-447. | F | H | A-23 |
| Q1-448. | F | H | A-24 |
| Q1-449. | F | H | A-25 |
| Q1-450. | F | H | A-26 |
| Q1-451. | F | H | A-27 |
| Q1-452. | F | H | A-28 |
| Q1-453. | F | H | —CH$_2$-4-OCH$_3$—C$_6$H$_4$ |
| Q1-454. | F | H | C(=O)OCH$_3$ |
| Q1-455. | F | H | C(=O)OC$_2$H$_5$ |
| Q1-456. | F | H | C(=O)NHCH$_3$ |
| Q1-457. | F | H | C(=O)NHC$_2$H$_5$ |
| Q1-458. | F | H | C(=O)NH—CH$_2$(CH$_3$)$_2$ |
| Q1-459. | F | H | C(=O)NH—CH$_2$CF$_3$ |
| Q1-460. | F | H | C(=O)NH—CH$_2$Cyclopropyl |
| Q1-461. | F | H | C(=O)NH—CH(CH$_3$)Cyclopropyl |
| Q1-462. | F | H | C(=O)NH—CH$_2$C(=O)NH—CH$_2$Cyclopropyl |
| Q1-463. | F | H | C(=O)NH—CH$_2$C(=O)NH—CH$_2$CF$_3$ |
| Q1-464. | F | H | C(=O)NH—CH$_2$(A-1) |
| Q1-465. | F | H | C(=O)NH—CH$_2$(A-2) |
| Q1-466. | F | H | CH$_2$C(=O)OCH$_3$ |
| Q1-467. | F | H | CH$_2$C(=O)OC$_2$H$_5$ |
| Q1-468. | F | H | CH$_2$C(=O)NHCH$_3$ |
| Q1-469. | F | H | CH$_2$C(=O)NHC$_2$H$_5$ |
| Q1-470. | F | H | CH$_2$C(=O)NH—CH$_2$(CH$_3$)$_2$ |
| Q1-471. | F | H | CH$_2$C(=O)NH—CH$_2$CF$_3$ |
| Q1-472. | F | H | CH$_2$C(=O)NH—CH$_2$Cyclopropyl |
| Q1-473. | F | H | CH$_2$C(=O)NH—CH(CH$_3$)Cyclopropyl |
| Q1-474. | F | H | CH$_2$C(=O)NH—CH$_2$C(=O)NH—CH$_2$Cyclopropyl |
| Q1-475. | F | H | CH$_2$C(=O)NH—CH$_2$C(=O)NH—CH$_2$CF$_3$ |
| Q1-476. | F | H | CH$_2$C(=O)NH—CH$_2$(A-1) |
| Q1-477. | F | H | CH$_2$C(=O)NH—CH$_2$(A-2) |
| Q1-478. | F | H | (CH$_2$)$_2$C(=O)OCH$_3$ |
| Q1-479. | F | H | (CH$_2$)$_2$C(=O)OC$_2$H$_5$ |
| Q1-480. | F | H | (CH$_2$)$_2$C(=O)NHCH$_3$ |
| Q1-481. | F | H | (CH$_2$)$_2$C(=O)NHC$_2$H$_5$ |
| Q1-482. | F | H | (CH$_2$)$_2$C(=O)NH—CH$_2$(CH$_3$)$_2$ |
| Q1-483. | F | H | (CH$_2$)$_2$C(=O)NH—CH$_2$CF$_3$ |
| Q1-484. | F | H | (CH$_2$)$_2$C(=O)NH—CH$_2$Cyclopropyl |
| Q1-485. | F | H | (CH$_2$)$_2$C(=O)NH—CH(CH$_3$)Cyclopropyl |
| Q1-486. | F | H | (CH$_2$)$_2$C(=O)NH—CH$_2$C(=O)NH—CH$_2$Cyclopropyl |
| Q1-487. | F | H | (CH$_2$)$_2$C(=O)NH—CH$_2$C(=O)NH—CH$_2$CF$_3$ |
| Q1-488. | F | H | (CH$_2$)$_2$C(=O)NH—CH$_2$(A-1) |
| Q1-489. | F | H | (CH$_2$)$_2$C(=O)NH—CH$_2$(A-2) |
| Q1-490. | F | H | SO$_2$CH$_3$ |
| Q1-491. | F | H | CF$_3$ |
| Q1-492. | F | H | CH$_2$CF$_3$ |
| Q1-493. | F | H | CH$_2$CH$_2$CF$_3$ |
| Q1-494. | F | H | CH$_2$CF(CF$_3$)$_2$ |
| Q1-495. | F | H | CH$_2$(CF$_2$)$_3$CF$_3$ |
| Q1-496. | F | F | H |
| Q1-497. | F | F | F |
| Q1-498. | F | F | CH$_3$ |
| Q1-499. | F | F | OCH$_3$ |
| Q1-500. | F | F | OCH$_2$CH$_3$ |
| Q1-501. | F | F | NHCH$_3$ |
| Q1-502. | F | F | NHCH$_2$CH$_3$ |
| Q1-503. | F | F | NHCH$_2$CH$_2$CH$_3$ |
| Q1-504. | F | F | NHCH$_2$CF$_3$ |
| Q1-505. | F | F | CH$_2$CH$_3$ |
| Q1-506. | F | F | CH$_2$CH$_2$CH$_3$ |
| Q1-507. | F | F | CH(CH$_3$)$_2$ |
| Q1-508. | F | F | Ph |
| Q1-509. | F | F | CH$_2$Ph |
| Q1-510. | F | F | 2-Cl—C$_6$H$_4$ |
| Q1-511. | F | F | 3-Cl—C$_6$H$_4$ |
| Q1-512. | F | F | 4-Cl—C$_6$H$_4$ |
| Q1-513. | F | F | 2-CH$_3$—C$_6$H$_4$ |
| Q1-514. | F | F | 3-CH$_3$—C$_6$H$_4$ |
| Q1-515. | F | F | 4-CF$_3$—C$_6$H$_4$ |
| Q1-516. | F | F | 2-CF$_3$—C$_6$H$_4$ |
| Q1-517. | F | F | 3-CF$_3$—C$_6$H$_4$ |
| Q1-518. | F | F | 4-CH$_3$—C$_6$H$_4$ |
| Q1-519. | F | F | 2-OCH$_3$—C$_6$H$_4$ |
| Q1-520. | F | F | 3-OCH$_3$—C$_6$H$_4$ |

TABLE Q1-continued

| Compound No | R¹ | R² | G |
|---|---|---|---|
| Q1-521. | F | F | 4-OCH₃—C₆H₄ |
| Q1-522. | F | F | 2-OCF₃—C₆H₄ |
| Q1-523. | F | F | 3-OCF₃—C₆H₄ |
| Q1-524. | F | F | 4-OCF₃—C₆H₄ |
| Q1-525. | F | F | —O—CH₂CH₂—O—CH₃ |
| Q1-526. | F | F | A-2 |
| Q1-527. | F | F | A-3 |
| Q1-528. | F | F | A-4 |
| Q1-529. | F | F | A-5 |
| Q1-530. | F | F | A-6 |
| Q1-531. | F | F | A-7 |
| Q1-532. | F | F | A-8 |
| Q1-533. | F | F | A-9 |
| Q1-534. | F | F | A-10 |
| Q1-535. | F | F | A-11 |
| Q1-536. | F | F | A-12 |
| Q1-537. | F | F | A-13 |
| Q1-538. | F | F | A-14 |
| Q1-539. | F | F | A-15 |
| Q1-540. | F | F | A-16 |
| Q1-541. | F | F | A-17 |
| Q1-542. | F | F | A-18 |
| Q1-543. | F | F | A-19 |
| Q1-544. | F | F | A-21 |
| Q1-545. | F | F | A-22 |
| Q1-546. | F | F | A-23 |
| Q1-547. | F | F | A-24 |
| Q1-548. | F | F | A-25 |
| Q1-549. | F | F | A-26 |
| Q1-550. | F | F | A-27 |
| Q1-551. | F | F | A-28 |
| Q1-552. | F | F | —CH₂-4-OCH₃—C₆H₄ |
| Q1-553. | F | F | C(=O)OCH₃ |
| Q1-554. | F | F | C(=O)OC₂H₅ |
| Q1-555. | F | F | C(=O)NHCH₃ |
| Q1-556. | F | F | C(=O)NHC₂H₅ |
| Q1-557. | F | F | C(=O)NH—CH₂(CH₃)₂ |
| Q1-558. | F | F | C(=O)NH—CH₂CF₃ |
| Q1-559. | F | F | C(=O)NH—CH₂Cyclopropyl |
| Q1-560. | F | F | C(=O)NH—CH(CH₃)Cyclopropyl |
| Q1-561. | F | F | C(=O)NH—CH₂C(=O)NH—CH₂Cyclopropyl |
| Q1-562. | F | F | C(=O)NH—CH₂C(=O)NH—CH₂CF₃ |
| Q1-563. | F | F | C(=O)NH—CH₂(A-1) |
| Q1-564. | F | F | C(=O)NH—CH₂(A-2) |
| Q1-565. | F | F | CH₂C(=O)OCH₃ |
| Q1-566. | F | F | CH₂C(=O)OC₂H₅ |
| Q1-567. | F | F | CH₂C(=O)NHCH₃ |
| Q1-568. | F | F | CH₂C(=O)NHC₂H₅ |
| Q1-569. | F | F | CH₂C(=O)NH—CH₂(CH₃)₂ |
| Q1-570. | F | F | CH₂C(=O)NH—CH₂CF₃ |
| Q1-571. | F | F | CH₂C(=O)NH—CH₂Cyclopropyl |
| Q1-572. | F | F | CH₂C(=O)NH—CH(CH₃)Cyclopropyl |
| Q1-573. | F | F | CH₂C(=O)NH—CH₂C(=O)NH—CH₂Cyclopropyl |
| Q1-574. | F | F | CH₂C(=O)NH—CH₂C(=O)NH—CH₂CF₃ |
| Q1-575. | F | F | CH₂C(=O)NH—CH₂(A-1) |
| Q1-576. | F | F | CH₂C(=O)NH—CH₂(A-2) |
| Q1-577. | F | F | (CH₂)₂C(=O)OCH₃ |
| Q1-578. | F | F | (CH₂)₂C(=O)OC₂H₅ |
| Q1-579. | F | F | (CH₂)₂C(=O)NHCH₃ |
| Q1-580. | F | F | (CH₂)₂C(=O)NHC₂H₅ |
| Q1-581. | F | F | (CH₂)₂C(=O)NH—CH₂(CH₃)₂ |
| Q1-582. | F | F | (CH₂)₂C(=O)NH—CH₂CF₃ |
| Q1-583. | F | F | (CH₂)₂C(=O)NH—CH₂Cyclopropyl |
| Q1-584. | F | F | (CH₂)₂C(=O)NH—CH(CH₃)Cyclopropyl |
| Q1-585. | F | F | (CH₂)₂C(=O)NH—CH₂C(=O)NH—CH₂Cyclopropyl |
| Q1-586. | F | F | (CH₂)₂C(=O)NH—CH₂C(=O)NH—CH₂CF₃ |
| Q1-587. | F | F | (CH₂)₂C(=O)NH—CH₂(A-1) |
| Q1-588. | F | F | (CH₂)₂C(=O)NH—CH₂(A-2) |
| Q1-589. | F | F | SO₂CH₃ |
| Q1-590. | F | F | CF₃ |
| Q1-591. | F | F | CH₂CF₃ |
| Q1-592. | F | F | CH₂CH₂CF₃ |
| Q1-593. | F | F | CH₂CF(CF₃)₂ |
| Q1-594. | F | F | CH₂(CF₂)₃CF₃ |
| Q1-595. | F | CH₃ | H |
| Q1-596. | F | CH₃ | F |
| Q1-597. | F | CH₃ | CH₃ |
| Q1-598. | F | CH₃ | OCH₃ |

TABLE Q1-continued

| Compound No | R¹ | R² | G |
|---|---|---|---|
| Q1-599. | F | CH₃ | OCH₂CH₃ |
| Q1-600. | F | CH₃ | NHCH₃ |
| Q1-601. | F | CH₃ | NHCH₂CH₃ |
| Q1-602. | F | CH₃ | NHCH₂CH₂CH₃ |
| Q1-603. | F | CH₃ | NHCH₂CF₃ |
| Q1-604. | F | CH₃ | CH₂CH₃ |
| Q1-605. | F | CH₃ | CH₂CH₂CH₃ |
| Q1-606. | F | CH₃ | CH(CH₃)₂ |
| Q1-607. | F | CH₃ | Ph |
| Q1-608. | F | CH₃ | CH₂Ph |
| Q1-609. | F | CH₃ | 2-Cl—C₆H₄ |
| Q1-610. | F | CH₃ | 3-Cl—C₆H₄ |
| Q1-611. | F | CH₃ | 4-Cl—C₆H₄ |
| Q1-612. | F | CH₃ | 2-CH₃—C₆H₄ |
| Q1-613. | F | CH₃ | 3-CH₃—C₆H₄ |
| Q1-614. | F | CH₃ | 4-CF₃—C₆H₄ |
| Q1-615. | F | CH₃ | 2-CF₃—C₆H₄ |
| Q1-616. | F | CH₃ | 3-CF₃—C₆H₄ |
| Q1-617. | F | CH₃ | 4-CH₃—C₆H₄ |
| Q1-618. | F | CH₃ | 2-OCH₃—C₆H₄ |
| Q1-619. | F | CH₃ | 3-OCH₃—C₆H₄ |
| Q1-620. | F | CH₃ | 4-OCH₃—C₆H₄ |
| Q1-621. | F | CH₃ | 2-OCF₃—C₆H₄ |
| Q1-622. | F | CH₃ | 3-OCF₃—C₆H₄ |
| Q1-623. | F | CH₃ | 4-OCF₃—C₆H₄ |
| Q1-624. | F | CH₃ | —O—CH₂CH₂—O—CH₃ |
| Q1-625. | F | CH₃ | A-2 |
| Q1-626. | F | CH₃ | A-3 |
| Q1-627. | F | CH₃ | A-4 |
| Q1-628. | F | CH₃ | A-5 |
| Q1-629. | F | CH₃ | A-6 |
| Q1-630. | F | CH₃ | A-7 |
| Q1-631. | F | CH₃ | A-8 |
| Q1-632. | F | CH₃ | A-9 |
| Q1-633. | F | CH₃ | A-10 |
| Q1-634. | F | CH₃ | A-11 |
| Q1-635. | F | CH₃ | A-12 |
| Q1-636. | F | CH₃ | A-13 |
| Q1-637. | F | CH₃ | A-14 |
| Q1-638. | F | CH₃ | A-15 |
| Q1-639. | F | CH₃ | A-16 |
| Q1-640. | F | CH₃ | A-17 |
| Q1-641. | F | CH₃ | A-18 |
| Q1-642. | F | CH₃ | A-19 |
| Q1-643. | F | CH₃ | A-21 |
| Q1-644. | F | CH₃ | A-22 |
| Q1-645. | F | CH₃ | A-23 |
| Q1-646. | F | CH₃ | A-24 |
| Q1-647. | F | CH₃ | A-25 |
| Q1-648. | F | CH₃ | A-26 |
| Q1-649. | F | CH₃ | A-27 |
| Q1-650. | F | CH₃ | A-28 |
| Q1-651. | F | CH₃ | —CH₂-4-OCH₃—C₆H₄ |
| Q1-652. | F | CH₃ | C(=O)OCH₃ |
| Q1-653. | F | CH₃ | C(=O)OC₂H₅ |
| Q1-654. | F | CH₃ | C(=O)NHCH₃ |
| Q1-655. | F | CH₃ | C(=O)NHC₂H₅ |
| Q1-656. | F | CH₃ | C(=O)NH—CH₂(CH₃)₂ |
| Q1-657. | F | CH₃ | C(=O)NH—CH₂CF₃ |
| Q1-658. | F | CH₃ | C(=O)NH—CH₂Cyclopropyl |
| Q1-659. | F | CH₃ | C(=O)NH—CH(CH₃)Cyclopropyl |
| Q1-660. | F | CH₃ | C(=O)NH—CH₂C(=O)NH—CH₂Cyclopropyl |
| Q1-661. | F | CH₃ | C(=O)NH—CH₂C(=O)NH—CH₂CF₃ |
| Q1-662. | F | CH₃ | C(=O)NH—CH₂(A-1) |
| Q1-663. | F | CH₃ | C(=O)NH—CH₂(A-2) |
| Q1-664. | F | CH₃ | CH₂C(=O)OCH₃ |
| Q1-665. | F | CH₃ | CH₂C(=O)OC₂H₅ |
| Q1-666. | F | CH₃ | CH₂C(=O)NHCH₃ |
| Q1-667. | F | CH₃ | CH₂C(=O)NHC₂H₅ |
| Q1-668. | F | CH₃ | CH₂C(=O)NH—CH₂(CH₃)₂ |
| Q1-669. | F | CH₃ | CH₂C(=O)NH—CH₂CF₃ |
| Q1-670. | F | CH₃ | CH₂C(=O)NH—CH₂Cyclopropyl |
| Q1-671. | F | CH₃ | CH₂C(=O)NH—CH(CH₃)Cyclopropyl |
| Q1-672. | F | CH₃ | CH₂C(=O)NH—CH₂C(=O)NH—CH₂Cyclopropyl |
| Q1-673. | F | CH₃ | CH₂C(=O)NH—CH₂C(=O)NH—CH₂CF₃ |
| Q1-674. | F | CH₃ | CH₂C(=O)NH—CH₂(A-1) |
| Q1-675. | F | CH₃ | CH₂C(=O)NH—CH₂(A-2) |
| Q1-676. | F | CH₃ | (CH₂)₂C(=O)OCH₃ |

TABLE Q1-continued

| Compound No | R¹ | R² | G |
|---|---|---|---|
| Q1-677. | F | CH₃ | (CH₂)₂C(=O)OC₂H₅ |
| Q1-678. | F | CH₃ | (CH₂)₂C(=O)NHCH₃ |
| Q1-679. | F | CH₃ | (CH₂)₂C(=O)NHC₂H₅ |
| Q1-680. | F | CH₃ | (CH₂)₂C(=O)NH—CH₂(CH₃)₂ |
| Q1-681. | F | CH₃ | (CH₂)₂C(=O)NH—CH₂CF₃ |
| Q1-682. | F | CH₃ | (CH₂)₂C(=O)NH—CH₂Cyclopropyl |
| Q1-683. | F | CH₃ | (CH₂)₂C(=O)NH—CH(CH₃)Cyclopropyl |
| Q1-684. | F | CH₃ | (CH₂)₂C(=O)NH—CH₂C(=O)NH—CH₂Cyclopropyl |
| Q1-685. | F | CH₃ | (CH₂)₂C(=O)NH—CH₂C(=O)NH—CH₂CF₃ |
| Q1-686. | F | CH₃ | (CH₂)₂C(=O)NH—CH₂(A-1) |
| Q1-687. | F | CH₃ | (CH₂)₂C(=O)NH—CH₂(A-2) |
| Q1-688. | F | CH₃ | SO₂CH₃ |
| Q1-689. | F | CH₃ | CF₃ |
| Q1-690. | F | CH₃ | CH₂CF₃ |
| Q1-691. | F | CH₃ | CH₂CH₂CF₃ |
| Q1-692. | F | CH₃ | CH₂CF(CF₃)₂ |
| Q1-693. | F | CH₃ | CH₂(CF₂)₃CF₃ |
| Q1-694. | CF₃ | CH₃ | H |
| Q1-695. | CF₃ | CH₃ | F |
| Q1-696. | CF₃ | CH₃ | CH₃ |
| Q1-697. | CF₃ | CH₃ | OCH₃ |
| Q1-698. | CF₃ | CH₃ | OCH₂CH₃ |
| Q1-699. | CF₃ | CH₃ | NHCH₃ |
| Q1-700. | CF₃ | CH₃ | NHCH₂CH₃ |
| Q1-701. | CF₃ | CH₃ | NHCH₂CH₂CH₃ |
| Q1-702. | CF₃ | CH₃ | NHCH₂CF₃ |
| Q1-703. | CF₃ | CH₃ | CH₂CH₃ |
| Q1-704. | CF₃ | CH₃ | CH₂CH₂CH₃ |
| Q1-705. | CF₃ | CH₃ | CH(CH₃)₂ |
| Q1-706. | CF₃ | CH₃ | Ph |
| Q1-707. | CF₃ | CH₃ | CH₂Ph |
| Q1-708. | CF₃ | CH₃ | 2-Cl—C₆H₄ |
| Q1-709. | CF₃ | CH₃ | 3-Cl—C₆H₄ |
| Q1-710. | CF₃ | CH₃ | 4-Cl—C₆H₄ |
| Q1-711. | CF₃ | CH₃ | 2-CH₃—C₆H₄ |
| Q1-712. | CF₃ | CH₃ | 3-CH₃—C₆H₄ |
| Q1-713. | CF₃ | CH₃ | 4-CF₃—C₆H₄ |
| Q1-714. | CF₃ | CH₃ | 2-CF₃—C₆H₄ |
| Q1-715. | CF₃ | CH₃ | 3-CF₃—C₆H₄ |
| Q1-716. | CF₃ | CH₃ | 4-CH₃—C₆H₄ |
| Q1-717. | CF₃ | CH₃ | 2-OCH₃—C₆H₄ |
| Q1-718. | CF₃ | CH₃ | 3-OCH₃—C₆H₄ |
| Q1-719. | CF₃ | CH₃ | 4-OCH₃—C₆H₄ |
| Q1-720. | CF₃ | CH₃ | 2-OCF₃—C₆H₄ |
| Q1-721. | CF₃ | CH₃ | 3-OCF₃—C₆H₄ |
| Q1-722. | CF₃ | CH₃ | 4-OCF₃—C₆H₄ |
| Q1-723. | CF₃ | CH₃ | —O—CH₂CH₂—O—CH₃ |
| Q1-724. | CF₃ | CH₃ | A-2 |
| Q1-725. | CF₃ | CH₃ | A-3 |
| Q1-726. | CF₃ | CH₃ | A-4 |
| Q1-727. | CF₃ | CH₃ | A-5 |
| Q1-728. | CF₃ | CH₃ | A-6 |
| Q1-729. | CF₃ | CH₃ | A-7 |
| Q1-730. | CF₃ | CH₃ | A-8 |
| Q1-731. | CF₃ | CH₃ | A-9 |
| Q1-732. | CF₃ | CH₃ | A-10 |
| Q1-733. | CF₃ | CH₃ | A-11 |
| Q1-734. | CF₃ | CH₃ | A-12 |
| Q1-735. | CF₃ | CH₃ | A-13 |
| Q1-736. | CF₃ | CH₃ | A-14 |
| Q1-737. | CF₃ | CH₃ | A-15 |
| Q1-738. | CF₃ | CH₃ | A-16 |
| Q1-739. | CF₃ | CH₃ | A-17 |
| Q1-740. | CF₃ | CH₃ | A-18 |
| Q1-741. | CF₃ | CH₃ | A-19 |
| Q1-742. | CF₃ | CH₃ | A-21 |
| Q1-743. | CF₃ | CH₃ | A-22 |
| Q1-744. | CF₃ | CH₃ | A-23 |
| Q1-745. | CF₃ | CH₃ | A-24 |
| Q1-746. | CF₃ | CH₃ | A-25 |
| Q1-747. | CF₃ | CH₃ | A-26 |
| Q1-748. | CF₃ | CH₃ | A-27 |
| Q1-749. | CF₃ | CH₃ | A-28 |
| Q1-750. | CF₃ | CH₃ | —CH₂-4-OCH₃—C₆H₄ |
| Q1-751. | CF₃ | CH₃ | C(=O)OCH₃ |
| Q1-752. | CF₃ | CH₃ | C(=O)OC₂H₅ |
| Q1-753. | CF₃ | CH₃ | C(=O)NHCH₃ |
| Q1-754. | CF₃ | CH₃ | C(=O)NHC₂H₅ |

TABLE Q1-continued

| Compound No | R$^1$ | R$^2$ | G |
|---|---|---|---|
| Q1-755. | CF$_3$ | CH$_3$ | C(=O)NH—CH$_2$(CH$_3$)$_2$ |
| Q1-756. | CF$_3$ | CH$_3$ | C(=O)NH—CH$_2$CF$_3$ |
| Q1-757. | CF$_3$ | CH$_3$ | C(=O)NH—CH$_2$Cyclopropyl |
| Q1-758. | CF$_3$ | CH$_3$ | C(=O)NH—CH(CH$_3$)Cyclopropyl |
| Q1-759. | CF$_3$ | CH$_3$ | C(=O)NH—CH$_2$C(=O)NH—CH$_2$Cyclopropyl |
| Q1-760. | CF$_3$ | CH$_3$ | C(=O)NH—CH$_2$C(=O)NH—CH$_2$CF$_3$ |
| Q1-761. | CF$_3$ | CH$_3$ | C(=O)NH—CH$_2$(A-1) |
| Q1-762. | CF$_3$ | CH$_3$ | C(=O)NH—CH$_2$(A-2) |
| Q1-763. | CF$_3$ | CH$_3$ | CH$_2$C(=O)OCH$_3$ |
| Q1-764. | CF$_3$ | CH$_3$ | CH$_2$C(=O)OC$_2$H$_5$ |
| Q1-765. | CF$_3$ | CH$_3$ | CH$_2$C(=O)NHCH$_3$ |
| Q1-766. | CF$_3$ | CH$_3$ | CH$_2$C(=O)NHC$_2$H$_5$ |
| Q1-767. | CF$_3$ | CH$_3$ | CH$_2$C(=O)NH—CH$_2$(CH$_3$)$_2$ |
| Q1-768. | CF$_3$ | CH$_3$ | CH$_2$C(=O)NH—CH$_2$CF$_3$ |
| Q1-769. | CF$_3$ | CH$_3$ | CH$_2$C(=O)NH—CH$_2$Cyclopropyl |
| Q1-770. | CF$_3$ | CH$_3$ | CH$_2$C(=O)NH—CH(CH$_3$)Cyclopropyl |
| Q1-771. | CF$_3$ | CH$_3$ | CH$_2$C(=O)NH—CH$_2$C(=O)NH—CH$_2$Cyclopropyl |
| Q1-772. | CF$_3$ | CH$_3$ | CH$_2$C(=O)NH—CH$_2$C(=O)NH—CH$_2$CF$_3$ |
| Q1-773. | CF$_3$ | CH$_3$ | CH$_2$C(=O)NH—CH$_2$(A-1) |
| Q1-774. | CF$_3$ | CH$_3$ | CH$_2$C(=O)NH—CH$_2$(A-2) |
| Q1-775. | CF$_3$ | CH$_3$ | (CH$_2$)$_2$C(=O)OCH$_3$ |
| Q1-776. | CF$_3$ | CH$_3$ | (CH$_2$)$_2$C(=O)OC$_2$H$_5$ |
| Q1-777. | CF$_3$ | CH$_3$ | (CH$_2$)$_2$C(=O)NHCH$_3$ |
| Q1-778. | CF$_3$ | CH$_3$ | (CH$_2$)$_2$C(=O)NHC$_2$H$_5$ |
| Q1-779. | CF$_3$ | CH$_3$ | (CH$_2$)$_2$C(=O)NH—CH$_2$(CH$_3$)$_2$ |
| Q1-780. | CF$_3$ | CH$_3$ | (CH$_2$)$_2$C(=O)NH—CH$_2$CF$_3$ |
| Q1-781. | CF$_3$ | CH$_3$ | (CH$_2$)$_2$C(=O)NH—CH$_2$Cyclopropyl |
| Q1-782. | CF$_3$ | CH$_3$ | (CH$_2$)$_2$C(=O)NH—CH(CH$_3$)Cyclopropyl |
| Q1-783. | CF$_3$ | CH$_3$ | (CH$_2$)$_2$C(=O)NH—CH$_2$C(=O)NH—CH$_2$Cyclopropyl |
| Q1-784. | CF$_3$ | CH$_3$ | (CH$_2$)$_2$C(=O)NH—CH$_2$C(=O)NH—CH$_2$CF$_3$ |
| Q1-785. | CF$_3$ | CH$_3$ | (CH$_2$)$_2$C(=O)NH—CH$_2$(A-1) |
| Q1-786. | CF$_3$ | CH$_3$ | (CH$_2$)$_2$C(=O)NH—CH$_2$(A-2) |
| Q1-787. | CF$_3$ | CH$_3$ | SO$_2$CH$_3$ |
| Q1-788. | CF$_3$ | CH$_3$ | CF$_3$ |
| Q1-789. | CF$_3$ | CH$_3$ | CH$_2$CF$_3$ |
| Q1-790. | CF$_3$ | CH$_3$ | CH$_2$CH$_2$CF$_3$ |
| Q1-791. | CF$_3$ | CH$_3$ | CH$_2$CF(CF$_3$)$_2$ |
| Q1-792. | CF$_3$ | CH$_3$ | CH$_2$(CF$_2$)$_3$CF$_3$ |

Table 309 to table 618 of preferred compounds
Compounds as defined in analogy to table 1 to table 308, but wherein the combination of R$^1$ and R$^2$ and G for a compound corresponds in each case to one row of Table Q2.

TABLE Q2

| Compound No | R$^1$ and R$^2$ | G |
|---|---|---|
| Q2-1. | =NOH | C(=O)OCH$_3$ |
| Q2-2. | =NOH | C(=O)OC$_2$H$_5$ |
| Q2-3. | =NOH | C(=O)NHCH$_3$ |
| Q2-4. | =NOH | C(=O)NHC$_2$H$_5$ |
| Q2-5. | =NOH | C(=O)NH—CH$_2$(CH$_3$)$_2$ |
| Q2-6. | =NOH | C(=O)NH—CH$_2$CF$_3$ |
| Q2-7. | =NOH | C(=O)NH—CH$_2$Cyclopropyl |
| Q2-8. | =NOH | C(=O)NH—CH(CH$_3$)Cyclopropyl |
| Q2-9. | =NOH | C(=O)NH—CH$_2$C(=O)NH—CH$_2$Cyclopropyl |
| Q2-10. | =NOH | C(=O)NH—CH$_2$C(=O)NH—CH$_2$CF$_3$ |
| Q2-11. | =NOH | C(=O)NH—CH$_2$(A-1) |
| Q2-12. | =NOH | C(=O)NH—CH$_2$(A-2) |
| Q2-13. | =NOH | SO$_2$CH$_3$ |
| Q2-14. | =NOH | CF$_3$ |
| Q2-15. | =NOH | CH$_2$CF$_3$ |
| Q2-16. | =NOCH$_3$ | C(=O)OCH$_3$ |
| Q2-17. | =NOCH$_3$ | C(=O)OC$_2$H$_5$ |
| Q2-18. | =NOCH$_3$ | C(=O)NHCH$_3$ |
| Q2-19. | =NOCH$_3$ | C(=O)NHC$_2$H$_5$ |
| Q2-20. | =NOCH$_3$ | C(=O)NH—CH$_2$(CH$_3$)$_2$ |
| Q2-21. | =NOCH$_3$ | C(=O)NH—CH$_2$CF$_3$ |
| Q2-22. | =NOCH$_3$ | C(=O)NH—CH$_2$Cyclopropyl |
| Q2-23. | =NOCH$_3$ | C(=O)NH—CH(CH$_3$)Cyclopropyl |
| Q2-24. | =NOCH$_3$ | C(=O)NH—CH$_2$C(=O)NH—CH$_2$Cyclopropyl |
| Q2-25. | =NOCH$_3$ | C(=O)NH—CH$_2$C(=O)NH—CH$_2$CF$_3$ |
| Q2-26. | =NOCH$_3$ | C(=O)NH—CH$_2$(A-1) |
| Q2-27. | =NOCH$_3$ | C(=O)NH—CH$_2$(A-2) |

TABLE Q2-continued

| Compound No | R¹ and R² | G |
|---|---|---|
| Q2-28. | =NOCH$_3$ | SO$_2$CH$_3$ |
| Q2-29. | =NOCH$_3$ | CF$_3$ |
| Q2-30. | =NOCH$_3$ | CH$_2$CF$_3$ |
| Q2-31. | =NOC$_2$H$_5$ | C(=O)OCH$_3$ |
| Q2-32. | =NOC$_2$H$_5$ | C(=O)OC$_2$H$_5$ |
| Q2-33. | =NOC$_2$H$_5$ | C(=O)NHCH$_3$ |
| Q2-34. | =NOC$_2$H$_5$ | C(=O)NHC$_2$H$_5$ |
| Q2-35. | =NOC$_2$H$_5$ | C(=O)NH—CH$_2$(CH$_3$)$_2$ |
| Q2-36. | =NOC$_2$H$_5$ | C(=O)NH—CH$_2$CF$_3$ |
| Q2-37. | =NOC$_2$H$_5$ | C(=O)NH—CH$_2$Cyclopropyl |
| Q2-38. | =NOC$_2$H$_5$ | C(=O)NH—CH(CH$_3$)Cyclopropyl |
| Q2-39. | =NOC$_2$H$_5$ | C(=O)NH—CH$_2$C(=O)NH—CH$_2$Cyclopropyl |
| Q2-40. | =NOC$_2$H$_5$ | C(=O)NH—CH$_2$C(=O)NH—CH$_2$CF$_3$ |
| Q2-41. | =NOC$_2$H$_5$ | C(=O)NH—CH$_2$(A-1) |
| Q2-42. | =NOC$_2$H$_5$ | C(=O)NH—CH$_2$(A-2) |
| Q2-43. | =NOC$_2$H$_5$ | SO$_2$CH$_3$ |
| Q2-44. | =NOC$_2$H$_5$ | CF$_3$ |
| Q2-45. | =NOC$_2$H$_5$ | CH$_2$CF$_3$ |
| Q2-46. | —CH$_2$CH$_2$— | H |
| Q2-47. | —CH2CH2— | CH$_3$ |
| Q2-48. | —CH$_2$CH$_2$— | CH$_2$CH$_3$ |
| Q2-49. | —CH$_2$CH$_2$— | CH$_2$CH$_2$CH$_3$ |
| Q2-50. | —CH$_2$CH$_2$— | CH(CH$_3$)$_2$ |
| Q2-51. | —CH$_2$CH$_2$CH$_2$— | H |
| Q2-52. | —CH$_2$CH$_2$CH$_2$— | CH$_3$ |
| Q2-53. | —CH$_2$CH$_2$CH$_2$— | CH$_2$CH$_3$ |
| Q2-54. | —CH2CH$_2$CH$_2$— | CH$_2$CH$_2$CH$_3$ |
| Q2-55. | —CH$_2$CH$_2$CH$_2$— | CH(CH$_3$)$_2$ |
| Q2-56. | —CH$_2$CH$_2$CH$_2$CH$_2$— | H |
| Q2-57. | —CH$_2$CH$_2$CH$_2$CH$_2$— | CH$_3$ |
| Q2-58. | —CH$_2$CH$_2$CH$_2$CH$_2$— | CH$_2$CH$_3$ |
| Q2-59. | —CH$_2$CH$_2$CH$_2$CH$_2$— | CH$_2$CH$_2$CH$_3$ |
| Q2-60. | —CH$_2$CH$_2$CH$_2$CH$_2$— | CH(CH$_3$)$_2$ |
| Q2-61. | =O | H |
| Q2-62. | =O | CH$_3$ |
| Q2-63. | =O | OCH$_3$ |
| Q2-64. | =O | OCH$_2$CH$_3$ |
| Q2-65. | =O | NHCH$_3$ |
| Q2-66. | =O | NHCH$_2$CH$_3$ |
| Q2-67. | =O | NHCH$_2$CH$_2$CH$_3$ |
| Q2-68. | =O | NHCH$_2$CF$_3$ |
| Q2-69. | =O | CH$_2$CH$_3$ |
| Q2-70. | =O | CH$_2$CH$_2$CH$_3$ |
| Q2-71. | =O | CH(CH$_3$)$_2$ |
| Q2-72. | =CH$_2$ | H |
| Q2-73. | =CH$_2$ | F |
| Q2-74. | =CH$_2$ | CH$_3$ |
| Q2-75. | =CH$_2$ | OCH$_3$ |
| Q2-76. | =CH$_2$ | OCH$_2$CH$_3$ |
| Q2-77. | =CH$_2$ | NHCH$_3$ |
| Q2-78. | =CH$_2$ | NHCH$_2$CH$_3$ |
| Q2-79. | =CH$_2$ | NHCH$_2$CH$_2$CH$_3$ |
| Q2-80. | =CH$_2$ | NHCH$_2$CF$_3$ |
| Q2-81. | =CH$_2$ | CH$_2$CH$_3$ |
| Q2-82. | =CH$_2$ | CH$_2$CH$_2$CH$_3$ |
| Q2-83. | =CH$_2$ | CH(CH$_3$)$_2$ |
| Q2-84. | =CH$_2$ | Ph |
| Q2-85. | =CH$_2$ | CH$_2$Ph |
| Q2-86. | =CH$_2$ | 2-Cl—C$_6$H$_4$ |
| Q2-87. | =CH$_2$ | 3-Cl—C$_6$H$_4$ |
| Q2-88. | =CH$_2$ | 4-Cl—C$_6$H$_4$ |
| Q2-89. | =CH$_2$ | 2-CH$_3$—C$_6$H$_4$ |
| Q2-90. | =CH$_2$ | 3-CH$_3$—C$_6$H$_4$ |
| Q2-91. | =CH$_2$ | 4-CF$_3$—C$_6$H$_4$ |
| Q2-92. | =CH$_2$ | 2-CF$_3$—C$_6$H$_4$ |
| Q2-93. | =CH$_2$ | 3-CF$_3$—C$_6$H$_4$ |
| Q2-94. | =CH$_2$ | 4-CH$_3$—C$_6$H$_4$ |
| Q2-95. | =CH$_2$ | 2-OCH$_3$—C$_6$H$_4$ |
| Q2-96. | =CH$_2$ | 3-OCH$_3$—C$_6$H$_4$ |
| Q2-97. | =CH$_2$ | 4-OCH$_3$—C$_6$H$_4$ |
| Q2-98. | =CH$_2$ | 2-OCF$_3$—C$_6$H$_4$ |
| Q2-99. | =CH$_2$ | 3-OCF$_3$—C$_6$H$_4$ |
| Q2-100. | =CH$_2$ | 4-OCF$_3$—C$_6$H$_4$ |
| Q2-101. | =CH$_2$ | —O—CH$_2$CH$_2$—O—CH$_3$ |
| Q2-102. | =CH$_2$ | A-2 |
| Q2-103. | =CH$_2$ | A-3 |
| Q2-104. | =CH$_2$ | A-4 |
| Q2-105. | =CH$_2$ | A-5 |

TABLE Q2-continued

| Compound No | R¹ and R² | G |
|---|---|---|
| Q2-106. | =CH₂ | A-6 |
| Q2-107. | =CH₂ | A-7 |
| Q2-108. | =CH₂ | A-8 |
| Q2-109. | =CH₂ | A-9 |
| Q2-110. | =CH₂ | A-10 |
| Q2-111. | =CH₂ | A-11 |
| Q2-112. | =CH₂ | A-12 |
| Q2-113. | =CH₂ | A-13 |
| Q2-114. | =CH₂ | A-14 |
| Q2-115. | =CH₂ | A-15 |
| Q2-116. | =CH₂ | A-16 |
| Q2-117. | =CH₂ | A-17 |
| Q2-118. | =CH₂ | A-18 |
| Q2-119. | =CH₂ | A-19 |
| Q2-120. | =CH₂ | A-21 |
| Q2-121. | =CH₂ | A-22 |
| Q2-122. | =CH₂ | A-23 |
| Q2-123. | =CH₂ | A-24 |
| Q2-124. | =CH₂ | A-25 |
| Q2-125. | =CH₂ | A-26 |
| Q2-126. | =CH₂ | A-27 |
| Q2-127. | =CH₂ | A-28 |
| Q2-128. | =CH₂ | —CH₂-4-OCH₃—C₆H₄ |
| Q2-129. | =CH₂ | C(=O)OCH₃ |
| Q2-130. | =CH₂ | C(=O)OC₂H₅ |
| Q2-131. | =CH₂ | C(=O)NHCH₃ |
| Q2-132. | =CH₂ | C(=O)NHC₂H₅ |
| Q2-133. | =CH₂ | C(=O)NH—CH₂(CH₃)₂ |
| Q2-134. | =CH₂ | C(=O)NH—CH₂CF₃ |
| Q2-135. | =CH₂ | C(=O)NH—CH₂Cyclopropyl |
| Q2-136. | =CH₂ | C(=O)NH—CH(CH₃)Cyclopropyl |
| Q2-137. | =CH₂ | C(=O)NH—CH₂C(=O)NH—CH₂Cyclopropyl |
| Q2-138. | =CH₂ | C(=O)NH—CH₂C(=O)NH—CH₂CF₃ |
| Q2-139. | =CH₂ | C(=O)NH—CH₂(A-1) |
| Q2-140. | =CH₂ | C(=O)NH—CH₂(A-2) |
| Q2-141. | =CH₂ | SO₂CH₃ |
| Q2-142. | =CH₂ | CF₃ |
| Q2-143. | =CH₂ | CH₂CF₃ |
| Q2-144. | =CH₂ | CH₂CH₂CF₃ |
| Q2-145. | =CH₂ | CH₂CF(CF₃)₂ |
| Q2-146. | =CH₂ | CH₂(CF₂)₃CF₃ |
| Q2-147. | =C(CH₃)₂ | H |
| Q2-148. | =C(CH₃)₂ | F |
| Q2-149. | =C(CH₃)₂ | CH₃ |
| Q2-150. | =C(CH₃)₂ | OCH₃ |
| Q2-151. | =C(CH₃)₂ | OCH₂CH₃ |
| Q2-152. | =C(CH₃)₂ | NHCH₃ |
| Q2-153. | =C(CH₃)₂ | NHCH₂CH₃ |
| Q2-154. | =C(CH₃)₂ | NHCH₂CH₂CH₃ |
| Q2-155. | =C(CH₃)₂ | NHCH₂CF₃ |
| Q2-156. | =C(CH₃)₂ | CH₂CH₃ |
| Q2-157. | =C(CH₃)₂ | CH₂CH₂CH₃ |
| Q2-158. | =C(CH₃)₂ | CH(CH₃)₂ |
| Q2-159. | =C(CH₃)₂ | Ph |
| Q2-160. | =C(CH₃)₂ | CH₂Ph |
| Q2-161. | =C(CH₃)₂ | 2-Cl—C₆H₄ |
| Q2-162. | =C(CH₃)₂ | 3-Cl—C₆H₄ |
| Q2-163. | =C(CH₃)₂ | 4-Cl—C₆H₄ |
| Q2-164. | =C(CH₃)₂ | 2-CH₃—C₆H₄ |
| Q2-165. | =C(CH₃)₂ | 3-CH₃—C₆H₄ |
| Q2-166. | =C(CH₃)₂ | 4-CF₃—C₆H₄ |
| Q2-167. | =C(CH₃)₂ | 2-CF₃—C₆H₄ |
| Q2-168. | =C(CH₃)₂ | 3-CF₃—C₆H₄ |
| Q2-169. | =C(CH₃)₂ | 4-CH₃—C₆H₄ |
| Q2-170. | =C(CH₃)₂ | 2-OCH₃—C₆H₄ |
| Q2-171. | =C(CH₃)₂ | 3-OCH₃—C₆H₄ |
| Q2-172. | =C(CH₃)₂ | 4-OCH₃—C₆H₄ |
| Q2-173. | =C(CH₃)₂ | 2-OCF₃—C₆H₄ |
| Q2-174. | =C(CH₃)₂ | 3-OCF₃—C₆H₄ |
| Q2-175. | =C(CH₃)₂ | 4-OCF₃—C₆H₄ |
| Q2-176. | =C(CH₃)₂ | —O—CH₂CH₂—O—CH₃ |
| Q2-177. | =C(CH₃)₂ | A-2 |
| Q2-178. | =C(CH₃)₂ | A-3 |
| Q2-179. | =C(CH₃)₂ | A-4 |
| Q2-180. | =C(CH₃)₂ | A-5 |
| Q2-181. | =C(CH₃)₂ | A-6 |
| Q2-182. | =C(CH₃)₂ | A-7 |
| Q2-183. | =C(CH₃)₂ | A-8 |

TABLE Q2-continued

| Compound No | R¹ and R² | G |
|---|---|---|
| Q2-184. | =C(CH$_3$)$_2$ | A-9 |
| Q2-185. | =C(CH$_3$)$_2$ | A-10 |
| Q2-186. | =C(CH$_3$)$_2$ | A-11 |
| Q2-187. | =C(CH$_3$)$_2$ | A-12 |
| Q2-188. | =C(CH$_3$)$_2$ | A-13 |
| Q2-189. | =C(CH$_3$)$_2$ | A-14 |
| Q2-190. | =C(CH$_3$)$_2$ | A-15 |
| Q2-191. | =C(CH$_3$)$_2$ | A-16 |
| Q2-192. | =C(CH$_3$)$_2$ | A-17 |
| Q2-193. | =C(CH$_3$)$_2$ | A-18 |
| Q2-194. | =C(CH$_3$)$_2$ | A-19 |
| Q2-195. | =C(CH$_3$)$_2$ | A-21 |
| Q2-196. | =C(CH$_3$)$_2$ | A-22 |
| Q2-197. | =C(CH$_3$)$_2$ | A-23 |
| Q2-198. | =C(CH$_3$)$_2$ | A-24 |
| Q2-199. | =C(CH$_3$)$_2$ | A-25 |
| Q2-200. | =C(CH$_3$)$_2$ | A-26 |
| Q2-201. | =C(CH$_3$)$_2$ | A-27 |
| Q2-202. | =C(CH$_3$)$_2$ | A-28 |
| Q2-203. | =C(CH$_3$)$_2$ | —CH$_2$-4-OCH$_3$—C$_6$H$_4$ |
| Q2-204. | =C(CH$_3$)$_2$ | C(=O)OCH$_3$ |
| Q2-205. | =C(CH$_3$)$_2$ | C(=O)OC$_2$H$_5$ |
| Q2-206. | =C(CH$_3$)$_2$ | C(=O)NHCH$_3$ |
| Q2-207. | =C(CH$_3$)$_2$ | C(=O)NHC$_2$H$_5$ |
| Q2-208. | =C(CH$_3$)$_2$ | C(=O)NH—CH$_2$(CH$_3$)$_2$ |
| Q2-209. | =C(CH$_3$)$_2$ | C(=O)NH—CH$_2$CF$_3$ |
| Q2-210. | =C(CH$_3$)$_2$ | C(=O)NH—CH$_2$Cyclopropyl |
| Q2-211. | =C(CH$_3$)$_2$ | C(=O)NH—CH(CH$_3$)Cyclopropyl |
| Q2-212. | =C(CH$_3$)$_2$ | C(=O)NH—CH$_2$C(=O)NH—CH$_2$Cyclopropyl |
| Q2-213. | =C(CH$_3$)$_2$ | C(=O)NH—CH$_2$C(=O)NH—CH$_2$CF$_3$ |
| Q2-214. | =C(CH$_3$)$_2$ | C(=O)NH—CH$_2$(A-1) |
| Q2-215. | =C(CH$_3$)$_2$ | C(=O)NH—CH$_2$(A-2) |
| Q2-216. | =C(CH$_3$)$_2$ | SO$_2$CH$_3$ |
| Q2-217. | =C(CH$_3$)$_2$ | CF$_3$ |
| Q2-218. | =C(CH$_3$)$_2$ | CH$_2$CF$_3$ |
| Q2-219. | =C(CH$_3$)$_2$ | CH$_2$CH$_2$CF$_3$ |
| Q2-220. | =C(CH$_3$)$_2$ | CH$_2$CF(CF$_3$)$_2$ |
| Q2-221. | =C(CH$_3$)$_2$ | CH$_2$(CF$_2$)$_3$CF$_3$ |

Table 619 to table 927 of preferred compounds

Compounds as defined in analogy to table 1 to table 308, but wherein the combination of R¹ and R² for a compound corresponds in each case to one row of Table Q3, and wherein G is not present (m=0).

TABLE Q3

| Compound No. | R¹ and R² |
|---|---|
| Q3-1. | C$_4$H$_6$ |
| Q3-2. | 2-F—C$_6$H$_4$ |
| Q3-3. | 3-F—C$_6$H$_4$ |
| Q3-4. | 4-F—C$_6$H$_4$ |
| Q3-5. | 2-Cl—C$_6$H$_4$ |
| Q3-6. | 3-Cl—C$_6$H$_4$ |
| Q3-7. | 4-Cl—C$_6$H$_4$ |
| Q3-8. | 2-CH$_3$—C$_6$H$_4$ |
| Q3-9. | 3-CH$_3$—C$_6$H$_4$ |
| Q3-10. | 4-CF$_3$—C$_6$H$_4$ |
| Q3-11. | 2-CF$_3$—C$_6$H$_4$ |
| Q3-12. | 3-CF$_3$—C$_6$H$_4$ |
| Q3-13. | 4-CH$_3$—C$_6$H$_4$ |
| Q3-14. | 2-OCH$_3$—C$_6$H$_4$ |
| Q3-15. | 3-OCH$_3$—C$_6$H$_4$ |
| Q3-16. | 4-OCH$_3$—C$_6$H$_4$ |
| Q3-17. | 2-OCF$_3$—C$_6$H$_4$ |
| Q3-18. | 3-OCF$_3$—C$_6$H$_4$ |
| Q3-19. | 4-OCF$_3$—C$_6$H$_4$ |
| Q3-20. | A-2 |
| Q3-21. | A-3 |
| Q3-22. | A-4 |
| Q3-23. | A-5 |
| Q3-24. | A-6 |
| Q3-25. | A-7 |
| Q3-26. | A-8 |
| Q3-27. | A-9 |
| Q3-28. | A-10 |
| Q3-29. | A-11 |
| Q3-30. | A-12 |
| Q3-31. | A-13 |
| Q3-32. | A-14 |
| Q3-33. | A-15 |
| Q3-34. | A-16 |
| Q3-35. | A-17 |
| Q3-36. | A-18 |
| Q3-37. | A-19 |
| Q3-38. | A-21 |
| Q3-39. | A-22 |
| Q3-40. | A-23 |
| Q3-41. | A-24 |
| Q3-42. | A-25 |
| Q3-43. | A-26 |
| Q3-44. | A-27 |
| Q3-45. | A-28 |

Preparation Methods

Methods for the preparation of substituted ketonic isoxazoline compounds of formula (I)

Compounds of formula I can be prepared according to the following methods and variations described in schemes 1-7 below. R¹-R⁵, A¹-A⁴, G, X, m, p and q are defined as above for formula I.

Compounds of formula I can, for example, be prepared by cycloaddition of styrene compounds of formula II with nitrile oxides derived from oximes of formula III as outlined in scheme 1. The reaction typically proceeds through the intermediacy of an in situ generated hydroxamic acid halogenide, normally a chloride, by reaction with a halogenating agent like chlorine, hypochloride, N-succinimide, or chloramine-T. The halogenating agent is combined with the oxime before addition, or in the presence of the styrene II. Depending on the conditions, amine bases such as pyridine or triethylamine may be necessary. The reaction can be run in a wide variety of solvents including DMF, toluene, dichloromethane, chlorobenzene, acetonitrile, tetrahydrofurane, di-ethylether, ethyl acetate or the like.

The corresponding styrene compounds of formula II can be prepared as e.g. described in WO 2005/085216 or WO 2007/094313, or more preferably as described in EP Application 09159246.9.

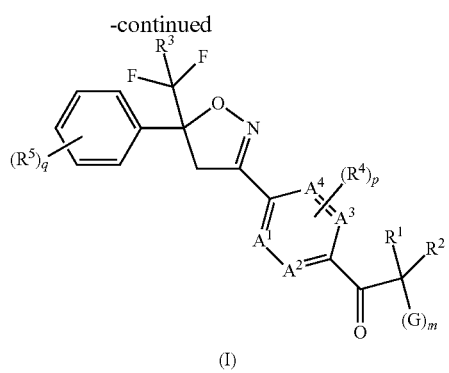

Scheme 1:

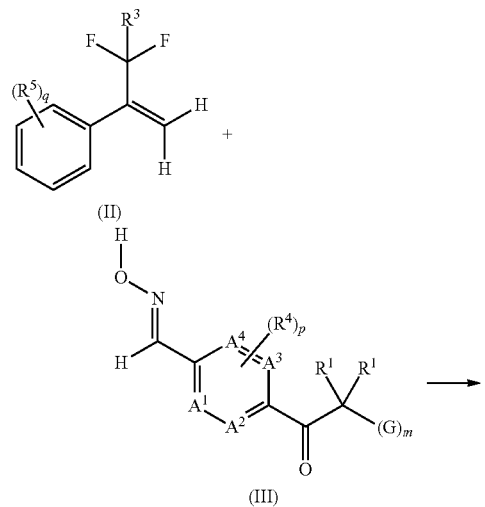

Compounds of formula I, can also be prepared as outlined in scheme 2 by reaction of an organometallic compound of formula IV with a carboxylic acid derivative. In scheme 2 Q may be a metal as for example $ZnT_2$, $MgT_2$, Li, Na, K, $SnT_3$, with T being a halogen; with LG being a leaving group such as halogen or OR or $S(O)_nR$, wherein R is $C_1$-$C_6$-alkyl, $C_1$-$C_6$-haloalkyl, a substituted phenyl, such as e.g. tosyl and n is 0-2; as described e.g. in WO 2008/156721 or by Dieter et al, Tetrahedron (2003), 59(7), 1083-1094. Compounds of formula I can also be prepared from secondary alcohols of compound VI by oxidation, as for example described in US 2007265321. Compounds of formula VI can be prepared by reaction of compounds of formula IV with an aldehyde, as for example described by Yamagishi et al, Journal of Organic Chemistry (2009), 74(16), 6350-6353.

Scheme 2:

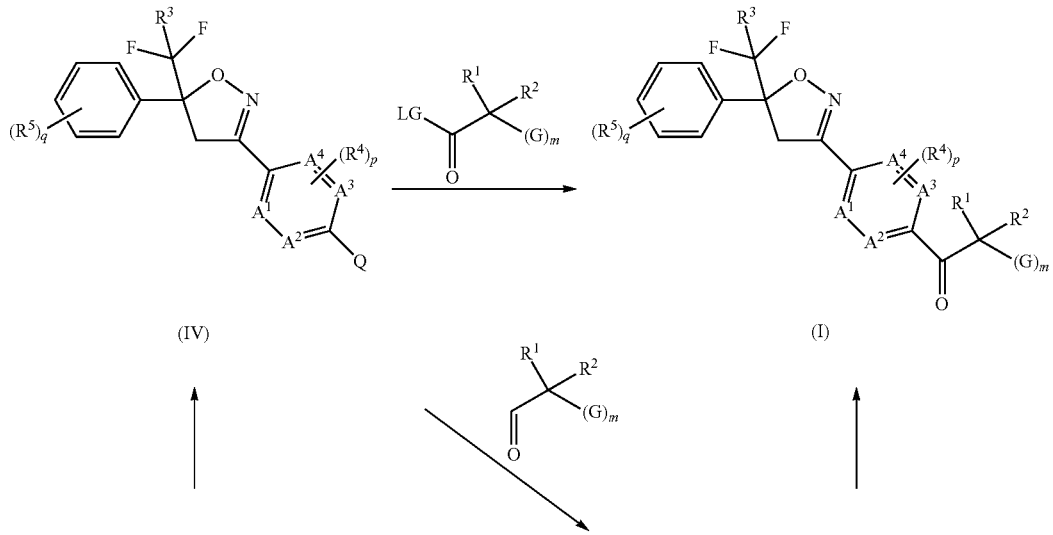

-continued

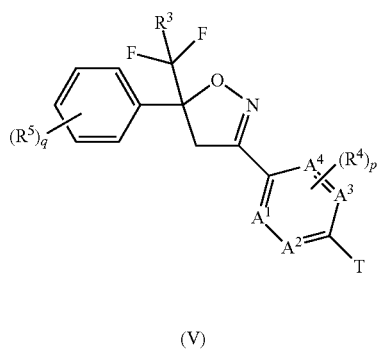

(V)

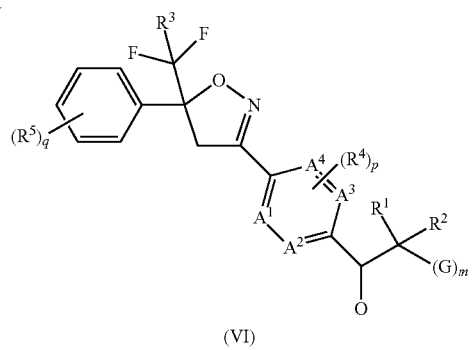

(VI)

The corresponding metal organyls of formula IV can be prepared by a halogen-metal exchange reaction of halides of formula V. The corresponding halides of formula V can be prepared as for example described in US 2007066617 or in EP Application 09159246.9 (wherein T is in formula V is Cl, Br. I).

Compounds of formula VI can also be prepared as outlined in scheme 3 by reaction of an aldehyde of formula IV with a appropriate nucleophile, as for example described by Joncour et al, Chem Med Chem (2008), 3(11), 1731-1739.

Compounds of formula IV in scheme 3 can be prepared by palladium catalyzed carbonylation of compounds of formula V, as for example described by Banard et al, Organic Process Research & Development (2008), 12(4), 566-574. Compounds of formula IV can also be prepared by reduction or a reduction/oxidation sequence of esters of formula IX, as for example described in WO 2007017468 (reduction) or in WO 2006128803 (reduction/oxidation sequence). Compounds of formula IX can be prepared by carbonylation of compounds of formula V, as for example described in WO 2005/085216.

Scheme 3:

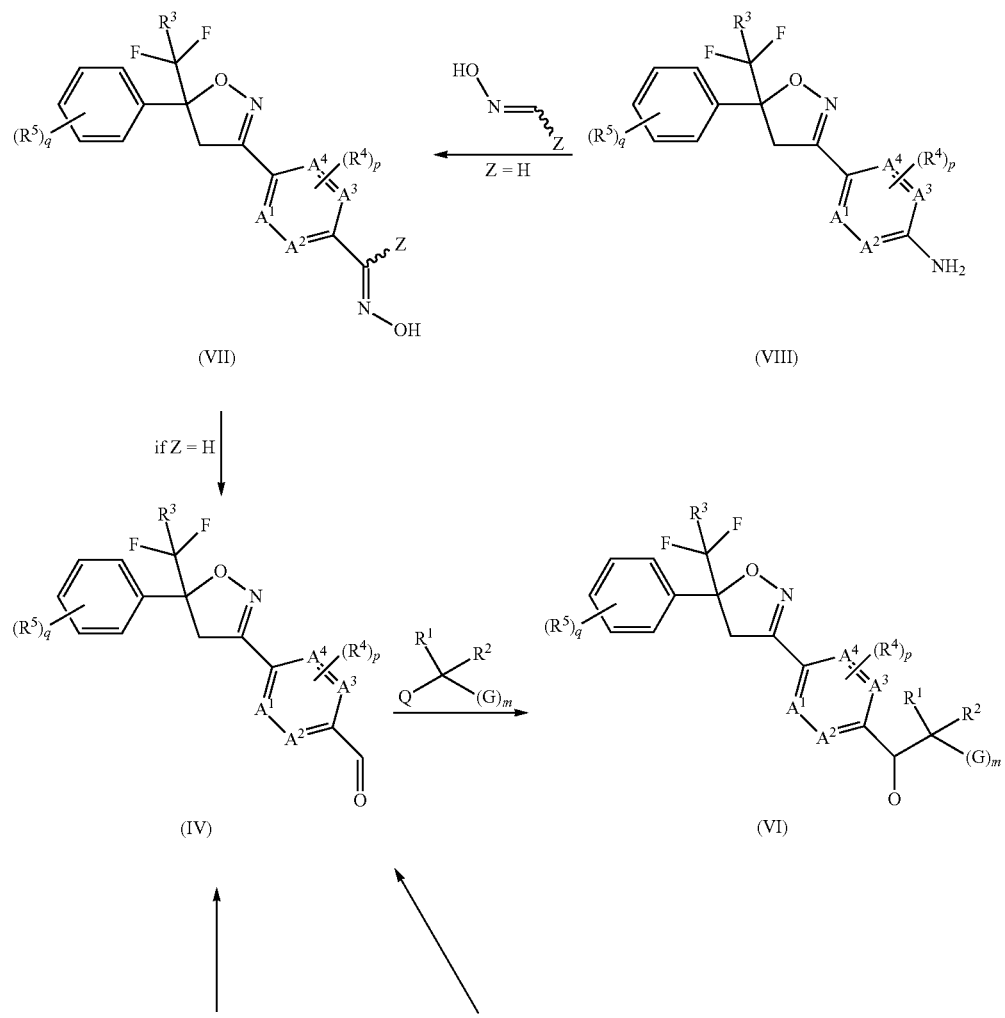

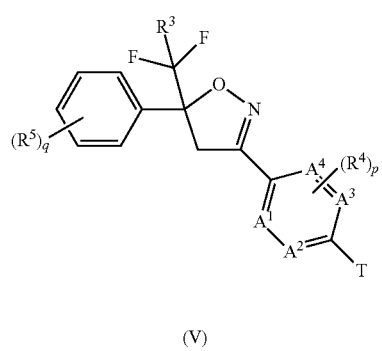

(V)

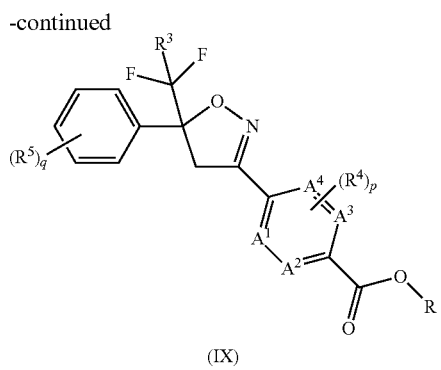

(IX)

The aldehydes of formula IV can also be prepared from the respective oximes (if Z is hydrogen) of formula VII by acidic hydrolysis, as for example described by Lin et al, Chemistry—A European Journal (2009), 15(10), 2305-2309. Compounds of formula VII can be prepared by diazotation of an amine of formula VIII and copper catalyzed reaction with a formoxime (Z is hydrogen) as in scheme 3 or a higher substituted oxime (Z is $C(R^1)(R^2)$-G) as in scheme 3a (see below), as for example described by Philipp et al, Justus Liebigs Annalen der Chemie (1936), 523, 285-289 or by Woodward et al, Tetrahedron (1958), 2, 1-57 or in EP Application 09159246.9. In case of the latter, compounds of formula I can then be prepared according to scheme 3a directly by acidic hydrolysis of compounds of formula VII (Z in this case equals $C(R^1)(R^2)$-G), as for example described by Singh et al, European Journal of Organic Chemistry (2008), (32), 5446-5460, and obtained after the diazotation of the amine of formula VIII with a the accordingly substituted oxime. The corresponding compounds of formula VIII can generally be prepared according to WO 2007/125984.

Scheme 3a

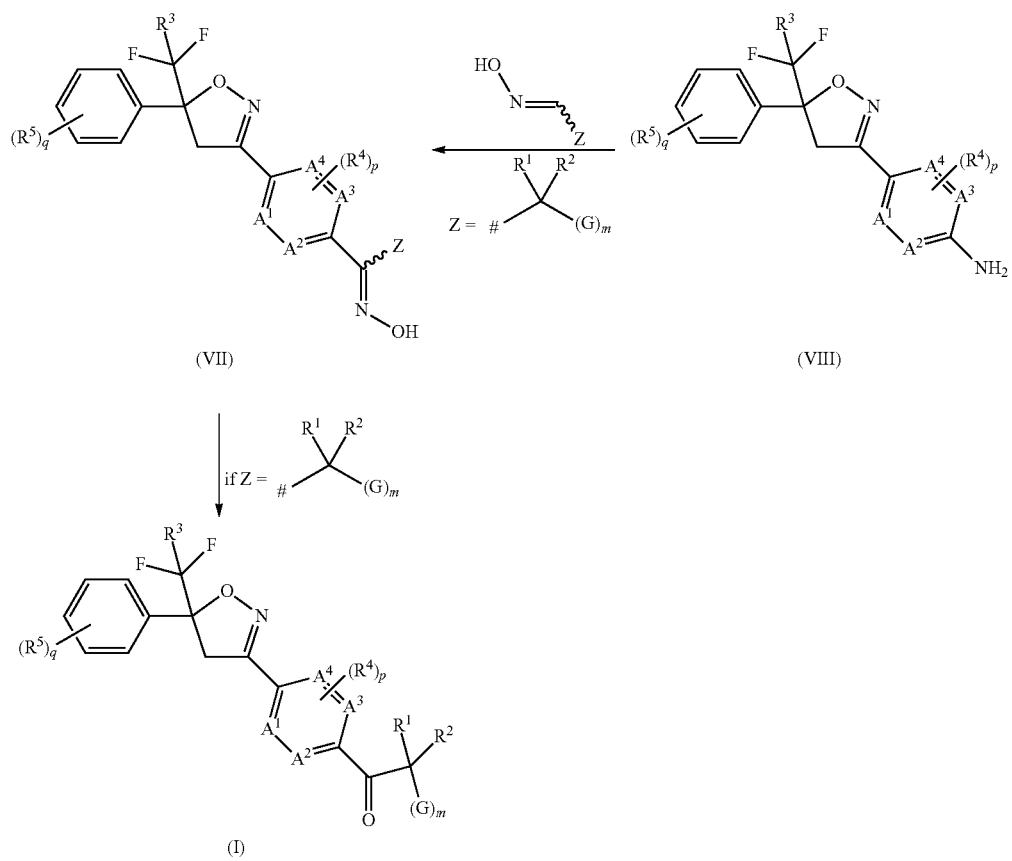

Compounds of formula I can also be prepared as outlined in scheme 4 by a Wacker type oxidation of an olefin of formula X, as for example described by Lu et al, Catalysis Letters (2009), 131(3-4), 517-525. The corresponding olefin of formula X can be prepared by transition metal catalyzed reaction of a halide of formula V with a boronic acid or a stannane. In scheme 4, W may be for example $B(OR)_2$ or $Sn(C_1-C_4-alkyl)_3$, T may be a halogen like for example Cl, Br or I or a leaving group LG as for example $OS(O)_2CF_3$ and E is hydrogen, alkyl, aryl or the like], as for example described by Giannini et al, Bioorganic & Medicinal Chemistry Letters (2009), 19(8), 2346-2349. Compounds of formula I can also be prepared by ozonolysis of compounds of formula XI as for example described by Gioiello et al, Journal of Organic Chemistry (2009), 74(9), 3520-3523. Alternatively, this reaction can be substituted by a dihydroxylation/glycol-cleavage-sequence, as for example described by Bogar et al, Organic Letters (2007), 9(17), 3401-3404.

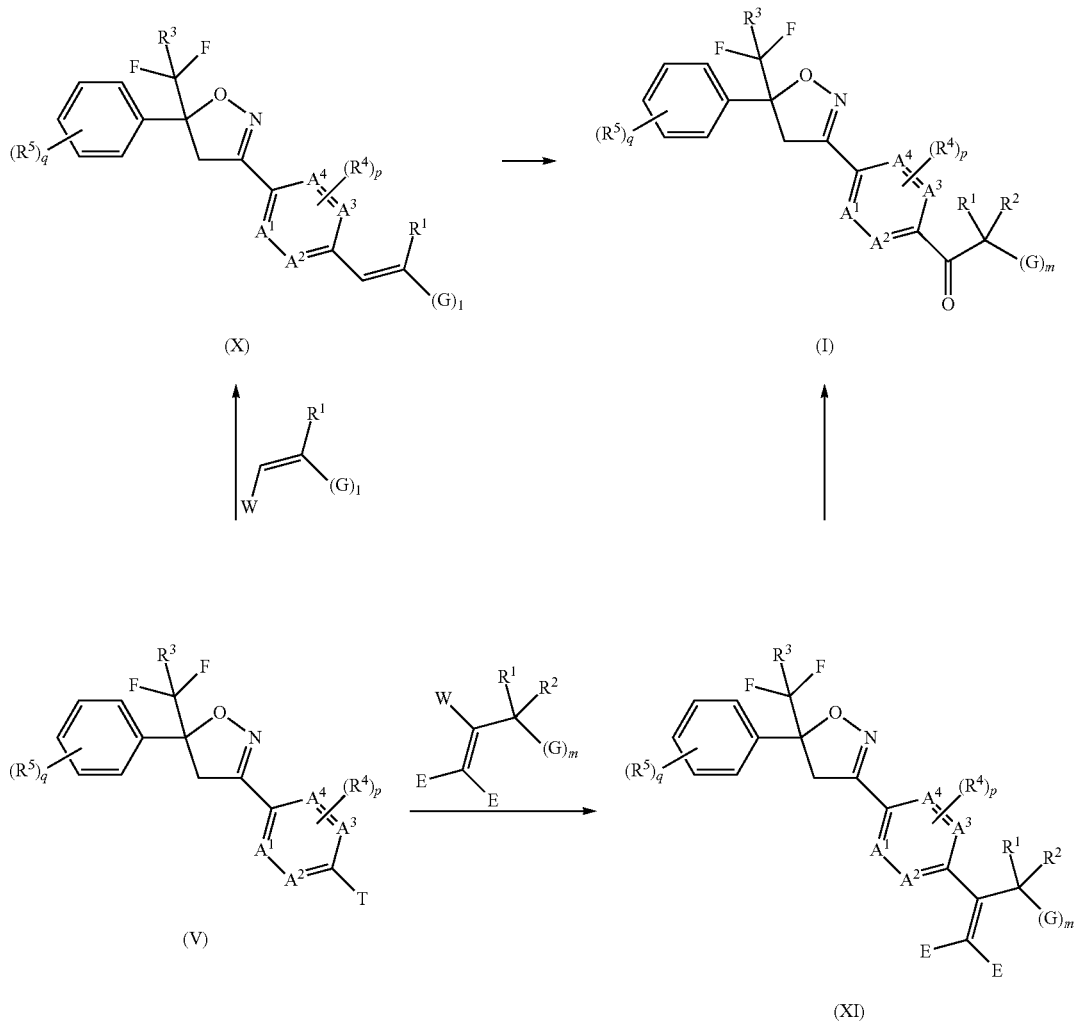

The corresponding compounds of formula XI can be prepared from compounds of formula V in the same manner as described above, wherein [W may be for example $B(OR)_2$ or $Sn(C_1-C_4-alkyl)_3$], as for example described by Konno et al, Journal of Organic Chemistry (2004), 69(6), 2188-2190.

Compounds of formula X and XI can also be prepared as outlined in scheme 5, wherein the variables W, T and E are defined in scheme 4, by reaction of an organometallic or a organoboron compound of formula XII, with a halogenated olefin, as for example described by Simard-Mercier et al, Journal of Organic Chemistry (2008), 73(15), 5899-5906.

Scheme 5:

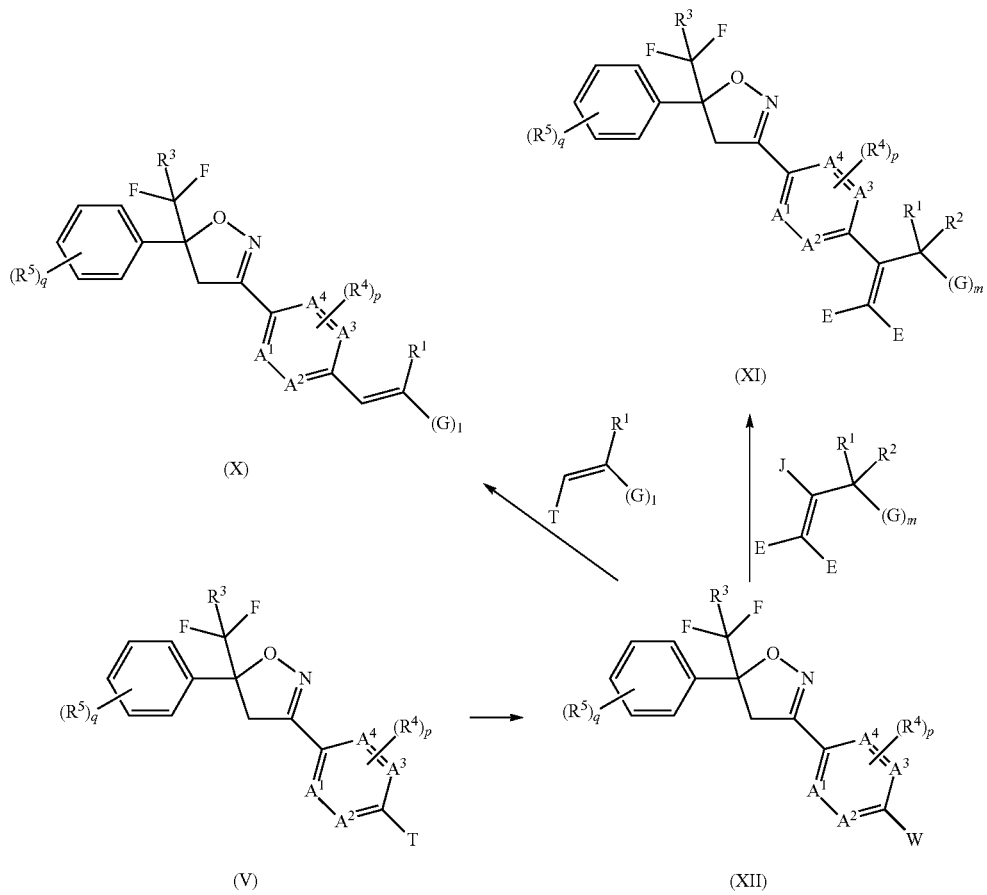

The corresponding compounds of formula XII can be prepared from halogens of formula V by halogen metal exchange, subsequent transmetalation or reaction with a boric ester or a diboron compound, as for example described by Liu et al, Journal of the American Chemical Society (2009), 131 (24), 8703-8707.

Compounds of formula III can be prepared as outlined in scheme 6 by reaction of an aldehyde of formula XIII with hydroxylamine as for example described in WO 2005/085216. Aldehyde compounds of formula XIII can for example be prepared by metalation of a halogenate of formula XIV (T may be a halogen as for example Cl, Br, I) and reaction with a formylation reagent or carbon monoxide as for example described in WO 2005/085216. The corresponding compounds of formula XIV can be prepared as for example described in WO 2009/127609.

Scheme 6:

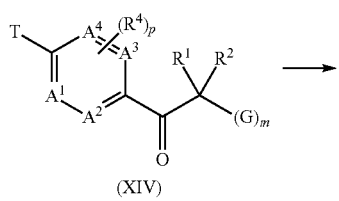

-continued

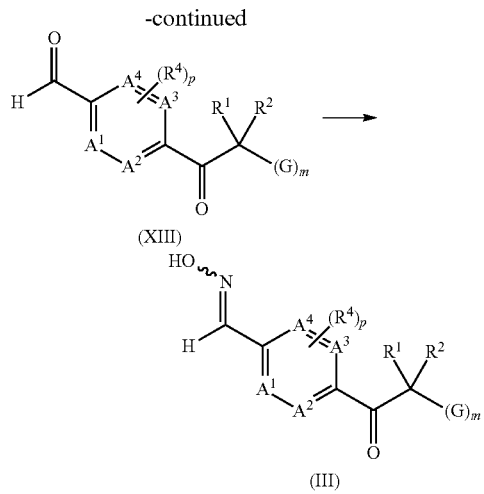

Compounds of formula I can be prepared as outlined in scheme 7 by alpha-alkylation of ketone of formula XV and quenching with an electrophile, as for example described by Zheng et al, Chemistry—A European Journal (2008), 14(32), 9864-9867. This may involve also a two step process via the intermediacy of an enol ether or a silyl enol ether and subsequent Mukaiyama-type reaction, as for example described by Mukaiyama et al, Chemistry Letters (1991), (6), 949-52.

Ketones of formula XV can be prepared from halides of formula V by a Heck-type reaction with an enol ether, as for example described in JP 2008-044858

Scheme 7:

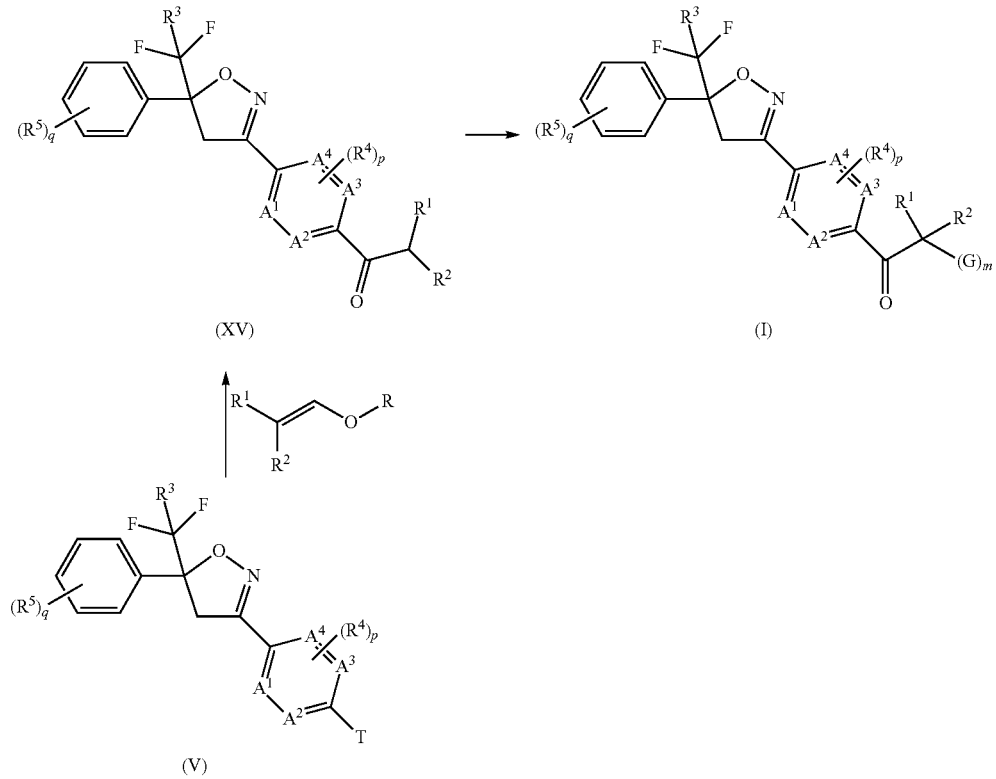

If individual compounds cannot be prepared via the above-described routes, they can be prepared by derivatization of other compounds I or by customary modifications of the synthesis routes described.

The reaction mixtures are worked up in the customary manner, for example by mixing with water, separating the phases, and, if appropriate, purifying the crude products by chromatography, for example on alumina or silica gel. Some of the intermediates and end products may be obtained in the form of colorless or pale brown viscous oils, which are freed or purified from volatile components under reduced pressure and at moderately elevated temperature. If the intermediates and end products are obtained as solids, they may be purified by recrystallization or digestion.

Pests

The compounds of the formula I, and their salts are in particular suitable for efficiently controlling arthropodal pests such as arachnids, myriapedes and insects as well as nematodes.

The compounds of the formula I are especially suitable for efficiently combating the following pests:

Insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis;* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera* ssp., *Diabrotica longicomis, Diabrotica semipunctata, Diabrotica 12-punctata Diabrotica speciosa, Diabrotica virgifera, Epilachna varivestis, Epitrix hirtipennis, Eutinobothrus brasiliensis,*

*Hylobius abietis, Hypera brunneipennis, Hypera postica, Ips typographus, Lema bilineata, Lema melanopus, Leptinotarsa decemlineata, Limonius californicus, Lissorhoptrus otyzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria;* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chtysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza forum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pomonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;* thrips (Thysanoptera), e.g. *Dichromothrips corbetti, Dichromothrips* ssp., *Frankliniella fusca, Frankliniella occidentalis, Frankliniella tritici, Scirtothrips citri, Thrips oryzae, Thrips palmi* and *Thrips tabaci,* termites (Isoptera), e.g. *Calotermes flavicollis, Leucotermes flavipes, Heterotermes aureus, Reticulitermes flavipes, Reticulitermes virginicus, Reticulitermes lucifugus, Reticulitermes santonensis, Reticulitermes grassei, Termes natalensis,* and *Coptotermes formosanus;* cockroaches (Blattaria—Blattodea), e.g. *Blattella germanica, Blattella asahinae, Periplaneta americana, Periplaneta japonica, Periplaneta brunnea, Periplaneta fulgginosa, Periplaneta australasiae,* and *Blatta orientalis;* bugs, aphids, leafhoppers, whiteflies, scale insects, cicadas (Hemiptera), e.g. *Acrostemum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mall, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiiand, Viteus vitifolii, Cimex lectularius, Cimex hemipterus, Reduvius senilis, Triatoma* spp., and *Arilus critatus;* ants, bees, wasps, sawflies (Hymenoptera), e.g. *Athalia rosae, Atta cephalotes, Atta capiguara, Atta cephalotes, Atta laevigata, Atta robusta, Atta sexdens, Atta texana, Crematogaster* spp., *Hoplocampa minuta, Hoplocampa testudinea, Lasius niger, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutilla occidentalis, Bombus* spp., *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile;* crickets, grasshoppers, locusts (Orthoptera), e.g. *Acheta domestica, ayllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina;* arachnoidea, such as arachnids (Acarina), e.g. of the families Argasidae, Ixodidae and Sarcoptidae, such as *Amblyomma americanum, Amblyomma variegatum, Ambryomma maculaturn, Argas persicus, Boophilus annulatus, Boophilus decoloratus, Boophilus microplus, Dermacentor silvarum, Dermacentor andersoni, Dermacentor variabilis, Hyaloma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and Eriophyidae spp. such as *Aculus schlechtendali, Phyllocoptrata oleivora* and *Eriophyes sheldoni;* Tarsonemidae spp. such as *Phytonemus pallidus* and *Polyphagotarsonemus latus;* Tenuipalpidae spp. such as *Brevipalpus phoenicis;* Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *Oligonychus pratensis;* Araneida, e.g. *Latrodectus mactans,* and *Loxosceles reclusa;* fleas (Siphonaptera), e.g. *Ctenocephalides felis, Ctenocephalides canis, Xenopsylla cheopis, Pulex irritans, Tunga penetrans,* and *Nosopsyllus fasciatus,* silverfish, firebrat (Thysanura), e.g. *Lepisma saccharina* and *Thermobia domestica,* centipedes (Chilopoda), e.g. *Scutigera coleoptrata,* millipedes (Diplopoda), e.g. *Narceus* spp.,

Earwigs (Dermaptera), e.g. *forficula auricularia,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.*

Collembola (springtails), e.g. *Onychiurus* ssp.

They are also suitable for controlling Nematodes: plant parasitic nematodes such as root knot nematodes, *Meloidogyne hapla, Meloidogyne incognita, Meloidogyne javanica,* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of the formula I and their salts are also useful for controlling arachnids (Arachnoidea), such as acarians (Acarina), e.g. of the families Argasidae, Ixodidae and Sarcoptidae, such as *Amblyomma americanum, Amblyomma variegatum, Argas persicus, Boophilus annulatus, Boophilus decoloratus, Boophilus microplus, Dermacentor silvarum, Hyalomma truncatum, Ixodes ricinus, Ixodes rubicundus, Ornithodorus moubata, Otobius megnini, Dermanyssus gallinae, Psoroptes ovis, Rhipicephalus appendiculatus, Rhipicephalus evertsi, Sarcoptes scabiei,* and Eriophyidae spp. such as *Aculus schlechtendali, Phyllocoptrata oleivora* and *Eriophyes sheldoni*; Tarsonemidae spp. such as *Phytonemus pallidus* and *Polyphagotarsonemus latus*; Tenuipalpidae spp. such as *Brevipalpus phoenicis*; Tetranychidae spp. such as *Tetranychus cinnabarinus, Tetranychus kanzawai, Tetranychus pacificus, Tetranychus telarius* and *Tetranychus urticae, Panonychus ulmi, Panonychus citri,* and *oligonychus pratensis.*

Compounds of the formula I are particularly useful for controlling insects, preferably sucking or piercing insects such as insects from the genera Thysanoptera, Diptera and Hemiptera, in particular the following species:

Thysanoptera: *Frankliniella fusca, Frankliniella occidentalis, Frankliniella tritici, Scirtothrips citri, Thrips oryzae, Thrips palmi* and *Thrips tabaci,*

Diptera, e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratitis capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Liriomyza sativae, Liriomyza trifolii, Lucilia caprina, Lucilia cuprina, Lucilia sericata, Lycoria pectoralis, Mansonia titillanus, Mayetiola destructor, Musca autumnalis, Musca domestica, Muscina stabulans, Oestrus ovis, Opomyza forum, Oscinella frit, Pegomya hysocyami, Phorbia antiqua, Phorbia brassicae, Phorbia coarctata, Phlebotomus argentipes, Psorophora columbiae, Psila rosae, Psorophora discolor, Prosimulium mixtum, Rhagoletis cerasi, Rhagoletis pornonella, Sarcophaga haemorrhoidalis, Sarcophaga* spp., *Simulium vittatum, Stomoxys calcitrans, Tabanus bovinus, Tabanus atratus, Tabanus lineola,* and *Tabanus similis, Tipula oleracea,* and *Tipula paludosa;*

Hemiptera, in particular aphids: *Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Brachycaudus cardui, Brachycaudus helichrysi, Brachycaudus persicae, Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viciae, Melanaphis pyrarius, Metopolophium dirhodum, Myzodes persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantiand,* and *Viteus vitifolii.*

Compounds of the formula I are particularly useful for controlling insects of the orders Hemiptera and Thysanoptera.

Formulations

For use in a method according to the present invention, the compounds I can be converted into the customary formulations, e.g. solutions, emulsions, suspensions, dusts, powders, pastes, granules and directly sprayable solutions. The use form depends on the particular purpose and application method. Formulations and application methods are chosen to ensure in each case a fine and uniform distribution of the compound of the formula I according to the present invention.

The formulations are prepared in a known manner (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S.

Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8), for example by extending the active compound with auxiliaries suitable for the formulation of agrochemicals, such as solvents and/or carriers, if desired emulsifiers, surfactants and dispersants, preservatives, antifoaming agents, anti-freezing agents, for seed treatment formulation also optionally colorants and/or binders and/or gelling agents.

Solvents/carriers, which are suitable, are e.g.:
solvents such as water, aromatic solvents (for example Solvesso products, xylene and the like), paraffins (for example mineral fractions), alcohols (for example methanol, butanol, pentanol, benzyl alcohol), ketones (for example cyclohexanone, gamma-butyrolactone), pyrrolidones (N-metyhl-pyrrolidone (NMP), N-octylpyrrolidone NOP), acetates (glycol diacetate), alkyl lactates, lactones such as g-butyrolactone, glycols, fatty acid dimethylamides, fatty acids and fatty acid esters, triglycerides, oils of vegetable or animal origin and modified oils such as alkylated plant oils. In principle, solvent mixtures may also be used.
carriers such as ground natural minerals and ground synthetic minerals, such as silica gels, finely divided silicic acid, silicates, talc, kaolin, attaclay, limestone, lime, chalk, bole, loess, clay, dolomite, diatomaceous earth, calcium sulfate and magnesium sulfate, magnesium oxide, ground synthetic materials, fertilizers, such as, for example, ammonium sulfate, ammonium phosphate, ammonium nitrate, ureas and products of vegetable origin, such as cereal meal, tree bark meal, wood meal and nutshell meal, cellulose powders and other solid carriers.

Suitable emulsifiers are nonionic and anionic emulsifiers (for example polyoxyethylene fatty alcohol ethers, alkylsulfonates and arylsulfonates).

Examples of dispersants are lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, Also anti-freezing agents such as glycerin, ethylene glycol, propylene glycol and bactericides such as can be added to the formulation.

Suitable antifoaming agents are for example antifoaming agents based on silicon or magnesium stearate.

Suitable preservatives are for example dichlorophen and benzyl alcohol hemiformal Suitable thickeners are compounds which confer a pseudoplastic flow behavior to the formulation, i.e. high viscosity at rest and low viscosity in the agitated stage. Mention may be made, in this context, for example, of commercial thickeners based on poly-saccharides, such as Xanthan Gum® (Kelzan® from Kelco), Rhodopol®23 (Rhone Poulenc) or Veegum® (from R.T. Vanderbilt), or organic phyllosilicates, such as Attaclay® (from Engelhardt). Antifoam agents suitable for the dispersions according to the invention are, for example, silicone emulsions (such as, for example, Silikon® SRE, Wacker or Rhodorsil® from Rhodia), long-chain alcohols, fatty acids, organofluorine compounds and mixtures thereof. Biocides can be added to stabilize the compositions according to the invention against attack by microorganisms. Suitable biocides are, for example, based on isothiazolones such as the compounds marketed under the trademarks Proxel® from Avecia (or Arch) or Acticide® RS from Thor Chemie and Kathon® MK from Rohm & Haas. Suitable antifreeze agents are organic polyols, for example ethylene glycol, propylene glycol or glycerol. These are usually employed in amounts of not more than 10% by weight, based on the total weight of the active compound composition. If appropriate, the active compound compositions according to the invention may comprise 1 to 5% by weight of buffer, based on the total amount of the formulation prepared, to regulate the pH, the amount and type of the buffer used depending on the chemical properties of the active compound or the active compounds. Examples of buffers are alkali metal salts of weak inorganic or organic acids, such as, for example, phosphoric acid, boronic acid, acetic acid, propionic acid, citric acid, fumaric acid, tartaric acid, oxalic acid and succinic acid.

Substances which are suitable for the preparation of directly sprayable solutions, emulsions, pastes or oil dispersions are mineral oil fractions of medium to high boiling point, such as kerosene or diesel oil, furthermore coal tar oils and oils of vegetable or animal origin, aliphatic, cyclic and aromatic hydrocarbons, for example toluene, xylene, paraffin, tetrahydronaphthalene, alkylated naphthalenes or their derivatives, methanol, ethanol, propanol, butanol, cyclohexanol, cyclohexanone, isophorone, strongly polar solvents, for example dimethyl sulfoxide, N-methylpyrrolidone and water.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

For seed treatment purposes, respective formulations can be diluted 2-10 fold leading to concentrations in the ready to use preparations of 0.01 to 60% by weight active compound by weight, preferably 0.1 to 40% by weight.

The compound of formula I can be used as such, in the form of their formulations or the use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; they are intended to ensure in each case the finest possible distribution of the active compounds according to the invention.

The following are examples of formulations:

1. Products for dilution with water. For seed treatment purposes, such products may be applied to the seed diluted or undiluted.

A) Water-Soluble Concentrates (SL, LS)

10 parts by weight of the active compound is dissolved in 90 parts by weight of water or a water-soluble solvent. As an alternative, wetters or other auxiliaries are added. The active compound dissolves upon dilution with water, whereby a formulation with 10% (w/w) of active compound is obtained.

B) Dispersible Concentrates (DC)

20 parts by weight of the active compound is dissolved in 70 parts by weight of cyclohexanone with addition of 10 parts by weight of a dispersant, for example polyvinylpyrrolidone. Dilution with water gives a dispersion, whereby a formulation with 20% (w/w) of active compounds is obtained.

C) Emulsifiable Concentrates (EC)

15 parts by weight of the active compounds is dissolved in 7 parts by weight of xylene with addition of calcium dodecylbenzenesulfonate and castor oil ethoxylate (in each case 5 parts by weight). Dilution with water gives an emulsion, whereby a formulation with 15% (w/w) of active compounds is obtained.

D) Emulsions (EW, EO, ES)

25 parts by weight of the active compound is dissolved in 35 parts by weight of xylene with addition of calcium dodecylbenzenesulfonate and castor oil ethoxylate (in each case 5 parts by weight). This mixture is introduced into 30 parts by weight of water by means of an emulsifier machine (e.g. Ultraturrax) and made into a homogeneous emulsion. Dilution with water gives an emulsion, whereby a formulation with 25% (w/w) of active compound is obtained.

E) Suspensions (SC, OD, FS)

In an agitated ball mill, 20 parts by weight of the active compound is comminuted with addition of 10 parts by weight of dispersants, wetters and 70 parts by weight of water or of an organic solvent to give a fine active compound suspension. Dilution with water gives a stable suspension of the active compound, whereby a formulation with 20% (w/w) of active compound is obtained.

F) Water-Dispersible Granules and Water-Soluble Granules (WG, SG)

50 parts by weight of the active compound is ground finely with addition of 50 parts by weight of dispersants and wetters and made as water-dispersible or water-soluble granules by means of technical appliances (for example extrusion, spray tower, fluidized bed). Dilution with water gives a stable dispersion or solution of the active compound, whereby a formulation with 50% (w/w) of active compound is obtained.

G) Water-Dispersible Powders and Water-Soluble Powders (WP, SP, SS, WS)

75 parts by weight of the active compound are ground in a rotor-stator mill with addition of 25 parts by weight of dispersants, wetters and silica gel. Dilution with water gives a stable dispersion or solution of the active compound, whereby a formulation with 75% (w/w) of active compound is obtained.

H) Gel-Formulation (GF)

In an agitated ball mill, 20 parts by weight of the active compound is comminuted with addition of 10 parts by weight of dispersants, 1 part by weight of a gelling agent wetters and 70 parts by weight of water or of an organic solvent to give a fine active compound suspension. Dilution with water gives a stable suspension of the active compound, whereby a formulation with 20% (w/w) of active compound is obtained.

2. Products to be applied undiluted for foliar applications. For seed treatment purposes, such products may be applied to the seed diluted or undiluted.

I) Dustable Powders (DP, DS)

5 parts by weight of the active compound are ground finely and mixed intimately with 95 parts by weight of finely divided kaolin. This gives a dustable product having 5% (w/w) of active compound.

J) Granules (GR, FG, GG, MG)

0.5 part by weight of the active compound is ground finely and associated with 95.5 parts by weight of carriers, whereby a formulation with 0.5% (w/w) of active compound is obtained. Current methods are extrusion, spray-drying or the fluidized bed. This gives granules to be applied undiluted for foliar use.

K) ULV solutions (UL)

10 parts by weight of the active compound is dissolved in 90 parts by weight of an organic solvent, for example xylene. This gives a product having 10% (w/w) of active compound, which is applied undiluted for foliar use.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within relatively wide ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even to apply the active ingredient without additives.

In the method of this invention compounds I may be applied with other active ingredients, for example with other pesticides, insecticides, herbicides, fertilizers such as ammonium nitrate, urea, potash, and superphosphate, phytotoxicants and plant growth regulators, safeners and nematicides. These additional ingredients may be used sequentially or in combination with the above-described compositions, if appropriate also added only immediately prior to use (tank mix). For example, the plant(s) may be sprayed with a composition of this invention either before or after being treated with other active ingredients.

The following list M of pesticides together with which the compounds according to the invention can be used and with which potential synergistic effects might be produced, is intended to illustrate the possible combinations, but not to impose any limitation:

M.1. Organo(thio)phosphate compounds: acephate, azamethiphos, azinphos-ethyl, azinphos-methyl, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, flupyrazophos, fosthiazate, heptenophos, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon, vamidothion;

M.2. Carbamate compounds: aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb, triazamate;

M.3. Pyrethroid compounds: acrinathrin, allethrin, d-cis-trans allethrin, d-trans allethrin, bifenthrin, bioallethrin, bioallethrin S-cylclopentenyl, bioresmethrin, cyclopothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, imiprothrin, metofluthrin, permethrin, phenothrin, prallethrin, profluthrin, pyrethrin (pyrethrum), resmethrin, silafluofen, tefluthrin, tetramethrin, tralomethrin, transfluthrin;

M.4. Juvenile hormone mimics: hydroprene, kinoprene, methoprene, fenoxycarb, pyriproxyfen;

M.5, Nicotinic receptor agonists/antagonists compounds: acetamiprid, bensultap, cartap hydrochloride, clothianidin, dinotefuran, imidacloprid, thiamethoxam, nitenpyram, nicotine, spinosad (allosteric agonist), spinetoram (allosteric agonist), thiacloprid, thiocyclam, thiosultap-sodium and AKD1022.

M.6. GABA gated chloride channel antagonist compounds: chlordane, endosulfan, gamma-HCH (lindane); ethiprole, fipronil, pyrafluprole, pyriprole M.7. Chloride channel activators: abamectin, emamectin benzoate, milbemectin, lepimectin;

M.8. METI I compounds: fenazaquin, fenpyroximate, pyrimidifen, pyridaben, tebufenpyrad, tolfenpyrad, flufenerim, rotenone;

M.9. METI II and III compounds: acequinocyl, fluacyprim, hydramethylnon;

M.10. Uncouplers of oxidative phosphorylation: chlorfenapyr, DNOC;

M.11. Inhibitors of oxidative phosphorylation: azocyclotin, cyhexatin, diafenthiuron, fenbutatin oxide, propargite, tetradifon;

M.12. Moulting disruptors: cyromazine, chromafenozide, halofenozide, methoxyfenozide, tebufenozide;

M.13. Synergists: piperonyl butoxide, tribufos;

M.14. Sodium channel blocker compounds: indoxacarb, metaflumizone;

M.15. Fumigants: methyl bromide, chloropicrin sulfuryl fluoride;

M.16. Selective feeding blockers: crylotie, pymetrozine, flonicamid;

M.17. Mite growth inhibitors: clofentezine, hexythiazox, etoxazole;

M.18. Chitin synthesis inhibitors: buprofezin, bistrifluoron, chlorfluazuron, diflubenzuron, flucycloxuron, flufenoxuron, hexaflumuron, lufenuron, novaluron, noviflumuron, teflubenzuron, triflumuron;

M.19. Lipid biosynthesis inhibitors: spirodiclofen, spiromesifen, spirotetramat;

M.20. Octapaminergic agonsits: amitraz;

M.21. Ryanodine receptor modulators: flubendiamide and the phtalamid compound (R)-, (S)-3-Chlor-N1-{2-methyl-4-[1,2,2,2-tetrafluor-1-(trifluormethyl)ethyl]phenyl}-N2-(1-methyl-2-methylsulfonylethyl)phthalamid (M21.1)

M.22. Other isoxazoline compounds: 4-[5-(3,5-Dichlorophenyl)-5-trifluoromethyl-4,5-dihydro-isoxazol-3-yl]-2-methyl-N-pyridin-2-ylmethyl-benzamide (M22.1), 4-[5-(3,5-Dichloro-phenyl)-5-trifluoromethyl-4,5-dihydro-isoxazol-3-yl]-2-methyl-N-(2,2,2-trifluoro-ethyl)-benzamide (M22.2), 4-[5-(3,5-Dichloro-phenyl)-5-trifluoromethyl-4,5-dihydro-isoxazol-3-yl]-2-methyl-N-[(2,2,2-trifluoro-ethylcarbamoyl)-methyl]-benzamide (M22.3), 4-[5-(3,5-Dichloro-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.4)-4-[5-(3,5-Dichlorophenyl)-5-trifluoromethyl-4,5-dihydro-isoxazol-3-yl]-N-[(methoxyimino)methyl]-2-methylbenzamide (M22.5), 4-[5-(3-Chloro-5-trifluoromethyl-phenyl)-5-trifluoromethyl-4,5-dihydro-isoxazol-3-yl]-2-methyl-N-[(2,2,2-trifluoro-ethylcarbamoyl)-methyl]-benzamide (M22.6), 4-[5-(3-Chloro-5-trifluoromethyl-phenyl)-5-trifluoromethyl-4,5-dihydro-isoxazol-3-yl]-naphthalene-1-carboxylic acid [(2,2,2-trifluoro-ethylcarbamoyl)-methyl]-amide (M22.7) and 5-[5-(3,5-Dichloro-4-fluoro-phenyl)-5-trifluoromethyl-4,5-dihydro-isoxazol-3-yl]-2-[1,2,4]triazol-1-yl-benzonitrile (M22.8);

M.23. Anthranilamide compounds: chloranthraniliprole, cyantraniliprole, 5-Bromo-2-(3-chloro-pyridin-2-yl)-2H-pyrazole-3-carboxylic acid [4-cyano-2-(1-cyclopropyl-ethylcarbamoyl)-6-methyl-phenyl]-amide (M23.1), 5-Bromo-2-(3-chloro-pyridin-2-yl)-2H-pyrazole-3-carboxylic acid [2-chloro-4-cyano-6-(1-cyclopropyl-ethylcarbamoyl)-phenyl]-amide (M23.2), 5-Bromo-2-(3-chloro-pyridin-2-yl)-2H-pyrazole-3-carboxylic acid [2-bromo-4-cyano-6-(1-cyclopropyl-ethylcarbamoyl)-phenyl]-amide (M23.3), 5-Bromo-2-(3-chloro-pyridin-2-yl)-2H-pyrazole-3-carboxylic acid [2-bromo-4-chloro-6-(1-cyclopropyl-ethylcarbamoyl)-phenyl]-amide (M23.4), 5-Bromo-2-(3-chloro-pyridin-2-yl)-2H-pyrazole-3-carboxylic acid [2,4-dichloro-6-(1-cyclopropyl-ethylcarbamoyl)-phenyl]-amide (M23.5), 5-Bromo-2-(3-chloro-pyridin-2-yl)-2H-pyrazole-3-carboxylic acid [4-chloro-2-(1-cyclopropyl-ethylcarbamoyl)-6-methyl-phenyl]-amide (M23.6), N'-(2-{[5-Bromo-2-(3-chloro-pyridin-2-yl)-2H-pyrazole-3-carbonyl]-amino}-5-chloro-3-methyl-benzoyl)-hydrazinecarboxylic acid methyl ester (M23.7), N'-(2-{[5-Bromo-2-(3-chloro-pyridin-2-yl)-2H-pyrazole-3-carbonyl]-amino}-5-chloro-3-methyl-benzoyl)-N'-methyl-hydrazinecarboxylic acid methyl ester (M23.8), N'-(2-{[5-Bromo-2-(3-chloro-pyridin-2-yl)-2H-pyrazole-3-carbonyl]-amino}-5-chloro-3-methyl-benzoyl)-N,N'-dimethyl-hydrazinecarboxylic acid methyl ester (M23.9), N'-(3,5-Dibromo-2-{[5-bromo-2-(3-chloro-pyridin-2-yl)-2H-pyrazole-3-carbonyl]-amino}-benzoyl)-hydrazinecarboxylic acid methyl ester (M23.10), N'-(3,5-Dibromo-2-{[5-bromo-2-(3-chloro-pyridin-2-yl)-2H-pyrazole-3-carbonyl]-amino}-benzoyl)-N'-methyl-hydrazinecarboxylic acid methyl ester (M23.11) and N'-(3,5-Dibromo-2-{[5-bromo-2-(3-chloro-pyridin-2-yl)-2H-pyrazole-3-carbonyl]-amino}-benzoyl)-N,N'-dimethyl-hydrazinecarboxylic acid methyl ester (M23.12);

M.24. Malononitrile compounds: 2-(2,2,3,3,4,4,5,5-octafluoropentyl)-2-(3,3,3-trifluoro-propyl)malononitrile ($CF_2H$—$CF_2$—$CF_2$—$CF_2$—$CH_2$—$C(CN)_2$—$CH_2$—$CH_2$—$CF_3$) (M24.1) and 2-(2,2,3,3,4,4,5,5-octafluoropentyl)-2-(3, 3,4,4,4-pentafluorobutyl)-malonodinitrile (CF$_2$H—CF$_2$—CF$_2$—CF$_2$—CH$_2$—C(CN)$_2$—CH$_2$—CH$_2$—CF$_2$—CF$_3$) (M24.2);

M.25. Microbial disruptors: *Bacillus thuringiensis* subsp. *Israelensi*, *Bacillus sphaericus*, *Bacillus thuringiensis* subsp. *Aizawai*, *Bacillus thuringiensis* subsp. *Kurstaki*, *Bacillus thuringiensis* subsp. *Tenebrionis*;

M.26. Aminofuranone compounds: 4-{[(6-Bromopyrid-3-yl)methyl](2-fluoroethyl)amino}furan-2(5H)-on (M26.1), 4-{[(6-Fluoropyrid-3-yl)methyl](2,2-difluoroethyl)amino}furan-2(5H)-on (M26.2), 4-{[(2-Chloro1,3-thiazolo-5-yl)methyl](2-fluoroethyl)amino}furan-2(5H)-on (M26.3), 4-{[(6-Chloropyrid-3-yl)methyl](2-fluoroethyl)amino}furan-2(5H)-on (M26.4), 4-{[(6-Chloropyrid-3-yl)methyl](2,2-difluoroethyl)amino}furan-2(5H)-on (M26.5), 4-{[(6-Chloro-5-fluoropyrid-3-yl)methyl](methyl)amino}furan-2(5H)-on (M26.6), 4-{[(5,6-Dichloropyrid-3-yl)methyl](2-fluoroethyl)amino}furan-2(5H)-on (M26.7), 4-{[(6-Chloro-5-fluoropyrid-3-yl)methyl](cyclopropyl)amino}furan-2(5H)-on (M26.8), 4-{[(6-Chloropyrid-3-yl)methyl](cyclopropyl)amino}furan-2(5H)-on (M26.9) and 4-{[(6-Chloropyrid-3-yl)methyl](methyl)amino}furan-2(5H)-on (M26.10);

M.27. Various compounds: aluminium phosphide, amidoflumet, benclothiaz, benzoximate, bifenazate, borax, bromopropylate, cyanide, cyenopyrafen, cyflumetofen, chinomethionate, dicofol, fluoroacetate, phosphine, pyridalyl, pyrifluquinazon, sulfur, organic sulfur compounds, tartar emetic, sulfoxaflor, N—R'-2,2-dihalo-1-R"cyclopropanecarboxamide-2-(2,6-dichloro-α,α,α-trifluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, 4-But-2-ynyloxy-6-(3,5-dimethyl-piperidin-1-yl)-2-fluoro-pyrimidine (M27.1), Cyclopropaneacetic acid, 1,1'-[(3S,4R,4aR,6S,6aS,12R,12aS,12bS)-4-[[(2-cyclopropylacetyl)oxy]methyl]-1,3,4,4a,5,6,6a,12,12a,12b-decahydro-12-hydroxy-4,6a,12b-trimethyl-11-oxo-9-(3-pyridinyl)-2H,11H-naphtho[2,1-b]pyrano[3,4-e]pyran-3,6-diyl]ester (M27.2) and 8-(2-Cyclopropylmethoxy-4-trifluoromethyl-phenoxy)-3-(6-trifluoromethyl-pyridazin-3-yl)-3-aza-bicyclo[3.2.1]octane (M27.3).

The commercially available compounds of the group M may be found in The Pesticide Manual, 13th Edition, British Crop Protection Council (2003) among other publications.

Paraoxon and their preparation have been described in Farm Chemicals Handbook, Volume 88, Meister Publishing Company, 2001. Flupyrazofos has been described in Pesticide Science 54, 1988, p. 237-243 and in U.S. Pat. No. 4,822,779. AKD 1022 and its preparation have been described in U.S. Pat. No. 6,300,348. The anthranilamides M23.1 to M23.6 have been described in WO 2008/72743 and WO 200872783, those M23.7 to M23.12 in WO2007/043677. The phthalamide M 21.1 is known from WO 2007/101540. The alkynylether compound M27.1 is described e.g. in JP 2006131529. Organic sulfur compounds have been described in WO 2007060839. The isoxazoline compounds M 22.1 to M 22.8 have been described in e.g. WO2005/085216, WO 2007/079162, WO 2007/026965, WO 2009/126668 and WO2009/051956. The aminofuranone compounds M 26.1 to M 26.10 have been described eg. in WO 2007/115644. The pyripyropene derivative M 27.2 has been described in WO 2008/66153 and WO 2008/108491. The pyridazin compound M 27.3 has been described in JP 2008/115155. Malononitrile compounds as those (M24.1) and (M24.2) have been described in WO 02/089579, WO 02/090320, WO 02/090321, WO 04/006677, WO 05/068423, WO 05/068432 and WO 05/063694.

Fungicidal mixing partners are those selected from the group consisting of acylalanines such as benalaxyl, metalaxyl, ofurace, oxadixyl, amine derivatives such as aldimorph, dodine, dodemorph, fenpropimorph, fenpropidin, guazatine, iminoctadine, spiroxamin, tridemorph, anilinopyrimidines such as pyrimethanil, mepanipyrim or cyrodinyl, antibiotics such as cycloheximid, griseofulvin, kasugamycin, natamycin, polyoxin or streptomycin, azoles such as bitertanol, bromoconazole, cyproconazole, difenoconazole, diniconazole, epoxiconazole, fenbuconazole, fluquiconazole, flusilazole, hexaconazole, imazalil, metconazole, myclobutanil, penconazole, propiconazole, prochloraz, prothioconazole, tebuconazole, triadimefon, triadimenol, triflumizol, triticonazole, flutriafol, dicarboximides such as iprodion, myclozolin, procymidon, vinclozolin, dithiocarbamates such as ferbam, nabam, maneb, mancozeb, metam, metiram, propineb, polycarbamate, thiram, ziram, zineb, heterocyclic compounds such as anilazine, benomyl, boscalid, carbendazim, carboxin, oxycarboxin, cyazofamid, dazomet, dithianon, famoxadon, fenamidon, fenarimol, fuberidazole, flutolanil, furametpyr, isoprothiolane, mepronil, nuarimol, probenazole, proquinazid, pyrifenox, pyroquilon, quinoxyfen, silthiofam, thiabendazole, thifluzamid, thiophanate-methyl, tiadinil, tricyclazole, triforine, copper fungicides such as Bordeaux mixture, copper acetate, copper oxychloride, basic copper sulfate, nitrophenyl derivatives such as binapacryl, dinocap, dinobuton, nitrophthalisopropyl, phenylpyrroles such as fenpiclonil or fludioxonil, sulfur, other fungicides such as acibenzolar-S-methyl, benthiavalicarb, carpropamid, chlorothalonil, cyflufenamid, cymoxanil, diclomezin, diclocymet, diethofencarb, edifenphos, ethaboxam, fenhexamid, fentin-acetate, fenoxanil, ferimzone, fluazinam, fosetyl, fosetyl-aluminum, iprovalicarb, hexachlorobenzene, metrafenon, pencycuron, propamocarb, phthalide, toloclofos-methyl, quintozene, zoxamid, strobilurins such as azoxystrobin, dimoxystrobin, fluoxastrobin, kresoxim-methyl, metominostrobin, orysastrobin, picoxystrobin or trifloxystrobin, sulfenic acid derivatives such as captafol, captan, dichlofluanid, folpet, tolylfluanid, cinnemamides and analogs such as dimethomorph, flumetover or flumorph.

Applications

The animal pest, i.e. the insects, arachnids and nematodes, the plant, soil or water in which the plant is growing can be contacted with the present compounds of formula I or composition(s) containing them by any application method known in the art. As such, "contacting" includes both direct contact (applying the compounds/compositions directly on the animal pest or plant—typically to the foliage, stem or roots of the plant) and indirect contact (applying the compounds/compositions to the locus of the animal pest or plant).

The compounds of formula I or the pesticidal compositions comprising them may be used to protect growing plants and crops from attack or infestation by animal pests, especially insects, acaridae or arachnids by contacting the plant/crop with a pesticidally effective amount of compounds of formula I. The term "crop" refers both to growing and harvested crops.

The compounds of the present invention and the compositions comprising them are particularly important in the control of a multitude of insects on various cultivated plants, such as cereal, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

The compounds of the present invention are employed as such or in form of compositions by treating the insects or the plants, plant propagation materials, such as seeds, soil, surfaces, materials or rooms to be protected from insecticidal attack with a insecticidally effective amount of the active compounds. The application can be carried out both before and after the infection of the plants, plant propagation materials, such as seeds, soil, surfaces, materials or rooms by the insects.

The present invention also includes a method of combating animal pests which comprises contacting the animal pests, their habit, breeding ground, food supply, cultivated plants, seed, soil, area, material or environment in which the animal pests are growing or may grow, or the materials, plants, seeds, soils, surfaces or spaces to be protected from animal attack or infestation with a pesticidally effective amount of a mixture of at least one active compound I.

Moreover, animal pests may be controlled by contacting the target pest, its food supply, habitat, breeding ground or its locus with a pesticidally effective amount of compounds of formula I. As such, the application may be carried out before or after the infection of the locus, growing crops, or harvested crops by the pest.

The compounds of the invention can also be applied preventively to places at which occurrence of the pests is expected.

The compounds of formula I may be also used to protect growing plants from attack or infestation by pests by contacting the plant with a pesticidally effective amount of compounds of formula I. As such, "contacting" includes both direct contact (applying the compounds/compositions directly on the pest and/or plant—typically to the foliage, stem or roots of the plant) and indirect contact (applying the compounds/compositions to the locus of the pest and/or plant).

"Locus" means a habitat, breeding ground, plant, seed, soil, area, material or environment in which a pest or parasite is growing or may grow.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "cultivated plants" is to be understood as including plants which have been modified by breeding, mutagenesis or genetic engineering. Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s) (oligo- or polypeptides) poly for example by glycosylation or polymer additions such as prenylated, acetylated or farnesylated moieties or PEG moieties (e.g. as disclosed in Biotechnol Prog. 2001 July-August; 17(4):720-8., Protein Eng Des Sel. 2004 January; 17(1):57-66, Nat. Protoc. 2007; 2(5):1225-35., Curr Opin Chem. Biol. 2006 October; 10(5): 487-91. Epub 2006 Aug. 28., Biomaterials. 2001 March; 22(5):405-17, Bioconjug Chem. 2005 January-February; 16(1):113-21).

The term "cultivated plants" is to be understood also including plants that have been rendered tolerant to applications of specific classes of herbicides, such as hydroxy-phenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A-0242236, EP-A-242246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), for example Clearfield® summer rape (Canola) being tolerant to imidazolinones, e.g. imazamox. Genetic engineering methods have been used to render cultivated plants, such as soybean, cotton, corn, beets and rape, tolerant to herbicides, such as glyphosate and glufosinate, some of which are commercially available under the trade names RoundupReady® (glyphosate) and LibertyLink® (glufosinate).

The term "cultivated plants" is to be understood also including plants that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, for example *Photorhabdus* spp. or *Xenorhabdus* spp.; toxins produced by animals, such as scorpion toxins, arachnid toxins, wasp toxins, or other insect-specific neurotoxins; toxins produced by fungi, such *Streptomycetes* toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, for example WO 02/015701). Further examples of such toxins or genetically-modified plants capable of synthesizing such toxins are disclosed, for example, in EP-A 374 753, WO 93/007278, WO 95/34656, EP-A 427 529, EP-A 451 878, WO 03/018810 and WO 03/052073. The methods for producing such genetically modified plants are generally known to the person skilled in the art and are described, for example, in the publications mentioned above. These insecticidal proteins contained in the genetically modified plants impart to the plants producing these proteins protection from harmful pests from certain taxonomic groups of arthropods, particularly to beetles (Coleoptera), flies (Diptera), and butterflies and moths (Lepidoptera) and to plant parasitic nematodes (Nematoda).

The term "cultivated plants" is to be understood also including plants that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, for example EP-A 0 392 225), plant disease resistance genes (for example potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, for example, in the publications mentioned above.

The term "cultivated plants" is to be understood also including plants that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

The term "cultivated plants" is to be understood also including plants that contain by the use of recombinant DNA techniques a modified amount of substances of content or new substances of content, specifically to improve human or animal nutrition, for example oil crops that produce health-promoting long-chain omega-3 fatty acids or unsaturated omega-9 fatty acids (e.g. Nexera® rape).

The term "cultivated plants" is to be understood also including plants that contain by the use of recombinant DNA techniques a modified amount of substances of content or new substances of content, specifically to improve raw material production, for example potatoes that produce increased amounts of amylopectin (e.g. Amflora® potato).

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment or of application to the pests dwelling place or nest, the quantity of active ingredient ranges from 0.0001 to 500 g per 100 m$^2$, preferably from 0.001 to 20 g per 100 m$^2$.

Customary application rates in the protection of materials are, for example, from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in treating crop plants, the rate of application of the active ingredients of this invention may be in the range of 0.1 g to 4000 g per hectare, desirably from 25 g to 600 g per hectare, more desirably from 50 g to 500 g per hectare.

The compounds of formula I are effective through both contact (via soil, glass, wall, bed net, carpet, plant parts or animal parts), and ingestion (bait, or plant part).

The compounds of the invention may also be applied against non-crop insect pests, such as ants, termites, wasps, flies, mosquitoes, crickets, or cockroaches. For use against said non-crop pests, compounds of formula I are preferably used in a bait composition.

The bait can be a liquid, a solid or a semisolid preparation (e.g. a gel). Solid baits can be formed into various shapes and forms suitable to the respective application e.g. granules, blocks, sticks, disks. Liquid baits can be filled into various devices to ensure proper application, e.g. open containers, spray devices, droplet sources, or evaporation sources. Gels can be based on aqueous or oily matrices and can be formulated to particular necessities in terms of stickyness, moisture retention or aging characteristics.

The bait employed in the composition is a product, which is sufficiently attractive to incite insects such as ants, termites, wasps, flies, mosquitoes, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or polyorganosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature and are known to those skilled in the art.

For use in bait compositions, the typical content of active ingredient is from 0.001 weight % to 15 weight %, desirably from 0.001 weight % to 5% weight % of active compound.

Formulations of compounds of formula I as aerosols (e.g in spray cans), oil sprays or pump sprays are highly suitable for the non-professional user for controlling pests such as flies, fleas, ticks, mosquitoes or cockroaches. Aerosol recipes are preferably composed of the active compound, solvents such as lower alcohols (e.g. methanol, ethanol, propanol, butanol), ketones (e.g. acetone, methyl ethyl ketone), paraffin hydrocarbons (e.g. kerosenes) having boiling ranges of approximately 50 to 250° C., dimethylformamide, N-methylpyrrolidone, dimethyl sulfoxide, aromatic hydrocarbons such as toluene, xylene, water, furthermore auxiliaries such as emulsifiers such as sorbitol monooleate, oleyl ethoxylate having 3-7 mol of ethylene oxide, fatty alcohol ethoxylate, perfume oils such as ethereal oils, esters of medium fatty acids with lower alcohols, aromatic carbonyl compounds, if appropriate stabilizers such as sodium benzoate, amphoteric surfactants, lower epoxides, triethyl orthoformate and, if required, propellants such as propane, butane, nitrogen, compressed air, dimethyl ether, carbon dioxide, nitrous oxide, or mixtures of these gases.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of formula I and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of formula I and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder. Suitable repellents for example are N,N-Diethyl-meta-toluamide (DEET), N,N-diethylphenylacetamide (DEPA), 1-(3-cyclohexan-1-yl-carbonyl)-2-methylpiperine, (2-hydroxymethylcyclohexyl)acetic acid lactone, 2-ethyl-1,3-hexandiol, indalone, Methylneodecanamide (MNDA), a pyrethroid not used for insect control such as {(+/−)-3-allyl-2-methyl-4-oxocyclopent-2-(+)-enyl-(+)-trans-chrysantemate (Esbiothrin), a repellent derived from or identical with plant ex-tracts like limonene, eugenol, (+)-Eucamalol (1), (−)-1-epi-eucamalol or crude plant ex-tracts from plants like *Eucalyptus maculata, Vitex rotundifolia, Cymbopogan martinii, Cymbopogan citratus* (lemon grass), *Cymopogan nartdus* (citronella). Suitable binders are selected for example from polymers and copolymers of vinyl esters of aliphatic acids (such as such as vinyl acetate and vinyl versatate), acrylic and methacrylic esters of alcohols, such as butyl acrylate, 2-ethylhexylacrylate, and methyl acrylate, mono- and di-ethylenically unsaturated hydrocarbons, such as styrene, and aliphatic diens, such as butadiene.

The impregnation of curtains and bednets is done in general by dipping the textile material into emulsions or dispersions of the insecticide or spraying them onto the nets.

The compounds of formula I and its compositions can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities). The compounds of formula I are applied not only to the surrounding soil surface or into the under-floor soil in order to protect wooden materials but it can also be applied to lumbered articles such as surfaces of the under-floor concrete, alcove posts, beams, plywoods, furniture, etc., wooden articles such as particle boards, half boards, etc. and vinyl articles such as coated electric wires, vinyl sheets, heat insulating material such as styrene foams, etc. In case of application against ants doing harm to crops or human beings, the ant controller of the present invention is applied to the crops or the surrounding soil, or is directly applied to the nest of ants or the like.

Seed Treatment

The compounds of formula I are also suitable for the treatment of seeds in order to protect the seed from insect pest, in particular from soil-living insect pests and the resulting plant's roots and shoots against soil pests and foliar insects.

The compounds of formula I are particularly useful for the protection of the seed from soil pests and the resulting plant's roots and shoots against soil pests and foliar insects. The protection of the resulting plant's roots and shoots is preferred. More preferred is the protection of resulting plant's shoots from piercing and sucking insects, wherein the protection from aphids is most preferred.

The present invention therefore comprises a method for the protection of seeds from insects, in particular from soil insects and of the seedlings' roots and shoots from insects, in particular from soil and foliar insects, said method comprising contacting the seeds before sowing and/or after pregermination with a compound of the general formula I or a salt thereof. Particularly preferred is a method, wherein the plant's roots and shoots are protected, more preferably a method, wherein the plants shoots are protected form piercing and sucking insects, most preferably aa method, wherein the plants shoots are protected from aphids.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

The term seed treatment comprises all suitable seed treatment techniques known in the art, such as seed dressing, seed coating, seed dusting, seed soaking and seed pelleting.

The present invention also comprises seeds coated with or containing the active compound.

The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment seeds from plants, which tolerate the action of herbicides or fungicides or insecticides owing to breeding, including genetic engineering methods.

For example, the active compound can be employed in treatment of seeds from plants, which are resistant to herbicides from the group consisting of the sulfonylureas, imidazolinones, glufosinate-ammonium or glyphosate-isopropylammonium and analogous active substances (see for example, EP-A-0242236, EP-A-242246) (WO 92/00377) (EP-A-0257993, U.S. Pat. No. 5,013,659) or in transgenic crop plants, for example cotton, with the capability of producing *Bacillus thuringiensis* toxins (Bt toxins) which make the plants resistant to certain pests (EP-A-0142924, EP-A-0193259), Furthermore, the active compound can be used also for the treatment of seeds from plants, which have modified characteristics in comparison with existing plants consist, which can be generated for example by traditional breeding methods and/or the generation of mutants, or by recombinant procedures). For example, a number of cases have been described of recombinant modifications of crop plants for the purpose of modifying the starch synthesized in the plants (e.g. WO 92/11376, WO 92/14827, WO 91/19806) or of transgenic crop plants having a modified fatty acid composition (WO 91/13972).

The seed treatment application of the active compound is carried out by spraying or by dusting the seeds before sowing of the plants and before emergence of the plants.

Compositions which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

Conventional seed treatment formulations include for example flowable concentrates FS, solutions LS, powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pre-germinated the latter In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of compounds of formula I for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

Seed Treatment formulations may additionally also comprise binders and optionally colorants.

Binders can be added to improve the adhesion of the active materials on the seeds after treatment. Suitable binders are homo- and copolymers from alkylene oxides like ethylene oxide or propylene oxide, polyvinylacetate, polyvinylalcohols, polyvinylpyrrolidones, and copolymers thereof, ethylene-vinyl acetate copolymers, acrylic homo- and copolymers, polyethyleneamines, polyethyleneamides and polyethyleneimines, poly-saccharides like celluloses, tylose and starch, polyolefin homo- and copolymers like olefin/maleic anhydride copolymers, polyurethanes, polyesters, polystyrene homo and copolymers Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of a Gelling Agent is Carrageen (Satiagel®)

In the treatment of seed, the application rates of the compounds I are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed.

The invention therefore also relates to seed comprising a compound of the formula I, or an agriculturally useful salt of I, as defined herein. The amount of the compound I or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

Animal Health

The compounds of formula I or the enantiomers or veterinarily acceptable salts thereof are in particular also suitable for being used for combating parasites in and on animals.

An object of the present invention is therefore also to provide new methods to control parasites in and on animals. Another object of the invention is to provide safer pesticides for animals. Another object of the invention is further to provide pesticides for animals that may be used in lower doses than existing pesticides. And another object of the invention is to provide pesticides for animals, which provide a long residual control of the parasites.

The invention also relates to compositions containing a parasiticidally effective amount of compounds of formula I or the enantiomers or veterinarily acceptable salts thereof and an acceptable carrier, for combating parasites in and on animals.

The present invention also provides a method for treating, controlling, preventing and protecting animals against infestation and infection by parasites, which comprises orally, topically or parenterally administering or applying to the animals a parasiticidally effective amount of a compound of formula I or the enantiomers or veterinarily acceptable salts thereof or a composition comprising it.

The invention also provides a process for the preparation of a composition for treating, controlling, preventing or protecting animals against infestation or infection by parasites which comprises a parasiticidally effective amount of a compound of formula I or the enantiomers or veterinarily acceptable salts thereof or a composition comprising it.

Activity of compounds against agricultural pests does not suggest their suitability for control of endo- and ectoparasites in and on animals which requires, for example, low, non-emetic dosages in the case of oral application, metabolic compatibility with the animal, low toxicity, and a safe handling.

Surprisingly it has now been found that compounds of formula I are suitable for combating endo- and ectoparasites in and on animals.

Compounds of formula I or the enantiomers or veterinarily acceptable salts thereof and compositions comprising them are preferably used for controlling and preventing infestations and infections animals including warm-blooded animals (including humans) and fish. They are for example suitable for controlling and preventing infestations and infections in mammals such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels.

Compounds of formula I or the enantiomers or veterinarily acceptable salts thereof and compositions comprising them are preferably used for controlling and preventing infestations and infections in domestic animals, such as dogs or cats.

Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of formula I or the enantiomers or veterinarily acceptable salts thereof and compositions comprising them are suitable for systemic and/or non-systemic control of ecto- and/or endoparasites. They are active against all or some stages of development.

The compounds of formula I are especially useful for combating ectoparasites.

The compounds of formula I are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans,* and *Nosopsyllus fasciatus,* cockroaches (Blattaria—Blattodea), e.g. *Blattella germanica, Blattella asahinae, Periplaneta americana, Periplaneta japonica, Periplaneta brunnea, Periplaneta fuligginosa, Periplaneta australasiae,* and *Blatta orientalis,* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia canicularis, Gasterophilus intestinalis, Glossina morsitans, Glossina palpalis, Glossina fuscipes, Glossina tachinoides, Haematobia irritans, Haplodiplosis equestris, Hippelates* spp., *Hypoderma lineata, Leptoconops torrens, Lucilia caprina, Lucilia cuprina, Lucilia sericata, Lycoria pectoralis, Mansonia* spp., *Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga* sp., *Simulium vittatum, Stomoxys calcitrans, Tabanus bovinus, Tabanus atratus, Tabanus lineola,* and *Tabanus similis,* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus.* ticks and parasitic mites (Parasitiformes): ticks (Ixodida), e.g. *Ixodes scapularis, Ixodes holocyclus, Ixodes pacificus, Rhiphicephalus sanguineus, Dermacentor andersoni, Dermacentor variabilis, Amblyomma americanum, Ambryomma maculatum, Ornithodorus hermsi, Ornithodorus turicata* and parasitic mites (Mesostigmata), e.g. *Ornithonyssus bacoti* and *Dermanyssus gallinae,*

Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp, Bugs (Heteropterida): *Cimex lectularius, Cimex hemipterus, Reduvius senilis, Triatoma* spp., *Rhodnius* ssp., *Panstrongylus* ssp. and *Arilus critatus,*

Anoplurida, e.g. *Haematopinus* spp., *Linognathus* spp., *Pediculus* spp., *Phtirus* spp., and *Solenopotes* spp, Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp, Roundworms Nematoda:

Wipeworms and Trichinosis (Trichosyringida), e.g. Trichinellidae (*Trichinella* spp.), (Trichuridae) *Trichuris* spp., *Capillaria* spp, Rhabditida, e.g. *Rhabditis* spp, *Strongyloides* spp., *Helicephalobus* spp, Strongylida, e.g. *Strongylus* spp., *Ancylostoma* spp., *Necator americanus, Bunostomum* spp. (Hookworm), *Trichostrongylus* spp., *Haemonchus contortus., Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capillaris, Protostrongylus* spp., *Angiostrongylus* spp., *Parelaphostrongylus* spp. *Aleurostrongylus abstrusus,* and *Dioctophyma renale,*

Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., and *Oxyuris equi,*

Camallanida, e.g. *Dracunculus medinensis* (guinea worm)

Spirurida, e.g. *Thelazia* spp. *Wuchereria* spp., *Brugia* spp., *Onchocerca* spp., *Dirofilari* spp.a, *Dipetalonema* spp., *Setaria* spp., *Elaeophora* spp., *Spirocerca lupi,* and *Habronema* spp., Thorny headed worms (Acanthocephala), e.g. *Acanthocephalus* spp., *Macracanthorhynchus hirudinaceus* and *Oncicola* spp, Planarians (Plathelminthes):

Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., and *Nanocyetes* spp, Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., and *Hymenolepis* spp.

The compounds of formula I and compositions containing them are particularly useful for the control of pests from the orders Diptera, Siphonaptera and Ixodida.

Moreover, the use of the compounds of formula I and compositions containing them for combating mosquitoes is especially preferred.

The use of the compounds of formula I and compositions containing them for combating flies is a further preferred embodiment of the present invention.

Furthermore, the use of the compounds of formula I and compositions containing them for combating fleas is especially preferred.

The use of the compounds of formula I and compositions containing them for combating ticks is a further preferred embodiment of the present invention.

The compounds of formula I also are especially useful for combating endoparasites (roundworms nematoda, thorny headed worms and planarians).

Administration can be carried out both prophylactically and therapeutically.

Administration of the active compounds is carried out directly or in the form of suitable preparations, orally, topically/dermally or parenterally.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations in which the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further ingredients such as acids, bases, buffer salts, preservatives, and solubilizers. The solutions are filtered and filled sterile.

Suitable solvents are physiologically tolerable solvents such as water, alkanols such as ethanol, butanol, benzyl alcohol, glycerol, propylene glycol, polyethylene glycols, N-methylpyrrolidone, 2-pyrrolidone, and mixtures thereof.

The active compounds can optionally be dissolved in physiologically tolerable vegetable or synthetic oils which are suitable for injection.

Suitable solubilizers are solvents which promote the dissolution of the active compound in the main solvent or prevent its precipitation. Examples are polyvinylpyrrolidone, polyvinyl alcohol, polyoxyethylated castor oil, and polyoxyethylated sorbitan ester.

Suitable preservatives are benzyl alcohol, trichlorobutanol, p-hydroxybenzoic acid esters, and n-butanol.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on.

Solutions for use on the skin are prepared according to the state of the art and according to what is described above for injection solutions, sterile procedures not being necessary.

Further suitable solvents are polypropylene glycol, phenyl ethanol, phenoxy ethanol, ester such as ethyl or butyl acetate, benzyl benzoate, ethers such as alkyleneglycol alkylether, e.g. dipropyleneglycol monomethylether, ketons such as acetone, methylethylketone, aromatic hydrocarbons, vegetable and synthetic oils, dimethylformamide, dimethylacetamide, transcutol, solketal, propylencarbonate, and mixtures thereof.

It may be advantageous to add thickeners during preparation. Suitable thickeners are inorganic thickeners such as bentonites, colloidal silicic acid, aluminium monostearate, organic thickeners such as cellulose derivatives, polyvinyl alcohols and their copolymers, acrylates and methacrylates.

Gels are applied to or spread on the skin or introduced into body cavities. Gels are prepared by treating solutions which have been prepared as described in the case of the injection solutions with sufficient thickener that a clear material having an ointment-like consistency results. The thickeners employed are the thickeners given above.

Pour-on formulations are poured or sprayed onto limited areas of the skin, the active compound penetrating the skin and acting systemically.

Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added.

Suitable solvents which are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether, di-ethylene glycol mono-butyl ether, ketones such as acetone, methyl ethyl ketone, cyclic carbonates such as propylene carbonate, ethylene carbonate, aromatic and/or aliphatic hydrocarbons, vegetable or synthetic oils, DMF, dimethylacetamide, n-alkylpyrrolidones such as methylpyrrolidone, n-butylpyrrolidone or n-octylpyrrolidone, N-methylpyrrolidone, 2-pyrrolidone, 2,2-dimethyl-4-oxy-methylene-1,3-dioxolane and glycerol formal.

Suitable colorants are all colorants permitted for use on animals and which can be dissolved or suspended.

Suitable absorption-promoting substances are, for example, DMSO, spreading oils such as isopropyl myristate, dipropylene glycol pelargonate, silicone oils and copolymers thereof with polyethers, fatty acid esters, triglycerides, fatty alcohols.

Suitable antioxidants are sulfites or metabisulfites such as potassium metabisulfite, ascorbic acid, butylhydroxytoluene, butylhydroxyanisole, tocopherol.

Suitable light stabilizers are, for example, novantisolic acid.

Suitable adhesives are, for example, cellulose derivatives, starch derivatives, polyacrylates, natural polymers such as alginates, gelatin.

Emulsions can be administered orally, dermally or as injections.

Emulsions are either of the water-in-oil type or of the oil-in-water type.

They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances.

Suitable hydrophobic phases (oils) are:
liquid paraffins, silicone oils, natural vegetable oils such as sesame oil, almond oil, castor oil, synthetic triglycerides such as caprylic/capric biglyceride, triglyceride mixture with vegetable fatty acids of the chain length $C_8$-$C_{12}$ or other specially selected natural fatty acids, partial glyceride mixtures of saturated or unsaturated fatty acids possibly also containing hydroxyl groups, mono- and diglycerides of the $C_8$-$C_{10}$ fatty acids, fatty acid esters such as ethyl stearate, di-n-butyryl adipate, hexyl laurate, dipropylene glycol perlargonate, esters of a branched fatty acid of medium chain length with saturated fatty alcohols of chain length $C_{16}$-$C_{18}$, isopropyl myristate, isopropyl palmitate, caprylic/capric acid esters of saturated fatty alcohols of chain length $C_{12}$-$C_{18}$, isopropyl stearate, oleyl oleate, decyl oleate, ethyl oleate, ethyl lactate, waxy fatty acid esters such as synthetic duck coccygeal gland fat, dibutyl phthalate, diisopropyl adipate, and ester mixtures related to the latter, fatty alcohols such as isotridecyl alcohol, 2-octyldodecanol, cetylstearyl alcohol, oleyl alcohol, and fatty acids such as oleic acid and mixtures thereof.

Suitable hydrophilic phases are: water, alcohols such as propylene glycol, glycerol, sorbitol and mixtures thereof.

Suitable emulsifiers are:
non-ionic surfactants, e.g. polyethoxylated castor oil, polyethoxylated sorbitan monooleate, sorbitan monostearate, glycerol monostearate, polyoxyethyl stearate, alkylphenol polyglycol ether;
ampholytic surfactants such as di-sodium N-lauryl-p-iminodipropionate or lecithin; anionic surfactants, such as sodium lauryl sulfate, fatty alcohol ether sulfates, mono/dialkyl polyglycol ether orthophosphoric acid ester monoethanolamine salt; cation-active surfactants, such as cetyltrimethylammonium chloride.

Suitable further auxiliaries are: substances which enhance the viscosity and stabilize the emulsion, such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silicic acid or mixtures of the substances mentioned.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers.

Liquid suspending agents are all homogeneous solvents and solvent mixtures.

Suitable wetting agents (dispersants) are the emulsifiers given above.

Other auxiliaries which may be mentioned are those given above.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form.

Suitable excipients are all physiologically tolerable solid inert substances. Those used are inorganic and organic substances. Inorganic substances are, for example, sodium chloride, carbonates such as calcium carbonate, hydrogencarbonates, aluminium oxides, titanium oxide, silicic acids, argillaceous earths, precipitated or colloidal silica, or phosphates. Organic substances are, for example, sugar, cellulose, foodstuffs and feeds such as milk powder, animal meal, grain meals and shreds, starches.

Suitable auxiliaries are preservatives, antioxidants, and/or colorants which have been mentioned above.

Other suitable auxiliaries are lubricants and glidants such as magnesium stearate, stearic acid, talc, bentonites, disintegration-promoting substances such as starch or crosslinked polyvinylpyrrolidone, binders such as starch, gelatin or linear polyvinylpyrrolidone, and dry binders such as microcrystalline cellulose.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

The compositions which can be used in the invention can comprise generally from about 0.001 to 95% of the compound of formula I.

Generally it is favorable to apply the compounds of formula I in total amounts of 0.5 mg/kg to 100 mg/kg per day, preferably 1 mg/kg to 50 mg/kg per day.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

In a preferred embodiment of the present invention, the compositions comprising the compounds of formula I them are applied dermally/topically.

In a further preferred embodiment, the topical application is conducted in the form of compound-containing shaped articles such as collars, medallions, ear tags, bands for fixing at body parts, and adhesive strips and foils.

Generally it is favorable to apply solid formulations which release compounds of formula I in total amounts of 10 mg/kg to 300 mg/kg, preferably 20 mg/kg to 200 mg/kg, most preferably 25 mg/kg to 160 mg/kg body weight of the treated animal in the course of three weeks.

For the preparation of the shaped articles, thermoplastic and flexible plastics as well as elastomers and thermoplastic elastomers are used. Suitable plastics and elastomers are polyvinyl resins, polyurethane, polyacrylate, epoxy resins, cellulose, cellulose derivatives, polyamides and polyester which are sufficiently compatible with the com-pounds of formula I. A detailed list of plastics and elastomers as well as preparation procedures for the shaped articles is given e.g. in WO 03/086075.

EXAMPLES

The present invention is now illustrated in further details by the following examples, without imposing any limitation thereto.

C. Compound Examples

Compounds can be characterized e.g. by coupled High Performance Liquid Chromatography/mass spectrometry (HPLC/MS), by $^1$H-NMR and/or by their melting points.

Analytical HPLC column: RP-18 column Chromolith Speed ROD from Merck KgaA, Germany). Elution: acetonitrile+0.1% trifluoroacetic acid (TFA)/water+0.1% trifluoroacetic acid (TFA) in a ratio of from 5:95 to 100:0 in 5 minutes at 40° C. (standard method); or in some cases from 5:95 to 100:0 in 4 minutes at 40° C. (characterized as method (B) in the table(s) below).

$^1$H-NMR, respectively $^{13}$C-NMR: The signals are characterized by chemical shift (ppm) vs. tetramethylsilane, respectively CDCl$_3$ for $^{13}$C-NMR, by their multiplicity and by their integral (relative number of hydrogen atoms given). The following abbreviations are used to characterize the multiplicity of the signals: m=multiplett, q=quartett, t=triplett, d=doublet and s=singulett.

C.1 Compound Examples 1

Compound examples 1-1 to 1-4 correspond to compound formula C.1:

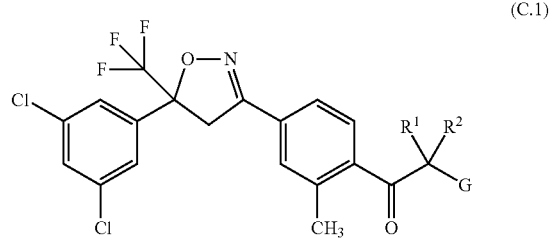

(C.1)

wherein R$^1$, R$^2$ and G of each compound example is defined table C.1 below.

TABLE C.1

| Compound Ex. | R$^1$ | R$^2$ | G | HPLC-MS: R$_t$(min) | and [M + H] |
|---|---|---|---|---|---|
| 1-1 | H | H | H | n.a. | n.a. |
| 1-2 | H | H | CH(CH$_3$)$_2$ | 4.220 | 458.05 |
| 1-3 | H | H | C(=O)—OCH$_2$CH$_3$ | 4.684 | 488.05 |
| 1-4 | H | H | C(=O)—OCH$_3$ | 4.945 | 474.00 |
| 1-5 | CH$_3$ | CH$_3$ | C(=O)—OCH$_3$ | 4.759 | 501.80 |
| 1-6 | CH$_3$ | H | CH$_3$ | 4.866 | 443.80 |
| 1-7 | H | H | CH$_3$ | 4.721 | 429.80 |
| 1-8 | H | H | C(=O)—N(CH$_3$)CH$_2$CH$_3$ | 4.490 | 500.80 |
| 1-9 | H | H | C(=O)—NHCH$_2$C(=O)—NCH$_2$CH$_3$ | 3.920 | 543.80 |
| 1-10 | H | H | C(=O)—NHCH$_2$CH$_2$CH$_3$ | 4.294 | 501.05 |
| 1-11 | H | H | C(=O)—NHCH$_3$ | 4.001 | 472.80 |
| 1-12 | H | H | CH$_2$C(=O)—OCH$_2$CH$_3$ | 4.668 | 502.05 |
| 1-13 | H | H | C(=O)—NHCH$_2$C(=O)—NCH$_2$CF$_3$ | 4.110 | 597.70 |
| 1-14 | H | H | C$_6$H$_5$ | 4.846 | 492.05 |
| 1-15 | H | H | 4-CH$_3$—C$_6$H$_4$ | 4.301 | 506.05 |
| 1-16 | H | H | CH$_2$CF$_3$ | 4.773 | 497.70 |
| 1-17 | =N—OH | | C(=O)—OCH$_3$ | 4.287 | 502.95 |
| 1-18 | =O | | OCH$_3$ | 4.465 | 459.95 |
| 1-19 | =CH—CH$_3$ | | H | 4.753 | 441.80 |
| 1-20 | =O | | NHCH$_3$ | 4.194 | 458.80 |
| 1-21 | —CH$_2$CH$_2$— | | H | 4.732 | 442.05 |
| 1-22 | H | H | C(=O)—N(CH$_2$CH$_3$)$_2$ | 3.990(B) | 515.05 |
| 1-23 | H | H | CH$_2$C(=O)—NHCH$_2$CH=CH$_2$ | 3.767(B) | 513.05 |
| 1-24 | H | H | CH$_2$CH$_2$C(=O)—NHCH(CH$_3$)cyclopropyl | 3.925 | 555.05 |
| 1-25 | =N—OCH$_2$C$_6$H$_5$ | | C(=O)—OCH$_3$ | 4.153(B) | 593.05 |
| 1-26 | H | H | CH$_2$C(=O)—NHCH(CH$_3$)$_2$ | 4.759 | 501.80 |
| 1-27 | H | H | CH$_2$CH$_2$CF$_3$ | 4.809 | 511.8 |
| 1-28 | H | H | C(=O)—NHCH$_2$CH$_3$ | 3.558(B) | 487.05 |
| 1-29 | H | H | CH$_2$C(=O)—NHCH$_3$ | 3.578(B) | 487.05 |
| 1-30 | =CH$_2$ | | CH$_2$CH$_2$C(=O)—NHCH(CH$_3$)$_2$ | 3.764(B) | 541.15 |
| 1-31 | H | H | CH$_2$C(=O)—NHCH$_2$CH$_2$CH$_3$ | 4.384 | 515.05 |
| 1-32 | H | H | CH$_2$C(=O)—NHCH$_2$cylopropyl | 3.833(B) | 527.05 |
| 1-33 | =N—OC$_2$H$_5$ | | C(=O)—OCH$_3$ | 4.051(B) | 531.0 |
| 1-34 | =N—OCH$_3$ | | C(=O)—OCH$_3$ | 4.555 | 516.50 |
| 1-35 | H | H | CH$_2$—cylopropyl | 4.943 | 470.05 |
| 1-36 | H | H | CH$_2$C(=O)—N(CH$_3$)C$_2$H$_5$ | 3.745(6) | 515.00 |
| 1-37 | =N—OC$_3$H$_7$ | | C(=O)—OCH$_3$ | 4.152(6) | 545.0 |
| 1-38 | H | H | CH$_2$CH$_2$C(=O)—NHC$_2$H$_5$ | 3.710 | 515.05 |
| 1-39 | H | H | CH$_2$CH$_2$C(=O)—NH C$_3$H$_7$ | 3.835(6) | 529.00 |
| 1-40 | H | H | CH$_2$CH$_2$C(=O)—N(CH$_3$)C$_2$H$_5$ | 3.913(6) | 529.00 |
| 1-41 | H | H | C(=O)—N(CH$_3$)$_2$ | 3.669(6) | 487.05 |
| 1-42 | H | H | C(=O)—NHCH(CH$_3$)$_2$ | 3.660(6) | 501.05 |
| 1-43 | H | H | C(=O)—NHCH$_2$CF$_3$ | 3.674(6) | 541.00 |
| 1-44 | H | H | C(=O)—NHCH(CH$_3$)cyclopropyl | 3.779(6) | 527.00 |

TABLE C.1-continued

| Compound Ex. | R¹ | R² | G | HPLC-MS: $R_t$(min) and [M + H] | |
|---|---|---|---|---|---|
| 1-45 | H | H | C(=O)—NHCH$_2$cylopropyl | 3.674(6) | 513.05 |
| 1-46 | H | H | CH$_2$C(=O)—N(CH$_2$CH$_3$)$_2$ | 4.618 | 529.15 |
| 1-47 | H | H | SO$_2$CH$_3$ | 4.155 | 493.95 |
| 1-48 | =CHN—CH$_2$CF$_3$ | | C(=O)—OCH$_3$ | 3.856 | 583.05 |
| 1-49 | =N—OCH$_2$—cylopropyl | | C(=O)—OCH$_3$ | 4.147(B) | 557.0 |
| 1-50 | H | H | CH$_2$CH$_2$C(=O)—NHCH$_3$ | 3.606 | 501.05 |
| 1-51 | H | H | CH$_2$CH$_2$C(=O)—N(CH$_3$)$_2$ | 3.784 | 515.05 |
| 1-52 | H | H | CH$_2$CH$_2$C(=O)—NHCH$_2$CH=CH$_2$ | 3.775 | 527.05 |
| 1-53 | H | H | CH$_2$C(=O)—NHCH$_2$CF$_3$ | 4.459 | 555.05 |
| 1-54 | H | H | CH$_2$CH$_2$C(=O)—NHCH$_2$CF$_3$ | 3.895(B) | 569.0 |
| 1-55 | H | H | CH$_2$CH$_2$C(=O)—N(CH$_2$CH$_3$)$_2$ | 3.999 | 543.05 |
| 1-56 | H | H | CH$_2$CH$_2$C(=O)—NHCH$_2$C≡CH | 3.728 | 525.05 |
| 1-57 | H | H | CH$_2$CH$_2$C(=O)—NHCH(CH$_3$)$_2$ | 3.695 | 529.15 |
| 1-58 | =CHN(CH$_3$)$_2$ | | C(=O)—NHCH$_2$CF$_3$ | 4.043(B) | 596.0 |
| 1-59 | =CHN(CH$_3$)$_2$ | | C(=O)—OCH$_3$ | 3.575(B) | 529.05 |
| 1-60 | H | H | CH$_2$CH$_2$C(=O)—NHCH$_2$cylopropyl | 3.838 | 541.05 |
| 1-61 | H | H | CH$_2$CH$_2$C(=O)—OCH$_3$ | 4.072(B) | 502.00 |
| 1-62 | H | H | CH$_2$C(=O)—NHCH$_2$C≡CH | 3.723 | 511.05 |

C.2 Compound Examples 2

Compound examples 2-1 correspond to compound formula C.2:

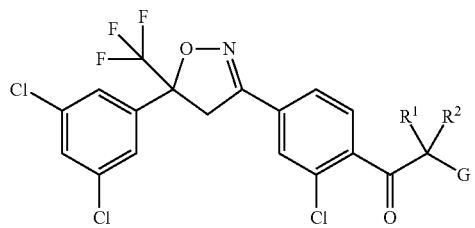

(formula C.2)

wherein R¹, R² and G of each compound example is defined table C.2 below.

TABLE C.2

| Compound Ex. | R¹ | R² | G |
|---|---|---|---|
| 2-1 | H | H | H |

C.3 Compound Examples 3

Compound examples 3-1 correspond to compound formula C.3:

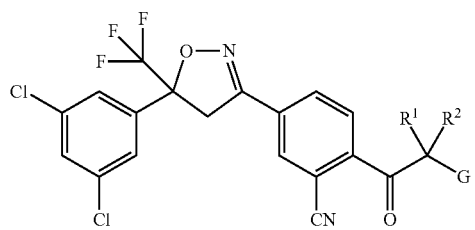

(formula C.3)

wherein R¹, R² and G of each compound example is defined table C.3 below.

TABLE C.3

| Compound Ex. | R¹ | R² | G |
|---|---|---|---|
| 3-1 | H | H | H |

C.4 Compound Examples 4

Compound examples 4-1 correspond to compound formula C.4:

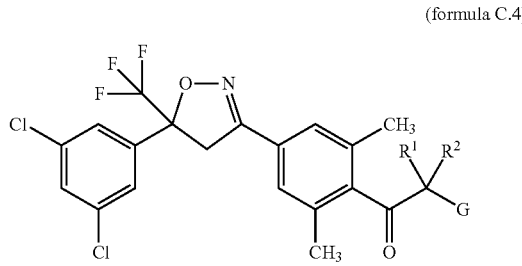

(formula C.4)

wherein R¹, R² and G of each compound example is defined table C.4 below.

TABLE C.4

| Compound Ex. | R¹ | R² | G | HPLC-MS: $R_t$ (min) and [M + H] | |
|---|---|---|---|---|---|
| 4-1 | H | H | H | 4.758 | 430.05 |

S. Synthesis Examples

S.1 Synthesis of 1-{4-[5-(3,5-Dichloro-phenyl)-5-trifluoromethyl-4,5-dihydro-isoxazol-3-yl]-2-methyl-phenyl}-ethanone (Compound 1-1 of table C.1)

A mixture of 3-(4-Bromo-3-methyl-phenyl)-5-(3,5-dichloro-phenyl)-5-trifluoromethyl-4,5-dihydro-isoxazole (500 mg), 1,4-butanediol-monovinyl ether (385 mg), 1,3-bis (diphenylphosphine)propane (dppp, 9 mg), palladium on charcoal (10%, 23 mg), dicylohexylmethylamine (259 mg) and n-butanol (3 mL) were stirred under an atmosphere of nitrogen at reflux over night. After cooling, ethyl acetate (30 mL) and aqueous hydrochloric acid (1 M, 20 mL) were added and the mixture was stirred at room temperature for 1 h. After filtration, the layers were separated, the organic layer was extracted with 1 M HCl, dried ($Na_2SO_4$) and evaporated in vacuum. Purification of the residue on silica gel afforded the title compound (270 mg, 60%).

Characterization by HPLC-MS: 4.224 min, M=415.60
Characterization by $^1$H-NMR (500 MHz, $CDCl_3$):
δ [delta]=2.53 (s, 3H), 2.60 (s, 3H), 3.71 (d, 1H), 4.11 (d, 1H), 7.42 (s, 1H), 7.52 (s, 3H), 7.58 (m, 1H), 7.73 (d, 1H) ppm.

S.2 Synthesis of 1-{4-[5-(3,5-Dichloro-phenyl)-5-trifluoromethyl-4,5-dihydro-isoxazol-3-yl]-2-methyl-phenyl}-3-methyl-butan-1-one (Compound 1-2 of table C.1)

Step 1: Synthesis of 1-{4-[5-(3,5-Dichloro-phenyl)-5-trifluoromethyl-4,5-dihydro-soxazol-3-yl]-2-methyl-phenyl}-3-methyl-butan-1-ol To a solution of 3-(4-Bromo-3-methyl-phenyl)-5-(3,5-dichloro-phenyl)-5-trifluoromethyl-4,5-dihydro-isoxazole (2.00 g) in ether (80 mL) was added tert.-butyllithium (1.6 M in pentane, 5.8 mL) at −78° C. After 10 min, a solution of $MgBr_2$ (0.15 M in THF, 58.9 mL) was added at this temperature. After another 15 min at −78° C., valeraldehyde (0.52 mL) was added and left for 1 h at this temperature, before the mixture was allowed to warm to room temperature. Saturated $NH_4Cl$ solution was added and the mixture was extracted with MTBE. The organic layer was separated and dried ($Na_2SO_4$). Evaporation in vacuum afforded a residue that was purified by flash chromatography on silica gel to afford the title compound (1.02 g, 50%).

Characterization by HPLC-MS: 3.935 min, M=460.00

Step 2: Synthesis of 1-{4-[5-(3,5-Dichloro-phenyl)-5-trifluoromethyl-4,5-dihydro-isoxazol-3-yl]-2-methyl-phenyl}-3-methyl-butan-1-one To a solution of 1-{4-[5-(3,5-Dichloro-phenyl)-5-trifluoromethyl-4,5-dihydro-soxazol-3-yl]-2-methyl-phenyl}-3-methyl-butan-1-ol (i.e. the product of Step 1, 1.20 g) in dichloromethane (50 mL) was added Dess-Martin reagent ([87413-09-0], 1.216 g) in small portions. After 30 min at room temperature, aqueous NaHCO3 solution was added, followed by Na2S2O4 solution. The organic layer was separated and washed with water and dried ($Na_2SO_4$). Evaporation in vacuum afforded a residue that was purified by flash chromatography on silica gel to afford the title compound (1.05 g, 88%).

Characterization by HPLC-MS: 4.220 min, M=458.05

B. Biological Examples

The activity of the compounds of formula I of the present invention could be demonstrated and evaluated in biological tests described in the following.

If not otherwise specified the test solutions were prepared as follow:

The active compound was dissolved at the desired concentration in a mixture of 1:1 (vol:vol) distilled water:acteon. The test solution was prepared at the day of use and in general at concentrations of ppm (wt/vol).

B.1 Diamond Back Moth (*Plutella xylostella*)

Leaves of Chinese cabbage were dipped in test solution and air-dried. Treated leaves were placed in petri dished lined with moist filter paper. Mortality was recorded 24, 72, and 120 hours after treatment.

In this test, the compounds 1-1 1-2, 1-16, 1-22, 1-23, 1-27, 1-28, 1-29, 1-31, 1-32, 1-35, 1-36, 1-38, 1-39, 1-40, 1-41, 1-42, 1-43, 1-44, 1-45, 1-46, 1-47, 1-48, 1-50, 1-51, 1-52, 1-53, 1-54, 1-55, 1-56, 1-57, 1-58 and 1-60, respectively, at 300 ppm showed a mortality of at least 75% in comparison with untreated controls.

B.2 Mediterranean Fruitfly (*Ceratitis capitata*)

For evaluating control of Mediterranean fruitfly (*Ceratitis capitata*) the test unit consisted of microtiter plates containing an insect diet and 50-80 *C. capitata* eggs.

The compounds were formulated using a solution containing 75% v/v water and 25% v/v DMSO. Different concentrations of formulated compounds were sprayed onto the insect diet at 5 μl, using a custom built micro atomizer, at two replications. After application, microtiter plates were incubated at about 28±1° C. and about 80±5% relative humidity for 5 days. Egg and larval mortality was then visually assessed.

In this test, the compounds 1-1, 1-2, 1-3, 1-6, 1-18, 1-23, 1-24, 1-26, 1-29, 1-31, 1-32, 1-38, 1-39, 1-40, 1-45, 1-46, 1-48, 1-50, 1-51, 1-52, 1-53, 1-54, 1-55, 1-56, 1-57, 1-58 and 1-60 respectively, at 2500 ppm showed a mortality of at least 75% in comparison with untreated controls.

B.3 Silverleaf Whitefly (*Bemisia argentifolii*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was placed into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding. Cups were covered with a reusable screened lid. Test plants were maintained in a growth room at about 25° C. and about 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, the compounds 1-1, 1-2, 1-23, 1-24, 1-26, 1-27, 1-29, 1-31, 1-36, 1-38, 1-39, 1-40, 1-41, 1-42, 1-44, 1-46, 1-50, 1-51, 1-52, 1-53, 1-54, 1-55, 1-56 and 1-57, respectively, at 300 ppm showed a mortality of at least 75% in comparison with untreated controls.

B.4 Southern Armyworm (*Spodoptera eridania*)

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Lima bean plants (variety Sieva) were grown 2 plants to a pot and selected for treatment at the 1$^{st}$ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compounds 1-1, 1-2, 1-5, 1-16, 1-22, 1-23, 1-24, 1-26, 1-27, 1-28, 1-29, 1-31, 1-32, 1-35, 1-36, 1-38, 1-39, 1-40, 1-41, 1-42, 1-43, 1-44, 1-45, 1-46, 1-47, 1-50, 1-51, 1-52, 1-53, 1-54, 1-55, 1-56, 1-57, 1-58 and 1-60, respectively, at 300 ppm showed a mortality of at least 75% in comparison with untreated controls.

B.5 Vetch aphid (*Megoura viciae*)

For evaluating control of vetch aphid (*Megoura viciae*) through contact or systemic means the test unit consisted of 24-well-microtiter plates containing broad bean leaf disks.

The compounds were formulated using a solution containing 75% v/v water and 25% v/v DMSO. Different concentrations of formulated compounds were sprayed onto the leaf disks at 2.5 µl, using a custom built micro atomizer, at two replications. After application, the leaf disks were air-dried and 5-8 adult aphids placed on the leaf disks inside the microtiter plate wells. The aphids were then allowed to suck on the treated leaf disks and incubated at about 23±1° C. and about 50±5% relative humidity for 5 days. Aphid mortality and fecundity was then visually assessed.

In this test, the compounds 1-1, 1-2, 1-23, 1-24, 1-26, 1-29, 1-31, 1-32, 1-38, 1-39, 1-40, 1-45, 1-46, 1-50, 1-51, 1-52, 1-53, 1-54, 1-55, 1-56, 1-57 and 1-60 respectively, at 2500 ppm showed a mortality of at least 75% in comparison with untreated controls.

B.6 Tobacco Budworm (*Heliothis virescens*) I

The active compounds were formulated in cyclohexanone as a 10,000 ppm solution supplied in tubes. The tubes were inserted into an automated electrostatic sprayer equipped with an atomizing nozzle and they served as stock solutions for which lower dilutions were made in 50% acetone:50% water (v/v). A nonionic surfactant (Kinetic®) was included in the solution at a volume of 0.01% (v/v).

Cotton plants were grown 2 plants to a pot and selected for treatment at the cotyledon stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 budworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, the compounds 1-1, 1-2, 1-3, 1-23, 1-24, 1-26, 1-29, 1-31, 1-32, 1-38, 1-39, 1-40, 1-45, 1-46, 1-50, 1-51, 1-52, 1-53, 1-54, 1-55, 1-56, 1-58, 1-60 and 1-61 respectively, at 2500 ppm showed a mortality of at least 75% in comparison with untreated controls.

B.7 Boll Weevil (*Anthonomus grandis*)

For evaluating control of boll weevil (*Anthonomus grandis*) the test unit consisted of 24-well-microtiter plates containing an insect diet and 20-30 *A. grandis* eggs.

The compounds were formulated using a solution containing 75% v/v water and 25% v/v DMSO. Different concentrations of formulated compounds were sprayed onto the insect diet at 20 µl, using a custom built micro atomizer, at two replications.

After application, microtiter plates were incubated at about 23±1° C. and about 50±5% relative humidity for 5 days. Egg and larval mortality was then visually assessed.

In this test, the compounds 1-1, 1-3, 1-23, 1-24, 1-26, 1-29, 1-31, 1-32, 1-38, 1-39, 1-40, 1-45, 1-46, 1-50, 1-51, 1-52, 1-53, 1-54, 1-55, 1-56, 1-57, 1-58, 1-60 and 1-61 respectively, at 2500 ppm showed a mortality of at least 75% in comparison with untreated controls.

B.8 Green Peach Aphid (*Myzus Persicae*)

For evaluating control of green peach aphid (*Myzus persicae*) through systemic means the test unit consisted of 96-well-microtiter plates containing liquid artificial diet under an artificial membrane.

The compounds were formulated using a solution containing 75% v/v water and 25% v/v DMSO. Different concentrations of formulated compounds were pipetted into the aphid diet, using a custom built pipetter, at two replications.

After application, 5-8 adult aphids were placed on the artificial membrane inside the microtiter plate wells. The aphids were then allowed to suck on the treated aphid diet and incubated at about 23±1° C. and about 50±5% relative humidity for 3 days. Aphid mortality and fecundity was then visually assessed.

In this test, the compounds 1-1, 1-2, 1-3, 1-18, 1-23, 1-24, 1-26, 1-29, 1-31, 1-32, 1-38, 1-39, 1-40, 1-45, 1-46, 1-50, 1-51, 1-52, 1-53, 1-54, 1-55, 1-56, 1-57, 1-58, and 1-60 respectively, at 2500 ppm showed a mortality of at least 75% in comparison with untreated controls.

The activity of compounds of formula I can also be evaluated by applying other biological assays, such as:

HB.1 Cotton Aphid (*Aphis gossypii*)

The active compounds are formulated in cyclohexanone as a 10,000 ppm solution supplied in tubes. The tubes are inserted into an automated electrostatic sprayer equipped with an atomizing nozzle and they serv as stock solutions for which lower dilutions are made in 50% acetone:50% water (v/v). A nonionic surfactant (Kinetic®) is included in the solution at a volume of 0.01% (v/v).

Cotton plants at the cotyledon stage are infested with aphids prior to treatment by placing a heavily infested leaf from the main aphid colony on top of each cotyledon. Aphids are allowed to transfer overnight to accomplish an infestation of 80-100 aphids per plant and the host leaf is removed. The infested plants are then sprayed by an automated electrostatic plant sprayer equipped with an atomizing spray nozzle. The plants are dried in the sprayer fume hood, removed from the sprayer, and then maintained in a growth room under fluorescent lighting in a 24-hr photoperiod at 25° C. and 20-40% relative humidity. Aphid mortality on the treated plants, relative to mortality on untreated control plants, is determined after 5 days.

HB.2 Cowpea Aphid (*aphis craccivora*)

Potted cowpea plants colonized with approximately 100-150 aphids of various stages are sprayed after the pest population has been recorded. Population reduction is assessed after 24, 72, and 120 hours.

HB.3 Orchid Thrips (*dichromothrips corbetti*)

*Dichromothrips corbetti* adults used for bioassay are obtained from a colony maintained continuously under laboratory conditions. For testing purposes, the test compound is diluted to a concentration of 300 ppm (wt compound: vol diluent) in a 1:1 mixture of acetone:water (vol:vol), plus 0.01% vol/vol Kinetic® surfactant.

Thrips potency of each compound is evaluated by using a floral-immersion technique. Plastic petri dishes are used as test arenas. All petals of individual, intact orchid flowers are dipped into treatment solution and allowed to dry. Treated flowers are placed into individual petri dishes along with 10-15 adult thrips. The petri dishes are then covered with lids. All test arenas are held under continuous light and a temperature of about 28° C. for duration of the assay. After 4 days, the numbers of live thrips are counted on each flower, and along inner walls of each petri dish. The level of thrips mortality is extrapolated from pre-treatment thrips numbers.

HB.4 Red Spider Mite (*Tetranychus kanzawai*)

The active compound is dissolved at the desired concentration in a mixture of 1:1 (v/v) distilled water:acetone. A surfactant (Alkamuls® EL 620) is added at the rate of 0.1% (v/v).

Potted cowpea beans of 7-10 days of age are cleaned with tap water and sprayed with 5 ml of the test solution using air driven hand atomizer. The treated plants are allowed to air dry and afterwards inculated with 20 or more mites by clipping a cassava leaf section with known mite population. Treated plants are placed inside a holding room at about 25-27° C. and about 50-60% relatice humidity.

Mortality is determined by counting the live mites 72 HAT. Percent mortality is assessed after 72 h.

HB.5 Western Flower Thrips (*Frankliniella occidentalis*)

Serial dilutions of each technical grade AI ire made in pure acetone. 0.5 ml of the treatment solution was deposited into the bottom of a glass vial (scintillation vial). The cap is screwed back onto the vial and inverted for about five seconds. The cap is subsequently removed and the vial laid on its side and rolled constantly, on a hot dog roller, until all the acetone had flashed off and the inner surface of the vial is dry. Cotton leave discs are also dipped simultaneously into the treatment solutions and allowed to dry. After the vials are dried, the leave discs are placed into the vials to serve as a food/water source for the thrips. Each treatment is replicated 5-fold. Western flower thrips are aspirated into the vials, approximately 5 larvae or adults/vial. Following treatment application the vials are held in a holding room under fluorescent light and constant 26° C. Thrips mortality is assessed at 2 DAT (days after treatment), counting all thrips both dead and alive.

If not otherwise specified in these tests, the test solutions are prepared as follow: The active compound is dissolved at the desired concentration in a mixture of 1:1 (vol:vol) distilled water:acteon. The test solution is prepared at the day of use and in general at concentrations of ppm (wt/vol).

BA. Animal Health

General test conditions of animal health glass vial contact assays

If not otherwise specified the tests are usually to be conducted as glass vial contact assays. Glass vials (20 ml scintillation vials) are used. Treatment solutions are mixed with technical grade chemicals diluted in acetone. Treatment solutions needed for the assays include generally 1 and 10 ppm (0.01 and 0.1 µg/cm$^2$, respectively), but optionally also 100 and/or 1000 ppm for first tier vials. As commercial standard, alphacypermethrin, is run at 1 ppm. As solvent control, acetone is used for the assay. Treatment solution is pipetted into the bottom of each vial. Each vial is turned on its side and placed onto a commercial grade hot dog roller without applying heat. The uncapped vials are allowed to roll to allow for the acetone treatment to vent off. After drying, the vials are placed into the compartmented vial shipping boxes. The workstation is prepared by chilling the table and plastic Petri dishes with the inside wall coated with Fluon. A weigh boat of 10% sugar water saturated cotton dental pellets is also prepared. The animal pests are collected into a tube with a rechargeable insect vacuum. The tube of animal pests is placed in a laboratory refrigerator until the animal pests are incapacitated. The animal pests are emptied into chilled Petri dish. A small cotton dental pellet is soaked in water or in 10 wt % sugar water, whereas the excess solution is gently squeezed out. The cotton dental pellet is placed into the bottom of each vial. For the test the animal pests are added to each vial and then the cap is loosely put on the vial to allow for ventilation. The test vials are hold at ambient room temperature in compartmented boxes. In general, the animal pests are observed for incapacitation at least at 4, 24, and 48 hours after infestation, or for a longer period, if required. Mortality is defined as an insect incapable of coordinated movement when agitated.

BA.1 Acrobat Ant Workers (*Crematogaster* sp.)

Treatment solutions are mixed with test compound diluted in acetone at concentrations of 10 and 100 ppm. Collected ants for placement in the vials are typically not chilled prior to infesting vials. Data are collected at 1, 2, and 4 days after infestation.

BA.2 Brown Dog Tick Adults (*Rhipicephalus sanguineus*)

Treatment solutions are mixed with test compound diluted in acetone at concentrations of 10 and 100 ppm. No food or water source is provided in the vials. Data are collected out to 5 days after infestation. Ticks are evaluated by rolling the vials on a preheated hotdog roller. Tick activity is stimulated within approx. 1-2 minutes.

BA.3 Cat Flea Adults (*Ctenocephalides felis*)

Treatment solutions are mixed with test compound diluted in acetone at concentrations of 10 and 100 ppm. The standard (alphacypermethrin) is used at 10 ppm. The cat flea adults fleas are incapacitated by placing the shipment vials of fleas in a laboratory freezer (−20° C.) for about 3 minutes. Upon removal from the freezer, the fleas are then emptied into a chilled Petri dish and covered. No food or water source is provided in the vials. Fleas are observed for incapacitation at 1, 2, and 3 days after infestation.

BA.4 German Cockroach Adults (*Blattella germanica*)

Treatment solutions are mixed with test compound diluted in acetone at concentrations of 10 and 100 ppm. The cockroaches are incapacitated by chilling them in a Fluon or petroleum jelly/mineral oil treated plastic tray that is placed onto a bed of ice set into a large plastic tub. Then the cockroaches are emptied into chilled Petri dish. The small cotton dental pellet soaked in water is added into the bottom of each vial. Test vials are hold at ambient room temperature in compartmented boxes, whereas the compartmented box are stored with the vials on its side. Data are collected at 4 hours, and 1, 2 days after infestation.

BA.5 House Fly Adults (*Musca domestica*)

Treatment solutions are mixed with test compound diluted in acetone at concentrations of 1 and 10 ppm. The small cotton dental pellet added is soaked in 10% sugar water. Flies are observed for incapacitation at 4, 24, and 48 hours after infestation.

BA.6 Yellowfever Mosquito Adults (*Aedes aegypti*)

BA.6.a Glass Vial Contact Assay (Test Conditions as Described Above)

Treatment solutions are mixed with test compound diluted in acetone at concentrations of 1 and 10 ppm. The mosquitoes are incapacitated by placing the entire cage into a walk-in cooler or lab refrigerator for 5-10 minutes. Chilled plastic Petri dish with the inside wall coated with Fluon and bottom lined with a piece of paper towel are placed within the cage. Mosquitoes are collected with a mouth aspirator and emptied into the Petri dish, quickly replacing the lid on the dish. The dish is removed from the cage and the small cotton dental pellet soaked in 10% sugar water is added into the bottom of each vial then placed onto the chill table. Flies are observed for incapacitation at 4, 24, and 48 hours after infestation.

BA.6.b Larval Mosquito Water Treatment Assay

The assay is conducted in 6-well polystyrene plates using one plate per treatment rate. Stock solutions are prepared at 100 and 1000 ppm. Screen rates are at 1 and 10 ppm. Distilled water is added to each well, control wells are treated with acetone. Temephos (Abate technical) is used as the standard at 0.1 ppm. Ten late third-instar yellowfever mosquito larvae (*Aedes aegypti*) in water are added to each well. One drop of liver powder solution (6 g in 100 ml distilled water) is added to each well as a food source daily. Plates are maintained at 22-25° C. and 25-50% RH (relative humidity) and observed daily for dead larvae and pupae at 1, 2, 3, and 5 days after treatment. Dead larvae and all pupae are removed daily. Mortality is defined as an insect incapable of coordinated movement when agitated.

We claim:

1. A compound of formula (I)

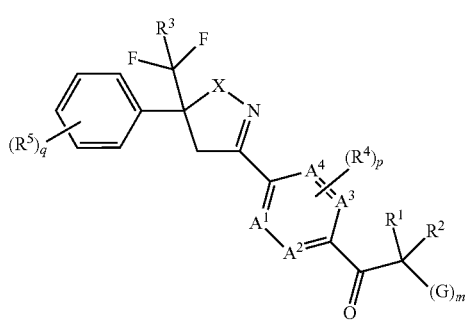

(I)

wherein $A^1$, $A^2$, $A^3$ and $A^4$ are N or CH, with the proviso that no more than two nitrogen are present in the ring;

X is O, S or $CH_2$;

p is 0, 1, 2, 3 or 4;

q is 0, 1, 2, 3, 4 or 5;

m is 0 or 1;

G is selected from the group consisting of hydrogen, nitro, cyano, —SCN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, wherein the carbon atoms of the aforementioned aliphatic and cyclo-aliphatic radicals may optionally be substituted with one or more $R^6$, which are independently selected from one another;
$NR^{9a}R^{9b}$, $S(O)_nR^7$, —$S(O)_nNR^{9a}R^{9b}$, $C(=O)R^6$, $C(=O)OR^7$, $C(=O)NR^{9a}R^{9b}$, $C(=S)R^6$, $C(=S)SR^7$, $C(=S)NR^{9a}R^{9b}$, $C(=NR^8)R^6$;

phenyl, optionally substituted with one or more substituents $R^{10}$, which are selected independently from one another, and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{10}$, selected independently from one another, and wherein the nitrogen and/or the sulfur atom(s) of the heterocyclic ring may optionally be oxidized;

$R^1$, $R^2$ are selected independent from one another from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, wherein the carbon atoms of the aforementioned aliphatic and cyclo-aliphatic radicals may optionally be substituted with one or more $R^6$, which are independently selected from one another;

$Si(R^{11})_2R^{12}$, $OR^7$, $OSO_2R^7$, $S(O)_nR^7$, $S(O)_nNR^{9a}R^{9b}$, $NR^{9a}R^{9b}$, $C(=O)NR^{9a}R^{9b}$, $C(=S)NR^{9a}R^{9b}$, $C(=O)OR^7$, phenyl, optionally substituted with one or more substituents $R^{10}$, which are independently selected from one another; and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{10}$, selected independently from one another, and wherein the nitrogen and/or the sulfur atom(s) of the heterocyclic ring may optionally be oxidized, or, $R^1$ and $R^2$ may together form =$CR^{13}R^{14}$; =$CR^{13}NR^{17a}R^{17b}$, =$S(O)_nR^{16}$; =$S(O)_nNR^{17a}R^{17b}$, =$NR^{17a}$, =$NOR^{16}$; =$NNR^{17a}$;

or $R^1$ and $R^2$ may form together with the carbon atoms to which $R^1$ and $R^2$ are bonded to a 3-, 4-, 5-, 6-, 7- or 8-membered saturated, partly or fully unsaturated or aromatic carbocyclic or heterocyclic ring optionally comprising 1, 2 or 3 heteroatoms selected from the group consisting of oxygen, nitrogen and sulfur and/or optionally substituted with k substituents $R^{10}$, selected independently from one another, and wherein the nitrogen and/or the sulfur atom(s) of the heterocyclic ring may optionally be oxidized;

$R^3$ is selected from the group consisting of hydrogen, halogen, hydroxyl, nitrile, SCN, $C_1$-$C_4$-alkyl, $C_1$-$C_4$-haloalkyl, $C_1$-$C_4$-alkoxy-$C_1$-$C_4$-alkyl, $C_1$-$C_4$-haloalkoxy-$C_3$-$C_6$-cycloalkyl $C_3$-$C_6$-halocycloalkyl and $C_1$-$C_4$-halothioalkyl;

$R^4$ is attached to a carbon atom of the ring and is selected, independently from each other if p>1, from the group consisting of hydrogen, halogen, cyano, azido, nitro, —SCN, $SF_5$, $C_1$-$C_6$-alkyl, $C_3$-$C_8$-cycloalkyl, $C_2$-$C_6$-alkenyl, $C_2$-$C_6$-alkynyl, wherein the carbon atoms of the aforementioned aliphatic and cyclo-aliphatic radicals may optionally be substituted with one or more $R^6$, which are independently selected from one another;

$Si(R^{11})_2R^{12}$, $OR^7$, —$OS(O)_nR^7$, $S(O)_nR^7$, $NR^{9a}R^{9b}$, $N(R^{9a})C(=O)R^6$, $C(=O)R^6$, —$C(=O)OR^7$, $C(=NR^8)R^6$, $C(=S)R^6$, phenyl, optionally substituted with one or more substituents independently selected from $R^{10}$, which are selected independently from one another; and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{10}$, independently selected from one another, and wherein the nitrogen and/or the sulfur atom(s) of the heterocyclic ring may optionally be oxidized, or, when p is 2 or more and two of $R^4$ are adjacent, the two adjacent $R^4$ may form a bridge selected from the group consisting of $CH_2CH_2CH_2CH_2$, $CH=CH—CH=CH$, $N=CH—CH=CH$, $CH=N—CH=CH$, $N=CH—N=CH$, $OCH_2CH_2CH_2$, $OCH=CHCH_2$, $CH_2OCH_2CH_2$, $OCH_2CH_2O$, $OCH_2OCH_2$, $CH_2CH_2CH_2$, $CH=CHCH_2$, $CH_2CH_2O$, $CH=CHO$, $CH_2OCH_2$, $CH_2C(=O)O$, $C(=O)OCH_2$, $O(CH_2)O$, $SCH_2CH_2CH_2$, $SCH=CHCH_2$, $CH_2SCH_2CH_2$, $SCH_2CH_2S$, $SCH_2SCH_2$, $CH_2CH_2S$, $CH=CHS$, $CH_2SCH_2$, $CH_2C(=S)S$, $C(=S)SCH_2$, $S(CH_2)S$, $CH_2CH_2NR^{9a}$, $CH_2CH=N$, $OCH=N$, $SCH=N$, and $CH=CH—NR^{9a}$, wherein the carbon atoms of the bridge may optionally be substituted with one or two substituents selected from the group consisting of $=O$, $OH$, $CH_3$, $OCH_3$, halogen, halomethyl or halomethoxy;

$R^5$ is selected independently from each other if q>1 from the group consisting of hydrogen, halogen, cyano, azido, nitro, SCN, $SF_5$, $C_1$-$C_6$-alkyl, $C_3$-$C_8$-cycloalkyl, $C_2$-$C_6$-alkenyl, $C_2$-$C_6$-alkynyl, wherein the carbon atoms of the aforementioned aliphatic and cyclo-aliphatic radicals may optionally be substituted with one or more $R^6$, which are independently selected from one another;

$Si(R^{11})_2R^{12}$, $OR^7$, $—OS(O)_nR^7$, $S(O)_nR^7$, $NR^{9a}R^{9b}$, $N(=R^{9a})C(=O)R^6$, $C(=O)R^6$, $C(=O)OR^7$, $C(=NR^8)R^6$, $C(=S)R^6$, phenyl, optionally substituted with one or more substituents $R^{10}$; which are independently selected from one another; and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{10}$, independently selected from one another, and wherein the nitrogen and/or the sulfur atom(s) of the heterocyclic ring may optionally be oxidized;

$R^6$ is selected from the group consisting of hydrogen, halogen, cyano, azido, nitro, $—SCN$, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $Si(R^{11})_2R^{12}$, $OR^{16}$, $OSO_2R^{16}$, $S(O)_nR^{16}$, $S(O)_nNR^{17a}R^{17b}{}_2$, $NR^{17a}R^{17b}$, $NR^{17a}C(=O)R^{16}C(=O)NR^{17a}R^{17b}$, $C(=S)NR^{17a}R^{17b}$, $C(=O)OR^{16}$, phenyl, optionally substituted with one or more substituents $R^{18}$, which are independently selected from one another; and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{18}$, selected independently from one another, and wherein the nitrogen and/or the sulfur atom(s) of the heterocyclic ring may optionally be oxidized;

or two $R^6$ present on one carbon atom may together form $=O$, $=CR^{13}R^{14}$; $=S(O)_nR^{16}$; $=S(O)_nNR^{17a}R^{17b}$, $=NR^{17a}$, $=NOR^{16}$; $=NNR^{17a}R^{17b}$;

or two $R^6$ may form a 3-, 4-, 5-, 6-, 7- or 8-membered saturated or partly unsaturated carbocyclic or heterocyclic ring together with the carbon atoms to which the two $R^6$ are bonded to;

$R^7$ is, independent from each other, selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_4$-$C_8$-alkylcycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $—Si(R^{11})_2R^{12}$, $S(O)_nR^{16}$, $—S(O)_nNR^{17a}R^{17b}$, $NR^{17a}R^{17b}$, $—N=CR^{13}R^{14}$, $—C(=O)R^{16}$, $C(=O)NR^{17a}R^{17b}$, $C(=S)NR^{17a}R^{17b}$, $C(=O)OR^{16}$, phenyl, optionally substituted with one or more substituents $R^{18}$; which are selected independently from one another; and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{18}$, selected independently from one another, and wherein the nitrogen and/or the sulfur atom(s) of the heterocyclic ring may optionally be oxidized;

$R^8$ is selected from the group consisting of hydrogen, nitro, cyano, $C_1$-$C_{10}$-alkyl, $C_3$-$C_8$-cycloalkyl, $C_2$-$C_{10}$-alkenyl, $C_2$-$C_{10}$-alkynyl, wherein the carbon atoms of the aforementioned aliphatic and cyclo-aliphatic radicals may optionally be substituted with one or more $R^{15}$, which are selected independently from one another; $NR^{17a}R^{17b}$, $Si(R^{11})_2R^{12}$, $OR^{16}$, $S(O)_nR^{16}$, $S(O)_nNR^{17a}R^{17b}$, $C(=O)R^{15}$, $—C(=O)OR^{16}$, $C(=O)NR^{17a}R^{17b}$, $C(=S)R^{15}$, $C(=S)SR^{16}$, $C(=S)NR^{17a}R^{17b}$; $C(=NR^{17a})R^{15}$;

phenyl, optionally substituted with one or more substituents $R^{18}$, which are selected independently from one another; and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{18}$, independently selected from one another, and wherein the nitrogen and/or the sulfur atom(s) of the heterocyclic ring may optionally be oxidized;

$R^{9a}$, $R^{9b}$ are selected independent from one another from the group consisting of hydrogen, $C_1$-$C_6$-alkyl, optionally substituted with one or more substituents $R^{10}$;

$C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $S(O)_nR^{16}$, $—S(O)_nNR^{17a}R^{17b}$, $C(=O)R^{15}$, $C(=O)OR^{16}$, $C(=C)NR^{17a}R^{17b}$, $C(=S)R^{15}$, $C(=S)SR^{16}$, $C(=S)NR^{17a}R^{17b}$, $C(=NR^{17a})R^{15}$, phenyl, optionally substituted with one or more substituents $R^{18}$, which are selected independently from one another;

a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized;
or,
$R^{9a}$ and $R^{9b}$ are together a $C_2$-$C_7$ alkylene chain and form a 3-, 4-, 5-, 6-, 7- or 8-membered saturated, partly saturated or unsaturated aromatic ring together with the nitrogen atom they are bonded to, wherein the alkylene chain may contain one or two heteroatoms selected from the group consisting of oxygen, sulfur and nitrogen, and may optionally be substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl;

phenyl, optionally substituted with one or more substituents $R^{18}$; which are selected independently from one another; or a 3-, 4-, 5-, 6-, or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{18}$, selected independently from one another, and wherein the nitrogen and/or the sulfur atom(s) of the heterocyclic ring may optionally be oxidized;

$R^{10}$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl, wherein the carbon atoms of the aforementioned aliphatic and cyclo-aliphatic radicals may optionally be substituted with one or more $R^{15}$, which are selected independently from one another;
$Si(R^{11})_2R^{12}$, $OR^{16}$, $OS(O)_nR^{16}$, —$S(O)_nR^{16}$, $S(O)_nNR^{17a}R^{17b}$, $NR^{17a}R^{17b}$, $C(=O)R^{15}$, $C(=O)OR^{16}$, —$C(=NR^{17a})R^{15}$, $C(=O)NR^{17a}R^{17b}$, $C(=S)NR^{17a}R^{17b}$, phenyl, optionally substituted with halogen, cyano, nitro, $C_1$-$C_6$-alkyl, $C_1$-$C_6$-haloalkyl, $C_1$-$C_6$-alkoxy or $C_1$-$C_6$-haloalkoxy; and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents selected independently from one another from the group consisting of halogen, cyano, $NO_2$, $C_1$-$C_6$-alkyl, $C_1$-$C_6$-haloalkyl, $C_1$-$C_6$-alkoxy and $C_1$-$C_6$-haloalkoxy, and wherein the nitrogen and/or the sulfur atom(s) of the heterocyclic ring may optionally be oxidized;
or two $R^{10}$ present together on one atom of a partly saturated heterocyclic may be =O, =$CR^{13}R^{14}$; =$S(O)_nR^{16}$; =$S(O)_nNR^{17a}R^{17b}$, =$NR^{17a}$, =$NOR^{16}$; or =$NNR^{17a}$;

or, two $R^{10}$ on adjacent carbon atoms may be a bridge selected from the group consisting of $CH_2CH_2CH_2CH_2$, CH=CH—CH=CH, N=CH—CH=CH, CH=N—CH=CH, N=CH—N=CH, $OCH_2CH_2CH_2$, OCH=$CHCH_2$, $CH_2OCH_2CH_2$, $OCH_2CH_2O$, $OCH_2OCH_2$, $CH_2CH_2CH_2$, CH=$CHCH_2$, $CH_2CH_2O$, CH=CHO, $CH_2OCH_2$, $CH_2C(=O)O$, $C(=O)OCH_2$, $O(CH_2)O$, $SCH_2CH_2$, SCH=$CHCH_2$, $CH_2SCH_2CH_2$, $SCH_2CH_2S$, $SCH_2SCH_2$, $CH_2CH_2S$, CH—CHS, $CH_2SCH_2$, $CH_2C(=S)S$, $C(=S)SCH_2$, $S(CH_2)S$, $CH_2CH_2NR^{9a}$, $CH_2CH=N$, CH=CH—$NR^{9a}$, OCH=N, and SCH=N and form together with the carbon atoms to which the two $R^{10}$ are bonded to a 5-membered or 6-membered partly saturated or unsaturated, aromatic carbocyclic or heterocyclic ring, wherein the ring may optionally be substituted with one or two substituents selected from the group consisting of =O, OH, $CH_3$, $OCH_3$, halogen, halomethyl and halomethoxy;

$R^{11}$, $R^{12}$ are selected independent from one another from the group consisting of hydrogen, halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_8$ cycloalkyl, $C_3$-$C_8$ halocycloalkyl, $C_1$-$C_6$ alkoxyalkyl, $C_1$-$C_6$ haloalkoxyalkyl, phenyl, optionally substituted with one or more substituents $R^{18}$; which are selected independently from one another; and a 3-, 4-, 5-, 6- to 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{18}$, selected independently from one another, and wherein the nitrogen and/or the sulfur atom(s) of the heterocyclic ring may optionally be oxidized;

$R^{13}$, $R^{14}$ are selected independent from one another from the group consisting of hydrogen, $C_1$-$C_4$ alkyl, $C_1$-$C_6$ cycloalkyl, $C_1$-$C_4$ alkoxyalkyl, phenyl and benzyl;

$R^{15}$ is selected from the group consisting of hydrogen, halogen, cyano, azido, nitro, OH, SH, SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, ($C_1$-$C_6$-alkyl)amino or di-($C_1$-$C_6$-alkyl)amino, ($C_1$-$C_6$-haloalkyl)amino, di-($C_1$-$C_6$-haloalkyl)amino, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cycloaliphatic radicals may be unsubstituted, partially or fully halogenated and/or oxygenated and/or may carry 1 or 2 radicals selected from $C_1$-$C_4$ alkoxy;

phenyl, benzyl, pyridyl, and phenoxy, wherein the last four radicals may be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino and di-($C_1$-$C_6$-alkyl)amino;

or two $R^{15}$ present on the same carbon atom may together be =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl);

$R^{16}$ is selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals may be unsubstituted, partially or fully halogenated and/or oxygenated and/or may carry 1 or 2 radicals selected from $C_1$-$C_4$ alkoxy cyclopropyl, halocyclopropyl;

phenyl, benzyl, pyridyl, and phenoxy, wherein the last four radicals may be unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

$R^{17a}$, $R^{17b}$ is selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $C_1$-$C_4$-alkoxy, $C_1$-$C_4$-alkyl, cyclopropyl, halocyclopropyl, pyridyl;

phenyl, benzyl, pyridyl, and phenoxy, wherein the four last mentioned radicals may be unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

or, $R^{17a}$ and $R^{17b}$ may together be a $C_2$-$C_6$ alkylene chain forming a 3- to 7-membered saturated, partly saturated or unsaturated ring together with the nitrogen atom $R^{17a}$ and $R^{17b}$ are bonded to, wherein the alkylene chain may contain 1 or 2 heteroatoms selected from the group consisting of oxygen, sulfur and nitrogen, and may optionally be substituted with halogen, $C_1$-$C_4$-haloalkyl, $C_1$-$C_4$-alkoxy or $C_1$-$C_4$-haloalkoxy, and wherein the nitrogen and/or the sulfur atom(s) of the heterocyclic ring may optionally be oxidized;

$R^{18}$ is selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $C_1$-$C_4$-alkoxy;

phenyl, benzyl, pyridyl, and phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy), ($C_1$-$C_6$-alkoxy)carbonyl;

or two $R^{18}$ present together on one atom of a partly saturated atom may be $=O$, $=N(C_1$-$C_6$-alkyl), $=NO(C_1$-$C_6$-alkyl), $=CH(C_1$-$C_4$-alkyl) or $=C(C_1$-$C_4$-alkyl)$C_1$-$C_4$-alkyl;

or, two $R^{18}$ on two adjacent carbon atoms may be together a $C_2$-$C_6$ alkylene chain, which form together with the carbon atom they are bonded to a 3-, 4-, 5-, 6- or 7-membered saturated, partly saturated or unsaturated aromatic, wherein the alkylene chain may contain 1 or 2 heteroatoms selected from the group consisting of oxygen, sulfur and nitrogen, and may optionally be substituted with halogen, $C_1$-$C_4$-haloalkyl, $C_1$-$C_4$-alkoxy or $C_1$-$C_4$-haloalkoxy, and wherein the nitrogen and/or the sulfur atom(s) of the heterocyclic ring may optionally be oxidized;

n is 0, 1 or 2;

k is an integer selected from 0 to 10;

or an enantiomer, diastereomer or salt thereof.

2. The compound of claim 1, wherein
$A^4$ is CH.

3. The compound of claim 1, wherein
$A^1$, $A^3$, $A^4$ are CH.

4. The compound of claim 1, wherein
X is O.

5. The compound of claim 1, wherein
$R^3$ is selected from the group consisting of hydrogen, halogen, hydroxyl, nitrile, SCN, $C_1$-$C_4$-haloalkyl, and $C_3$-$C_6$-halocycloalkyl.

6. The compound of claim 1, wherein
$R^3$ is selected from the group consisting of halogen, $C_1$-$C_4$-alkyl, $C_1$-$C_4$-haloalkyl.

7. The compound of claim 1, wherein
$R^3$ is selected from the group consisting of chlorine, bromine and fluorine.

8. The compound of claim 1, wherein
$R^1$, $R^2$ are selected independent from one another from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, wherein the carbon atoms of the aforementioned aliphatic and cyclo-aliphatic radicals may optionally be substituted with one or more $R^6$, which are independently selected from one another, $Si(R^{11})_2 R^{12}$, $OR^7$, $OSO_2R^7$, $S(O)_n R^7$, $S(O)_n NR^{9a}R^{9b}$ $NR^{9a}R^{9b}$, $C(=O)NR^{9a}R^{9b}$, $C(=S)NR^{9a}R^{9b}$, $C(=O)OR^7$, phenyl, optionally substituted with one or more substituents $R^{10}$, which are independently selected from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, selected independently from one another, and wherein the nitrogen and/or the sulfur atom(s) of the heterocyclic ring may optionally be oxidized; and m is 1.

9. The compound of claim 1, wherein
$R^1$ and $R^2$ may together form $=CR^{13}R^{14}$; $=CR^{13}NR^{17a}R^{17b}$; $=S(O)_n R^{16}$; $=S(O)_n NR^{17a}R^{17b}$; $=NR^{17a}$; $=NOR^{16}$; $=NNR^{17a}$; or may form together with the carbon atom to which $R^1$ and $R^2$ are bonded to a 3-, 4-, 5-, 6-, 7- or 8-membered saturated, partly unsaturated carbocyclic or heterocyclic ring optionally comprising 1, 2 or 3 heteroatoms selected from oxygen, nitrogen and/or sulfur and/or optionally substituted with k substituents $R^{10}$, selected independently from one another, and wherein the nitrogen and/or the sulfur atom(s) of the heterocyclic ring may optionally be oxidized;

m is 1; and

G is selected from the group consisting of hydrogen, cyano, —SCN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, wherein the carbon atoms of the aforementioned aliphatic and cyclo-aliphatic radicals may optionally be substituted with one or more $R^6$, which are independently selected from one another, or
$NR^{9a}R^{9b}$, $S(O)_n R^7$, $-S(O)_n NR^{9a}R^{9b}$, $C(=O)R^6$, $C(=O)OR^7$, $C(=O)NR^{9a}R^{9b}$, $C(=NR^8)R^6$;

phenyl, optionally substituted with one or more substituents $R^{10}$, selected independently from one another;

a 3-, 4-, 5-, 6- or 7-membered saturated, partly saturated, partly or fully unsaturated or aromatic heterocyclic ring comprising 1, 2 or 3 heteroatoms selected from oxygen, nitrogen and/or sulfur, optionally substituted with k substituents $R^{10}$, selected independently from one another, and wherein the nitrogen and/or the sulfur atom(s) of the heterocyclic ring may optionally be oxidized.

10. The compound of claim 1, wherein $R^1$ and $R^2$ may form together with the carbon atom to which $R^1$ and $R^2$ are bonded to a 5- or 6-membered carboaromatic or heteroaromatic ring, optionally comprising 1, 2 or 3 heteroatoms selected from oxygen nitrogen and/or sulfur and/or optionally substituted with k substituents $R^{10}$, selected independently from one another; and m is 0.

11. The compound of claim 1, wherein q is 1; and $R^5$ is selected from the group consisting of hydrogen, halogen, cyano, $C_1$-$C_6$-alkyl, $C_1$-$C_6$-alkyl, $C_3$-$C_8$-cycloalkyl, wherein the five last aliphatic and cyclo-aliphatic radicals may optionally be substituted with one or more $R^{15}$, selected independently from one another;

$Si(R^{11})_2R^{12}$, $OR^7$, $OS(O)_nR^7$, $S(O)_nR^7$, $NR^{9a}R^{9b}$, $N(R^{9a})C(=O)R^6$, $C(=O)R^6$, $C(=O)OR^7$, $C(=NR^{9a})R^6$ and $C(=S)R^6$; and $R^5$ is substituted in position 3.

12. The compound of claim 1, wherein q is 2; and both $R^5$ are selected independently from one another from the group consisting of hydrogen, halogen, cyano, $OR^7$, $C_1$-$C_6$-alkyl, $C_3$-$C_8$-cycloalkyl, wherein the carbon atoms of the two last aliphatic and cyclo-aliphatic radicals may optionally be substituted with one or more $R^6$ and are selected independently from one another; and the two $R^5$ are substituted in position 3 and 5.

13. The compound of claim 1, and of formula (I-2)

(I-2)

wherein $R^3$ is selected from the group consisting of halogen, $C_1$-$C_4$-alkyl, $C_1$-$C_4$-haloalkyl.

14. The compound of claim 1, and of formula (I-3)

(I-3)

wherein $R^3$ is selected from the group consisting of halogen, $C_1$-$C_4$-alkyl, $C_1$-$C_4$-haloalkyl.

15. The compound of claim 1, and of formula (I-4)

(I-4)

wherein $R^3$ is selected from the group consisting of halogen, $C_1$-$C_4$-alkyl, $C_1$-$C_4$-haloalkyl;

p is 0, 1 or 2;

$R^4$ is selected independently from p from the group consisting of hydrogen, halogen, cyano, azido, nitro, —SCN, $SF_5$, $C_1$-$C_6$-alkyl, $C_3$-$C_8$-cycloalkyl, $C_2$-$C_6$-alkenyl, $C_2$-$C_6$-alkynyl, wherein the carbon atoms of the aforementioned aliphatic and cyclo-aliphatic radicals may optionally be substituted with one or more $R^6$, which are independently selected from one another, $Si(R^{11})_2R^{12}$, $OR^7$, —$OS(O)_nR^7$, $S(O)nR^7$, $NR^{9a}R^{9b}$, $N(R^{9a})C(=O)R^6$, $C(=O)R^6$, $C(=O)OR^7$, $C(=NR^{9a})R^6$, $C(=S)R^6$, phenyl, optionally substituted with one or more substituents independently selected from $R^{10}$, which are selected independently from one another, a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{10}$, independently selected from one another, and wherein the nitrogen and/or the sulfur atom(s) of the heterocyclic ring may optionally be oxidized, or, when p is 2 and two of $R^4$ are adjacent, the two adjacent $R^4$ may be a bridge selected from the group consisting of $CH_2CH_2CH_2CH_2$, $CH=CH$—

CH=CH, N=CH—CH=CH, CH=N—CH=CH, N=CH—N=CH, OCH$_2$CH$_2$CH$_2$, OCH=CHCH$_2$, CH$_2$OCH$_2$CH$_2$, OCH$_2$CH$_2$O, OCH$_2$OCH$_2$, CH$_2$CH$_2$CH$_2$, CH=CHCH$_2$, CH$_2$CH$_2$O, CH=CHO, CH$_2$OCH$_2$, CH$_2$C(=O)O, C(=O)OCH$_2$, O(CH$_2$)O, SCH$_2$CH$_2$CH$_2$, SCH=CHCH$_2$, CH$_2$SCH$_2$CH$_2$, SCH$_2$CH$_2$S, SCH$_2$SCH$_2$, CH$_2$CH$_2$S, CH=CHS, CH$_2$SCH$_2$, CH$_2$C(=S)S, C(=S)SCH$_2$, S(CH$_2$)S, CH$_2$CH$_2$NR$^{9a}$, CH$_2$CH=N, CH=CH—NR$^{9a}$, OCH=N, SCH=N;

R$^{5a}$ and R$^{5c}$ are selected independently from one another from the group consisting of hydrogen, halogen, cyano, nitro, SCN, SF$_5$, C$_1$-C$_6$-alkyl, C$_3$-C$_8$-cycloalkyl, wherein the carbon atoms of the two last aliphatic and cyclo-aliphatic radicals may optionally be substituted with one or more R$^6$, selected independently from one another, OR$^7$, S(O)nR$^7$, NR$^{9a}$R$^{9b}$, C(=O)R$^6$, —C(=O)OR$^7$, C(=NR$^8$)R$^6$, C(=S)NR$^6$; and R$^{5b}$ is selected from the group consisting of hydrogen, halogen, cyano, nitro, —SCN, SF$_5$, C$_1$-C$_6$-alkyl, C$_1$-C$_6$-alkyl, C$_3$-C$_8$-cycloalkyl, C$_2$-C$_6$-alkenyl, C$_2$-C$_6$-alkynyl, wherein the five last aliphatic and cyclo-aliphatic radicals may optionally be substituted with one or more R$^6$, selected independently from one another, Si(R$^{11}$)$_2$R$^{12}$, OR$^7$, OS(O)$_n$R$^7$, S(O)$_n$R$^7$, NR$^{9a}$R$^{9b}$, N(R$^{9a}$)C(=O)R$^6$, CHO, C(=O)R$^6$, C(=O)OR$^7$, C(=NR$^9$)R$^6$, C(=S)NR$^6$, phenyl, optionally substituted with one or more substituents R$^{10}$, which are selected independently from one another;

a 3-, 4-, 5-, 6- to 7-membered saturated, partly saturated or unsaturated aromatic heterocyclic ring comprising 1, 2 or 3 heteroatoms selected from oxygen, nitrogen and/or sulfur, optionally substituted with k substituents R$^{10}$, independently selected from one another, and wherein the nitrogen and/or the sulfur atom(s) of the heterocyclic ring may optionally be oxidized.

16. The compound of claim 1, and of formula (I-5)

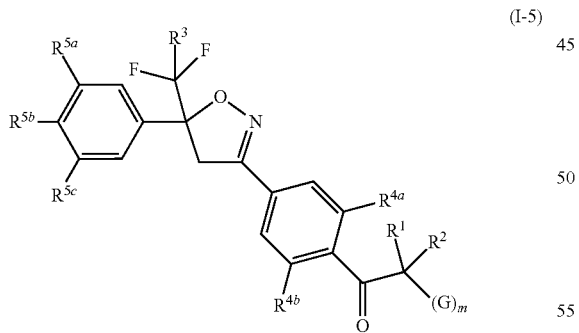

(I-5)

wherein
R$^3$ is selected from the group consisting of halogen, C$_1$-C$_4$-alkyl, C$_1$-C$_4$-haloalkyl;
R$^{4a}$ and R$^{4b}$ are selected independently from one another from the group consisting of hydrogen, halogen, cyano, azido, nitro, —SCN, SF$_5$, C$_1$-C$_6$-alkyl, C$_3$-C$_8$-cycloalkyl, wherein the carbon atoms of the last two aliphatic and cyclo-aliphatic radicals may optionally be substituted with one or more R$^6$, which are independently selected from one another, OR$^7$, —OS(O)$_n$R$^7$, S(O)nR$^7$, NR$^{9a}$R$^{9b}$, N(R$^{9a}$)C(=O)R$^6$, CHO, C(=O)R$^6$, —C(=O)OR$^7$, C(=NR$^{9a}$)R$^6$, C(=S)R$^6$, phenyl, optionally substituted with one or more substituents independently selected from R$^{10}$, which are selected independently from one another, a 3-, 4-, 5-, 6- or 7-membered saturated, partly saturated or unsaturated aromatic heterocyclic ring;

R$^{5a}$ and R$^{5c}$ are selected independently from one another from the group consisting of hydrogen, halogen, cyano, nitro, SCN, SF$_5$, C$_1$-C$_6$-alkyl, C$_3$-C$_8$-cycloalkyl, wherein the carbon atoms of the two last aliphatic and cyclo-aliphatic radicals may optionally be substituted with one or more R$^6$, selected independently from one another, OR$^7$, S(O)nR$^7$, NR$^{9a}$R$^{9b}$, C(=O)R$^6$, —C(=O)OR$^7$, C(=NR$^8$)R$^6$, C(=S)NR$^6$;

and

R$^{5b}$ is selected from the group consisting of hydrogen, halogen, cyano, nitro, —SCN, SF$_5$, C$_1$-C$_6$-alkyl, C$_1$-C$_6$-alkyl, C$_3$-C$_8$-cycloalkyl, C$_2$-C$_6$-alkenyl, C$_2$-C$_6$-alkynyl, wherein the aliphatic chains of the five last radicals may optionally be substituted with one or more R$^6$, selected independently from one another, Si(R$^{11}$)$_2$R$^{12}$, OR$^7$, OS(O)$_n$R$^7$, S(O)$_n$R$^7$, NR$^{9a}$R$^{9b}$, N(R$^{9a}$)C(=O)R$^6$, C(=O)R$^6$, C(=O)OR$^7$, C(=NR$^{9a}$)R$^6$, C(=S)NR$^6$, phenyl, optionally substituted with one or more substituents R$^{10}$, which are selected independently from one another;

a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents R$^{10}$, independently selected from one another, and wherein the nitrogen and/or the sulfur atom(s) of the heterocyclic ring may optionally be oxidized.

17. The compound of claim 16 and of formula (I-5), wherein
R$^{4a}$ and R$^{4b}$ are selected independently from one another from the group consisting of hydrogen, halogen, cyano, nitro, SCN, C$_1$-C$_6$-alkyl, C$_3$-C$_8$-cycloalkyl, wherein the carbon atoms of the of the last two aliphatic and cyclo-aliphatic radicals may optionally be substituted with one or more R$^6$, which are independently selected from one another, OR$^7$, —OS(O)$_n$R$^7$, S(O)nR$^7$, NR$^{9a}$R$^{9b}$, N(R$^{9a}$)C(=O)R$^6$, C(=O)R$^6$, —C(=O)OR$^7$, C(=NR$^{9a}$)R$^6$, C(=S)R$^6$;

R$^{5a}$ and R$^{5c}$ are selected independently from one another from the group consisting of hydrogen, halogen, cyano, OR$^7$, C$_1$-C$_6$-alkyl, C$_3$-C$_8$-cycloalkyl, wherein the carbon atoms of the two last aliphatic and cyclo-aliphatic radicals may optionally be substituted with one or more R$^6$, selected independently from one another;

and

R$^{5b}$ is selected from the group consisting of hydrogen, halogen, cyano, C$_1$-C$_6$-alkyl, C$_1$-C$_6$-alkyl, C$_3$-C$_8$-cycloalkyl, wherein the five last aliphatic and cyclo-aliphatic radicals may optionally be substituted with one or more R$^{15}$, selected independently from one another, Si(R$^{11}$)$_2$R$^{12}$, OR$^7$, OS(O)$_n$R$^7$, S(O)$_n$R$^7$, NR$^{9a}$R$^{9b}$, N(R$^{9a}$)C(=O)R$^6$, C(=O)R$^6$, C(=O)OR$^7$, C(=NR$^{9a}$)R$^6$ and C(=S)R$^6$.

18. The compound of claim 16, wherein
the ketonic isoxazoline compounds is an enantiomer of formula (I-S)

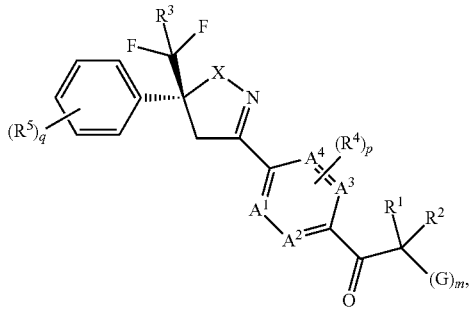

(I-S)

having the S-configuration.

19. The compound of claim 16, wherein
the ketonic isoxazoline compounds is an enantiomer of formula (I-R)

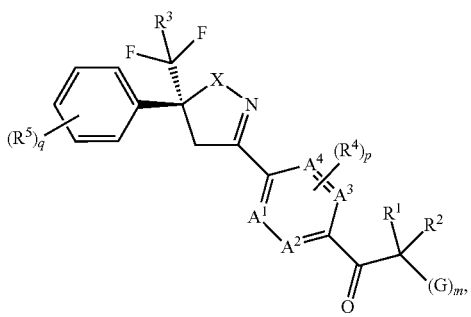

(I-R)

having the R-configuration.

20. A compound of formula (I-A)

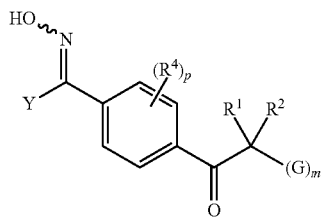

(I-A)

wherein
Y is hydrogen or halogen;
p is 0, 1, 2, 3 or 4;
m is 0 or 1;
G is selected from the group consisting of hydrogen, nitro, cyano, —SCN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, wherein the carbon atoms of the aforementioned aliphatic and cyclo-aliphatic radicals may optionally be substituted with one or more $R^6$, which are independently selected from one another;

$NR^{9a}R^{9b}$, $S(O)_nR^7$, —$S(O)_nNR^{9a}R^{9b}$, $C(=O)R^6$, $C(=O)OR^7$, $C(=O)NR^{9a}R^{9b}$, $C(=S)R^6$, $C(=S)SR^7$, $C(=S)NR^{9a}R^{9b}$, $C(=NR^8)R^6$;

phenyl, optionally substituted with one or more substituents $R^{10}$, which are selected independently from one another, and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{10}$, selected independently from one another, and wherein the nitrogen and/or the sulfur atom(s) of the heterocyclic ring may optionally be oxidized;

$R^1$, $R^2$ are selected independent from one another from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, wherein the carbon atoms of the aforementioned aliphatic and cyclo-aliphatic radicals may optionally be substituted with one or more $R^6$, which are independently selected from one another;

$Si(R^{11})_2R^{12}$, $OR^7$, $OSO_2R^7$, $S(O)_nR^7$, $S(O)_nNR^{9a}R^{9b}$, $NR^{9a}R^{9b}$, $C(=O)NR^{9a}R^{9b}$, $C(=S)NR^{9a}R^{9b}$, $C(=O)OR^7$, phenyl, optionally substituted with one or more substituents $R^{10}$, which are independently selected from one another; and a 2-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{10}$, selected independently from one another, and wherein the nitrogen and/or the sulfur atom(s) of the heterocyclic ring may optionally be oxidized, or, $R^1$ and $R^2$ may together form =$CR^{13}R^{14}$; =$CR^{13}NR^{17a}R^{17b}$, =$S(O)_nR^{16}$; =$S(O)_nNR^{17a}R^{17b}$, =$NR^{17a}$; =$NOR^{16}$; =$NNR^{17a}$;

or $R^1$ and $R^2$ may form together with the carbon atoms to which $R^1$ and $R^2$ are bonded to a 3-, 4-, 5-, 6-, 7- or 8-membered saturated, partly or fully unsaturated or aromatic carbocyclic or heterocyclic ring optionally comprising 1, 2 or 3 heteroatoms selected from the group consisting of oxygen, nitrogen and sulfur and/or optionally substituted with k substituents $R^{10}$, selected independently from one another, and wherein the nitrogen and/or the sulfur atom(s) of the heterocyclic ring may optionally be oxidized;

$R^4$ is attached to a carbon atom of the ring and is selected, independently from each other if p>1, from the group consisting of hydrogen, halogen, cyano, azido, nitro, —SCN, $SF_5$, $C_1$-$C_6$-alkyl, $C_3$-$C_8$-cycloalkyl, $C_2$-$C_6$-alkenyl, $C_2$-$C_6$-alkynyl, wherein the carbon atoms of the aforementioned aliphatic and cyclo-aliphatic radicals may optionally be substituted with one or more $R^6$, which are independently selected from one another;

$Si(R^{11})_2R^{12}$, $OR^7$, —$OS(O)_nR^7$, $S(O)_nR^7$, $NR^{9a}R^{9b}$, $N(R^{9a})C(=O)R^6$, $C(=O)R^6$, —$C(=O)OR^7$, $C(=NR^8)R^6$, $C(=S)R^6$, phenyl, optionally substituted with one or more substituents independently selected from $R^{10}$, which are selected independently from one another; and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{10}$, independently selected from one another, and wherein the nitrogen and/or the sulfur atom(s) of the heterocyclic ring may optionally be oxidized, or, when p is 2 or more and two of $R^4$ are adjacent, the two adjacent $R^4$ may form a bridge selected from the group consisting of $CH_2CH_2CH_2CH_2$, CH=CH—CH=CH, N=CH—CH=CH, CH=N—CH=CH, N=CH—N=CH, $OCH_2CH_2CH_2$, OCH=CHCH$_2$, $CH_2OCH_2CH_2$, $OCH_2CH_2O$, $OCH_2OCH_2$, $CH_2CH_2CH_2$, CH=CHCH$_2$, $CH_2CH_2O$, CH=CHO, $CH_2OCH_2$, $CH_2C(=O)O$, C(=O)OCH$_2$, O(CH$_2$)O, $SCH_2CH_2CH_2$, SCH=CHCH$_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, C(=S)SCH$_2$, S(CH$_2$)S, $CH_2CH_2NR^{9a}$, $CH_2CH=N$, OCH=N, SCH=N, and CH=CH—NR$^{9a}$, wherein the carbon atoms of the bridge may optionally be substituted with one or two substituents selected from the group consisting of =O, OH, CH$_3$, OCH$_3$, halogen, halomethyl or halomethoxy;

$R^5$ is selected from the group consisting of hydrogen, halogen, cyano, azido, nitro, —SCN, SF$_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, $Si(R^{11})_2R^{12}$, $OR^{16}$, $OSO_2R^{16}$, $S(O)_nR^{16}$, $S(O)_nNR^{17a}R^{17b}$, $NR^{17a}R^{17b}$, $NR^{17a}C(=O)R^{16}C(=O)NR^{17a}R^{17b}$, C(=S)NR$^{17a}$R$^{17b}$, C(=O)OR$^{16}$, phenyl, optionally substituted with one or more substituents $R^{10}$, which are independently selected from one another; and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{10}$, selected independently from one another, and wherein the nitrogen and/or the sulfur atom(s) of the heterocyclic ring may optionally be oxidized;

or two $R^6$ present on one carbon atom may together form =O, =CR$^{13}$R$^{14}$; =S(O)$_n$R$^{16}$; =S(O)$_n$NR$^{17a}$R$^{17b}$, =NR$^{17a}$, =NOR$^{16}$; =NNR$^{17a}$R$^{17b}$;

or two $R^6$ may form a 3-, 4-, 5-, 6-, 7- or 8-membered saturated or partly unsaturated carbocyclic or heterocyclic ring together with the carbon atoms to which the two $R^6$ are bonded to;

$R^7$ is, independent from each other, selected from the group consisting of hydrogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_4$-$C_8$-alkylcycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, —Si(R$^{11}$)$_2$R$^{12}$, S(O)$_n$R$^{16}$, —S(O)$_n$NR$^{17a}$R$^{17b}$, NR$^{17a}$R$^{17b}$, —N=CR$^{13}$R$^{14}$, —C(=O)R$^{16}$, C(=O)NR$^{17a}$R$^{17b}$, C(=S)NR$^{17a}$R$^{17b}$, C(=O)OR$^{16}$, phenyl, optionally substituted with one or more substituents $R^{18}$; which are selected independently from one another;

a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{18}$, selected independently from one another, and wherein the nitrogen and/or the sulfur atom(s) of the heterocyclic ring may optionally be oxidized;

$R^8$ is selected from the group consisting of hydrogen, nitro, cyano, $C_1$-$C_{10}$-alkyl, $C_3$-$C_8$-cycloalkyl, $C_2$-$C_{10}$-alkenyl, $C_2$-$C_{10}$-alkynyl, wherein the carbon atoms of the aforementioned aliphatic and cyclo-aliphatic radicals may optionally be substituted with one or more $R^{15}$, which are selected independently from one another;

NR$^{17a}$R$^{17b}$, Si(R$^{11}$)$_2$R$^{12}$, OR$^{16}$, S(O)$_n$R$^{16}$, S(O)$_n$NR$^{17a}$R$^{17b}$, C(=O)R$^{15}$, —C(=O)OR$^{16}$, C(=O)NR$^{17a}$R$^{17b}$, C(=S)R$^{15}$, C(=S)SR$^{16}$, C(=S)NR$^{17a}$R$^{17b}$; C(=NR$^{17a}$)R$^{15}$;

phenyl, optionally substituted with one or more substituents $R^{18}$, which are selected independently from one another; and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{18}$, independently selected from one another, and wherein the nitrogen and/or the sulfur atom(s) of the heterocyclic ring may optionally be oxidized;

$R^{9a}$, $R^{9b}$ are selected independent from one another from the group consisting of hydrogen, $C_1$-$C_6$-alkyl, optionally substituted with one or more substituents $R^{10}$;

$C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, S(O)$_n$R$^{16}$, —S(O)$_n$NR$^{17a}$R$^{17b}$, C(=O)R$^{15}$, C(=O)OR$^{16}$, C(=O)NR$^{17a}$R$^{17b}$, C(=S)R$^{15}$, C(=S)SR$^{16}$, C(=S)NR$^{17a}$R$^{17b}$, C(=NR$^{17a}$)R$^{15}$, phenyl, optionally substituted with one or more substituents $R^{18}$, which are selected independently from one another;

a 3-, 4-, 5-, 6- or 7-membered saturated, partly saturated or unsaturated aromatic heterocyclic ring comprising 1, 2 or 3 heteroatoms selected from oxygen, nitrogen and/or sulfur, optionally substituted with k substituents $R^{18}$, selected independently from one another, and wherein the nitrogen and/or the sulfur atom(s) of the heterocyclic ring may optionally be oxidized;

or, $R^{9a}$ and $R^{9b}$ are together a $C_2$-$C_7$ alkylene chain and form a 3-, 4-, 5-, 6-, 7- or 8-membered saturated, partly saturated or unsaturated aromatic ring together with the nitrogen atom they are bonded to, wherein the alkylene chain may contain one or two heteroatoms selected from the group consisting of oxygen, sulfur and nitrogen, and may optionally be substituted with halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl;

phenyl, optionally substituted with one or more substituents $R^{18}$; which are selected independently from one another; or a 3-, 4-, 5-, 6-, or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{18}$, selected independently from one another, and wherein the nitrogen and/or the sulfur atom(s) of the heterocyclic ring may optionally be oxidized;

$R^{10}$ is selected from the group consisting of hydrogen, halogen, cyano, azido, nitro, SCN, $SF_5$, $C_1$-$C_{10}$-alkyl, $C_3$-$C_8$-cycloalkyl, $C_2$-$C_{10}$-alkenyl, $C_2$-$C_{10}$-alkynyl, wherein the carbon atoms of the aforementioned aliphatic and cyclo-aliphatic radicals may optionally be substituted with one or more $R^{15}$, which are selected independently from one another;

$Si(R^{11})_2R^{12}$, $OR^{16}$, $OS(O)_nR^{16}$, —$S(O)_nR^{16}$, $S(O)_nNR^{17a}R^{17b}$, $NR^{17a}R^{17b}$, $C(=O)R^{15}$, $C(=O)OR^{16}$, —$C(=NR^{17a})R^{15}$, $C(=O)NR^{17a}R^{17b}$, $C(=S)NR^{17a}R^{17b}$, phenyl, optionally substituted with halogen, cyano, nitro, $C_1$-$C_6$-alkyl, $C_1$-$C_6$-haloalkyl, $C_1$-$C_6$-alkoxy or $C_1$-$C_6$-haloalkoxy; and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents selected independently from one another from the group consisting of halogen, cyano, $NO_2$, $C_1$-$C_6$-alkyl, $C_1$-$C_6$-haloalkyl, $C_1$-$C_6$-alkoxy and $C_1$-$C_6$-haloalkoxy, and wherein the nitrogen and/or the sulfur atom(s) of the heterocyclic ring may optionally be oxidized;

or two $R^{10}$ present together on one atom of a partly saturated heterocyclic may be =O, =$CR^{13}R^{14}$; =$S(O)_nR^{16}$; =$S(O)_nNR^{17a}R^{17b}$, =$NR^{17a}$, =$NOR^{16}$; or =$NNR^{17a}$;

or, two $R^{10}$ on adjacent carbon atoms may be a bridge selected from the group consisting of $CH_2CH_2CH_2CH_2$, CH=CH—CH=CH, N=CH—CH=CH, CH=N—CH=CH, N=CH—N=CH, $OCH_2CH_2CH_2$, OCH=$CHCH_2$, $CH_2OCH_2CH_2$, $OCH_2CH_2O$, $OCH_2OCH_2$, $CH_2CH_2CH_2$, CH=$CHCH_2$, $CH_2CH_2O$, CH=CHO, $CH_2OCH_2$, $CH_2C(=O)O$, $C(=O)OCH_2$, $O(CH_2)O$, $SCH_2CH_2CH_2$, SCH=$CHCH_2$, $CH_2SCH_2CH_2$, $SCH_2CH_2S$, $SCH_2SCH_2$, $CH_2CH_2S$, CH—CHS, $CH_2SCH_2$, $CH_2C(=S)S$, $C(=S)SCH_2$, $S(CH_2)S$, $CH_2CH_2NR^{9a}$, $CH_2CH=N$, CH=CH—$NR^{9a}$, OCH=N, and SCH=N and form together with the carbon atoms to which the two $R^{10}$ are bonded to a 5-membered or 6-membered partly saturated or unsaturated, aromatic carbocyclic or heterocyclic ring, wherein the ring may optionally be substituted with one or two substituents selected from the group consisting of =O, OH, $CH_3$, $OCH_3$, halogen, halomethyl and halomethoxy;

$R^{11}$, $R^{12}$ are selected independent from one another from the group consisting of hydrogen, halogen, $C_1$-$C_6$ alkyl, $C_1$-$C_6$ haloalkyl, $C_1$-$C_6$ alkoxyalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_8$ cycloalkyl, $C_3$-$C_8$ halocycloalkyl, $C_1$-$C_6$ alkoxyalkyl, $C_1$-$C_6$ haloalkoxyalkyl, phenyl, optionally substituted with one or more substituents $R^{18}$; which are selected independently from one another; and a 3-, 4-, 5-, 6- to 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{18}$, selected independently from one another, and wherein the nitrogen and/or the sulfur atom(s) of the heterocyclic ring may optionally be oxidized;

$R^{13}$, $R^{14}$ are selected independent from one another from the group consisting of hydrogen, $C_1$-$C_4$ alkyl, $C_1$-$C_6$ cycloalkyl, $C_1$-$C_4$ alkoxyalkyl, phenyl and benzyl;

$R^{15}$ is selected from the group consisting of hydrogen, halogen, cyano, azido, nitro, OH, SH, SCN, $SF_5$, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, ($C_1$-$C_6$-alkyl)amino or di-($C_1$-$C_6$-alkyl)amino, ($C_1$-$C_6$-haloalkyl)amino, di-($C_1$-$C_6$-haloalkyl)amino, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $C_1$-$C_4$ alkoxy;

phenyl, benzyl, pyridyl, and phenoxy, wherein the last four radicals may be unsubstituted, partially or fully halogenated and/or to carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy, ($C_1$-$C_6$-alkoxy)carbonyl, ($C_1$-$C_6$-alkyl)amino and di-($C_1$-$C_6$-alkyl)amino;

or two $R^{15}$ present on the same carbon atom may together be =O, =CH($C_1$-$C_4$-alkyl), =C($C_1$-$C_4$-alkyl)$C_1$-$C_4$-alkyl, =N($C_1$-$C_6$-alkyl) or =NO($C_1$-$C_6$-alkyl);

$R^{16}$ is selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned radicals may be unsubstituted, partially or fully halogenated and/or oxygenated and/or may carry 1 or 2 radicals selected from $C_1$-$C_4$ alkoxy cyclopropyl, halocyclopropyl;

phenyl, benzyl, pyridyl, and phenoxy, wherein the last four radicals may be unsubstituted, partially or fully halogenated and/or carry 1, 2 or 3 substituents selected from the group consisting of $C_1$-$C_6$-alkyl, $C_1$-$C_6$-haloalkyl, $C_1$-$C_6$-alkoxy, $C_1$-$C_6$ haloalkoxy and ($C_1$-$C_6$-alkoxy)carbonyl;

$R^{17a}$, $R^{17b}$ is selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $C_1$-$C_4$-alkoxy, $C_1$-$C_4$-alkyl, cyclopropyl, halocyclopropyl, pyridyl;

phenyl, benzyl, pyridyl, and phenoxy, wherein the four last mentioned radicals may be unsubstituted, partially or fully halogenated and/or carry 1, 2 or 3 substituents selected from the group consisting of $C_1$-$C_6$- alkyl, $C_1$-$C_6$-haloalkyl, $C_1$-$C_6$-alkoxy, $C_1$-$C_6$ haloalkoxy and ($C_1$-$C_6$-alkoxy)carbonyl;

or, $R^{17a}$ and $R^{17b}$ may together be a $C_2$-$C_6$ alkylene chain forming a 3- to 7-membered saturated, partly saturated or unsaturated ring together with the nitrogen atom $R^{17a}$ and $R^{17b}$ are bonded to, wherein the alkylene chain may contain 1 or 2 heteroatoms selected from the group consisting of oxygen, sulfur and nitrogen, and may optionally be substituted with halogen, $C_1$-$C_4$-haloalkyl, $C_1$-$C_4$-alkoxy or $C_1$-$C_4$-haloalkoxy, and wherein the nitrogen and/or the sulfur atom(s) of the heterocyclic ring may optionally be oxidized;

$R^{18}$ is selected from the group consisting of hydrogen, cyano, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, trimethylsilyl, triethylsilyl, tertbutyldimethylsilyl, $C_1$-$C_6$-alkyl, $C_2$-$C_6$-alkenyl, $C_2$-$C_6$-alkynyl, $C_3$-$C_8$-cycloalkyl, wherein the four last mentioned aliphatic and cyclo-aliphatic radicals may be unsubstituted, partially or fully halogenated and/or oxygenated and/or may carry 1 or 2 radicals selected from $C_1$-$C_4$-alkoxy;

phenyl, benzyl, pyridyl, and phenoxy, wherein the four last mentioned radicals may be unsubstituted, partially or fully halogenated and/or carry 1, 2 or 3 substituents selected from $C_1$-$C_6$-alkyl, $C_1$-$C_6$-haloalkyl, $C_1$-$C_6$-alkoxy, $C_1$-$C_6$ haloalkoxy), ($C_1$-$C_6$-alkoxy)carbonyl;

or two $R^{18}$ present together on one atom of a partly saturated atom may be =O, =N($C_1$-$C_6$-alkyl), =NO($C_1$-$C_6$-alkyl), =CH($C_1$-$C_4$-alkyl) or =C($C_1$-$C_4$-alkyl)$C_1$-$C_4$-alkyl;

or, two $R^{18}$ on two adjacent carbon atoms may be together a $C_2$-$C_6$ alkylene chain, which form together with the carbon atom they are bonded to a 3-, 4-, 5-, 6- or 7-membered saturated, partly saturated or unsaturated aromatic, wherein the alkylene chain may contain 1 or 2 heteroatoms selected from the group consisting of oxygen, sulfur and nitrogen, and may optionally be substituted with halogen, $C_1$-$C_4$-haloalkyl, $C_1$-$C_4$-alkoxy or $C_1$-$C_4$-haloalkoxy, and wherein the nitrogen and/or the sulfur atom(s) of the heterocyclic ring may optionally be oxidized;

n is 0, 1 or 2;

and k is an integer selected from 0 to 10.

21. A compound of formula (I-B)

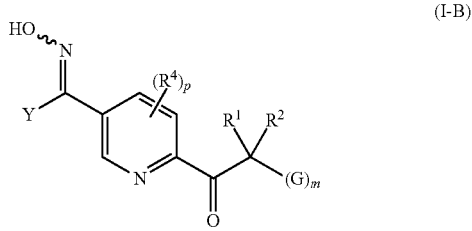

(I-B)

wherein

Y is hydrogen or halogen;

and wherein p is 0, 1, 2, 3 or 4;

m is 0 or 1;

G is selected from the group consisting of hydrogen, nitro, cyano, —SCN, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, wherein the carbon atoms of the aforementioned aliphatic and cyclo-aliphatic radicals may optionally be substituted with one or more $R^6$, which are independently selected from one another;

$NR^{9a}R^{9b}$, $S(O)_nR^7$, —$S(O)_nNR^{9a}R^{9b}$, $C(=O)R^6$, $C(=O)OR^7$, $C(=O)NR^{9a}R^{9b}$, $C(=S)R^6$, $C(=S)SR^7$, $C(=S)NR^{9a}R^{9b}$, $C(=NR^8)R^6$;

phenyl, optionally substituted with one or more substituents $R^{10}$, which are selected independently from one another, and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{10}$, selected independently from one another, and wherein the nitrogen and/or the sulfur atom(s) of the heterocyclic ring may optionally be oxidized;

$R^1$, $R^2$ are selected independent from one another from the group consisting of halogen, cyano, azido, nitro, —SCN, $SF_5$, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$ haloalkynyl, wherein the carbon atoms of the aforementioned aliphatic and cyclo-aliphatic radicals may optionally be substituted with one or more $R^6$, which are independently selected from one another;

$Si(R^{11})_2R^{12}$, $OR^7$, $OSO_2R^7$, $S(O)_nR^7$, $S(O)_nNR^{9a}R^{9b}$, $NR^{9a}R^{9b}$, $C(=O)NR^{9a}R^{9b}$, $C(=S)NR^{9a}R^{9b}$, $C(=O)OR^7$, phenyl, optionally substituted with one or more substituents $R^{10}$, which are independently selected from one another; and a 2-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{10}$, selected independently from one another, and wherein the nitrogen and/or the sulfur atom(s) of the heterocyclic ring may optionally be oxidized, or $R^1$ and $R^2$ may together form =$CR^{13}R^{14}$; =$CR^{13}NR^{17a}R^{17b}$, =$S(O)_nR^{16}$; =$S(O)_n$ $NR^{17a}R^{17b}$, =$NR^{17a}$; =$NOR^{16}$; =$NNR^{17a}$;

or $R^1$ and $R^2$ may form together with the carbon atoms to which $R^1$ and $R^2$ are bonded to a 3-, 4-, 5-, 6-, 7- or 8-membered saturated, partly or fully unsaturated or aromatic carbocyclic or heterocyclic ring optionally comprising 1, 2 or 3 heteroatoms selected from the group consisting of oxygen, nitrogen and sulfur and/or optionally substituted with k substituents $R^{10}$, selected independently from one another, and wherein the nitrogen and/or the sulfur atom(s) of the heterocyclic ring may optionally be oxidized; and $R^4$ is attached to a carbon atom of the ring and is selected, independently from each other if p>1, from the group consisting of hydrogen, halogen, cyano, azido, nitro, —SCN, $SF_5$, $C_1$-$C_6$-alkyl, $C_3$-$C_8$-cycloalkyl, $C_2$-$C_6$- alkenyl, $C_2$-$C_6$-alkynyl, wherein the carbon atoms of the aforementioned aliphatic and cyclo-aliphatic radicals may optionally be substituted with one or more $R^6$, which are independently selected from one another;
Si($R^{11}$)$_2$$R^{12}$, $OR^7$, —OS(O)$_n$$R^7$, S(O)$_n$$R^7$, $NR^{9a}R^{9b}$, $N(R^{9a})C(=O)R^6$, $C(=O)R^6$, —C(=O)O$R^7$, $C(=NR^8)R^6$, $C(=S)R^6$, phenyl, optionally substituted with one or more substituents independently selected from $R^{10}$, which are selected independently from one another; and a 3-, 4-, 5-, 6- or 7-membered saturated, partly saturated or unsaturated aromatic heterocyclic ring comprising 1, 2 or 3 heteroatoms selected from the group consisting of oxygen, nitrogen and sulfur, optionally substituted with k substituents $R^{10}$, independently selected from one another, and wherein the nitrogen and/or the sulfur atom(s) of the heterocyclic ring may optionally be oxidized, or, when p is 2 or more and two of $R^4$ are adjacent, the two adjacent $R^4$ may form a bridge selected from the group consisting of $CH_2CH_2CH_2CH_2$, CH=CH—CH=CH, N=CH—CH=CH, CH=N—CH=CH, N=CH—N=CH, $OCH_2CH_2CH_2$, OCH=CHCH$_2$, $CH_2OCH_2CH_2$, $OCH_2CH_2O$, $OCH_2OCH_2$, $CH_2CH_2CH_2$, CH=CHCH$_2$, $CH_2CH_2O$, CH=CHO, $CH_2OCH_2$, $CH_2C(=O)O$, C(=O)OCH$_2$, $O(CH_2)O$, $SCH_2CH_2CH_2$, SCH=CHCH$_2$, $CH_2SCH_2CH_2$, $SCH_2CH_2S$, $SCH_2SCH_2$, $CH_2CH_2S$, CH=CHS, $CH_2SCH_2$, $CH_2C(=S)S$, C(=S)SCH$_2$, S(CH$_2$)S, $CH_2CH_2NR^{9a}$, $CH_2CH=N$, OCH=N, SCH=N, and CH=CH—$NR^{9a}$, wherein the carbon atoms of the bridge may optionally be substituted with one or two substituents selected from the group consisting of =O, OH, $CH_3$, $OCH_3$, halogen, halomethyl or halomethoxy.

22. An agricultural composition comprising at least one compound of the formula I, as defined in claim 1, an enantiomer, diastereoisomer and/or an agriculturally acceptable salt thereof, and at least one inert liquid and/or solid agriculturally acceptable carrier.

23. A veterinary composition comprising at least one compound of the formula I, as defined in claim 1, an enantiomer, diastereoisomer and/or a veterinarily acceptable salt thereof, and at least one inert liquid and/or solid veterinarily acceptable carrier.

24. A method for controlling or combating invertebrate pests which method comprises treating the pests, their food supply, their habitat or their breeding ground or a plant, plant propagation material, soil, area, material or environment in which the pests are growing or may grow, with a pesticidally effective amount of at least one compound of claim 1.

25. A method for protecting materials, plants, plant propagation material, soils, surfaces or spaces from invertebrate pest attack or infestation comprising applying a pesticidally effective amount of at least one compound of claim 1, to the materials, plants, plant propagation material, soils, surfaces or spaces.

26. The method as claimed in claim 25, for protecting plants from attack or infestation by invertebrate pests, which method comprises treating the plants with a pesticidally effective amount of at least one compound of claim 1.

27. The method as claimed in claim 25, for protecting plant propagation material and/or the plants which grow therefrom from attack or infestation by invertebrate pests, which method comprises treating the plant propagation material with a pesticidally effective amount of at least one compound of claim 1.

28. The method according to claim 23, wherein the plant propagation material are seeds.

29. Plant propagation material treated with at least one compound of claim 1.

30. The plant propagation material according to claim 28, wherein the plant propagation material are seeds.

31. A method for treating or protecting an animal from infestation or infection by invertebrate pests which comprises bringing the animal in contact with a pesticidally effective amount of at least one compound of claim 1.

* * * * *